US010851065B2

(12) United States Patent
Bock et al.

(10) Patent No.: US 10,851,065 B2
(45) Date of Patent: Dec. 1, 2020

(54) TETRASUBSTITUTED ALKENE COMPOUNDS AND THEIR USE

(71) Applicant: Eisai R&D Management Co., Ltd., Tokyo (JP)

(72) Inventors: Mark Bock, Boston, MA (US); Ming-Hong Hao, Quincy, MA (US); Manav Korpal, Winchester, MA (US); Vijay Kumar Nyavanandi, Andhra Pradesh (IN); Xiaoling Puyang, Cambridge, MA (US); Susanta Samajdar, Kamataka (IN); Peter Gerard Smith, Arlington, MA (US); John Wang, Andover, MA (US); Guo Zhu Zheng, Lexington, MA (US); Ping Zhu, Boxborough, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/713,107

(22) Filed: Sep. 22, 2017

(65) Prior Publication Data

US 2018/0127378 A1   May 10, 2018

Related U.S. Application Data

(63) Continuation of application No. 15/167,373, filed on May 27, 2016, now Pat. No. 9,796,683.

(60) Provisional application No. 62/269,745, filed on Dec. 18, 2015, provisional application No. 62/168,529, filed on May 29, 2015, provisional application No. 62/168,581, filed on May 29, 2015.

(51) Int. Cl.
| | |
|---|---|
| *A01N 43/00* | (2006.01) |
| *A01N 43/46* | (2006.01) |
| *A61K 31/55* | (2006.01) |
| *C07D 231/56* | (2006.01) |
| *C07D 403/12* | (2006.01) |
| *C07D 471/14* | (2006.01) |
| *C07D 403/06* | (2006.01) |
| *C07D 401/06* | (2006.01) |
| *C07D 401/14* | (2006.01) |

(52) U.S. Cl.
CPC ......... *C07D 231/56* (2013.01); *C07D 401/06* (2013.01); *C07D 401/14* (2013.01); *C07D 403/06* (2013.01); *C07D 403/12* (2013.01); *C07D 471/14* (2013.01)

(58) Field of Classification Search
USPC ....................................................... 514/333
See application file for complete search history.

(56) References Cited

U.S. PATENT DOCUMENTS

| | | | |
|---|---|---|---|
| 5,552,412 A | 9/1996 | Cameron et al. | |
| 8,063,249 B1 | 11/2011 | Kushner et al. | |
| 8,299,112 B2 | 10/2012 | Smith et al. | |
| 8,455,534 B2 | 6/2013 | Smith et al. | |
| 8,785,501 B2 | 7/2014 | Witt-Enderby et al. | |
| 9,399,646 B2 | 7/2016 | Smith et al. | |
| 9,796,683 B2 | 10/2017 | Bock et al. | |
| 2002/0103229 A1 | 8/2002 | Bhagwat et al. | |
| 2013/0231333 A1 | 9/2013 | Smith et al. | |
| 2013/0336962 A1 | 12/2013 | Andersen et al. | |
| 2014/0199236 A1 | 7/2014 | Chen et al. | |
| 2015/0105403 A1 | 4/2015 | Smith et al. | |
| 2018/0127378 A1 | 5/2018 | Bock et al. | |

FOREIGN PATENT DOCUMENTS

| | | |
|---|---|---|
| EA | 000815 B1 | 4/2000 |
| EP | 0 802 184 A1 | 10/1997 |
| GB | 2483736 A | 3/2012 |
| RU | 2130454 C1 | 5/1999 |
| WO | 9010638 A1 | 9/1990 |
| WO | WO 90/10638 A1 | 9/1990 |
| WO | 2007058626 A1 | 5/2007 |
| WO | WO 2007058626 A1 | 5/2007 |
| WO | 2009120999 A2 | 10/2009 |
| WO | WO 2009120999 A2 | 10/2009 |
| WO | 2011129837 A1 | 10/2011 |
| WO | WO 2011129837 A1 | 10/2011 |
| WO | 2012037410 A2 | 3/2012 |
| WO | 2012037411 A2 | 3/2012 |
| WO | WO 2012/037410 A2 | 3/2012 |
| WO | WO 2012/037411 A2 | 3/2012 |
| WO | WO 2012037411 A2 | 3/2012 |
| WO | 2013056178 A2 | 4/2013 |
| WO | WO 2013/056178 A2 | 4/2013 |
| WO | 2013142266 A1 | 9/2013 |
| WO | WO 2013142266 A1 | 9/2013 |
| WO | 2014205136 A1 | 12/2014 |

(Continued)

OTHER PUBLICATIONS

International Search Report and Written Opinion for PCT/US16/34764, dated Aug. 30, 2016.
Search History accompanying International Search Report for PCT/US2016/34764 dated Aug. 1, 2016.
PubChem, Compound Summary for CID 69281185, dated Dec. 1, 2012.
PubChem, Compound Summary for CID 89780731, dated Feb. 13, 2015.

(Continued)

*Primary Examiner* — Layla Soroush
(74) *Attorney, Agent, or Firm* — Buchanan Ingersoll & Rooney PC

(57) ABSTRACT

Disclosed herein are compounds, or pharmaceutically acceptable salts thereof, and methods of using the compounds for treating breast cancer by administration to a subject in need thereof a therapeutically effective amount of the compounds or pharmaceutically acceptable salts thereof. The breast cancer may be an ER-positive breast cancer and/or the subject in need of treatment may express a mutant ER-α protein.

20 Claims, 5 Drawing Sheets

Specification includes a Sequence Listing.

(56) References Cited

FOREIGN PATENT DOCUMENTS

| WO | 2014205138 A1 | 12/2014 |
| --- | --- | --- |
| WO | WO 2014/205136 A1 | 12/2014 |
| WO | WO 2014/205138 A1 | 12/2014 |
| WO | 2015000868 A1 | 1/2015 |
| WO | WO 2015/000868 A1 | 1/2015 |
| WO | 2015136016 A2 | 9/2015 |
| WO | WO 2015/136016 A2 | 9/2015 |
| WO | 2016055982 A1 | 4/2016 |
| WO | 2016097071 A1 | 6/2016 |
| WO | 2016196346 A1 | 12/2016 |

OTHER PUBLICATIONS

International Search Report and Written Opinion for PCT/US2016/34774, dated Sep. 7, 2016.
Search History accompanying International Search Report for PCT/US16/34774 dated Jul. 26, 2016.
International Search Report and Written Opinion for PCT/US2016/034782, dated Aug. 23, 2016.
Search History accompanying International Search Report for PCT/US2016/034782 dated Jul. 25, 2016.
Non-Final Office Action in U.S. Appl. No. 15/167,373, dated Dec. 23, 2016.
Response to Non-Final Office Action in U.S. Appl. No. 15/167,373, dated Mar. 22, 2017.
Notice of Allowance in U.S. Appl. No. 15/167,373, dated Jun. 21, 2017.
Mattras et al., "Identification by MALDI-TOF Mass Spectrometry of 17α-Bromoacetamidopropylestradiol Covalent Attachment Sites on Estrogen Receptor α", Biochemistry, 2002, pp. 15713-15727, vol. 41, No. 52.
Reese et al., "Mutagenesis of Cysteines in the Hormone Binding Domain of the Human Estrogen Receptor", The Journal of Biological Chemistry, Jun. 1991, pp. 10880-10887, vol. 266, No. 17.
Fisher et al., "Endometrial Cancer in Tamoxifen-Treated Breast Cancer Patients: Findings From the National Surgical Adjuvant Breast and Bowel Project (NSABP) B-14", Journal of the National Cancer Institute, Apr. 1994, pp. 527-537, vol. 86, No. 7.
Li et al., "Endocrine-Therapy-Resistant ESR1 Variants Revealed by Genomic Characterization of Breast-Cancer-Derived Xenografts", Cell Reports, Sep. 2013, pp. 1116-1130, vol. 4.
Jeselsohn et al., "Emergence of Constitutively Active Estrogen Receptor-α Mutations in Pretreated Advanced Estrogen Receptor-Positive Breast Cancer", Clin Cancer Res, Apr. 2014, pp. 1757-1767, vol. 20, No. 7.
Merenbakh-Lamin et al., "D538G Mutation in Estrogen Receptor-α: A Novel Mechanism for Acquired Endocrine Resistance in Breast Cancer", Cancer Res, Dec. 2013, pp. 6856-6864, vol. 72, No. 23.
Osborne et al., "Role of the Estrogen Receptor Coactivator AIB1 (SRC-3) and HER-2/neu in Tamoxifen Resistance in Breast Cancer", Journal of the National Cancer Institute, Mar. 2003, pp. 353-361, vol. 95, No. 5.
Segal et al., "Estrogen Receptor Mutations in Breast Cancer—New Focus on an Old Target", Clin Cancer Res, Apr. 2014, pp. 1724-1726, vol. 20, No. 7.
Shou et al., "Mechanisms of Tamoxifen Resistance: Increased Estrogen Receptor-HER2/neu Cross-Talk in ER/HER2-Positive Breast Cancer", Journal of the National Cancer Institute, Jun. 2004, pp. 926-935, vol. 96, No. 12.
Toy et al., "ESR1 ligand-binding domain mutations in hormone-resistant breast cancer", Nature Genetics, Dec. 2013, pp. 1439-1445, vol. 45, No. 12.
Van Leeuwen et al., "Risk of endometrial cancer after tamoxifen treatment of breast cancer", The Lancet, Feb. 1994, pp. 448-452, vol. 343.
Yu et al., "Ex vivo culture of circulating breast tumor cells for individualized testing of drug susceptibility", Science Mag, Jul. 2014, pp. 216-220, vol. 345, issue 6193.
Robinson et al., "Activating ESR1 mutations in hormone-resistant metastatic breast cancer", Nature Genetics, Dec. 2013, pp. 1446-1451, vol. 45, No. 12.
Lai et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts", Journal of Medicinal Chemistry, 2015, pp. 4888-4904, vol. 58.
Keely et al., "Design, Synthesis and Biochemical Evaluation of Estrogen Receptor Ligand Conjugates as Tumour Targeting Agents", Letters in Drug Design & Discovery, 2012, pp. 295-304, vol. 9, No. 3.
McDonnell, "The Molecular Pharmacology of SERMs", TEM, 1999, pp. 301-311, vol. 10, No. 8.
Wang et al., "A second binding site for hydroxytamoxifen within the coactivator-binding groove of estrogen receptor 3", PNAS, pp. 9908-9911, Jun. 2006, vol. 103, No. 26.
Coser et al., "Global analysis of ligand sensitivity of estrogen inducible and suppressible genes in MCF7BUS breast cancer cells by DNA microarray", PNAS, Nov. 2003, pp. 13994-13999, vol. 100, No. 24.
The Cancer Genome Atlas Research Network, "Integrated genomic characterization of endometrial carcinoma", Nature, 2013, pp. 1-5, vol. 000.
Fisher et al., "Endometrial Cancer in Tamoxifen-Treated Breast Cancer Patients: Findings From the National Surgical Adjuvant Breast and Bowel Project (NSABP) B-14", Journal of the National Cancer Institute, Apr. 1994, pp. 527-637, vol. 86, No. 7.
Osborne et al., "Mechanisms of Endocrine Resistance in Breast Cancer", Annu. Rev. Med., 2011, pp. 233-247, vol. 62.
Wang et al., "A second binding site for hydroxytamoxifen within the coactivator-binding groove of estrogen receptor β", PNAS, pp. 9908-9911, Jun. 2006, vol. 103, No. 26.
Office Action dated Oct. 18, 2019, by the Russian Patent Office in corresponding Russian Patent Application No. 2017146408/04(079322) and an English Translation of the Office Action. (16 pages).
"International Search Report and Written Opinion", International Search Report and Written Opinion for PCT/US2017/063047 dated Feb. 28, 2018.
International Search Report and Written Opinion for PCT/JP2017/042335 filed Nov. 27, 2017, dated Feb. 20, 2018.
Harlow, K.W., et al., Identification of Cysteine 530 as the Covalent Attachment Site of an Affinity-labeling Estrogen (Ketononestrol Aziridine) and Antiestrogen(Tamoxifen Aziridine) in the Human Estrogen Receptor, The Journal of Biological Chemistry, 1989, 17476-17485, vol. 264, No. 29, Issue of Oct. 15, The American Society for Biochemistry and Molecular Biology, Inc.

SEQUENCE LISTING

```
<160> NUMBER OF SEQ ID NOS: 8

<210> SEQ ID NO 1
<211> LENGTH: 39
<212> TYPE: DNA
<213> ORGANISM: artificial sequence
<220> FEATURE:
<223> OTHER INFORMATION: mutagenesis primer

<400> SEQUENCE: 1
aagaacgtgg tgccctctc tgacctgctg ctggagatg                    39

<210> SEQ ID NO 2
<211> LENGTH: 39
<212> TYPE: DNA
<213> ORGANISM: artificial sequence
<220> FEATURE:
<223> OTHER INFORMATION: mutagenesis primer

<400> SEQUENCE: 2
catctccagc agcaggtcag agaggggcac cacgttctt                   39

<210> SEQ ID NO 3
<211> LENGTH: 39
<212> TYPE: DNA
<213> ORGANISM: artificial sequence
```

<220> FEATURE:
<223> OTHER INFORMATION: mutagenesis primer

<400> SEQUENCE: 3
aagaacgtgg tgcccctcaa tgacctgctg ctggagatg           39

<210> SEQ ID NO 4
<211> LENGTH: 39
<212> TYPE: DNA
<213> ORGANISM: artificial sequence
<220> FEATURE:
<223> OTHER INFORMATION: mutagenesis primer

<400> SEQUENCE: 4
catctccagc agcaggtcat tgaggggcac cacgttctt           39

<210> SEQ ID NO 5
<211> LENGTH: 39
<212> TYPE: DNA
<213> ORGANISM: artificial sequence
<220> FEATURE:
<223> OTHER INFORMATION: mutagenesis primer

<400> SEQUENCE: 5
aagaacgtgg tgcccctctg tgacctgctg ctggagatg           39

<210> SEQ ID NO 6
<211> LENGTH: 39
<212> TYPE: DNA
<213> ORGANISM: artificial sequence
<220> FEATURE:
<223> OTHER INFORMATION: mutagenesis primer

<400> SEQUENCE: 6
catctccagc agcaggtcac agaggggcac cacgttctt           39

<210> SEQ ID NO 7
<211> LENGTH: 39
<212> TYPE: DNA
<213> ORGANISM: artificial sequence
<220> FEATURE:
<223> OTHER INFORMATION: mutagenesis primer

<400> SEQUENCE: 7
aacgtggtgc ccctctatgg cctgctgctg gagatgctg           39

<210> SEQ ID NO 8
<211> LENGTH: 39
<212> TYPE: DNA
<213> ORGANISM: artificial sequence
<220> FEATURE:
<223> OTHER INFORMATION: mutagenesis primer

<400> SEQUENCE: 8
cagcatctcc agcagcaggc catagagggg caccacgtt           39

TETRASUBSTITUTED ALKENE COMPOUNDS AND THEIR USE

CROSS-REFERENCE TO RELATED APPLICATIONS

This application is a continuation of U.S. patent application Ser. No. 15/167,373, filed on May 27, 2016 which claims priority to U.S. Provisional Application No. 62/168,581, filed on May 29, 2015, to U.S. Provisional Patent Application No. 62/168,529, filed on May 29, 2015, and to U.S. Provisional Application No. 62/269,745, filed on Dec. 18, 2015, all of which are incorporated by reference herein.

BACKGROUND

Breast cancer is the most commonly diagnosed malignancy among women today with nearly 200,000/1.7 million new cases diagnosed in the US/worldwide each year respectively. Since about 70% of breast tumors are positive for the estrogen receptor alpha (ERα)—a key oncogenic driver in this subset of tumors—several classes of therapies have been developed to antagonize ERα function, including 1) selective estrogen receptor downregulators (SERDs) of which fulvestrant is an example, 2) selective estrogen receptor modulators (SERMs) of which tamoxifen is an example and 3) aromatase inhibitors that reduce systemic levels of estrogen. These therapies have been largely effective in the clinic reducing occurrence and progression of ERα+ breast tumors. However there are on-target liabilities associated with these different classes of compounds. For example, tamoxifen has been shown to activate signaling activity in the endometrium leading to an increase in risk of endometrial cancers in the clinic (Fisher et al., (1994) *J Natl Cancer Inst*. April 6; 86(7):527-37; van Leeuwen et al., (1994) *Lancet* February 19; 343(8895):448-52). In contrast, since fulvestrant is a pure antagonist, it can lead to loss of bone density in post-menopausal women as ERα activity is critical for bone building. In addition to on-target side effects, clinical resistance is also beginning to emerge to these classes of ERα antagonists highlighting the need to develop next-generation compounds.

Several mechanisms of resistance have been identified using in vitro and in vivo models of resistance to various endocrine therapies. These include increased ERα/HER2 "crosstalk" (Shou et al., (2004) *J Natl Cancer Inst*. June 16; 96(12):926-35), aberrant expression of ERα coactivators/corepressors (Osborne et al., (2003) *J Natl Cancer Inst*. March 5; 95(5):353-61) or loss of ERα altogether to allow ER-independent growth (Osborne C K, Schiff R (2011) *Annu Rev Med* 62: 233-47).

In the hopes of identifying clinically relevant mechanisms of resistance, great effort has also recently gone into deeply characterizing the genetics of endocrine-therapy resistant metastases isolated from patients. Several independent labs have recently published the multitude of genetic lesions observed in the resistant vs the primary tumors (Li et al., (2013) *Cell Rep*. September 26; 4(6):1116-30; Robinson et al., (2013) *Nat Genet*. December; 45(12):1446-51; Toy et al., (2013) *Nat Genet*. 2013 December; 45(12):1439-45). Among these are the highly recurrent mutations in the ligand-binding domain of ESR1 (gene which encodes ERα protein) found to be significantly enriched in about 20% of resistant tumors relative to endocrine therapy naïve tumors (Jeselsohn et al., (2014) *Clin Cancer Res*. April 1; 20(7): 1757-67; Toy et al., (2013) *Nat Genet*. 2013 December; 45(12):1439-45; Robinson et al., (2013) *Nat Genet*. December; 45(12):1446-51; Merenbakh-Lamin et al., (2013) *Cancer Res*. December 1; 73(23):6856-64; Yu et al., (2014) *Science* July 11; 345(6193):216-20; Segal and Dowsett (2014), *Clin Cancer Res* April 1; 20(7): 1724-6), suggesting the potential for these mutations to functionally drive clinical resistance. In contrast to the enrichment in ESR1 mutations observed in therapy-resistant tumors, mutations in other cancer-related genes failed to show such a robust enrichment strongly implying the importance of ERα mutations in promoting resistance (Jeselsohn et al., (2014) *Clin Cancer Res*. April 1; 20(7):1757-67).

ER+ breast cancer patients on average are treated with seven independent therapies including chemotherapies and various anti-estrogen therapies such as tamoxifen, fulvestrant and aromatase inhibitors. Recent genomic profiling has revealed that the ERα pathway remains a critical driver of tumor growth in the resistant setting as activating mutations in ERα have emerged. Thus, it is critical that more potent ER-directed therapies be developed that can overcome resistance in the clinical setting. Hence, there is a need for novel compounds that can potently suppress the growth of both wild-type (WT) and ER α-mutant positive tumors.

SUMMARY

Described herein are novel compounds useful for treating cancer. In embodiments, such novel compounds are described by Formula II:

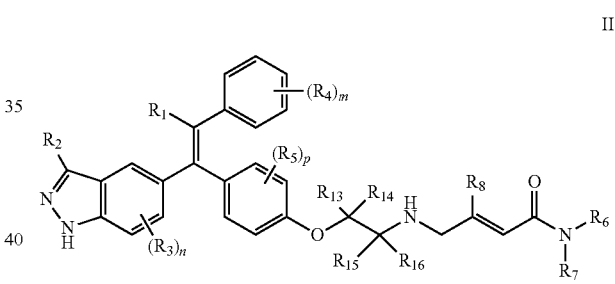

II wherein: $R_1$ is selected from the group consisting of methyl, ethyl, cyclobutyl, cyclopropyl and —$CH_2CH_2Cl$, propyl, isopropyl, —$CH_2CF_3$, and —$CH_2CH_2F$; $R_2$ is selected from the group consisting of H and F; n is 0-1; $R_3$ is F; m is 0-2; $R_4$ are the same or different and are independently selected from the group consisting of F, $CF_3$, Cl, isopropyl, —$OCH_3$, —$OCHF_2$, —$OCF_3$, ethyl and methyl; p is 0-1; $R_5$ is F; $R_6$ and $R_7$ are the same or different and are independently selected from the group consisting of methyl, ethyl, propyl, —$CH_2CH_2OH$ and

wherein r is 1 or 2; or, wherein $R_6$ and $R_7$ form a 4-6 membered heterocyclic ring with the N to which they are attached, wherein said heterocyclic ring optionally includes an oxygen atom, and wherein said heterocyclic ring is optionally substituted with F, or —$CH_2F$; $R_8$ is selected from the group consisting of H and —$CH_3$; and $R_{13}$, $R_{14}$, $R_{15}$, and $R_{16}$ are independently selected from the group consisting of —H or —$CH_3$; or pharmaceutically acceptable salts thereof.

In further embodiments, such novel compounds are described by Formula I:

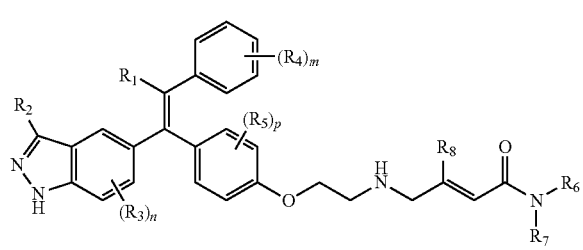

wherein: $R_1$ is selected from the group consisting of methyl, ethyl, cyclobutyl, cyclopropyl and —$CH_2CH_2Cl$; $R_2$ is selected from the group consisting of H and F; n is 0-1; $R_3$ is F; m is 0-2; $R_4$ are the same or different and are independently selected from the group consisting of F, $CF_3$, Cl, isopropyl, —$OCH_3$, —$OCHF_2$, —$OCF_3$, ethyl and methyl; p is 0-1; $R_5$ is F; $R_6$ and $R_7$ are the same or different and are independently selected from the group consisting of methyl, ethyl, propyl, —$CH_2CH_2OH$ and

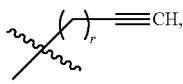

wherein r is 1 or 2; or, wherein $R_6$ and $R_7$ form a 4-6 membered heterocyclic ring with the N to which they are attached, wherein said heterocyclic ring optionally includes an oxygen atom, and wherein said heterocyclic ring is optionally substituted with F, or —$CH_2F$; $R_8$ is selected from the group consisting of H and —$CH_3$; or pharmaceutically acceptable salts thereof.

In embodiments, the compounds of Formula I may have the following preferred permutations or preferred combination of permutations: $R_1$ is ethyl or cyclobutyl; $R_6$ and $R_7$ are both methyl; $R_8$ is H; $R_2$ is H or F; m is 2 and one of $R_4$ is F and the other $R_4$ is Cl; m is 2 and both of $R_4$ are F; m is 0; $R_3$ is F; n is 0; p is 1 and $R_5$ is F; and p is 0.

In embodiments, the compounds of Formula I have the following permutation: $R_1$ is ethyl; $R_2$ is H; n is 0; m is 0; p is 0; $R_6$ and $R_7$ are the same and are methyl; $R_8$ is H; or pharmaceutically acceptable salts thereof.

In embodiments, the compounds of Formula I have the following permutation: $R_1$ is ethyl; $R_2$ is F; n is 0; m is 2 and one $R_4$ is F and one $R_4$ is Cl; p is 0; $R_6$ and $R_7$ are the same and are methyl; $R_8$ is H; or pharmaceutically acceptable salts thereof.

In embodiments, the compounds of Formula I are selected from the group consisting of (E)-4-((2-(4-((E)-1-(1H-indazol-5-yl)-2-phenylbut-1-en-1-yl)phenoxy)ethyl)amino)-N,N-dimethylbut-2-enamide; (E)-4-((2-(4-((E)-1-(3-fluoro-1H-indazol-5-yl)-2-phenyl but-1-en-1-yl) phenoxy)ethyl) amino)-N,N-dimethylbut-2-enamide; (E)-4-((2-(4-((E)-1-(3-fluoro-1H-indazol-5-yl)-2-(3-fluoro-5-(trifluoromethyl) phenyl)but-1-en-1-yl)phenoxy)ethyl)amino)-N,N-dimethylbut-2-enamide; (E)-4-((2-(4-((E)-1-(4-fluoro-1H-indazol-5-yl)-2-phenyl but-1-en-1-yl) phenoxy) ethyl)amino)-N,N-dimethylbut-2-enamide; (E)-4-((2-(4-((E)-2-(3,5-difluorophenyl)-1-(1H-indazol-5-yl)but-1-en-1-yl) phenoxy)ethyl)amino)-N,N-dimethylbut-2-enamide; (E)-4-((2-(4-((E)-2-(3,4-difluorophenyl)-1-(1H-indazol-5-yl)but-1-en-1-yl) phenoxy)ethyl)amino)-N,N-dimethylbut-2-enamide; (E)-4-((2-(4-((E)-2-(3-chloro-5-fluorophenyl)-1-(1H-indazol-5-yl)but-1-en-1-yl) phenoxy)ethyl)amino)-N,N-dimethylbut-2-enamide; (E)-4-((2-(4-((E)-1-(1H-indazol-5-yl)-2-phenylbut-1-en-1-yl)phenoxy) ethyl) amino)-N-methyl-N-(prop-2-yn-1-yl)but-2-enamide; (E)-4-((2-(4-((E)-1-(1H-indazol-5-yl)-2-phenylbut-1-en-1-yl)phenoxy) ethyl) amino)-N-(but-3-yn-1-yl)-N-methylbut-2-enamide; (E)-4-((2-(4-((E)-1-(1H-indazol-5-yl)-2-phenylbut-1-en-1-yl)phenoxy)ethyl) amino)-1-(azetidin-1-yl)but-2-en-1-one; (E)-4-((2-(4-((E)-1-(1H-indazol-5-yl)-2-phenylbut-1-en-1-yl)phenoxy)ethyl) amino)-1-(pyrrolidin-1-yl)but-2-en-1-one; (E)-4-((2-(4-((E)-1-(1H-indazol-5-yl)-2-phenylbut-1-en-1-yl)phenoxy)ethyl) amino)-1-(piperidin-1-yl)but-2-en-1-one; (E)-4-((2-(4-((E)-2-cyclobutyl-1-(1H-indazol-5-yl)-2-phenylvinyl)phenoxy) ethyl)amino)-N,N-dimethylbut-2-enamide; (E)-4-((2-(4-((E)-2-cyclobutyl-1-(3-fluoro-1H-indazol-5-yl)-2-phenylvinyl) phenoxy)ethyl)amino)-N,N-dimethylbut-2-enamide 2,2,2-trifluoro acetate; (E)-4-((2-(4-((E)-1-(1H-indazol-5-yl)-2-phenylbut-1-en-1-yl)phenoxy) ethyl) amino)-1-morpholinobut-2-en-1-one; (E)-4-((2-(4-((E)-1-(1H-indazol-5-yl)-2-phenylbut-1-en-1-yl)phenoxy) ethyl) amino)-N-ethyl-N-methylbut-2-enamide; (E)-4-((2-(4-((E)-1-(1H-indazol-5-yl)-2-phenylbut-1-en-1-yl) phenoxy)ethyl) amino)-N-methyl-N-propylbut-2-enamide; (E)-4-((2-(4-((E)-1-(1H-indazol-5-yl)-2-phenylbut-1-en-1-yl)phenoxy)ethyl)amino)-N-(2-hydroxyethyl)-N-methyl-but-2-enamide; (E)-4-((2-(4-((E)-2-(2-chloro-4-fluorophenyl)-1-(3-fluoro-1H-indazol-5-yl)but-1-en-1-yl)phenoxy) ethyl)amino)-N,N-dimethylbut-2-enamide; (E)-4-((2-(4-((E)-1-(1H-indazol-5-yl)-2-phenylbut-1-en-1-yl)phenoxy) ethyl) amino)-N,N,3-trimethylbut-2-enamide; (Z)-4-((2-(4-((E)-1-(1H-indazol-5-yl)-2-phenylbut-1-en-1-yl)phenoxy) ethyl) amino)-N,N-dimethylbut-2-enamide; (E)-4-((2-(4-((E)-2-cyclobutyl-1-(1H-indazol-5-yl)-2-phenylvinyl) phenoxy) ethyl)amino)-1-morpholinobut-2-en-1-one; (E)-4-((2-(4-((E)-2-cyclobutyl-1-(4-fluoro-1H-indazol-5-yl)-2-phenylvinyl) phenoxy)ethyl)amino)-N,N-dimethylbut-2-enamide; (E)-4-((2-((5-((Z)-1-(1H-indazol-5-yl)-2-phenylbut-1-en-1-yl)pyridin-2-yl) oxy)ethyl)amino)-N,N-dimethylbut-2-enamide; (E)-4-((2-(4-((E)-1-(1H-indazol-5-yl)-2-(o-tolyl)but-1-en-1-yl)phenoxy) ethyl)amino)-N-(2-hydroxyethyl)-N-methylbut-2-enamide; (E)-4-((2-(4-((E)-2-(2-chloro-4-fluorophenyl)-1-(3-fluoro-1H-indazol-5-yl) but-1-en-1-yl)phenoxy)ethyl)amino)-N-(2-hydroxyethyl)-N-methylbut-2-enamide; (E)-4-((2-(4-((E)-1-(1H-indazol-5-yl)-2-(4-isopropyl phenyl)but-1-en-1-yl) phenoxy)ethyl) amino)-N,N-dimethylbut-2-enamide; (E)-4-((2-(4-((E)-4-chloro-1-(1H-indazol-5-yl)-2-phenyl but-1-en-1-yl) phenoxy) ethyl)amino)-N,N-dimethylbut-2-enamide; (E)-4-((2-(4-((E)-1-(1H-indazol-5-yl)-2-(4-isopropyl phenyl)but-1-en-1-yl) phenoxy)ethyl)amino)-N,N-dimethylbut-2-enamide; (E)-4-((2-(4-((E)-2-(2-(difluoromethoxy)phenyl)-1-(1H-indazol-5-yl)but-1-en-1-yl)phenoxy)ethyl)amino)-N,N-dimethylbut-2-enamide; (E)-4-((2-(4-((E)-1-(1H-indazol-5-yl)-2-(2-(trifluoro-methoxy)phenyl)but-1-en-1-yl) phenoxy)ethyl)amino)-N,N-dimethylbut-2-enamide; (E)-4-((2-(4-((E)-1-(1H-indazol-5-yl)-2-(2-isopropyl phenyl)but-1-en-1-yl) phenoxy)ethyl)amino)-N,N-dimethylbut-2-enamide; (E)-4-((2-(4-((E)-2-(2-ethylphenyl)-1-(1H-indazol-5-yl) but-1-en-1-yl)phenoxy) ethyl)amino)-N,N-dimethylbut-2-enamide; (E)-4-((2-(4-((E)-1-(1H-indazol-5-yl)-2-(o-tolyl)but-1-en-1-yl)phenoxy)ethyl) amino)-N,N-dimethylbut-2-enamide; (E)-4-((2-((5-((Z)-1-(1H-indazol-5-yl)-2-phenylbut-1-en-1-yl)pyrimidin-2-yl) oxy)ethyl) amino)-N,N-dimethylbut-2-enamide; (E)-1-(azetidin-1-yl)-4-((2-(4-((E)-2-cyclobutyl-1-(1H-indazol-5-yl)-2- phenylvinyl) phenoxy)ethyl)amino)but-2-en-1-one; (E)-1-(azetidin-1-yl)-4-((2-(4-((E)-2-cyclobutyl-1-(3-fluoro-1H-indazol-5-yl)-2-phenylvinyl)phenoxy)ethyl)amino)but-2-en-1-one; (E)-4-((2-(4-((E)-2-cyclobutyl-1-(1H-indazol-5-yl)-2-phenylvinyl) phenoxy) ethyl)amino)-N-(2-hydroxyethyl)-N-methylbut-2-enamide; (E)-1-(azetidin-1-yl)-4-((2-(4-((E)-2-cyclobutyl-1-(1H-indazol-5-yl)-2-(o-tolyl) vinyl)phenoxy)ethyl)amino)but-2-en-1-one; (E)-4-((2-(4-((E)-1-(3-fluoro-1H-indazol-5-yl)-2-(2-fluoro phenyl)but-1-en-1-yl)phenoxy)ethyl)amino)-N,N-dimethylbut-2-enamide; (E)-4-((2-(4-((E)-1-(3-fluoro-1H-indazol-5-yl)-2-(3-fluoro phenyl)but-1-en-1-yl) phenoxy)ethyl)amino)-N,N-dimethylbut-2-enamide; (E)-4-((2-(4-((E)-1-(3-fluoro-1H-indazol-5-yl)-2-(3-fluorophenyl)but-1-en-1-yl) phenoxy)ethyl)amino)-N,N-dimethylbut-2-enamide; (E)-4-((2-(4-((E)-2-(2-chloro-4-fluorophenyl)-2-cyclobutyl-1-(3-fluoro-1H-indazol-5-yl)vinyl)phenoxy)ethyl)amino)-N,N-dimethylbut-2-enamide; (E)-4-((2-(2-fluoro-4-((Z)-1-(3-fluoro-1H-indazol-5-yl)-2-phenylbut-1-en-1-yl) phenoxy)ethyl)amino)-N,N-dimethylbut-2-enamide; (E)-4-((2-(4-((E)-2-(2,6-difluorophenyl)-1-(3-fluoro-1H-indazol-5-yl)but-1-en-1-yl)phenoxy)ethyl)amino)-N,N-dimethylbut-2-enamide; (E)-4-((2-(4-((E)-1-(3-fluoro-1H-indazol-5-yl)-2-(pyridin-3-yl)but-1-en-1-yl)phenoxy)ethyl)amino)-N,N-dimethylbut-2-enamide; (E)-4-((2-(4-((E)-1-(3-fluoro-1H-indazol-5-yl)-2-(pyridin-4-yl)but-1-en-1-yl) phenoxy)ethyl)amino)-N,N-dimethylbut-2-enamide; (E)-4-((2-(4-((E)-1-(1H-indazol-5-yl)-2-phenylprop-1-en-1-yl) phenoxy)ethyl)amino)-N,N-dimethylbut-2-enamide; (E)-4-((2-(4-((E)-2-cyclopropyl-1-(1H-indazol-5-yl)-2-phenylvinyl)phenoxy)ethyl)amino)-N,N-dimethylbut-2-enamide; (E)-4-((2-(4-((E)-2-(2-chloro-4-fluorophenyl)-1-(4-fluoro-1H-indazol-5-yl)but-1-en-1-yl)phenoxy)ethyl)amino)-N,N-dimethylbut-2-enamide; (E)-4-((2-((5-((Z)-2-(2-chloro-4-fluorophenyl)-1-(3-fluoro-1H-indazol-5-yl)but-1-en-1-yl)pyridin-2-yl)oxy)ethyl)amino)-N,N-dimethylbut-2-enamide; (E)-4-((2-((5-((Z)-2-(2-chloro-4-fluorophenyl)-4,4,4-trifluoro-1-(3-fluoro-1H-indazol-5-yl)but-1-en-1-yl)pyridin-2-yl)oxy)ethyl)amino)-N,N-dimethylbut-2-enamide; (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide; (E)-N,N-dimethyl-4-((2-(4-((E)-4,4,4-trifluoro-1-(3-fluoro-1H-indazol-5-yl)-2-(3-fluoropyridin-4-yl)but-1-en-1-yl)phenoxy)ethyl)amino) but-2-enamide; (E)-N,N-dimethyl-4-((2-((5-((Z)-4,4,4-trifluoro-1-(3-fluoro-1H-indazol-5-yl)-2-(3-fluoropyridin-4-yl)but-1-en-1-yl)pyridin-2-yl)oxy)ethyl)amino)but-2-enamide; (E)-N,N-dimethyl-4-((2-(4-((E)-2-phenyl-1-(1H-pyrazolo[4,3-b]pyridin-5-yl)but-1-en-1-yl)phenoxy)ethyl) amino)but-2-enamide; (E)-4-((2-(3-fluoro-4-((Z)-1-(3-fluoro-1H-indazol-5-yl)-2-phenylbut-1-en-1-yl)phenoxy) ethyl)amino)-N,N-dimethylbut-2-enamide; (E)-4-((2-(4-((E)-2-(2,4-difluorophenyl)-1-(3-fluoro-1H-indazol-5-yl) but-1-en-1-yl)phenoxy)ethyl)amino)-N,N-dimethylbut-2-enamide; (E)-4-((2-(4-((E)-1-(3,6-difluoro-1H-indazol-5-yl)-2-phenylbut-1-en-1-yl)phenoxy)ethyl)amino)-N,N-dimethylbut-2-enamide; (E)-4-((2-(4-((E)-1-(3-fluoro-1H-indazol-5-yl)-2-(pyridin-2-yl)but-1-en-1-yl)phenoxy)ethyl) amino)-N,N-dimethylbut-2-enamide; (E)-4-((2-((5-((Z)-1-(3-fluoro-1H-indazol-5-yl)-2-phenylbut-1-en-1-yl)pyridin-2-yl)oxy)ethyl)amino)-N,N-dimethylbut-2-enamide; (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino) but-2-enamide; (E)-4-((2-((5-((Z)-2-cyclobutyl-1-(3-fluoro-1H-indazol-5-yl)-2-phenylvinyl)pyridin-2-yl)oxy)ethyl) amino)-N,N-dimethylbut-2-enamide; (E)-4-((2-(4-((E)-2-(2-chlorophenyl)-1-(3-fluoro-1H-indazol-5-yl)but-1-en-1-yl)phenoxy)ethyl)amino)-N,N-dimethylbut-2-enamide; (E)-4-((2-(4-((E)-2-(2-chloro-4-fluorophenyl)-1-(1H-indazol-5-yl)but-1-en-1-yl)phenoxy)ethyl)amino)-N,N-dimethylbut-2-enamide; (E)-4-((2-(4-((E)-1-(3-fluoro-1H-indazol-5-yl)-2-(pyridin-4-yl)but-1-en-1-yl)phenoxy)ethyl)amino)-N-(2-hydroxyethyl)-N-methylbut-2-enamide; (E)-4-((2-(4-((E)-1-(7-fluoro-1H-indazol-5-yl)-2-phenylbut-1-en-1-yl)phenoxy)ethyl)amino)-N,N-dimethylbut-2-enamide; (E)-4-((2-(4-((E)-1-(3-fluoro-1H-indazol-5-yl)-2-phenylpent-1-en-1-yl)phenoxy)ethyl)amino)-N,N-dimethylbut-2-enamide; (E)-4-((2-(4-((E)-1-(3,7-difluoro-1H-indazol-5-yl)-2-phenylbut-1-en-1-yl)phenoxy)ethyl)amino)-N,N-dimethylbut-2-enamide; (E)-4-((2-(4-((E)-2-(2,5-difluorophenyl)-1-(3-fluoro-1H-indazol-5-yl)but-1-en-1-yl)phenoxy)ethyl)amino)-N,N-dimethylbut-2-enamide; (E)-4-((2-(4-((E)-1-(3-fluoro-1H-indazol-5-yl)-2-(3-fluoropyridin-4-yl)but-1-en-1-yl)phenoxy)ethyl)amino)-N,N-dimethylbut-2-enamide; (E)-4-((2-(4-((E)-1-(3-fluoro-1H-indazol-5-yl)-3-methyl-2-phenylbut-1-en-1-yl)phenoxy)ethyl)amino)-N,N-dimethylbut-2-enamide; (E)-5-((2-(4-((E)-4-fluoro-1-(3-fluoro-1H-indazol-5-yl)-2-phenylbut-1-en-1-yl)phenoxy)ethyl)amino)-N,N-dimethylpent-2-enamide; (E)-5-((2-(4-((E)-2-(2-chloro-4-fluorophenyl)-1-(3-fluoro-1H-indazol-5-yl)but-1-en-1-yl) phenoxy)ethyl)amino)-N,N-dimethylpent-2-enamide; (E)-4-((2-(4-((E)-2-(2-chloro-4-fluorophenyl)-1-(3-fluoro-1H-indazol-5-yl)but-1-en-1-yl)phenoxy)ethyl)amino)-N,N,2-trimethylbut-2-enamide; (E)-4-((2-(4-((E)-2-(2-chloro-4-fluorophenyl)-4,4,4-trifluoro-1-(3-fluoro-1H-indazol-5-yl) but-1-en-1-yl)phenoxy)ethyl)amino)-N,N-dimethylbut-2-enamide; (E)-4-((2-(4-((E)-1-(1H-indazol-5-yl)-2-(phenyl-d5)but-1-en-1-yl)phenoxy)ethyl)amino)-N,N-dimethylbut-2-enamide; (E)-4-((2-(4-((E)-1-(1H-indazol-5-yl)-2-phenylbut-1-en-1-yl)phenoxy)ethyl)amino)-N,N-dimethylpent-2-enamide; (E)-4-((2-(4-((E)-1-(1H-indazol-5-yl)-2-phenylbut-1-en-1-yl)phenoxy)propyl)amino)-N,N-dimethylbut-2-enamide; (E)-4-((1-(4-((E)-1-(1H-indazol-5-yl)-2-phenylbut-1-en-1-yl)phenoxy)propan-2-yl)amino)-N,N-dimethylbut-2-enamide; (E)-4-((2-((6-((Z)-1-(3-fluoro-1H-indazol-5-yl)-2-phenylbut-1-en-1-yl)pyridin-3-yl)oxy) ethyl)amino)-N,N-dimethylbut-2-enamide; (E)-4-((3-(4-((E)-1-(1H-indazol-5-yl)-2-phenylbut-1-en-1-yl)phenoxy) propyl)amino)-N,N-dimethylbut-2-enamide; (E)-4-((3-(4-((E)-1-(1H-indazol-5-yl)-2-phenylbut-1-en-1-yl)phenoxy) butan-2-yl)amino)-N,N-dimethylbut-2-enamide; (E)-4-((1-(4-((E)-1-(1H-indazol-5-yl)-2-phenylbut-1-en-1-yl) phenoxy)-2-methylpropan-2-yl)amino)-N,N-dimethylbut-2-enamide; (E)-4-((2-(4-((E)-1-(1H-indazol-5-yl)-2-phenylbut-1-en-1-yl)phenoxy)-2-methylpropyl)amino)-N,N-dimethylbut-2-enamide; and (E)-4-((2-(4-((E)-2-cyclobutyl-1-(3-fluoro-1H-indazol-5-yl)-2-phenylvinyl) phenoxy)ethyl)amino)-N-(2-hydroxyethyl)-N-methylbut-2-enamide, and pharmaceutically acceptable salts thereof.

In some embodiments, such novel compounds are described by Formula III:

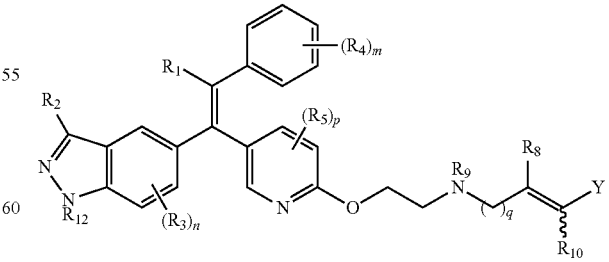

III wherein: R$_1$ is selected from the group consisting of C$_1$-C$_6$ alkyl, —CH$_2$CF$_3$, C$_3$-C$_6$ cycloalkyl and a 4-6 membered heterocyclic ring; R$_2$ is selected from the group consisting of H, halogen, hydroxy, C$_1$-C$_3$ alkyl, C$_3$-C$_4$ cycloalkyl and C$_4$ heterocyclic ring; $R_3$ are the same or different, and are independently selected from the group consisting of H, halogen, $C_1$-$C_6$ alkyl and $C_1$-$C_3$ alkoxy optionally substituted with at least one halogen; n is 0-3; $R_4$ are the same or different and are independently selected from the group consisting of H, halogen, $C_1$-$C_6$ alkyl, and $OR_{11}$, wherein $R_{11}$ is selected from the group consisting of $C_3$-$C_6$ cycloalkyl, $C_1$-$C_6$ alkyl, aryl, heteroaryl and a 4-6 membered heterocyclic ring; m is 0-5; $R_5$ are the same or different and are independently selected from the group consisting of H, halogen, $C_1$-$C_4$ alkyl, $C_1$-$C_4$ alkoxy, $C_3$-$C_4$ cycloalkyl, $C_3$-$C_6$ cycloalkoxy and $C_4$ heterocycle; p is 0-3; q is 1-2; $R_8$ and $R_{10}$ are the same or different and are independently selected from the group consisting of halogen, H and $C_1$-$C_3$ alkyl; $R_9$ is selected from the group consisting of H, $C_1$-$C_6$ alkyl and $C_3$-$C_6$ cycloalkyl; Y is selected from the group consisting of —$S(O)_2R_6$, —$S(O)_2NR_6R_7$, —$C(O)NR_6R_7$, —$C(O)R_6$, —$C(O)OR_6$, —CN; or wherein Y and $R_{10}$ both represent —$CF_3$; $R_6$ and $R_7$ are the same or different and are independently selected from the group consisting of H, $C_1$-$C_6$ alkyl, $C_3$-$C_6$ cycloalkyl, aryl, heteroaryl and a 4-6 membered heterocyclic ring wherein said alkyl is saturated or unsaturated or wherein $R_6$ and $R_7$ form a 4-6 membered heterocyclic ring with the N to which they are attached, optionally also containing an O atom; $R_{12}$ is selected from the group consisting of H, $C_3$-$C_4$ cycloalkyl and $C_1$-$C_6$ alkyl; and wherein any carbon containing moiety of $R_1$-$R_{12}$ may be optionally substituted with one or more halogen atoms, fluoromethane, difluoromethane or trifluoromethane, or —OH; or pharmaceutically acceptable salts thereof.

In a further embodiment, $R_1$ is selected from the group consisting of $C_1$-$C_6$ alkyl, $C_3$-$C_6$ cycloalkyl and a 4-6 membered heterocyclic ring. In a further embodiment, R1 is —$CH_2CF_3$. In more specific embodiments, such novel compounds are described by Formula III, wherein: $R_2$ is selected from the group consisting of H, halogen, methyl and ethyl; $R_3$ are the same or different, and are independently selected from the group consisting of H, halogen, methyl and ethyl; $R_4$ are the same or different and are independently selected from the group consisting of H, halogen, $C_1$-$C_6$ alkyl and $C_1$-$C_6$ alkoxy; $R_5$ are the same or different and are independently selected from the group consisting of H, halogen, methyl and ethyl; $R_8$ and $R_{10}$ are the same or different and are independently selected from the group consisting of H and methyl; $R_9$ is selected from the group consisting of H, methyl and ethyl; and $R_6$ and $R_7$ are the same or different and are independently selected from the group consisting of H and $C_1$-$C_6$ alkyl or wherein $R_6$ and $R_7$ form a 4-6 atom heterocyclic ring with the N to which they are attached, optionally also containing an O atom. In further embodiments, $R_1$ is cyclobutyl, ethyl, or —$CH_2CF_3$; $R_2$ is —H or —F; n is 0; m is 0 or 2, and when m is 2, then one $R_4$ is —Cl and the other $R_4$ is —F; p is 0; Y is —$CON(CH_3)_2$, and $R_8$, $R_9$, $R_{10}$, and $R_{12}$ are all —H.

In some embodiments, such novel compounds are described by Formula IV:

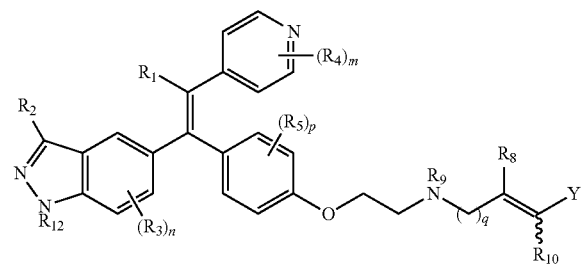

IV wherein: $R_1$ is selected from the group consisting of $C_1$-$C_6$ alkyl, $C_3$-$C_6$ cycloalkyl and a 4-6 membered heterocyclic ring; $R_2$ is selected from the group consisting of H, halogen, hydroxy, $C_1$-$C_3$ alkyl, $C_3$-$C_4$ cycloalkyl and $C_4$ heterocyclic ring; $R_3$ are the same or different, and are independently selected from the group consisting of H, halogen, $C_1$-$C_6$ alkyl and $C_1$-$C_3$ alkoxy optionally substituted with at least one halogen; n is 0-3; $R_4$ are the same or different and are independently selected from the group consisting of H, halogen, $C_1$-$C_6$ alkyl, and $OR_1$, wherein $R_{11}$ is selected from the group consisting of $C_3$-$C_6$ cycloalkyl, $C_1$-$C_6$ alkyl, aryl, heteroaryl and a 4-6 membered heterocyclic ring; m is 0-4; $R_5$ are the same or different and are independently selected from the group consisting of H, halogen, $C_1$-$C_4$ alkyl, $C_1$-$C_4$ alkoxy, $C_3$-$C_4$ cycloalkyl, $C_3$-$C_6$ cycloalkoxy and $C_4$ heterocycle; p is 0-4; q is 1-2; $R_8$ and $R_9$ are the same or different and are independently selected from the group consisting of halogen, H and $C_1$-$C_3$ alkyl; $R_9$ is selected from the group consisting of H, $C_1$-$C_6$ alkyl and $C_3$-$C_6$ cycloalkyl; Y is selected from the group consisting of —$S(O)_2R_6$, —$S(O)_2NR_6R_7$, —$C(O)NR_6R_7$, —$C(O)R_6$, —$C(O)OR_6$, —CN; or wherein Y and $R_{10}$ both represent —$CF_3$; $R_6$ and $R_7$ are the same or different and are independently selected from the group consisting of H, $C_1$-$C_6$ alkyl, $C_3$-$C_6$ cycloalkyl, aryl, heteroaryl and a 4-6 membered heterocyclic ring wherein said alkyl is saturated or unsaturated or wherein $R_6$ and $R_7$ form a 4-6 membered heterocyclic ring with the N to which they are attached, optionally also containing an O atom; $R_{12}$ is selected from the group consisting of H, $C_3$-$C_4$ cycloalkyl and $C_1$-$C_6$ alkyl; and wherein any carbon containing moiety of $R_1$-$R_{12}$ may be optionally substituted with one or more halogen atoms, fluoromethane, difluoromethane or trifluoromethane, or —OH; or pharmaceutically acceptable salts thereof.

In more specific embodiments, such novel compounds are described by Formula IV, wherein: $R_2$ is selected from the group consisting of H, halogen, methyl and ethyl; $R_3$ are the same or different, and are independently selected from the group consisting of H, halogen, methyl and ethyl; $R_4$ are the same or different and are independently selected from the group consisting of H, halogen, $C_1$-$C_6$ alkyl and $C_1$-$C_6$ alkoxy; $R_5$ are the same or different and are independently selected from the group consisting of H, halogen, methyl and ethyl; $R_8$ and $R_{10}$ are the same or different and are independently selected from the group consisting of H and methyl; $R_9$ is selected from the group consisting of H, methyl and ethyl; and $R_6$ and $R_7$ are the same or different and are independently selected from the group consisting of H and $C_1$-$C_6$ alkyl or wherein $R_6$ and $R_7$ form a 4-6 atom heterocyclic ring with the N to which they are attached, optionally also containing an O atom.

In some embodiments, the compounds of Formula III or Formula IV have the following permutations or combinations of permutations: Y is —$C(O)NR_6R_7$; $R_6$ and $R_7$ are methyl; $R_8$ and $R_{10}$ are both H; $R_1$ is ethyl or cyclobutyl; $R_9$ is H; $R_2$ is F or H; m is 2 and one of $R_4$ is F and the other $R_4$ is Cl; m is 2 and both of $R_4$ are F; m is 0; n is 1 and $R_3$ is F; n is 0; p is 1 and $R_5$ is F; or p is 0.

An embodiment may provide a compound having the following formula:

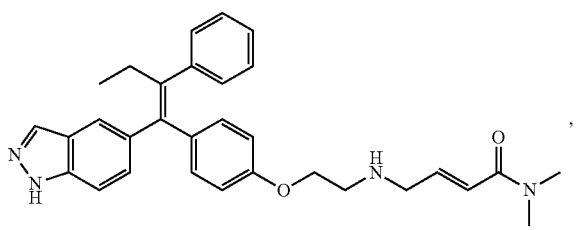 [SMILES: CC/C(=C(/c1ccc(OCCNC/C=C/C(=O)N(C)C)cc1)c1ccc2[nH]ncc2c1)c1ccccc1]

or a pharmaceutically acceptable salt thereof.

An embodiment may provide a compound having the following formula:

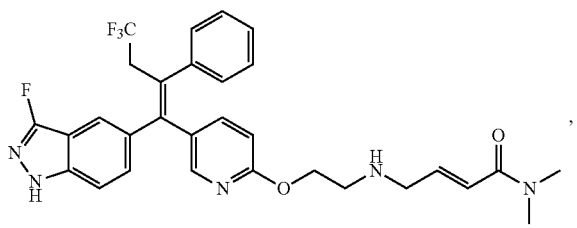 [SMILES: CN(C)C(=O)/C=C/CNCCOc1ccc(/C(=C(/CC(F)(F)F)c2ccccc2)c2ccc3[nH]nc(F)c3c2)cn1]

or a pharmaceutically acceptable salt thereof.

An embodiment may provide a compound having the following formula:

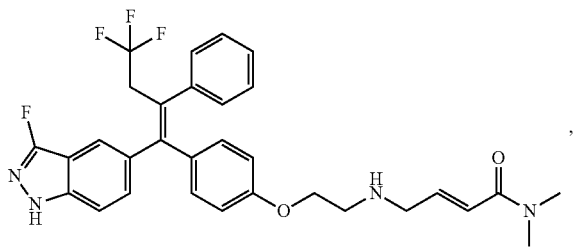 [SMILES: CN(C)C(=O)/C=C/CNCCOc1ccc(/C(=C(/CC(F)(F)F)c2ccccc2)c2ccc3[nH]nc(F)c3c2)cc1]

or a pharmaceutically acceptable salt thereof.

A further embodiment may provide a method of treating breast cancer comprising administering to a subject a compound according to any one of the preceding paragraphs. The breast cancer may be an ER-positive breast cancer. The subject may express a mutant ER-α protein. An embodiment may provide use of a compound as in the paragraphs above for treating breast cancer. In some embodiments the breast cancer is an ER-positive breast cancer. In some embodiments said subject expresses a mutant ER-α protein. In some embodiments a compound as presented above is used in the preparation of a medicament for treatment of breast cancer.

In embodiments, the compounds disclosed herein are useful for inhibiting the cell culture growth of MCF7 ER-alpha (wildtype) and MCF7 ER-alpha (Y537S mutant) cells. Other compounds (e.g., tamoxifen, raloxifene and fulvestrant) known to inhibit the cell culture growth of MCF7 ER-alpha (wildtype) cells are currently used to treat breast cancer in human patients. Hence, the compounds disclosed herein are useful for treating ER-alpha expressing breast cancer in human patients, and are useful for treating Y537S mutant ER-alpha expressing breast cancer in human patients.

In embodiments, the compounds disclosed herein are useful for treating breast cancer. In embodiments, the breast cancer is ER-α+. In embodiments, the breast cancer expresses an ER-α mutation, which is L536Q (Robinson et al. *Nat Genet.* 2013 December; 45(12)), L536R (Toy et al. *Nat Genet.* 2013 December; 45(12):1439-45), Y537S (Toy et al. *Nat Genet.* 2013 December; 45(12):1439-45; Robinson et al. *Nat Genet.* 2013 December; 45(12); Jeselsohn et al. *Clin Cancer Res.* 2014 Apr. 1; 20(7):1757-67), Y537N (Toy et al. *Nat Genet.* 2013 December; 45(12):1439-45; Jeselsohn et al. *Clin Cancer Res.* 2014 Apr. 1; 20(7):1757-67), Y537C (Toy et al. *Nat Genet.* 2013 December; 45(12):1439-45; Jeselsohn et al. *Clin Cancer Res.* 2014 Apr. 1; 20(7): 1757-67) and D538G (Toy et al. *Nat Genet.* 2013 December; 45(12): 1439-45; Robinson et al. *Nat Genet.* 2013 December; 45(12); Jeselsohn et al. *Clin Cancer Res.* 2014 Apr. 1; 20(7):1757-67; Merenbakh-Lamin et al. *Cancer Res.* 2013 Dec. 1; 73(23):6856-64); and Yu et al., (2014) *Science* July 11; 345(6193):216-20, all of which are incorporated by reference in their entireties for their teachings of ER-α mutations.

DETAILED DESCRIPTION

Figure 1:
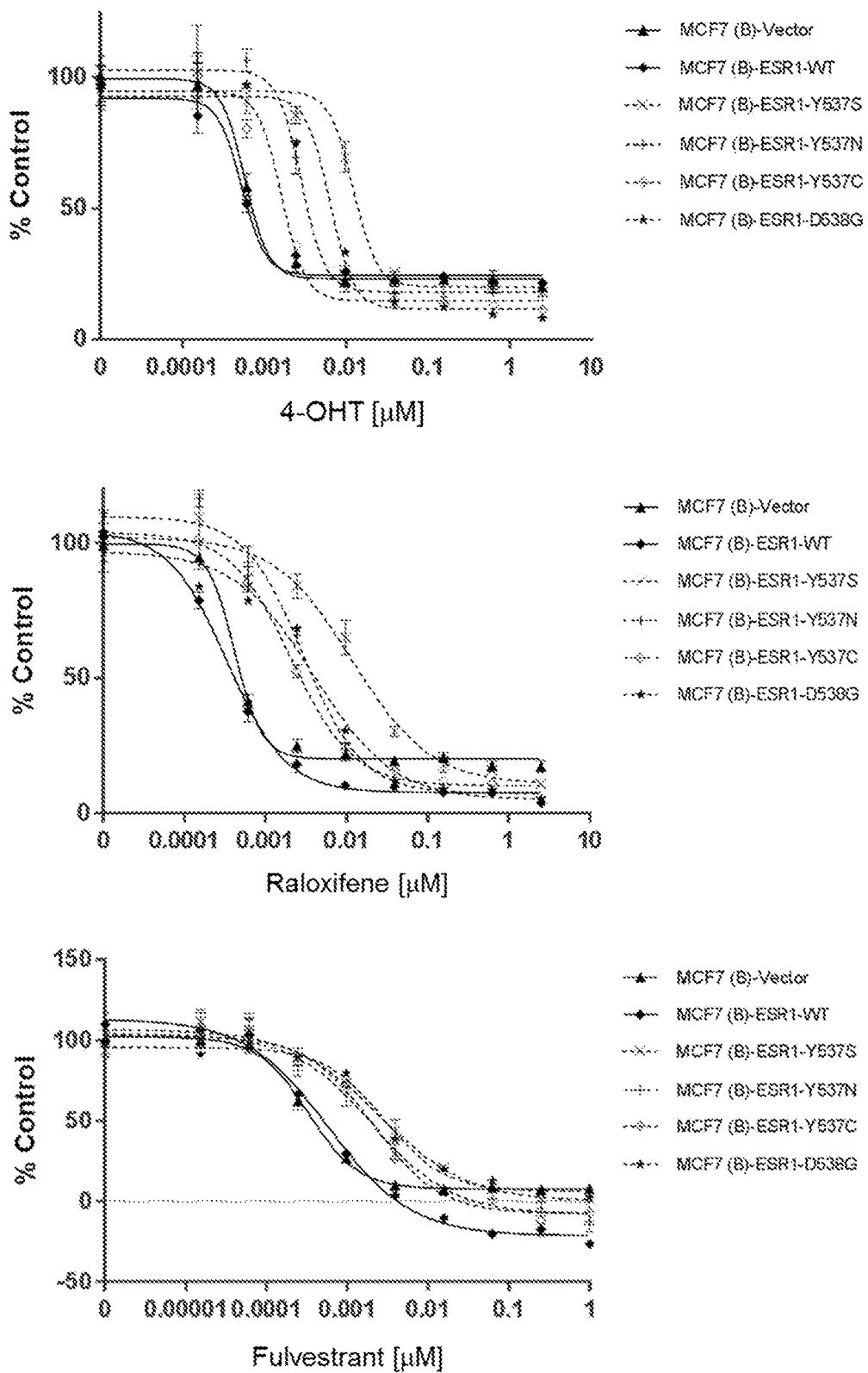
FIG. 1 shows in vitro proliferation effects of wild-type and mutant ER-bearing MCF7 lines to clinical therapies 4-hydroxytamoxifen (4-OHT), raloxifene and fulvestrant, where phenotypic resistance observed in mutant-bearing lines relative to control lines to existing clinical compounds, whereby MCF7 cells engineered to overexpress various $ERα^{MUT}$ showed partial resistance to various endocrine therapies.

All publications and patent documents cited herein are incorporated herein by reference as if each such publication or document was specifically and individually indicated to be incorporated herein by reference. Where the text of this disclosure and the text of one or more documents incorporated by reference conflicts, this disclosure controls. Citation of publications and patent documents is not intended as an admission that any is pertinent prior art, nor does it constitute any admission as to the contents or date of the same. The embodiments described herein having now been described by way of written description, those of skill in the art will recognize that the embodiments described herein may be practiced in a variety of embodiments and that the description and examples provided herein are for purposes of illustration and not limitation of the claims.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon ring having 3 to 7 carbon atoms (e.g., $C_3$-$C_7$). Examples of cycloalkyl include, but are not limited to, cyclopropyl, cyclobutyl, cyclopentyl, cyclohexyl, cycloheptyl, cyclopentenyl, cyclohexenyl, and cycloheptenyl.

The term "heterocycloalkyl" refers to a saturated or unsaturated nonaromatic 3-8 membered monocyclic groups, 7-10 membered fused bicyclic groups having one or more heteroatoms (such as O, N, or S), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, tetrahydrothiophene, dihydropyranyl, pyranyl, morpholinyl, 1,4-diazepanyl, 1,4-oxazepanyl, and the like.

Additional examples of heterocycloalkyl groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "optionally substituted alkyl" refers to unsubstituted alkyl or alkyl having designated substituents replacing one or more hydrogen atoms on one or more carbons of the hydrocarbon backbone. Such substituents may include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl(benzyl)). An "alkylaryl" moiety is an aryl substituted with an alkyl (e.g., methylphenyl).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents may include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents may include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR' wherein R' is H or other substituents, as defined). The nitrogen and sulfur heteroatoms may optionally be oxidized (i.e., N—O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., bicyclic. Non-limiting example of such aryl groups include, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline).

The cycloalkyl, heterocycloalkyl, aryl, or heteroaryl ring may be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups may also be fused with alicyclic or heterocyclic rings, which are not aromatic so as to form a multicyclic system (e.g., tetralin, methylenedioxyphenyl).

When a bond to a substituent is shown to cross a bond connecting two atoms in a ring (as shown by the examples below with substituent R), then such substituent may be bonded to any atom in the ring.

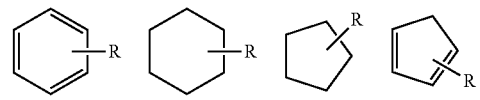

When any variable (e.g., R$_1$) occurs more than one time in any constituent or formula for a compound, its definition at each occurrence is independent of its definition at every other occurrence. Thus, for example, if a group is shown to be substituted with 0-2 R$_1$ moieties, then the group may optionally be substituted with up to two R$_1$ moieties and R$_1$ at each occurrence is selected independently from the definition of R$_1$.

The term "hydroxy" or "hydroxyl" includes groups with an —OH or —O$^-$.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups may be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Calm et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Calm et al., Experientia 1956, 12, 81; Cahn, J. Chem. Educ. 1964, 41, 116).

In the present specification, each incidence of a chiral center within a structural formula, such as the non-limiting example shown here:

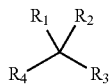

is meant to depict all possible stereoisomers. In contrast, a chiral center drawn with hatches and wedges, such as the non-limiting example shown here:

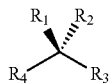

is meant to depict the stereoisomer as indicated (here in this $sp^3$ hybridized carbon chiral center, $R_3$ and $R_4$ are in the plane of the paper, $R_1$ is above the plane of paper, and $R_2$ is behind the plane of paper).

"Geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

In the present specification, each incidence within a structural formula including a wavy line adjacent to a double bond as shown:

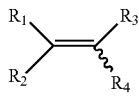

is meant to depict both geometric isomers. In contrast, such structures drawn without a wavy line is meant to depict a compound having the geometric configuration as drawn.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Where the present specification depicts a compound prone to tautomerization, but only depicts one of the tautomers, it is understood that all tautomers are included as part of the meaning of the chemical depicted. It is to be understood that the compounds disclosed herein may be depicted as different tautomers. It should also be understood that when compounds have tautomeric forms, all tautomeric forms are intended to be included, and the naming of the compounds does not exclude any tautomer form.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine.

Furthermore, the structures and other compounds disclosed herein include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The term "crystal polymorphs", "polymorphs" or "crystal forms" means crystal structures in which a compound (or a salt or solvate thereof) may crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds may be prepared by crystallization under different conditions. It is understood that the compounds disclosed herein may exist in crystalline form, crystal form mixture, or anhydride or hydrate thereof.

The compounds disclosed herein include the compounds themselves, as well as their salts and solvates, if applicable. A salt, for example, may be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt may also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms.

Additionally, the compounds disclosed herein, for example, the salts of the compounds, may exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, "pharmaceutically acceptable salts" refer to derivatives of the compounds disclosed herein wherein the parent compound is modified by making acid or base salts thereof.

Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt may be 1:1, or any ratio other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

Chemicals as named or depicted are intended to include all naturally occurring isotopes of atoms occurring in the present compounds. Isotopes include those atoms having the same atomic number but different mass numbers. By way of general example and without limitation, isotopes of $^1H$ hydrogen include tritium and deuterium, and isotopes of $^{12}C$ carbon include $^{13}C$ and $^{14}C$.

It will be understood that some compounds, and isomers, salts, esters and solvates thereof, of the compounds disclosed herein may exhibit greater in vivo or in vitro activity than others. It will also be appreciated that some cancers may be treated more effectively than others, and may be treated more effectively in certain species of subjects that others, using the compounds, and isomers, salts, esters and solvates thereof, of the compounds disclosed herein.

As used herein, "treating" means administering to a subject a pharmaceutical composition to ameliorate, reduce or lessen the symptoms of a disease. As used herein, "treating" or "treat" describes the management and care of a subject for the purpose of combating a disease, condition, or disorder and includes the administration of a compound disclosed herein, or a pharmaceutically acceptable salt, polymorph or solvate thereof, to alleviate the symptoms or complications of a disease, condition or disorder, or to eliminate the disease, condition or disorder. The term "treat" may also include treatment of a cell in vitro or an animal model.

Treating cancer may result in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer may result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer may result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%.

Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer may result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

As used herein, "subject" or "subjects" refers to any animal, such as mammals including rodents (e.g., mice or rats), dogs, primates, lemurs or humans.

Treating cancer may result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in increase in average survival time of a population in comparison to a population receiving monotherapy with a drug that is not a compound disclosed herein, or a pharmaceutically acceptable salt thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in a decrease in the mortality rate of a population of treated subjects in comparison to a population receiving carrier alone. Treating cancer may result in a decrease in the mortality rate of a population of treated subjects in comparison to an untreated population. Treating cancer may result in a decrease in the mortality rate of a population of treated subjects in comparison to a population receiving monotherapy with a drug that is not a compound disclosed herein, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer may result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate may be measured according to a change in tumor diameter per unit time.

Treating cancer may result in a decrease in tumor regrowth, for example, following attempts to remove it surgically. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder may result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder may result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells may be equivalent to the mitotic index.

Treating or preventing a cell proliferative disorder may result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder may result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology may be measured by microscopy, e.g., using an inverted tissue culture microscope. An abnormal cellular morphology may take the form of nuclear pleiomorphism.

As used herein, the term "alleviate" is meant to describe a process by which the severity of a sign or symptom of a disorder is decreased. Importantly, a sign or symptom may be alleviated without being eliminated. In a preferred embodiment, the administration of pharmaceutical compositions disclosed herein leads to the elimination of a sign or symptom, however, elimination is not required. Effective dosages are expected to decrease the severity of a sign or symptom. For instance, a sign or symptom of a disorder such as cancer, which may occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of embodiments described herein, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by non-health-care professionals.

A "pharmaceutical composition" is a formulation containing a compound disclosed herein in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound disclosed herein include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The present disclosure also provides pharmaceutical compositions comprising any compound disclosed herein in combination with at least one pharmaceutically acceptable excipient or carrier.

A pharmaceutical composition disclosed herein is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application may include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH may be adjusted with acids or bases, such as hydrochloric acid or sodium hydroxide. The parenteral preparation may be enclosed in ampoules, disposable syringes or multiple dose vials made of glass or plastic.

A compound or pharmaceutical composition disclosed herein may be administered to a subject in many of the well-known methods currently used for chemotherapeutic treatment. For example, for treatment of cancers, a compound disclosed herein may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect may be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation may be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount may be estimated initially either in cell culture assays, e.g., of neoplastic cells, or in animal models, usually rats, mice, rabbits, dogs, or pigs. The animal model may also be used to determine the appropriate concentration range and route of administration. Such information may then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds disclosed herein may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that may be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier may be a solvent or dispersion medium containing, for example, water, ethanol, polyol (for example, glycerol, propylene glycol, and liquid polyethylene glycol, and the like), and suitable mixtures thereof. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions may be brought about by including in the composition an agent which delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier for use as a mouthwash, wherein the compound in the fluid carrier is applied orally and swished and expectorated or swallowed. Pharmaceutically compatible binding agents, and/or adjuvant materials may be included as part of the composition. The tablets, pills, capsules, troches and the like may contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The active compounds may be prepared with pharmaceutically acceptable carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. Methods for preparation of such formulations will be apparent to those skilled in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the compounds disclosed herein are dictated by and directly dependent on the unique characteristics of the active compound and the particular therapeutic effect to be achieved.

In therapeutic applications, the dosages of the pharmaceutical compositions used in accordance with embodiments described herein vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages may range from about 0.01 mg/kg per day to about 5000 mg/kg per day. In preferred aspects, dosages may range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions may be included in a container, pack, or dispenser together with instructions for administration.

Techniques for formulation and administration of the compounds disclosed herein may be found in Remington: the Science and Practice of Pharmacy, $19^{th}$ edition, Mack Publishing Co., Easton, Pa. (1995). In an embodiment, the compounds described herein, and the pharmaceutically acceptable salts thereof, may be used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

Exemplary cancers that may be treated using one or more compounds disclosed herein include, but are not limited to, breast cancer, uterine endometrial, ovarian carcinoma, sarcoma, thyroid carcinoma, prostate, lung adenocarcinoma, and hepatocellular carcinoma.

In embodiments, the compounds disclosed herein may be useful for treating breast cancer. In embodiments, the breast cancer is ER-α+. In embodiments, the breast cancer expresses an ER-α mutation, which may be L536Q (Robinson et al. *Nat Genet.* 2013 December; 45(12)), L536R (Toy et al. *Nat Genet.* 2013 December; 45(12):1439-45), Y537S (Toy et al. *Nat Genet.* 2013 December; 45(12):1439-45; Robinson et al. *Nat Genet.* 2013 December; 45(12); Jeselsohn et al. *Clin Cancer Res.* 2014 Apr. 1; 20(7):1757-67), Y537N (Toy et al. *Nat Genet.* 2013 December; 45(12): 1439-45; Jeselsohn et al. *Clin Cancer Res.* 2014 Apr. 1; 20(7):1757-67), Y537C (Toy et al. *Nat Genet.* 2013 December; 45(12):1439-45; Jeselsohn et al. *Clin Cancer Res.* 2014 Apr. 1; 20(7): 1757-67) and D538G (Toy et al. *Nat Genet.* 2013 December; 45(12): 1439-45; Robinson et al. *Nat Genet.* 2013 December; 45(12); Jeselsohn et al. *Clin Cancer Res.* 2014 Apr. 1; 20(7):1757-67; Merenbakh-Lamin et al. *Cancer Res.* 2013 Dec. 1; 73(23):6856-64), all of which are incorporated by reference in their entireties for their teachings of ER-α mutations.

Thus, the compounds disclosed herein may be also useful for additional indications and genotypes. ESR1 mutations (Y537C/N) were recently discovered in 4 of 373 cases of endometrial cancers (Kandoth et al. *Nature* 2013 May 2; 497(7447):67-73; Robinson et al. *Nat Genet.* 2013 December; 45(12)). Since it has been shown that ESR1 mutations Y537C/N significantly drive resistance to currently marketed SOC therapies, the compounds disclosed herein may be useful for treating $ER\alpha^{MUT}$ endometrial cancers.

Exemplary cell proliferative disorders that may be treated using one or more compounds disclosed herein include, but are not limited to breast cancer, a precancer or precancerous condition of the breast, benign growths or lesions of the breast, and malignant growths or lesions of the breast, and metastatic lesions in tissue and organs in the body other than the breast. Cell proliferative disorders of the breast may include hyperplasia, metaplasia, and dysplasia of the breast.

A breast cancer that is to be treated may arise in a male or female subject. A breast cancer that is to be treated may arise in a premenopausal female subject or a postmenopausal female subject. A breast cancer that is to be treated may arise in a subject 30 years old or older, or a subject younger than 30 years old. A breast cancer that is to be treated has arisen in a subject 50 years old or older, or a subject younger than 50 years old. A breast cancer that is to be treated may arise in a subject 70 years old or older, or a subject younger than 70 years old.

A compound disclosed herein, or a pharmaceutically acceptable salt thereof, may be used to treat or prevent a cell proliferative disorder of the breast, or to treat or prevent breast cancer, in a subject having an increased risk of developing breast cancer relative to the population at large, or used to identify suitable candidates for such purposes. A subject with an increased risk of developing breast cancer relative to the population at large is a female subject with a family history or personal history of breast cancer. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old.

A cancer that is to be treated may include a tumor that has been determined to be less than or equal to about 2 centimeters in diameter. A cancer that is to be treated may include a tumor that has been determined to be from about 2 to about 5 centimeters in diameter. A cancer that is to be treated may include a tumor that has been determined to be greater than or equal to about 3 centimeters in diameter. A cancer that is to be treated may include a tumor that has been determined to be greater than 5 centimeters in diameter. A cancer that is to be treated may be classified by microscopic appearance as well differentiated, moderately differentiated, poorly differentiated, or undifferentiated. A cancer that is to be treated may be classified by microscopic appearance with respect to mitosis count (e.g., amount of cell division) or nuclear pleiomorphism (e.g., change in cells). A cancer that is to be treated may be classified by microscopic appearance as being associated with areas of necrosis (e.g., areas of dying or degenerating cells). A cancer that is to be treated may be classified as having an abnormal karyotype, having an abnormal number of chromosomes, or having one or more chromosomes that are abnormal in appearance. A cancer that is to be treated may be classified as being aneuploid, triploid, tetraploid, or as having an altered ploidy. A cancer that is to be treated may be classified as having a chromosomal translocation, or a deletion or duplication of an entire chromosome, or a region of deletion, duplication or amplification of a portion of a chromosome.

The compounds, or pharmaceutically acceptable salts thereof may be administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds may be selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian may readily determine and prescribe the effective amount of the drug required to prevent, counter, or arrest the progress of the condition.

EXAMPLES

Hereby are provided non-limiting examples of embodiments of compounds disclosed herein. If there is any discrepancy between a compound's depicted chemical structure and its chemical name, the depicted chemical structure will control.

TABLE 1

Viability Screen Results (see Example 101 below)

| Compound # | Structure | GI50 WT (nM) | GI50 MUT (Y537S) (nM) |
|---|---|---|---|
| 1 | 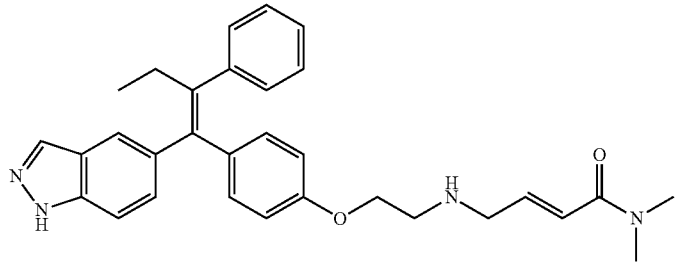 | 1.69 ± 0.54 (2) | 20.59 ± 7.01 (2) |

TABLE 1-continued

Viability Screen Results (see Example 101 below)

| Compound # | Structure | GI50 WT (nM) | GI50 MUT (Y537S) (nM) |
|---|---|---|---|
| 2 | 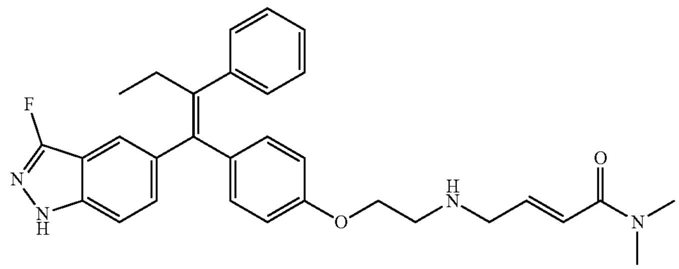 | 5.56 ± 2.84 (2) | 64.85 ± 37.24 (2) |
| 3 | 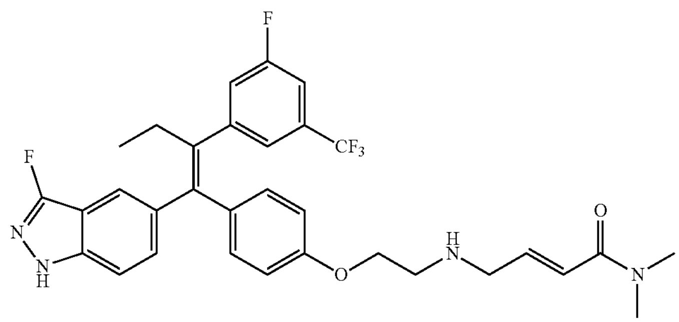 [SMILES: CC/C(=C(/c1ccc(OCCNC/C=C/C(=O)N(C)C)cc1)c1ccc2[nH]nc(F)c2c1)c1cc(F)cc(C(F)(F)F)c1] | 6.95 ± 2.47 (2) | 159.04 ± 91.80 (2) |
| 4 | 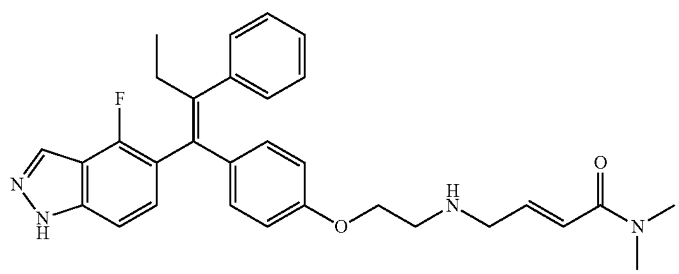 [SMILES: CC/C(=C(/c1ccc(OCCNC/C=C/C(=O)N(C)C)cc1)c1ccc2[nH]ncc2c1F)c1ccccc1] | 4.55 ± 3.34 (2) | 36.29 ± 15.99 (2) |
| 5 | 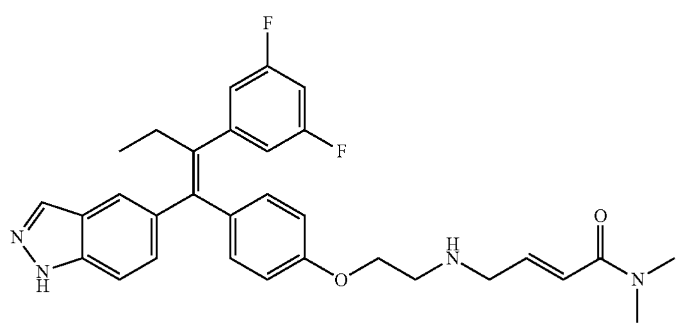 [SMILES: CC/C(=C(/c1ccc(OCCNC/C=C/C(=O)N(C)C)cc1)c1ccc2[nH]ncc2c1)c1cc(F)cc(F)c1] | 8.44 ± 3.87 (2) | 81.42 ± 45.75 (2) |
| 6 | 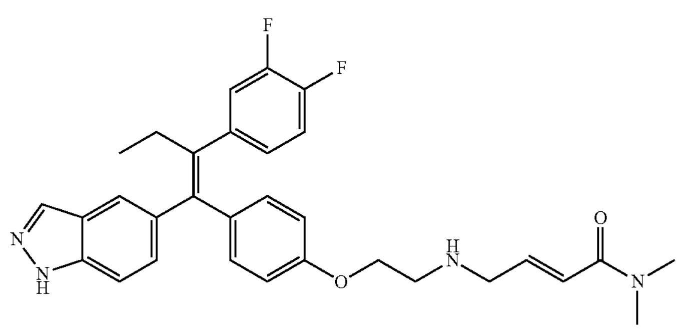 [SMILES: CC/C(=C(/c1ccc(OCCNC/C=C/C(=O)N(C)C)cc1)c1ccc2[nH]ncc2c1)c1ccc(F)c(F)c1] | 2.93 ± 2.83 (2) | 111.21 ± 124.43 (2) |

TABLE 1-continued

Viability Screen Results (see Example 101 below)

| Compound # | Structure | GI50 WT (nM) | GI50 MUT (Y537S) (nM) |
| --- | --- | --- | --- |
| 7 | 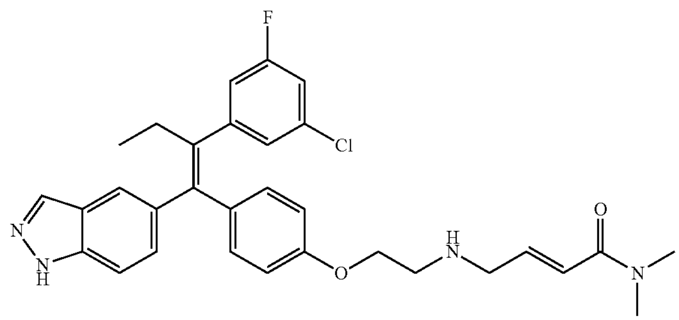 [SMILES: CC/C(=C(/c1ccc(OCCNC/C=C/C(=O)N(C)C)cc1)c1ccc2[nH]ncc2c1)c1cc(F)cc(Cl)c1] | 1.92 | 74.09 ± 55.2 (2) |
| 8 | 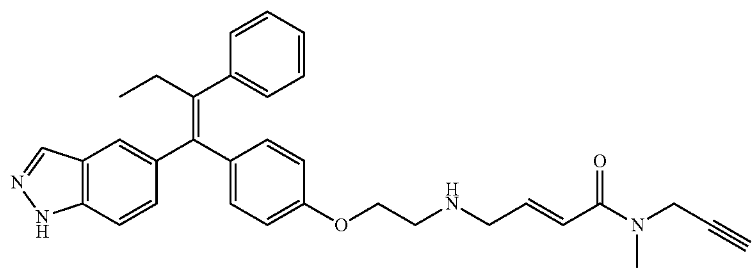 [SMILES: C#CCN(C)C(=O)/C=C/CNCCOc1ccc(/C(=C(/CC)c2ccccc2)c2ccc3[nH]ncc3c2)cc1] | 1.59 | 22.31 |
| 9 | 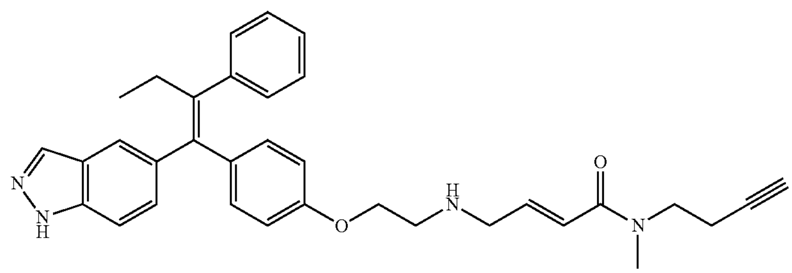 [SMILES: C#CCCN(C)C(=O)/C=C/CNCCOc1ccc(/C(=C(/CC)c2ccccc2)c2ccc3[nH]ncc3c2)cc1] | 5.57 | 117.8 |
| 10 | 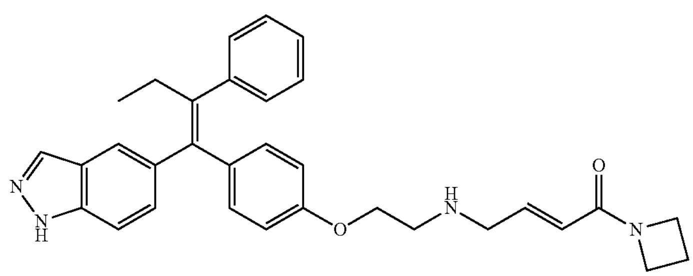 [SMILES: CC/C(=C(/c1ccc(OCCNC/C=C/C(=O)N2CCC2)cc1)c1ccc2[nH]ncc2c1)c1ccccc1] | 2.22 ± 2.34 (3) | 21.22 ± 17.22 (3) |
| 11 | 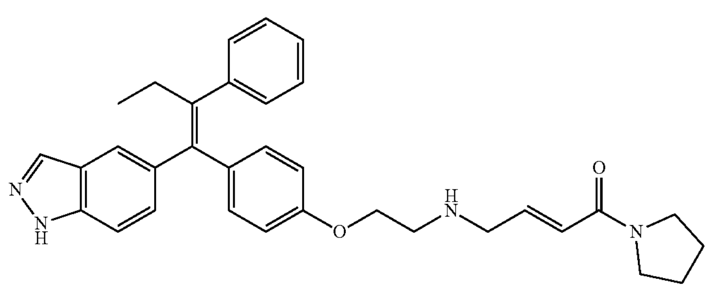 [SMILES: CC/C(=C(/c1ccc(OCCNC/C=C/C(=O)N2CCCC2)cc1)c1ccc2[nH]ncc2c1)c1ccccc1] | 0.76 | 13.97 |

TABLE 1-continued

Viability Screen Results (see Example 101 below)

| Compound # | Structure | GI50 WT (nM) | GI50 MUT (Y537S) (nM) |
|---|---|---|---|
| 12 | 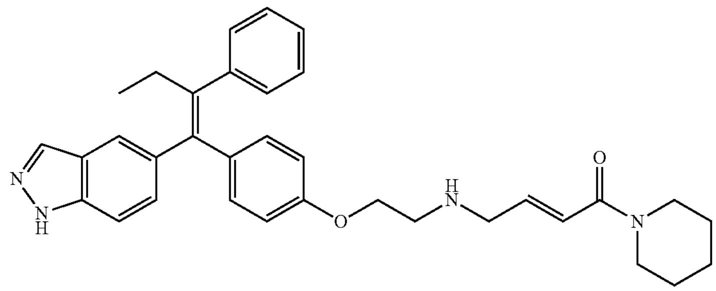 [SMILES: CC/C(=C(/c1ccc(OCCNC/C=C/C(=O)N2CCCCC2)cc1)c1ccc2[nH]ncc2c1)c1ccccc1] | 1.69 | 36.68 |
| 13 | 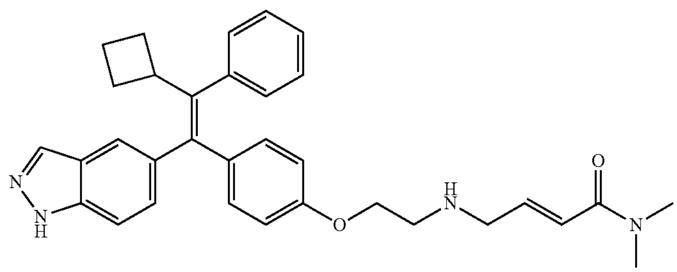 [SMILES: CN(C)C(=O)/C=C/CNCCOc1ccc(/C(=C(\c2ccccc2)C2CCC2)c2ccc3[nH]ncc3c2)cc1] | 2.08 ± 1.57 (3) | 20.02 ± 13.71 (3) |
| 14 | 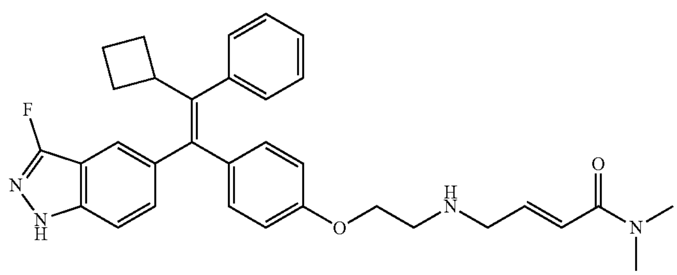 [SMILES: CN(C)C(=O)/C=C/CNCCOc1ccc(/C(=C(\c2ccccc2)C2CCC2)c2ccc3[nH]nc(F)c3c2)cc1] | 2.46 ± 1.43 (2) | 30.67 ± 4.02 (2) |
| 15 | 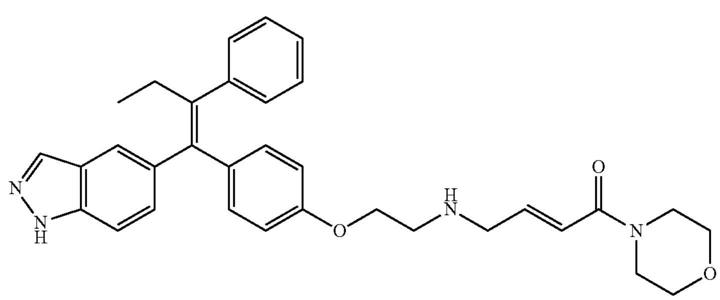 [SMILES: CC/C(=C(/c1ccc(OCCNC/C=C/C(=O)N2CCOCC2)cc1)c1ccc2[nH]ncc2c1)c1ccccc1] | 1.84 ± 1.09 (3) | 25.53 ± 13.78 (3) |
| 16 | 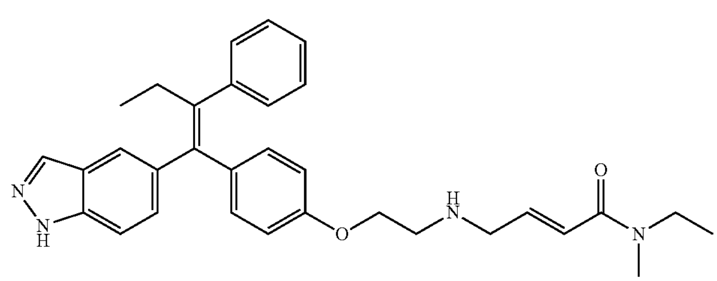 [SMILES: CC/C(=C(/c1ccc(OCCNC/C=C/C(=O)N(C)CC)cc1)c1ccc2[nH]ncc2c1)c1ccccc1] | 1.66 | 21.89 |

TABLE 1-continued

Viability Screen Results (see Example 101 below)

| Compound # | Structure | GI50 WT (nM) | GI50 MUT (Y537S) (nM) |
|---|---|---|---|
| 17 | 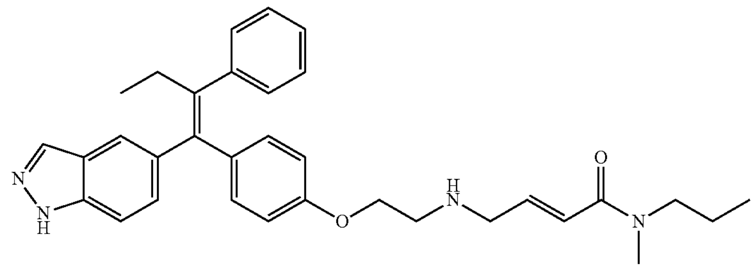 [SMILES: CCCN(C)C(=O)/C=C/CNCCOc1ccc(/C(=C(/CC)c2ccccc2)c2ccc3[nH]ncc3c2)cc1] | 2.18 | 25.18 |
| 18 | 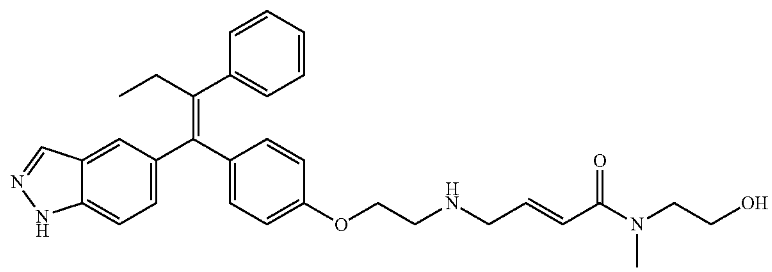 [SMILES: CC/C(=C(/c1ccc(OCCNC/C=C/C(=O)N(C)CCO)cc1)c1ccc2[nH]ncc2c1)c1ccccc1] | 1.63 ± 1.41 (3) | 21.35 ± 15.03 (3) |
| 19 | 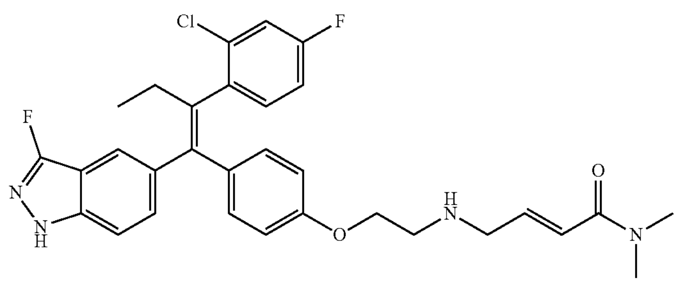 [SMILES: CC/C(=C(/c1ccc(OCCNC/C=C/C(=O)N(C)C)cc1)c1ccc2[nH]nc(F)c2c1)c1ccc(F)cc1Cl] | 1.58 | 18.57 |
| 21 | 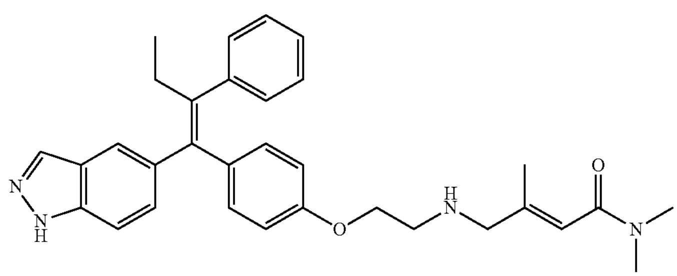 [SMILES: CC/C(=C(/c1ccc(OCCNC/C(C)=C/C(=O)N(C)C)cc1)c1ccc2[nH]ncc2c1)c1ccccc1] | 26.57 ± 21.84 (2) | 153.62 ± 51.68 (2) |
| 22 | 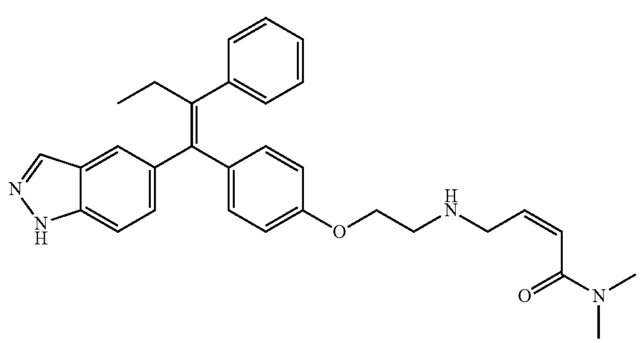 [SMILES: CC/C(=C(/c1ccc(OCCNC/C=C\C(=O)N(C)C)cc1)c1ccc2[nH]ncc2c1)c1ccccc1] | 2.42 ± 1.95 (2) | 21.64 ± 0.26 (2) |

TABLE 1-continued

Viability Screen Results (see Example 101 below)

| Compound # | Structure | GI50 WT (nM) | GI50 MUT (Y537S) (nM) |
|---|---|---|---|
| 23 | 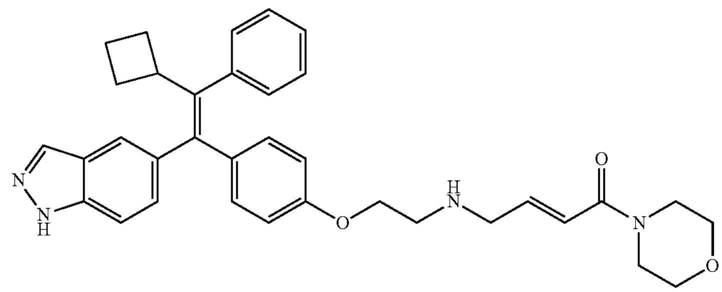 [SMILES: O=C(/C=C/CNCCOc1ccc(/C(=C(\c2ccccc2)C2CCC2)c2ccc3[nH]ncc3c2)cc1)N1CCOCC1] | 1.52 ± 1.05 (2) | 24.23 ± 6.57 (2) |
| 24 | 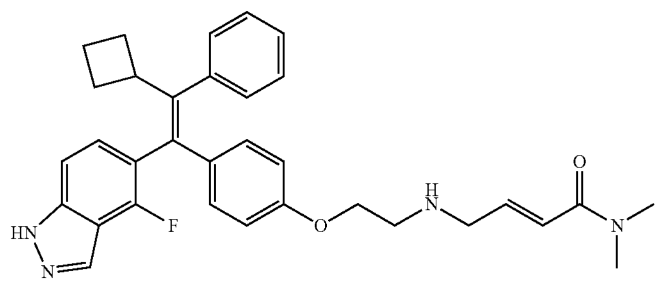 [SMILES: CN(C)C(=O)/C=C/CNCCOc1ccc(/C(=C(\c2ccccc2)C2CCC2)c2ccc3[nH]ncc3c2F)cc1] | 1.05 ± 0.30 (2) | 19.86 ± 3.58 (2) |
| 25 | 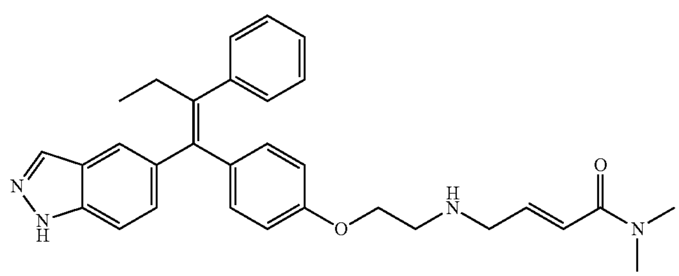 [SMILES: CC/C(=C(/c1ccc(OCCNC/C=C/C(=O)N(C)C)cc1)c1ccc2[nH]ncc2c1)c1ccccc1] | 1.15 ± 0.30 (2) | 19.64 ± 4.26 (2) |
| 26 | 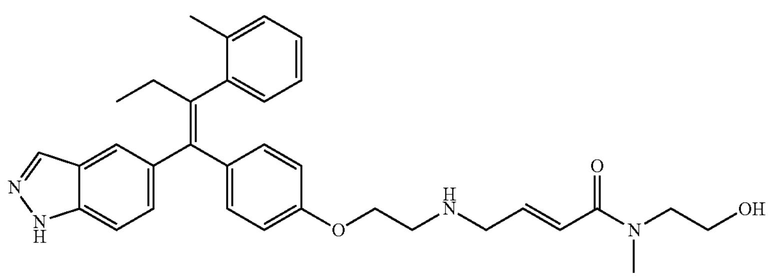 [SMILES: CC/C(=C(/c1ccc(OCCNC/C=C/C(=O)N(C)CCO)cc1)c1ccc2[nH]ncc2c1)c1ccccc1C] | 2.18 ± 0.87 (2) | 32.48 ± 16.72 (2) |
| 28 | 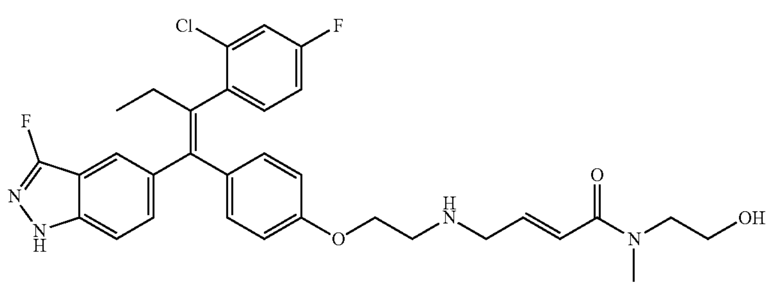 [SMILES: CC/C(=C(/c1ccc(OCCNC/C=C/C(=O)N(C)CCO)cc1)c1ccc2[nH]nc(F)c2c1)c1ccc(F)cc1Cl] | 3.16 | 69.7 |

TABLE 1-continued

Viability Screen Results (see Example 101 below)

| Compound # | Structure | GI50 WT (nM) | GI50 MUT (Y537S) (nM) |
|---|---|---|---|
| 29 | 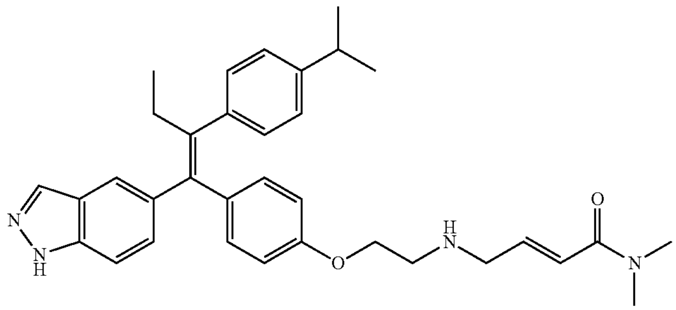 [SMILES: CC/C(=C(/c1ccc(OCCNC/C=C/C(=O)N(C)C)cc1)c1ccc2[nH]ncc2c1)c1ccc(C(C)C)cc1] | 3.37 | 58.66 |
| 30 | 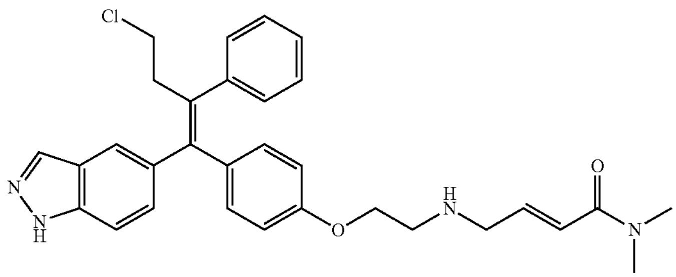 [SMILES: CN(C)C(=O)/C=C/CNCCOc1ccc(/C(=C(/CCCl)c2ccccc2)c2ccc3[nH]ncc3c2)cc1] | 2.74 ± 1.06 (2) | 61.26 ± 9.98 (2) |
| 31 | 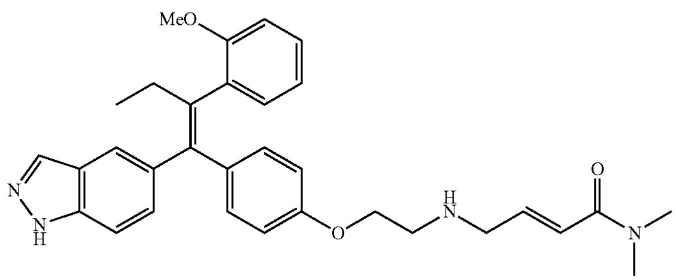 [SMILES: CC/C(=C(/c1ccc(OCCNC/C=C/C(=O)N(C)C)cc1)c1ccc2[nH]ncc2c1)c1ccccc1OC] | 0.83 | 13.09 |
| 32 | 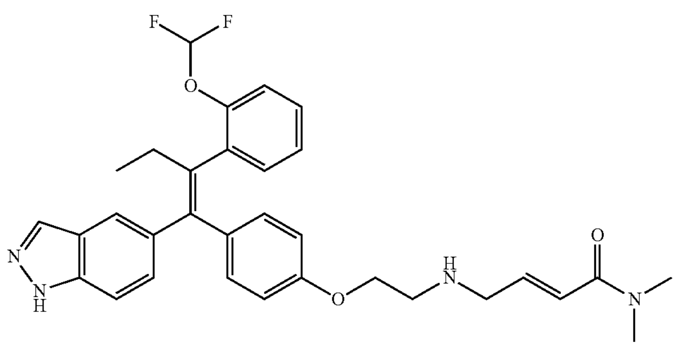 [SMILES: CC/C(=C(/c1ccc(OCCNC/C=C/C(=O)N(C)C)cc1)c1ccc2[nH]ncc2c1)c1ccccc1OC(F)F] | 1.28 | 22.89 |
| 33 | 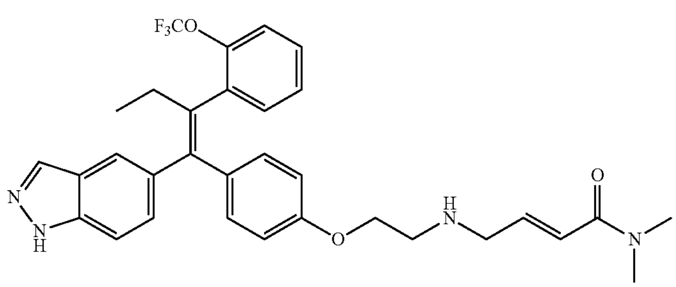 [SMILES: CC/C(=C(/c1ccc(OCCNC/C=C/C(=O)N(C)C)cc1)c1ccc2[nH]ncc2c1)c1ccccc1OC(F)(F)F] | 2.5 | 29.3 |

TABLE 1-continued

Viability Screen Results (see Example 101 below)

| Compound # | Structure | GI50 WT (nM) | GI50 MUT (Y537S) (nM) |
|---|---|---|---|
| 34 | 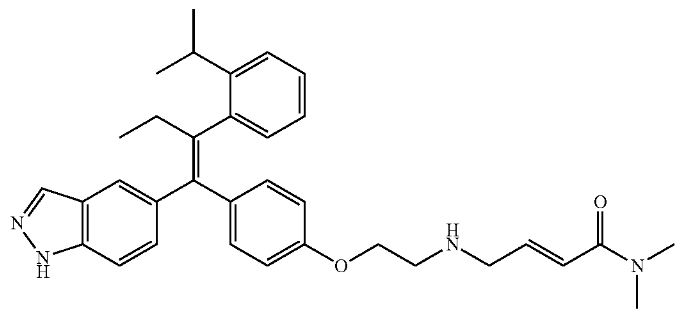 [SMILES: CC/C(=C(/c1ccc(OCCNC/C=C/C(=O)N(C)C)cc1)c1ccc2[nH]ncc2c1)c1ccccc1C(C)C] | 10.52 | 93.62 |
| 35 | 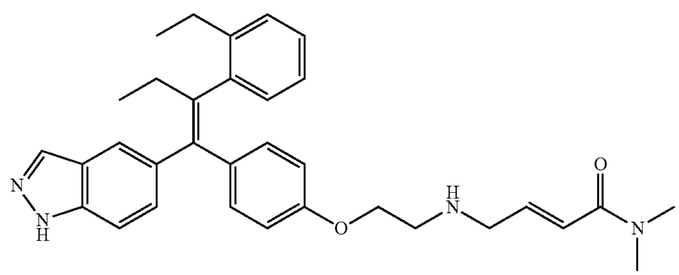 [SMILES: CC/C(=C(/c1ccc(OCCNC/C=C/C(=O)N(C)C)cc1)c1ccc2[nH]ncc2c1)c1ccccc1CC] | 6.22 ± 0.58 (2) | 47.82 ± 15.58 (2) |
| 36 | 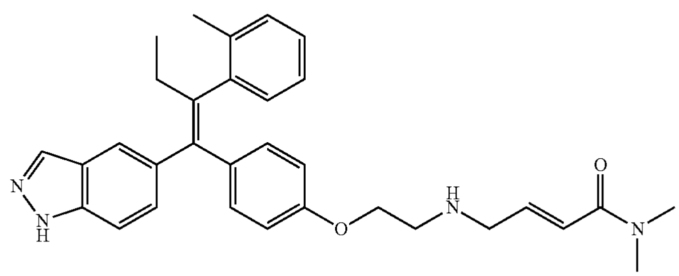 [SMILES: CC/C(=C(/c1ccc(OCCNC/C=C/C(=O)N(C)C)cc1)c1ccc2[nH]ncc2c1)c1ccccc1C] | 4.96 ± 3.10 (3) | 25.04 ± 21.87 (3) |
| 38 | 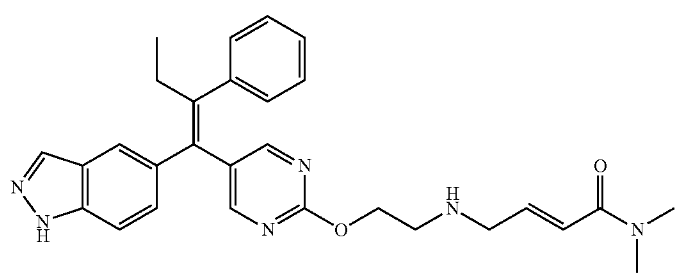 [SMILES: CC/C(=C(/c1cnc(OCCNC/C=C/C(=O)N(C)C)nc1)c1ccc2[nH]ncc2c1)c1ccccc1] | 8.23 ± 5.32 (3) | 158.56 ± 127.8 (3) |
| 39 | 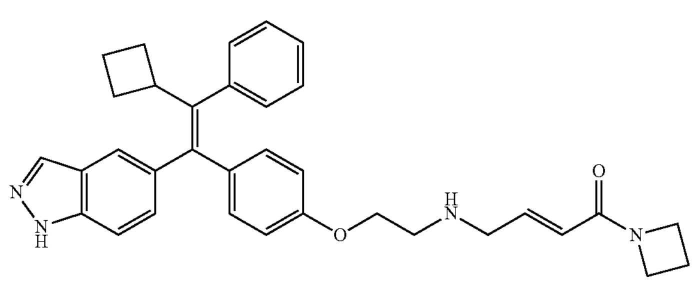 [SMILES: O=C(/C=C/CNCCOc1ccc(/C(=C(\c2ccccc2)C2CCC2)c2ccc3[nH]ncc3c2)cc1)N1CCC1] | 1.79 ± 0.47 (2) | 31.82 ± 4.85 (2) |

TABLE 1-continued

Viability Screen Results (see Example 101 below)

| Compound # | Structure | GI50 WT (nM) | GI50 MUT (Y537S) (nM) |
|---|---|---|---|
| 40 | 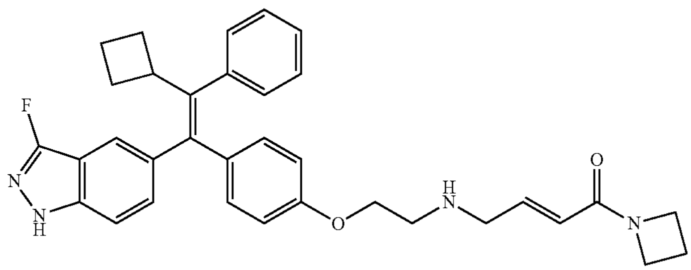 [SMILES: O=C(/C=C/CNCCOc1ccc(/C(=C(\c2ccccc2)C2CCC2)c2ccc3[nH]nc(F)c3c2)cc1)N1CCC1] | 7.52 ± 4.52 (3) | 94.55 ± 20.82 (3) |
| 41 | 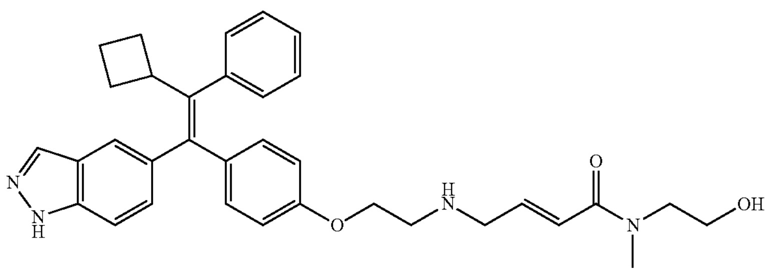 [SMILES: CN(CCO)C(=O)/C=C/CNCCOc1ccc(/C(=C(\c2ccccc2)C2CCC2)c2ccc3[nH]ncc3c2)cc1] | 3.84 | 66.31 |
| 42 | 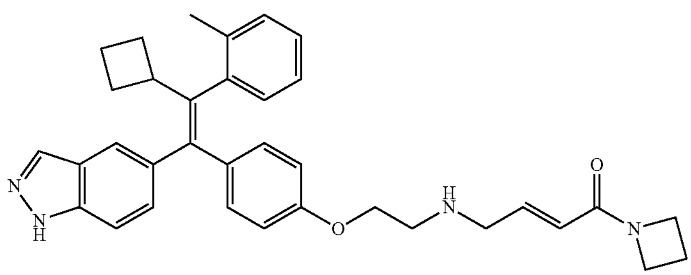 [SMILES: Cc1ccccc1/C(=C(\c1ccc(OCCNC/C=C/C(=O)N2CCC2)cc1)c1ccc2[nH]ncc2c1)C1CCC1] | 2.68 ± 1.66 (2) | 69.43 ± 29.08 (2) |
| 43 | 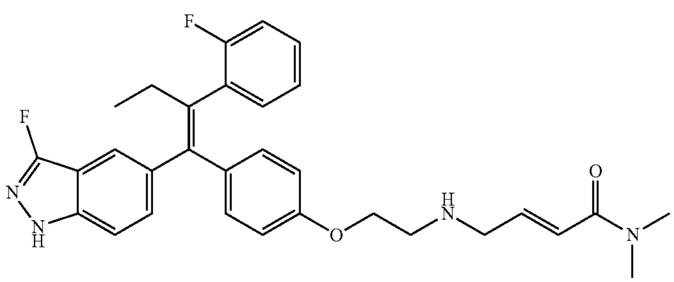 [SMILES: CC/C(=C(/c1ccc(OCCNC/C=C/C(=O)N(C)C)cc1)c1ccc2[nH]nc(F)c2c1)c1ccccc1F] | 1.94 | 47.31 |
| 44 | 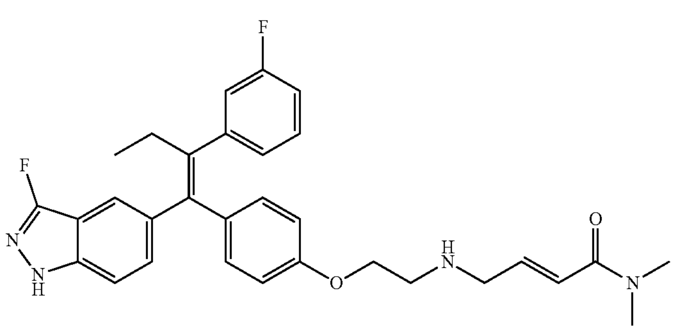 [SMILES: CC/C(=C(/c1ccc(OCCNC/C=C/C(=O)N(C)C)cc1)c1ccc2[nH]nc(F)c2c1)c1cccc(F)c1] | 4.91 | 179.86 |

TABLE 1-continued

Viability Screen Results (see Example 101 below)

| Compound # | Structure | GI50 WT (nM) | GI50 MUT (Y537S) (nM) |
|---|---|---|---|
| 45 | 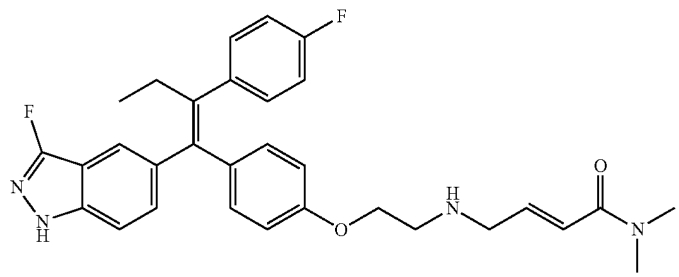 [SMILES: CC/C(=C(/c1ccc(OCCNC/C=C/C(=O)N(C)C)cc1)c1ccc2[nH]nc(F)c2c1)c1ccc(F)cc1] | 4.14 | 103.76 |
| 46 | 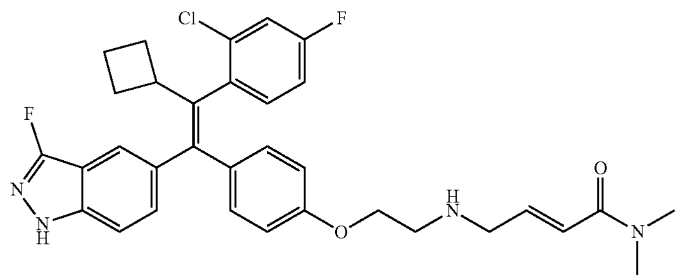 [SMILES: CN(C)C(=O)/C=C/CNCCOc1ccc(/C(=C(\c2ccc(F)cc2Cl)C2CCC2)c2ccc3[nH]nc(F)c3c2)cc1] | 0.95 | 12.36 |
| 49 | 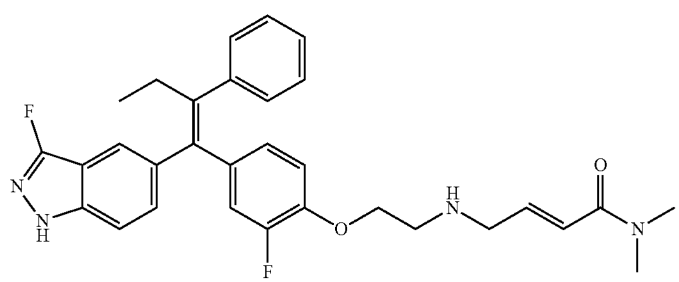 [SMILES: CC/C(=C(/c1ccc(OCCNC/C=C/C(=O)N(C)C)c(F)c1)c1ccc2[nH]nc(F)c2c1)c1ccccc1] | 5.4 | 288.09 |
| 50 | 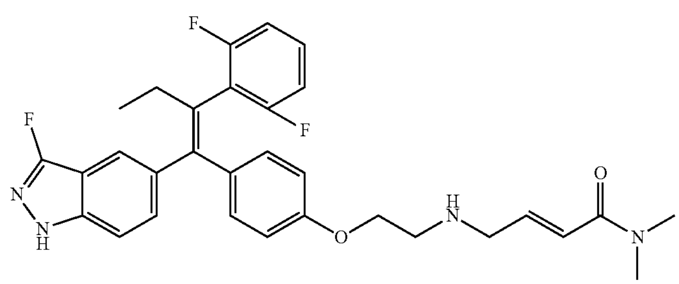 [SMILES: CC/C(=C(/c1ccc(OCCNC/C=C/C(=O)N(C)C)cc1)c1ccc2[nH]nc(F)c2c1)c1c(F)cccc1F] | 2.46 | 67.53 |
| 51 | 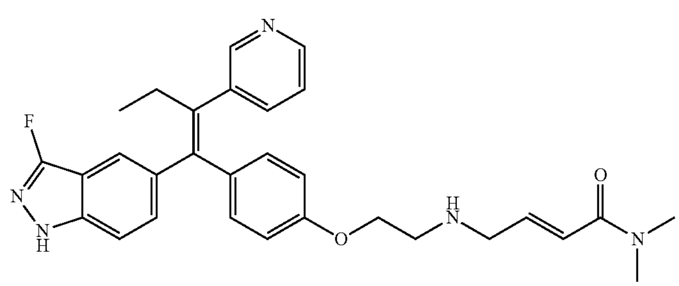 [SMILES: CC/C(=C(/c1ccc(OCCNC/C=C/C(=O)N(C)C)cc1)c1ccc2[nH]nc(F)c2c1)c1cccnc1] | 20.89 | 347 |

TABLE 1-continued

Viability Screen Results (see Example 101 below)

| Compound # | Structure | GI50 WT (nM) | GI50 MUT (Y537S) (nM) |
|---|---|---|---|
| 52 | 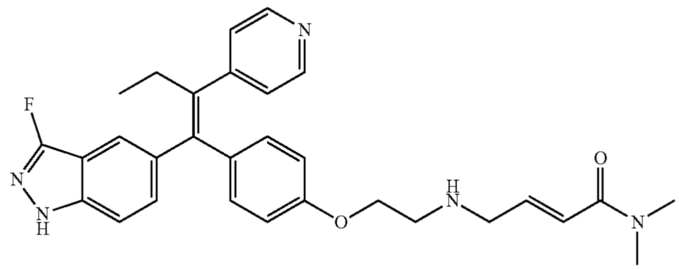 [SMILES: CC/C(=C(/c1ccc(OCCNC/C=C/C(=O)N(C)C)cc1)c1ccc2[nH]nc(F)c2c1)c1ccncc1] | 2.9 | 85.75 |
| 53 | 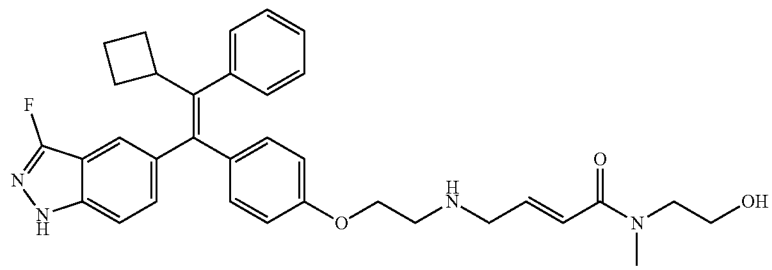 [SMILES: CN(CCO)C(=O)/C=C/CNCCOc1ccc(/C(=C(\c2ccccc2)C2CCC2)c2ccc3[nH]nc(F)c3c2)cc1] | 3.59 | 76.55 |
| 54 | 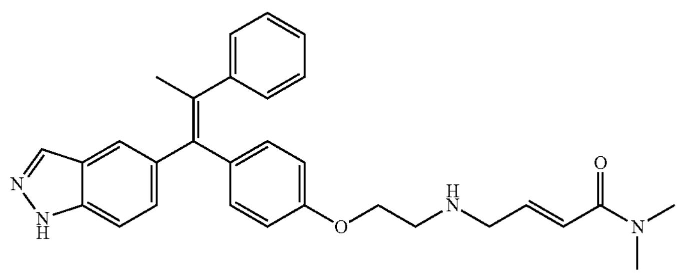 [SMILES: C/C(=C(/c1ccc(OCCNC/C=C/C(=O)N(C)C)cc1)c1ccc2[nH]ncc2c1)c1ccccc1] | 7.97 ± 1.65 (2) | 160.02 ± 39.63 (2) |
| 56 | 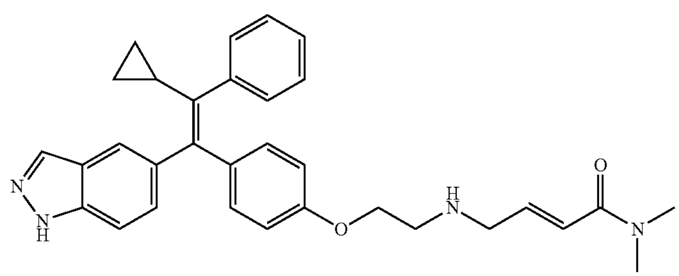 [SMILES: CN(C)C(=O)/C=C/CNCCOc1ccc(/C(=C(\c2ccccc2)C2CC2)c2ccc3[nH]ncc3c2)cc1] | 3.78 ± 1.75 (2) | 63.59 ± 18.38 (2) |
| 57 | 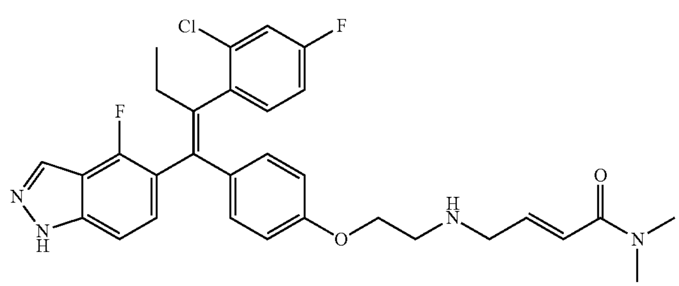 [SMILES: CC/C(=C(/c1ccc(OCCNC/C=C/C(=O)N(C)C)cc1)c1ccc2[nH]ncc2c1F)c1ccc(F)cc1Cl] | 1.9 | 36.2 |

TABLE 1-continued

Viability Screen Results (see Example 101 below)

| Compound # | Structure | GI50 WT (nM) | GI50 MUT (Y537S) (nM) |
|---|---|---|---|
| 58 | 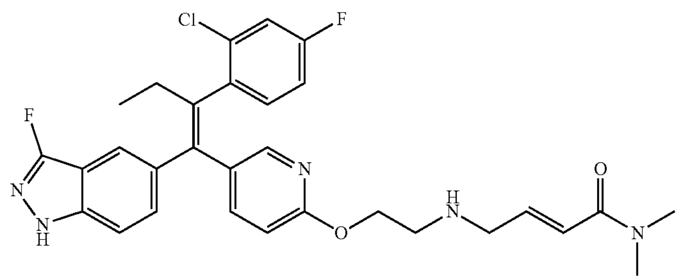 | 1.3 ± 0.4 (n = 2) | 17.9 ± 4.5 (n = 2) |
| 59 | 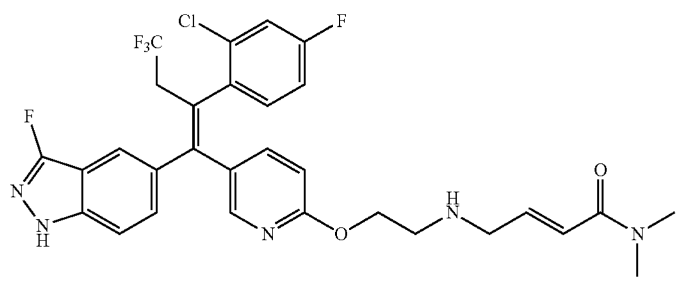 [SMILES: CN(C)C(=O)/C=C/CNCCOc1ccc(/C(=C(/CC(F)(F)F)c2ccc(F)cc2Cl)c2ccc3[nH]nc(F)c3c2)cn1] | 0.33 ± 0.18 (n = 2) | 15.24 ± 3.7 (n = 2) |
| 60 | 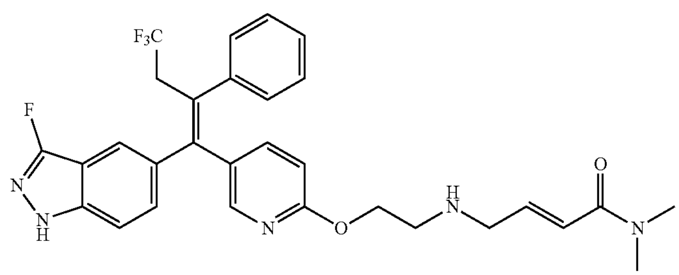 [SMILES: CN(C)C(=O)/C=C/CNCCOc1ccc(/C(=C(/CC(F)(F)F)c2ccccc2)c2ccc3[nH]nc(F)c3c2)cn1] | 0.34 | 4.26 |
| 61 | 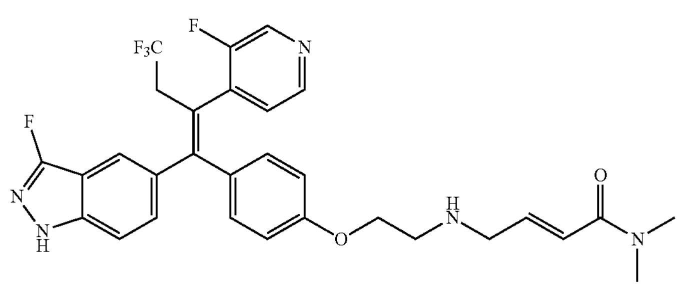 [SMILES: CN(C)C(=O)/C=C/CNCCOc1ccc(/C(=C(/CC(F)(F)F)c2ccncc2F)c2ccc3[nH]nc(F)c3c2)cc1] | 0.30 ± 0.1 (n = 2) | 4.0 ± 1.5 (n = 2) |
| 62 | 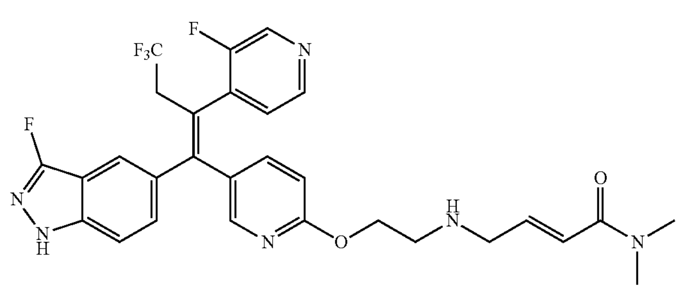 [SMILES: CN(C)C(=O)/C=C/CNCCOc1ccc(/C(=C(/CC(F)(F)F)c2ccncc2F)c2ccc3[nH]nc(F)c3c2)cn1] | 0.3 | 1.3 |

TABLE 1-continued

Viability Screen Results (see Example 101 below)

| Compound # | Structure | GI50 WT (nM) | GI50 MUT (Y537S) (nM) |
|---|---|---|---|
| 63 | 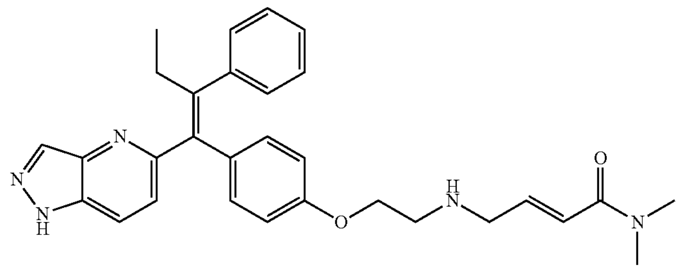 [SMILES: CC/C(=C(/c1ccc(OCCNC/C=C/C(=O)N(C)C)cc1)c1ccc2[nH]ncc2n1)c1ccccc1] | 2.8 | 65.7 |
| 64 | 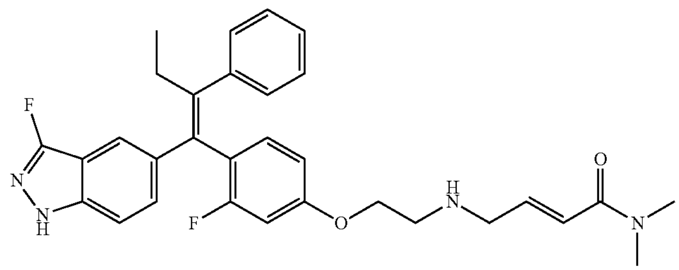 [SMILES: CC/C(=C(\c1ccc2[nH]nc(F)c2c1)c1ccc(OCCNC/C=C/C(=O)N(C)C)cc1F)c1ccccc1] | 3.1 | 58.3 |
| 65 | 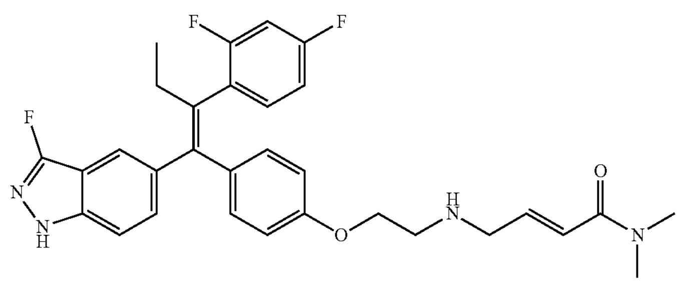 [SMILES: CC/C(=C(/c1ccc(OCCNC/C=C/C(=O)N(C)C)cc1)c1ccc2[nH]nc(F)c2c1)c1ccc(F)cc1F] | 4.0 | 66.0 |
| 66 | 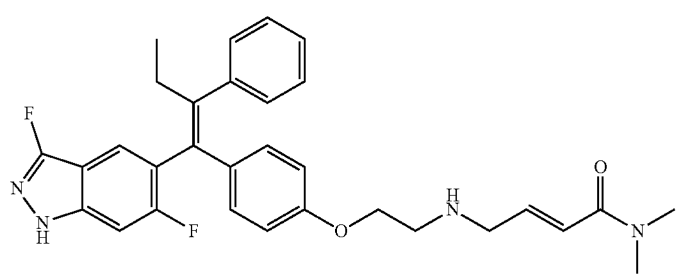 [SMILES: CC/C(=C(/c1ccc(OCCNC/C=C/C(=O)N(C)C)cc1)c1cc2c(F)n[nH]c2cc1F)c1ccccc1] | 32.1 | 826.8 |
| 67 | 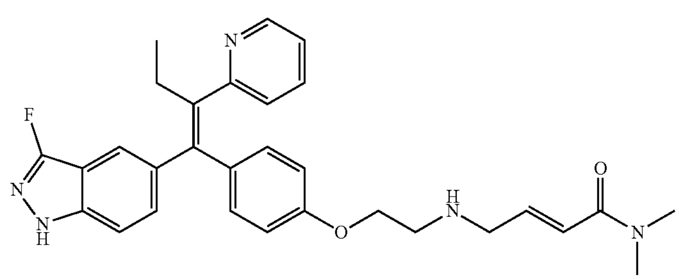 [SMILES: CC/C(=C(/c1ccc(OCCNC/C=C/C(=O)N(C)C)cc1)c1ccc2[nH]nc(F)c2c1)c1ccccn1] | 10.5 | 192.9 |

TABLE 1-continued

Viability Screen Results (see Example 101 below)

| Compound # | Structure | GI50 WT (nM) | GI50 MUT (Y537S) (nM) |
|---|---|---|---|
| 68 | 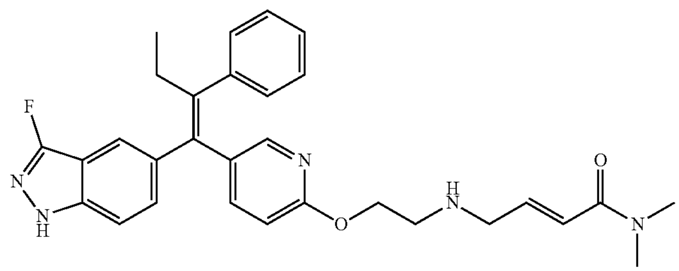 [SMILES: CC/C(=C(/c1ccc(OCCNC/C=C/C(=O)N(C)C)nc1)c1ccc2[nH]nc(F)c2c1)c1ccccc1] | 2.8 | 30.3 |
| 69 | 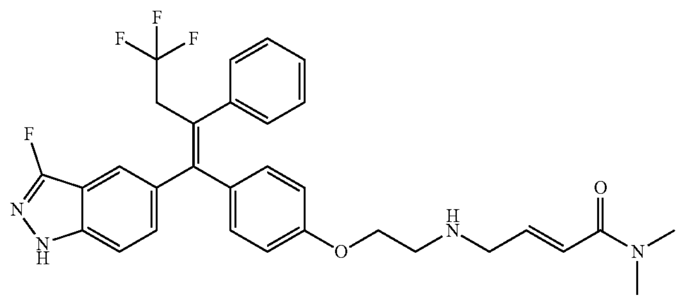 [SMILES: CN(C)C(=O)/C=C/CNCCOc1ccc(/C(=C(/CC(F)(F)F)c2ccccc2)c2ccc3[nH]nc(F)c3c2)cc1] | 1.0 | 16.2 |
| 72 | 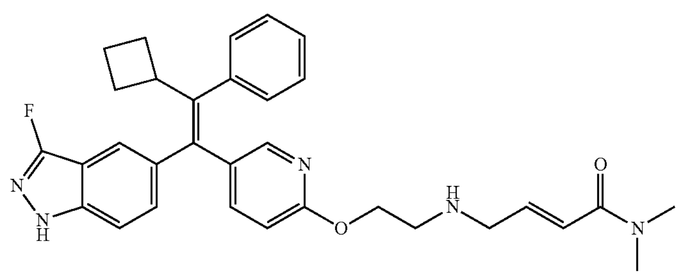 [SMILES: CN(C)C(=O)/C=C/CNCCOc1ccc(/C(=C(\c2ccccc2)C2CCC2)c2ccc3[nH]nc(F)c3c2)cn1] | 2.0 | 32.7 |
| 73 | 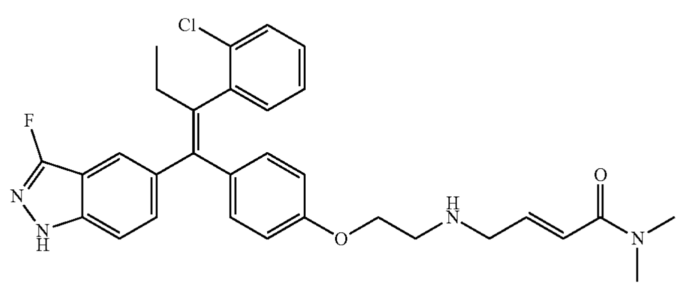 [SMILES: CC/C(=C(/c1ccc(OCCNC/C=C/C(=O)N(C)C)cc1)c1ccc2[nH]nc(F)c2c1)c1ccccc1Cl] | 1.7 | 40.5 |
| 74 | 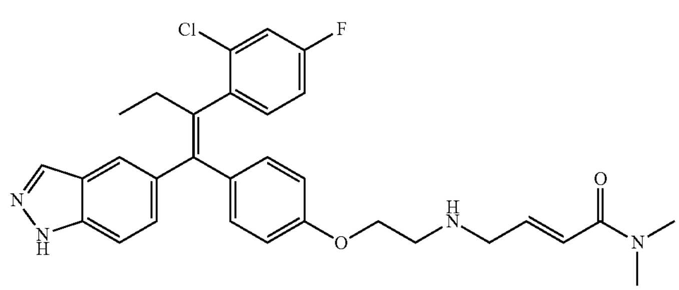 [SMILES: CC/C(=C(/c1ccc(OCCNC/C=C/C(=O)N(C)C)cc1)c1ccc2[nH]ncc2c1)c1ccc(F)cc1Cl] | 1.8 ± 0.5 (n = 2) | 28.8 ± 14.0 (n = 2) |

TABLE 1-continued

Viability Screen Results (see Example 101 below)

| Compound # | Structure | GI50 WT (nM) | GI50 MUT (Y537S) (nM) |
|---|---|---|---|
| 75 | 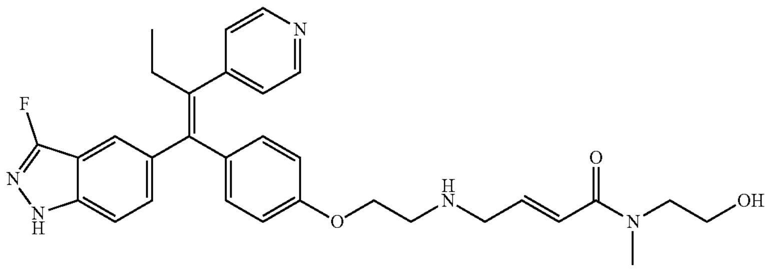 [SMILES: CC/C(=C(/c1ccc(OCCNC/C=C/C(=O)N(C)CCO)cc1)c1ccc2[nH]nc(F)c2c1)c1ccncc1] | 3.2 | 72.2 |
| 76 | 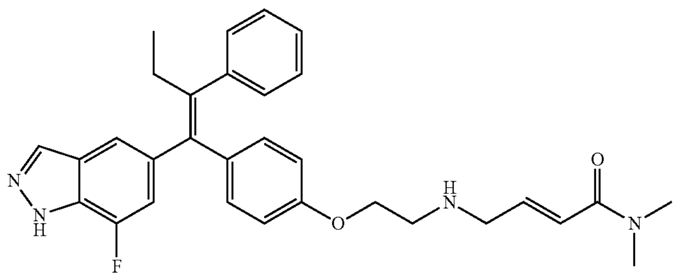 [SMILES: CC/C(=C(/c1ccc(OCCNC/C=C/C(=O)N(C)C)cc1)c1cc(F)c2[nH]ncc2c1)c1ccccc1] | 1.2 | 32.2 |
| 77 | 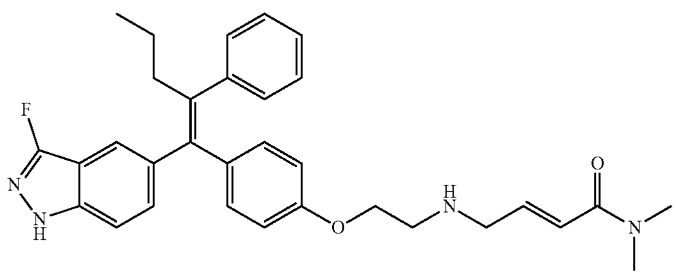 [SMILES: CCC/C(=C(/c1ccc(OCCNC/C=C/C(=O)N(C)C)cc1)c1ccc2[nH]nc(F)c2c1)c1ccccc1] | 2.4 | 35.0 |
| 79 | 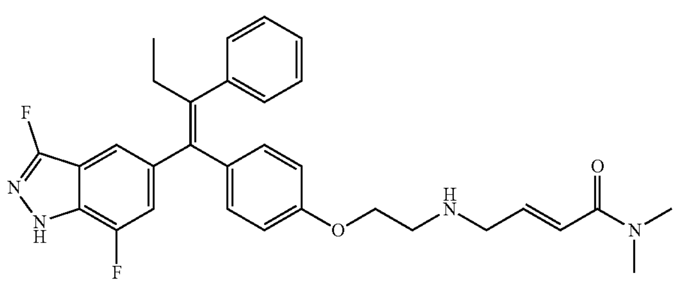 [SMILES: CC/C(=C(/c1ccc(OCCNC/C=C/C(=O)N(C)C)cc1)c1cc(F)c2[nH]nc(F)c2c1)c1ccccc1] | 6.9 | 92.5 |
| 80 | 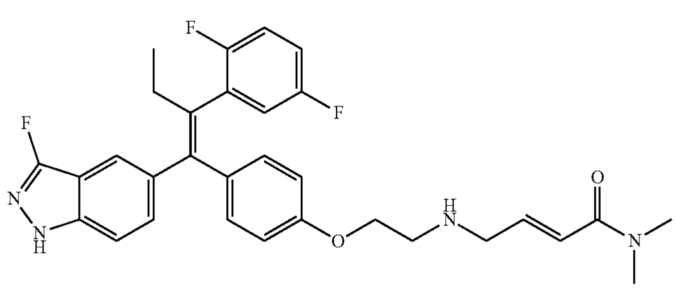 [SMILES: CC/C(=C(/c1ccc(OCCNC/C=C/C(=O)N(C)C)cc1)c1ccc2[nH]nc(F)c2c1)c1cc(F)ccc1F] | 2 | 33.6 |

TABLE 1-continued

Viability Screen Results (see Example 101 below)

| Compound # | Structure | GI50 WT (nM) | GI50 MUT (Y537S) (nM) |
|---|---|---|---|
| 81 | 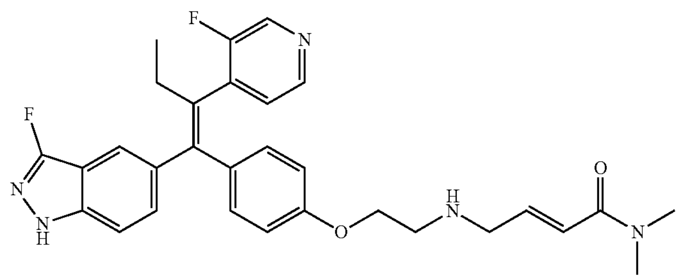 [SMILES: CC/C(=C(/c1ccc(OCCNC/C=C/C(=O)N(C)C)cc1)c1ccc2[nH]nc(F)c2c1)c1ccncc1F] | 0.3 | 13.0 |
| 82 | 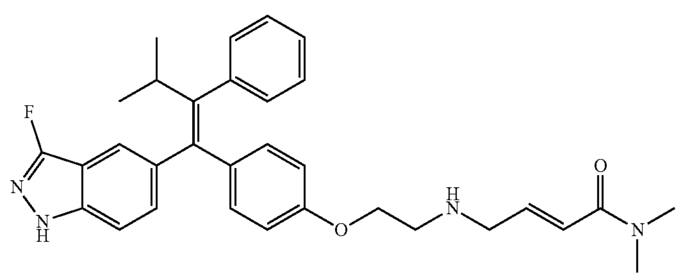 [SMILES: CC(C)/C(=C(/c1ccc(OCCNC/C=C/C(=O)N(C)C)cc1)c1ccc2[nH]nc(F)c2c1)c1ccccc1] | 4.65 ± 2.9 (n = 2) | 93.66 ± 6.3 (n = 2) |
| 84 | 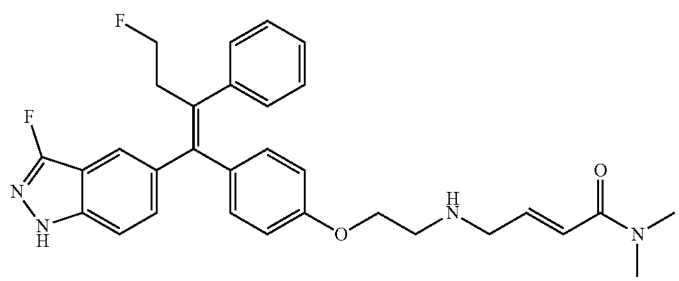 [SMILES: CN(C)C(=O)/C=C/CNCCOc1ccc(/C(=C(/CCF)c2ccccc2)c2ccc3[nH]nc(F)c3c2)cc1] | 2.15 ± 0.15 (n = 2) | 34.93 ± 1.5 (n = 2) |
| 85 | 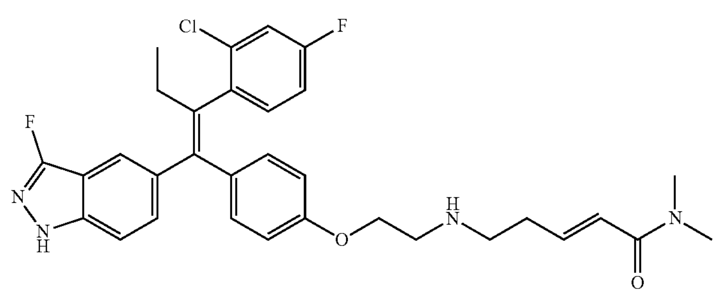 [SMILES: CC/C(=C(/c1ccc(OCCNCC/C=C/C(=O)N(C)C)cc1)c1ccc2[nH]nc(F)c2c1)c1ccc(F)cc1Cl] | 1.56 ± 0.56 (n = 2) | 28.40 ± 2.9 (n = 2) |
| 86 | 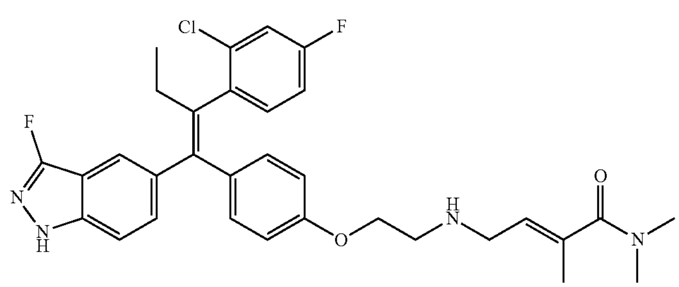 [SMILES: CC/C(=C(/c1ccc(OCCNC/C=C(\C)C(=O)N(C)C)cc1)c1ccc2[nH]nc(F)c2c1)c1ccc(F)cc1Cl] | 1.73 ± 1.0 (n = 2) | 29.43 ± 4.7 (n = 2) |

TABLE 1-continued
Viability Screen Results (see Example 101 below)
| Compound # | Structure | GI50 WT (nM) | GI50 MUT (Y537S) (nM) |
|---|---|---|---|
| 87 | 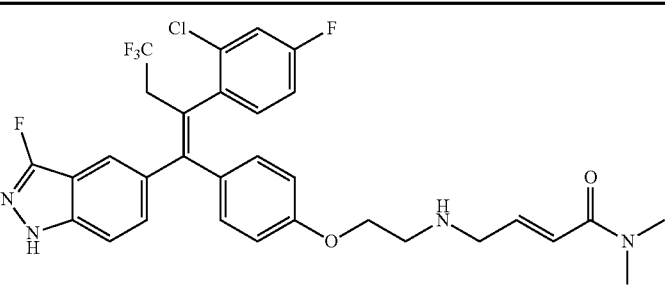 | 0.25 | 21.91 |
| 88 | 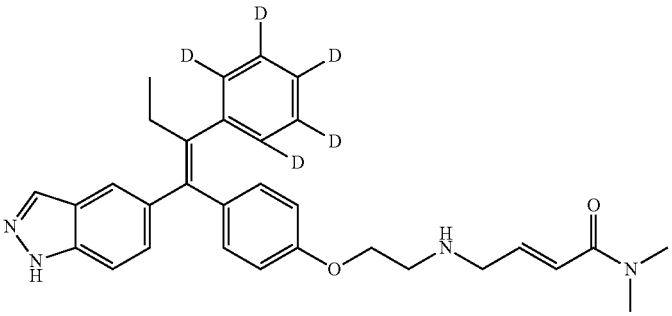 [SMILES: [2H]c1c([2H])c([2H])c(/C(CC)=C(\c2ccc(OCCNC/C=C/C(=O)N(C)C)cc2)c2ccc3[nH]ncc3c2)c([2H])c1[2H]] | 0.7 | 12.5 |
| 89 | 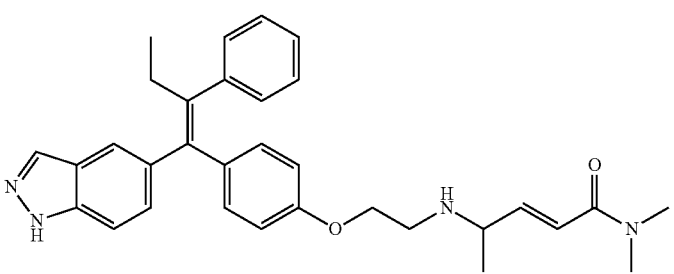 [SMILES: CC/C(=C(/c1ccc(OCCNC(C)/C=C/C(=O)N(C)C)cc1)c1ccc2[nH]ncc2c1)c1ccccc1] | 2.8 | 35 |
| 90 | 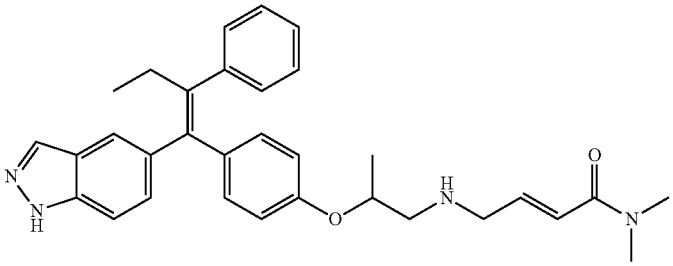 [SMILES: CC/C(=C(/c1ccc(OC(C)CNC/C=C/C(=O)N(C)C)cc1)c1ccc2[nH]ncc2c1)c1ccccc1] | 2.5 | 22.7 |
| 92 | 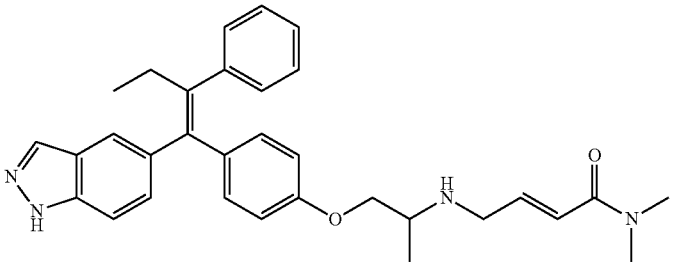 [SMILES: CC/C(=C(/c1ccc(OCC(C)NC/C=C/C(=O)N(C)C)cc1)c1ccc2[nH]ncc2c1)c1ccccc1] | 2.3 | 26.9 |

TABLE 1-continued

Viability Screen Results (see Example 101 below)

| Compound # | Structure | GI50 WT (nM) | GI50 MUT (Y537S) (nM) |
|---|---|---|---|
| 93 | 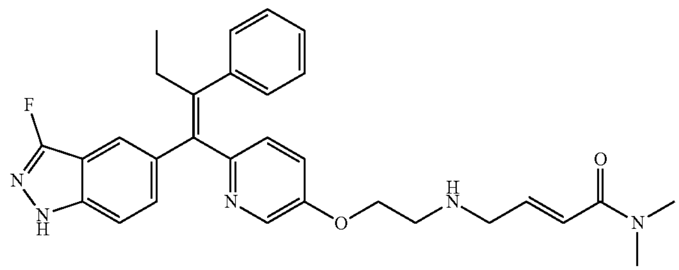 [SMILES: CC/C(=C(\c1ccc2[nH]nc(F)c2c1)c1ccc(OCCNC/C=C/C(=O)N(C)C)cn1)c1ccccc1] | 12.4 | 368.9 |
| 95 | 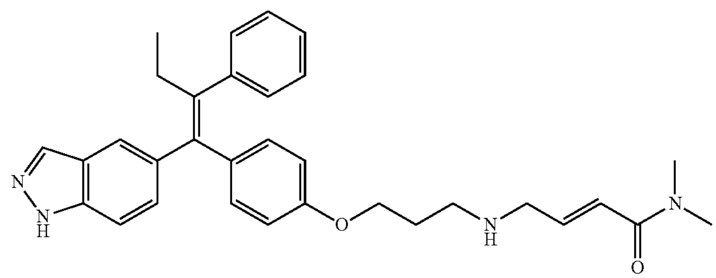 [SMILES: CC/C(=C(/c1ccc(OCCCNC/C=C/C(=O)N(C)C)cc1)c1ccc2[nH]ncc2c1)c1ccccc1] | 1.8 | 32.4 |
| 96 | 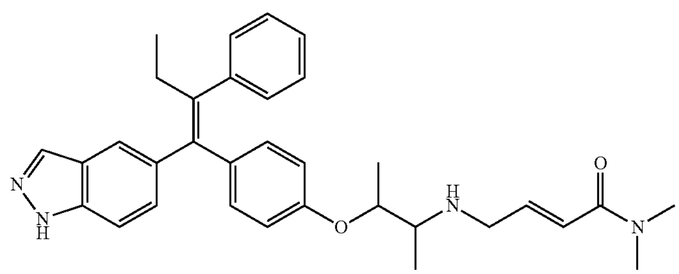 [SMILES: CC/C(=C(/c1ccc(OC(C)C(C)NC/C=C/C(=O)N(C)C)cc1)c1ccc2[nH]ncc2c1)c1ccccc1] | 2 | 27.2 |
| 98 | 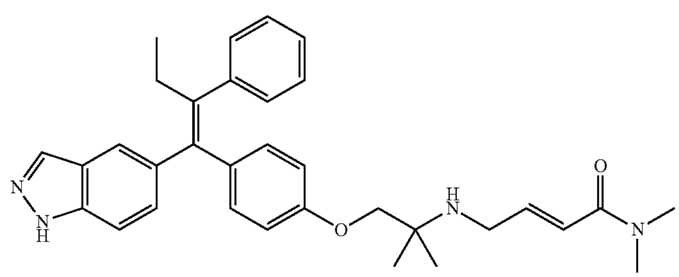 [SMILES: CC/C(=C(/c1ccc(OCC(C)(C)NC/C=C/C(=O)N(C)C)cc1)c1ccc2[nH]ncc2c1)c1ccccc1] | 0.4 | 13.4 |
| 99 | 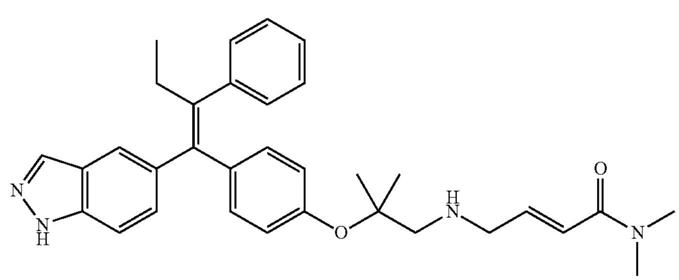 [SMILES: CC/C(=C(/c1ccc(OC(C)(C)CNC/C=C/C(=O)N(C)C)cc1)c1ccc2[nH]ncc2c1)c1ccccc1] | 2.7 | 81.4 |

General Procedures

The following abbreviations may be used herein:
ACN: Acetonitrile
BOC: tert-butyloxycarbonyl
CAN: ceric ammonium nitrate
Conc.: concentrated
Cs$_2$CO$_3$: Cesium carbonate
DABCO: 1,4-Diazabicyclo[2.2.2]octane
DCM: Dichloromethane DHP: Dihydropyran
DIPEA: N,N-diisopropylethylamine, Hunig's base
DMA: Dimethylacetamide
DMF: Dimethylformamide
DMSO: dimethylsulfoxide
DPEphos: (Oxydi-2,1-phenylene)bis(diphenylphosphine)
EDCI.HCl: N-(3-Dimethylaminopropyl)-N-ethylcarbodiimide hydrochloride
EtOH: Ethanol
EtOAc: Ethyl acetate
$Et_3N$: Triethylamine
Ex.: Example
h: Hours
HATU: 1-[Bis(dimethylamino)methylene]-1H-1,2,3-triazolo[4,5-b]pyridinium 3-oxid hexafluorophosphate
HCl: Hydrochloric acid
HMPA: Hexamethylphosphoramide
HPLC: High-performance liquid chromatography
$H_2SO_4$: Sulfuric acid
IPA: Isopropyl alcohol
K2CO3: Potassium carbonate
KOH: Potassium hydroxide
LCMS: Liquid chromatography—mass spectrometry
MeOH: Methanol
$Na_2CO_3$: Sodium carbonate
NBS: n-bromosuccinimide
nBuLi: n-Butyllithium
$NH_4Cl$: Ammonium chloride
$NH_4OH$: Ammonium hydroxide
NMR: nuclear magnetic resonance
on or o.n.: overnight
Pd/C: Palladium (0) on carbon
$Pd_2(dba)_3$: Tris(dibenzylideneacetone)dipalladium(0)
PPTS: pyridinium p-toluenesulfonate
PTSA: p-toluenesulfonic acid
RT or r.t.: room temperature
TBAF: Tetrabutylammonium fluoride
TEA: Triethylamine
TFA: Trifluoroacetic acid
THF: Tetrahydrofuran
TLC: Thin-layer chromatography
Pt/C: Platinum (0) on carbon Unless indicated otherwise, $^1H$ NMR spectra were taken on a Varian Mercury Plus 400 MHz NMR.

Scheme 1:
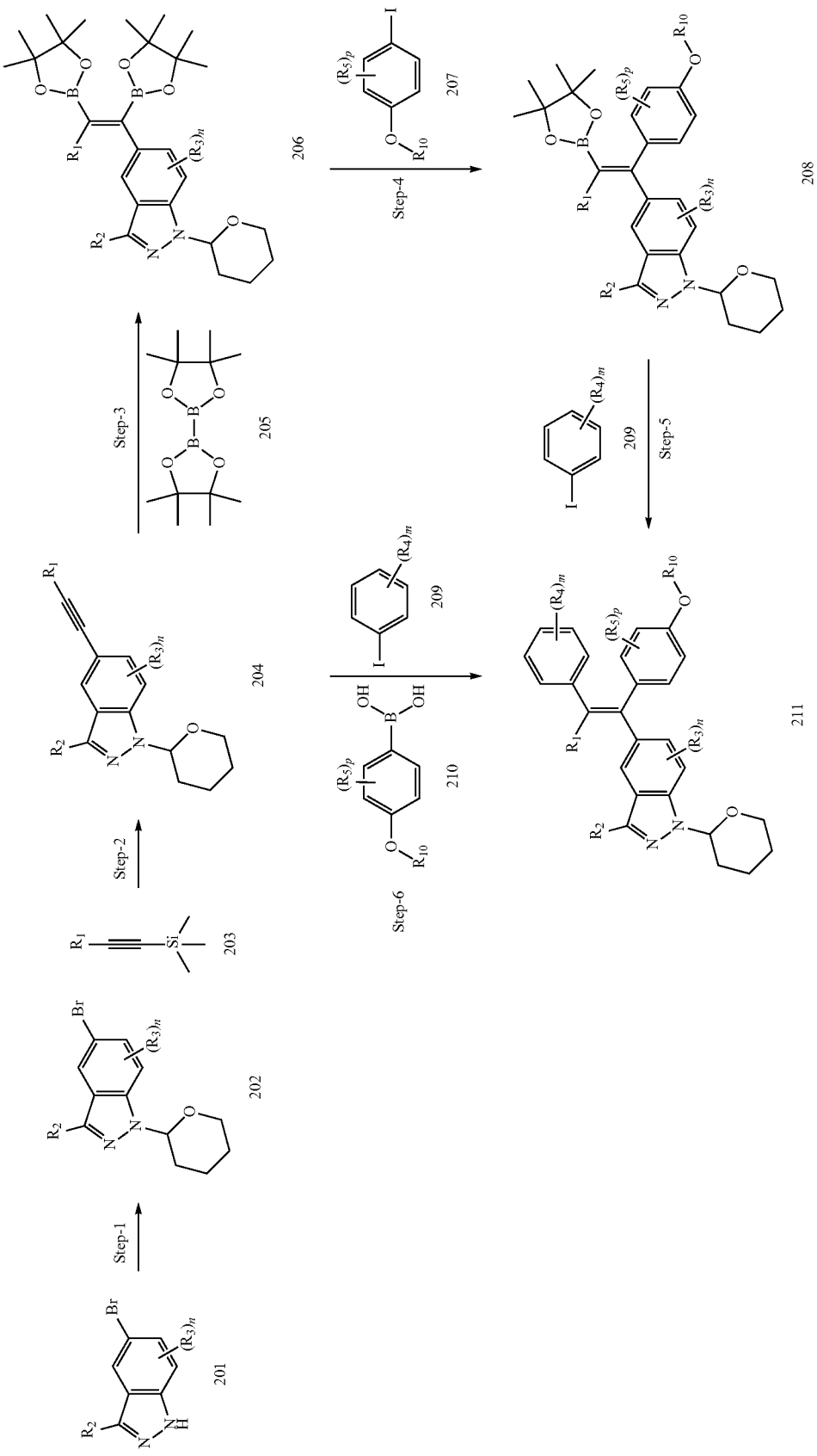

Step-1:

To a stirred solution of 5-bromo-1H-indazole (201, 23.5 mmol) in dry dichloromethane (50 mL) at 23° C. was added dihydro pyran (9.9 g, 118 mmol) followed by addition of pyridinium p-toluene sulfonate (0.6 g, 2.4 mmol). The resulting mixture was stirred at room 23° C. temperature for 16 h. Upon completion by TLC, the reaction mixture was quenched with water (50 mL) and extracted with dichloromethane (2×100 mL). The combined organic extracts were washed with water, brine, dried over sodium sulphate and concentrated. The crude material was purified by column chromatography over 230-400 mesh silica using 4-5% ethyl acetate in hexane to afford 5-bromo-1-(tetrahydro-2H-pyran-2-yl)-1H-indazole (202, 20 mmol, 86%) as a pale yellow oil.

Step-2a:

To a stirred solution of 5-bromo-1-(tetrahydro-2H-pyran-2-yl)-1H-indazole (202, 3.6 mmol) in 10 mL of MeOH:DMA:$H_2O$ (1:1:1), in a sealed tube, were added copper iodide (0.068 g, 0.3 mmol) and cesium carbonate (1.62 g, 4.9 mmol) at 23° C. This mixture was degassed with three vacuum/$N_2$ cycles, and then but-1-yn-1-yltrimethylsilane (203, 0.899 g, 7.1 mmol) followed by Pd(PPh$_3$)$_2$Cl$_2$ (0.125 g, 0.1 mmol) were added. The pressure tube was sealed and heated at 80° C. for 1-12 h. Upon completion by TLC, the reaction mixture was quenched with water (10 mL) and extracted with ethyl acetate (2×50 mL). The combined organic extracts were washed with water, brine, dried over sodium sulphate and concentrated. The crude product was purified over 230-400 mesh silica column chromatography using 4-5% ethyl acetate in hexane to afford 204 (1.4 mmol, 55%) as a pale yellow oil.

Step-2b:

To a stirred solution of 5-bromo-3-fluoro-1-(tetrahydro-2H-pyran-2-yl)-1H-indazole (202, 2.5 g, 8.3 mmol) in 30 mL of DMA, in a sealed tube, were added copper iodide (79 mg, 0.41 mmol) and cesium carbonate (4 g, 12.4 mmol) at room temperature. reaction mixture was degassed with three vacuum/$N_2$ cycles, (cyclobutylethynyl)trimethylsilane (203, 1.78 g, 11.74 mmol) followed by Pd(OAc)$_2$ (92 mg, 0.41 mmol) and dppf (228 mg, 0.041 mmol) were added. The pressure tube was sealed and heated at 90° C. for 2 h. Upon completion by TLC, the reaction mixture was cooled to room temperature and diluted with water (25 mL), extracted with ethyl acetate (100 mL). The combined organic extracts were washed with water followed by brine. The organic layer was dried over anhydrous sodium sulphate and concentrated under reduced pressure. The crude product was purified over 230-400 mesh silica column chromatography using 10% ethyl acetate in n-hexane as an eluent to afford 5-(cyclobutylethynyl)-3-fluoro-1-(tetrahydro-2H-pyran-2-yl)-1H-indazole (204, 2.15 g, 86%).

Step-3:

To a stirred solution of 204 (39.37 mmol) in 2-methyl THF (80 mL), was added bis(pinacolato) diboron (10.09 g, 39.76 mmol), tetrakis(triphenylphosphine)platinum(0) (372 mg, 0.299 mmol) under nitrogen atmosphere, reaction mixture was refluxed for 6 h. After completion of reaction, reaction mixture was diluted with water and extracted with EtOAc. The Organic layer was dried over anhydrous sodium sulphate and concentrated under reduced pressure. The crude material was used in next step without further purification (206, 39 mmol, quantitative) as brown color oil.

Step-4:

To a stirred solution of 207 (2.34 g, 10.61 mmol), bis(triphenylphosphine) palladium(II) dichloride (372 mg, 0.530 mmol), cesium carbonate (6.9 g, 21.23 mmol) and 2-methyl THF (60 mL) were added. This mixture was degassed with nitrogen and water (5 mL) was added. This mixture was stirred at room temperature for 12 h. After completion of reaction, reaction mixture was diluted with water and extracted with EtOAc. The Organic layer was dried over anhydrous sodium sulphate and concentrated under reduced pressure. The crude material was purified by column chromatography over 230-400 mesh silica gel using MeOH in dichloromethane (1.6:98.4) to afford 208 (5.5 mmol, 43%).

Step-5:

To a stirred solution of 208 (1.8 mmol) in 2-methyl THF (30 mL), iodobenzene (209, 1.8 mmol), 4M aqueous KOH (5 mL) and Pd(PPh$_3$)$_2$Cl$_2$ (63 mg, 0.09 mmol) were added and the mixture was degassed with nitrogen for 15 min and heated at 80-90° C. for 8-12 h. Upon completion, the reaction mixture was diluted with EtOAc. Organic layer was washed with water followed by brine, dried over anhydrous sodium sulphate, filtered and concentrated. The crude product was purified by silica gel chromatography (2:8 EtOAc in n-hexane) to give a desired product (211, 0.74 mmol, 41%).

Step-6:

To a solution of 5-(but-1-yn-1-yl)-1-(tetrahydro-2H-pyran-2-yl)-1H-indazole (204, 27.5 mmol), iodobenzene (209, 17 g, 82.7 mmol), 4-hydroxy phenyl boronic acid (210, 11.4 g, 82.7 mmol), in N,N-dimethyl formamide/water (2:1, 50 mL) was added K$_2$CO$_3$ (11.4 g, 82.7 mmol). The contents were degassed with three vacuum/$N_2$ cycles, and then heated at 45° C. for 1 h until the solution was homogeneous. A solution of Pd(PhCN)$_2$Cl$_2$ (0.528 g, 1.4 mmol) in N,N-dimethyl formamide (1 mL) was added and the resulting mixture was stirred at 45° C. for 16 h. Upon completion by TLC, the reaction mixture was quenched with water (500 mL) and extracted with ethyl acetate (2×500 mL). The combined organic extracts were washed with water, brine, dried over sodium sulphate and concentrated. The crude material was purified over 230-400 mesh silica column chromatography using 20% ethyl acetate in hexane to afford the desired compound (211, 11.8 mmol, 43%) as a pale yellow oil.

Scheme 2:
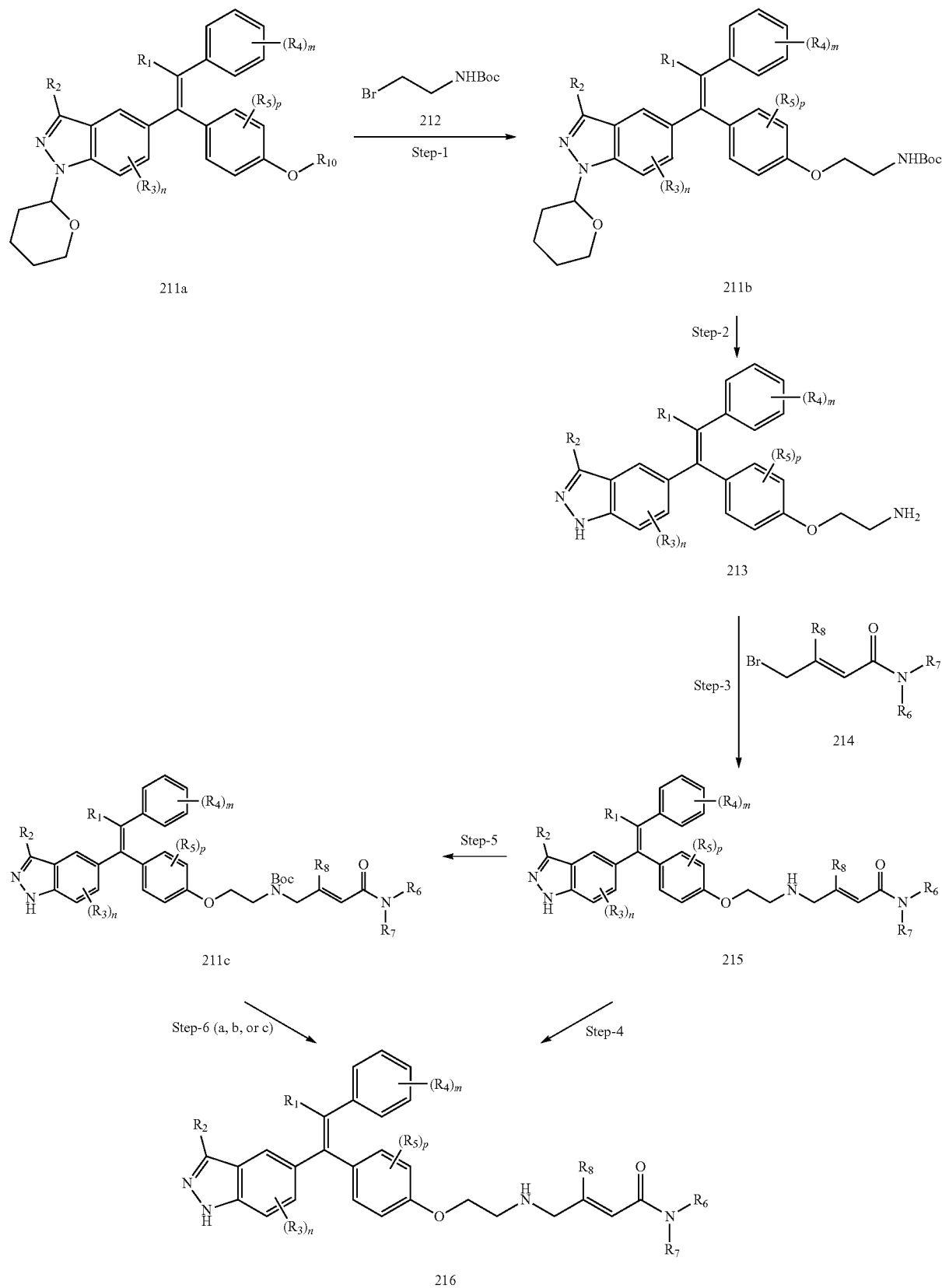

Step-1:

To a solution of 211a (3.4 mmol) in DMF (30 mL), at 0° C., were added sequentially potassium carbonate (1.4 g, 10.1 mmol) and tert-butyl (2-bromoethyl)-carbamate (212, 8.5 mmol). The reaction mixture was stirred at 80° C. for 16 h, was diluted with ethyl acetate, washed with water, brine, dried over sodium sulphate and concentrated under reduced pressure. The crude material was purified by column chromatography over 230-400 mesh silica gel using 15% ethyl acetate in n-hexane to afford the desired product (211b, 1.8 mmol, 53%) as a light brown colour gummy mass.

Step-2a:

To a stirred solution of 211b (2.5 mmol) in ethanol (10 mL) was added at 0° C., 2M HCl in ether (10 mL). The reaction mixture was stirred for 16-24 h at 23° C. After completion of reaction, reaction mixture was basified with saturated NaHCO$_3$, extracted with 10% MeOH in dichloromethane. Organic layer was concentrated under reduced pressure and the crude material was purified by column chromatography over 230-400 mesh silica gel using (4-5%) MeOH in DCM to afford the desire product (13, 1.25 mmol, 50%) as a brown coloured semi solid.

Step-2b:

To a stirred solution of 211 (1.5 g, 2.3 mmol) in ethanol (3 mL) was added at 0° C., 2M HCl in dithey ether (15 mL). The reaction mixture was stirred for 24 h at room temperature. After completion of reaction, reaction mixture was basified with saturated NaHCO$_3$, extracted with ethyl acetate. Organic layer was concentrated under reduced pressure to afford crude desired product (213, 1.1 g crude).

Step-3a:

To a stirred solution of 213 (1.24 mmol) in DMF (5 mL) was added at 0° C., (E)-4-bromo-N,N-dimethylbut-2-enamide (214, 1.24 mmol) and DIPEA (0.321 g, 2.49 mmol). The reaction mixture was stirred for 12-48 h at 23° C., was diluted with cold water (50 mL) and extracted with dichloromethane. The organic layer was washed with water followed by brine, dried over anhydrous sodium sulphate and concentrated under reduced pressure to give a crude mixture of 215.

Step-3b:

To a stirred solution of 213 (1.1 g, 2 mmol) in DMF (22 mL) was added DIPEA (0.62 g, 4 mmol) at room temperature, stirred for 15 min at same temperature. A solution of (E)-4-bromo-N,N-dimethylbut-2-enamide and (E)-4-chloro-N,N-dimethylbut-2-enamide mixture (214, 0.41 g, 2 mmol) in DMF (5 mL) was added drop wise, reaction mixture was stirred for 16 h at room temperature, after completion of reaction (monitored by TLC), reaction mixture was diluted with cold water (50 mL) and extracted with dichloromethane. The organic layer was washed with water followed by saturated NaCl solution, dried over anhydrous sodium sulphate and concentrated under reduced pressure to deliver crude product 215 (1.8 g).

Step-4:

The crude material obtained from previous step was purified by preparative HPLC to afford pure isomer 216 (0.06 mmol, 5%) as a white solid. The $^1$H NMR, HPLC and MS data were collected.

Step-5:

To a stirred solution of 215 (1.25 mmol) in DCM (10 mL) was added di-tert-butyl dicarbonate (0.546 g, 2.5 mmol). The reaction mixture was stirred for 1 h at 23° C., after completion of reaction, reaction mixture was diluted with cold water (50 mL) and extracted with dichloromethane (100 mL). The organic layer was washed with water followed by brine, dried over anhydrous sodium sulphate and concentrated under reduced pressure. Crude compound was purified by column chromatography using 2% MeOH in DCM to afford 211c (0.63 mmol, 50%) as a light brown semi-solid.

Step-6a:

To a stirred solution of 211c (0.622 mmol) in MeOH (5 mL) was added at 0° C., 2M HCl in ether (10 mL). The reaction mixture was stirred for 16 h at 23° C. After completion of reaction, reaction mixture was basified with saturated NaHCO$_3$, extracted with 10% MeOH in DCM. Organic layer was concentrated under reduced pressure to obtain crude compound (215, 0.07 mmol) as an off-white solid. Crude compound was purified by preparative HPLC to afford desired pure isomer (216, 0.03 mmol, 4.1%) as an white solid. The $^1$H NMR, HPLC and MS data were collected.

Step-6b:

To a stirred solution of 211c (0.081 mmol) in dichloromethane (1.2 mL) at 0° C., was added TFA (0.3 mL). The reaction mixture was stirred at 23° C. for 30 min to 2 h. After completion of reaction, the solution was basified with saturated NaHCO$_3$ solution and extracted with dichloromethane. Combined organic layer was dried over anhydrous sodium sulfate and concentrated under reduced pressure. The crude material was purified by preparative HPLC to afford desired pure isomer (216, 0.12 mmol, 33.3%) as an white solid. The $^1$H NMR, HPLC and MS data were collected.

Step-6c:

To a stirred solution of 211c (0.504 mmol) in EtOH (3 mL) was added at 0° C., 2M HCl in diethyl ether (5 mL). The reaction mixture was stirred for 12 h at room temperature. After completion of reaction (monitored by TLC), reaction mixture was basified with saturated NaHCO$_3$ solution at 0° C., extracted with 10% MeOH in dichloromethane. The organic layer was washed with water, saturated NaCl solution and concentrated under reduced pressure to obtain crude compound, crude compound was purified by preparative TLC to afford desired compound 216 (74 mg, 27%).

Scheme 3:

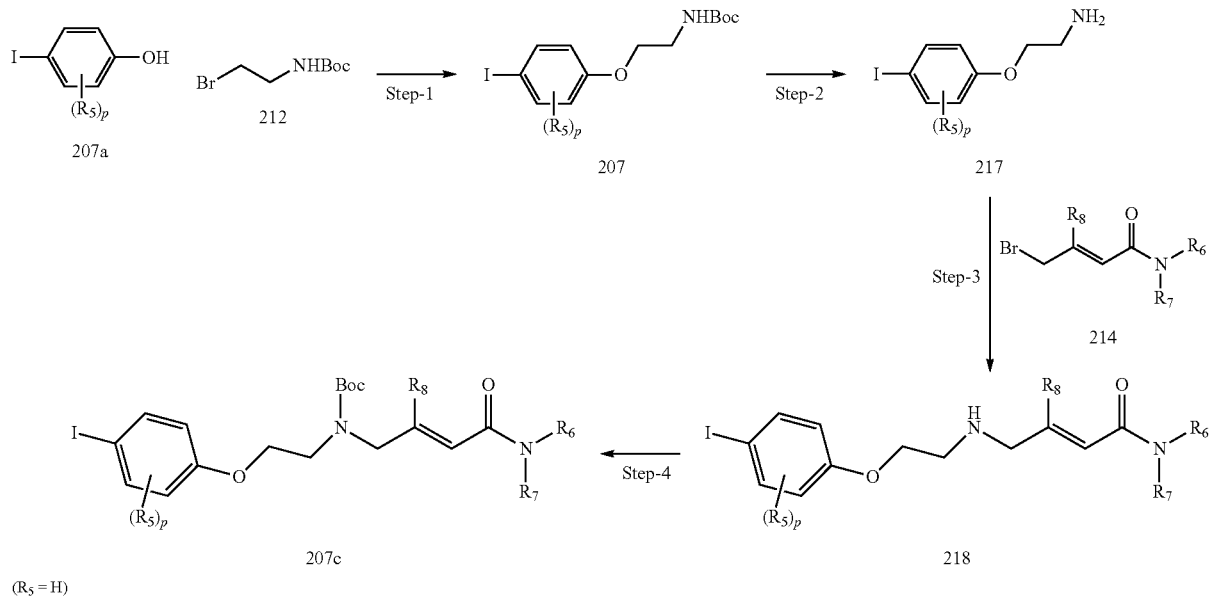

(R5 = H)

Step-1:
To a stirred solution of 4-iodophenol (207a, 227 mmol) in DMF (750 mL) was added potassium carbonate (188 g, 1.363 mol) and stirred for 30 min at 23° C., to the above mixture tert-butyl (2-bromoethyl)carbamate (212, 71.27 g, 318 mmol) was added. The contents were stirred at 70° C. for 12 h. After completion of reaction, reaction mixture was poured onto ice cold water, solid separated was filtered and dried under reduced pressure to obtain desired compound tert-butyl (2-(4-iodophenoxy)-ethyl)carbamate as an off-white solid (207b, 220 mmol, 97%).

Step-2:
To a stirred solution of tert-butyl (2-(4-iodophenoxy) ethyl)carbamate (207b, 68.6 mmol) in ethanol (50 mL) was added at 0° C., 2M HCl in ether (250 mL). The reaction mixture was stirred for 12 h at 23° C. After completion of reaction, reaction mixture was basified with saturated NaHCO₃, extracted with 10% MeOH in DCM. Organic layer was concentrated under reduced pressure and the crude material was used in next step without further purification (217, 60 mmol, 88%).

Step-3:
To a stirred solution of 2-(4-iodophenoxy)ethan-1-amine (217, 60.6 mmol) in DMF (65 mL) was added at 0° C., 4-bromo-N,N-dimethylbut-2-enamide (214, 42.4 mmol) and DIPEA (11.72 g, 90.9 mmol). The reaction mixture was stirred for 5 h at room temperature, was diluted with cold water (250 mL) and extracted with dichloromethane. The organic layer was washed with water followed by brine, dried over anhydrous sodium sulphate and concentrated under reduced pressure. The crude material was used in next step without further purification (218, 50 mmol, 83%, crude).

Step-4:
To a stirred solution of 218 (50.26 mmol) in dry dichloromethane (150 mL) was added DIPEA (6.4 g, 50.2 mmol) at 0° C., stirred for 15 min at 0° C. To the above reaction mixture, was added di-tert-butyl dicarbonate (13.1 g, 60.3 mmol), resulting mixture was stirred at 23° C. for 12 h. Upon completion by TLC, the reaction mixture was cooled to 0° C., quenched with ice cold water (500 mL) and extracted with dichloromethane (500 mL). The combined organic extracts were washed with water, followed by brine, dried over anhydrous sodium sulphate and concentrated under reduced pressure. The crude material was purified by column chromatography over 230-400 mesh silica using 3% MeOH in dichloromethane as an eluent to afford 207c (19 mmol, 37.8%).

Scheme 4:

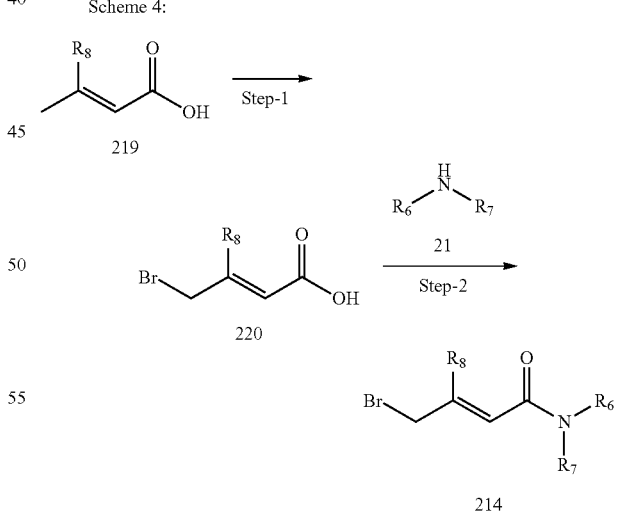

Step-1:
To a stirred solution of but-2-enoic acid (219, 116.0 mmol) in benzene (150 mL) was added N-Bromo succinamide (31.4 g, 120.0 mmol) followed by Benzoyl peroxide (0.200 g, 1.4 mmol) at 23° C. The reaction mixture was heated to reflux for 4 h, which resulted in precipitation of succinamide crystals. The crystals were filtered off and the filtrate was concentrated. The crude was recrystallized with minimum amount of hexane and washed with hexane to afford 4-bromobut-2-enoic acid (220, 42.5 mmol, 37%) as a white solid.

Step-2:

bromobut-2-enoic acid (220, 9 mmol) was taken in dichloromethane (30 mL) and cooled to 0° C. To this solution oxalyl chloride (1.6 mL, 18 mmol), DMF (0.1 mL) were added and stirred for 0.5 h at 23° C. The reaction mixture was concentrated under nitrogen atmosphere, residue was diluted with THF (30 mL), cooled to 0° C. and was basified with DIPEA (3.1 mL, 18 mmol). To this mixture, an amine (221, 9 mmol) was added slowly as a solution in dichloromethane and the contents were stirred at 23° C. for 1 h. The volatiles were removed by concentration under reduced pressure and the residue was partitioned between water and ethyl acetate. The organic layer was washed with water, brine, dried over sodium sulphate and concentrated. The crude material was purified by column chromatography over 230-400 mesh silica gel using 3-7% ethyl acetate in hexane to afford the desired amide (214, 0.85 mmol, 9.4%) as a brown colour liquid.

Scheme 5:

Compounds of formula III may be prepared by substituting the following compound for Compound 207 in Step-4 of Scheme 1:

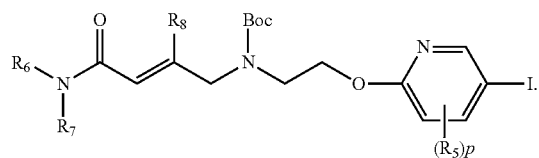

The compound shown here in Scheme 5 may be prepared by using the process as outlined in Scheme 3 by substituting the appropriate pyridyl for compound 207a.

Scheme 6:

Compounds of formula IV may be prepared by substituting the following compound for Compound 209 in Step-5 or Step-6 of Scheme 1:

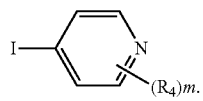

Example 1: Synthesis of (E)-4-((2-(4-((E)-1-(1H-indazol-5-yl)-2-phenylbut-1-en-1-yl)phenoxy) ethyl) amino)-N,N-dimethylbut-2-enamide (Compound 1)

Step-1: Synthesis of 5-bromo-1-(tetrahydro-2H-pyran-2-yl)-1H-indazole

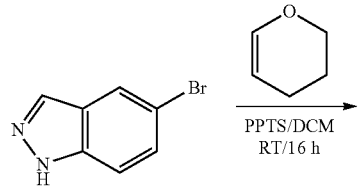

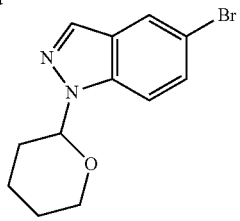

The reaction was carried out according to Scheme 1, Step-1, substituting 5-bromo-1H-indazole (5 g, 23.5 mmol) for Compound 201. The crude material was purified by column chromatography over 230-400 mesh silica using 4-5% ethyl acetate in hexane to afford the title compound of Ex. 1 Step-1 (12.6 g, 86%) as a pale yellow oil.

Step-2: Synthesis of but-1-yn-1-yltrimethylsilane

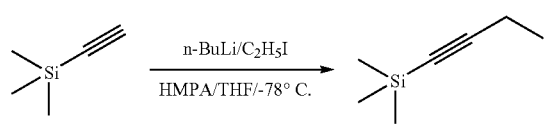

To a stirred solution of (trimethylsilyl)acetylene (116 g, 1.19 mol) in dry THF (400 mL) was added n-BuLi (2.5M in THF, 500 mL) at −78° C. over 2 h. The resulting mixture was warmed to 0° C. for 10 min. The reaction mixture was again cooled to −78° C., HMPA (234 g, 1.13 mol) was added to the above mixture and stirred at −78° C. for 30 min. To the above reaction mixture iodoethane (200 g, 1.28 mol) was added and the resulting mixture was stirred at room temperature for 16 h. After completion of reaction, the reaction mixture was quenched with water, extracted with ethyl acetate (1000 mL). The organic layer was washed with brine, dried over anhydrous sodium sulphate and concentrated under reduced pressure. The product but-1-yn-1-yltrimethylsilane was distilled between 125-135° C. to afford the title compound of Ex. 1 Step-2 (91 g, 61%) as a colourless liquid.

Step-3: Synthesis of 5-(but-1-yn-1-yl)-1-(tetrahydro-2H-pyran-2-yl)-1H-indazole

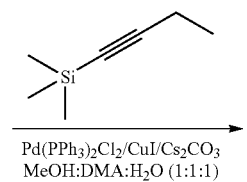

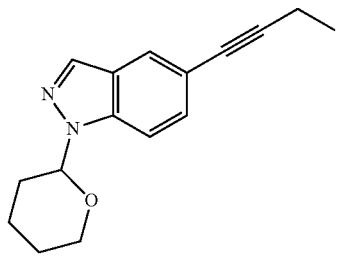

The reaction was carried out according to Scheme 1, Step-2a, using 5-bromo-1-(tetrahydro-2H-pyran-2-yl)-1H-indazole (1 g, 3.6 mmol) for compound 202. The crude product was purified over 230-400 mesh silica column chromatography using 4-5% ethyl acetate in hexane to afford the title compound of Ex. 1 Step-3 (0.5 g, 55%) as a pale yellow oil.

Step-4: Synthesis of (E)-4-(2-phenyl-1-(1-(tetrahydro-2H-pyran-2-yl)-1H-indazol-5-yl) but-1-en-1-yl)phenol

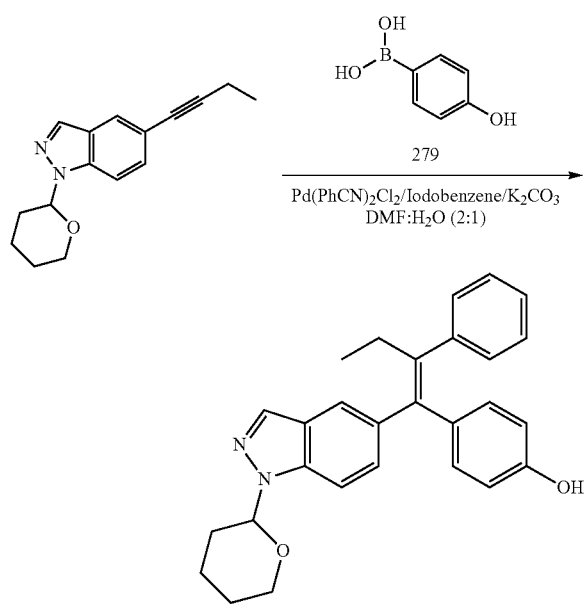

The reaction was carried out according to Scheme 1, Step-6 using 5-(but-1-yn-1-yl)-1-(tetrahydro-2H-pyran-2-yl)-1H-indazole (7 g, 27.5 mmol) for compound 204, iodobenzene (17 g, 82.7 mmol), and 4-hydroxy phenyl boronic acid (11.4 g, 82.7 mmol) for compound 210. The crude material was purified over 230-400 mesh silica column chromatography using 20% ethyl acetate in hexane to the title compound of Ex. 1 Step-4 (5 g, 43%) as a pale yellow oil.

Step-5: Synthesis of (E)-2-(2-(4-(2-phenyl-1-(1-(tetrahydro-2H-pyran-2-yl)-1H-indazol-5-yl) but-1-en-1-yl) phenoxy) ethyl) isoindoline-1,3-dione

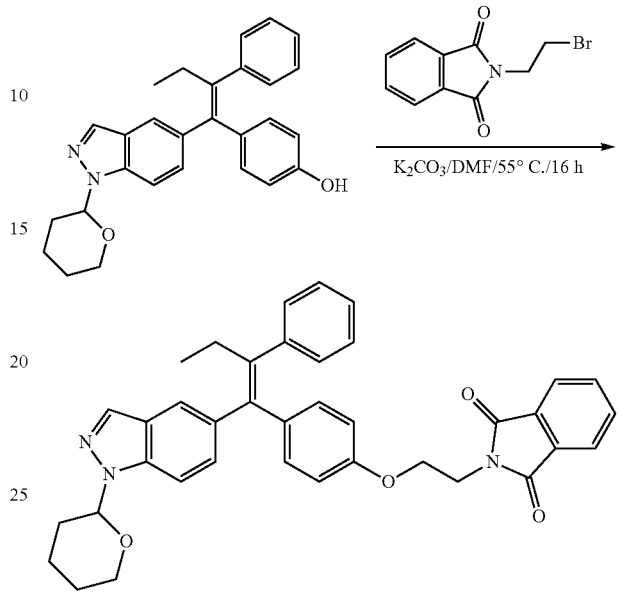

The reaction was carried out according to Scheme 2, Step-1 substituting (E)-4-(2-phenyl-1-(1-(tetrahydro-2H-pyran-2-yl)-1H-indazol-5-yl)but-1-en-1-yl) phenol (1 g, 2.3 mmol) for compound 211a and 2-(2-bromoethyl) isoindoline-1,3-dione (6 g, 23.5 mmol) for compound 212. The reaction mixture was stirred at 55° C. for 16 h, was diluted with ethyl acetate, washed with water, brine, dried over sodium sulphate and concentrated under reduced pressure. The crude material was purified by silica gel chromatography using 30-35% ethyl acetate in n-hexane to afford the title compound of Ex. 1 Step-5 (0.5 g, 36%) as a light brown colour gummy mass.

Step-6: Synthesis of (E)-2-(4-(2-phenyl-1-(1-(tetrahydro-2H-pyran-2-yl)-1H-indazol-5-yl) but-1-en-1-yl) phenoxy) ethan-1-amine

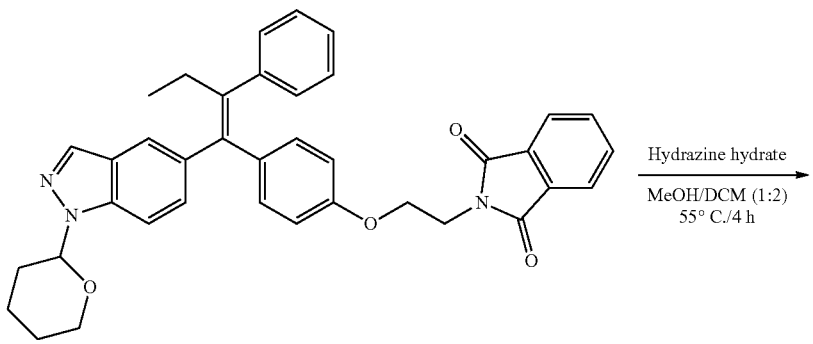

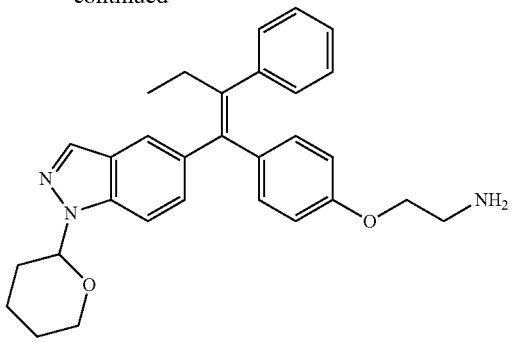

To a solution of (E)-2-(2-(4-(2-phenyl-1-(1-(tetrahydro-2H-pyran-2-yl)-1H-indazol-5-yl)but-1-en-1-yl)phenoxy)ethyl)isoindoline-1,3-dione (1 g, 1.6 mmol) in MeOH/DCM (1:2, 20 mL) was added hydrazine hydrate (14 mL) at room temperature. The reaction mixture was stirred at 55° C. for 4 h, quenched with NH$_4$OH and extracted with dichloromethane. The organic layer was washed with water, brine, dried over sodium sulphate and concentrated under reduced pressure. The crude material was purified by column chromatography over 100-200 mesh silica gel using 3% methanol in DCM to afford the title compound of Ex. 1 Step-6 (0.500 g, 64%) as a gummy compound.

Step-7: Synthesis of
(E)-4-bromo-N,N-dimethylbut-2-enamide

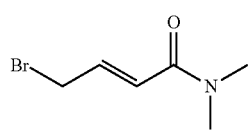

Step-7.1: Synthesis of (E)-4-bromobut-2-enoic acid

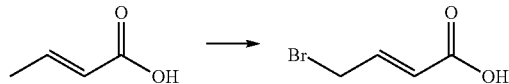

To a stirred solution of (E)-but-2-enoic acid (10.0 g, 116.0 mmol) in benzene (150 mL) was added N-Bromosuccinamide (31.4 g, 120.0 mmol) followed by Benzoyl peroxide (0.200 g, 1.4 mmol) at 23° C. The reaction mixture was heated to reflux for 4 h, which resulted in precipitation of succinamide crystals. The crystals were filtered off and the filtrate was concentrated. The crude was recrystallized with minimum amount of hexane and washed with hexane to afford (E)-4-bromobut-2-enoic acid (6.97 g, 37%) as a white solid.

Step-7.2: Synthesis of
(E)-4-bromo-N,N-dimethylbut-2-enamide

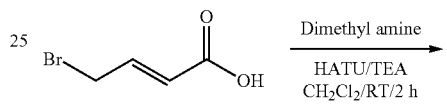

(E)-4-bromobut-2-enoic acid (2 g, 12.2 mmol) was taken in dichloromethane (20 mL) and at 0° C. were added HATU (5.5 g, 14 mmol), triethyl amine (2.56 mL, 18.4 mmol) and stirred for 10 min at RT. To this mixture N,N-dimethyl amine (9.2 mL, 18 mmol) was added slowly and the contents were stirred at room temperature for 2 h. The volatiles were removed under reduced pressure and the residue was partitioned between water and ethyl acetate. The organic layer was washed with water, brine, dried over sodium sulphate and concentrated. The crude material was purified by column chromatography over 100-200 silica gel using 20% ethyl acetate in n-hexane to afford (E)-4-bromo-N,N-dimethylbut-2-enamide (0.4 g, 17%) as a pale green colour liquid.

Step-8: Synthesis of (E)-N,N-dimethyl-4-((2-(4-((E)-2-phenyl-1-(1-(tetrahydro-2H-pyran-2-yl)-1H-indazol-5-yl) but-1-en-1-yl) phenoxy) ethyl) amino) but-2-enamide

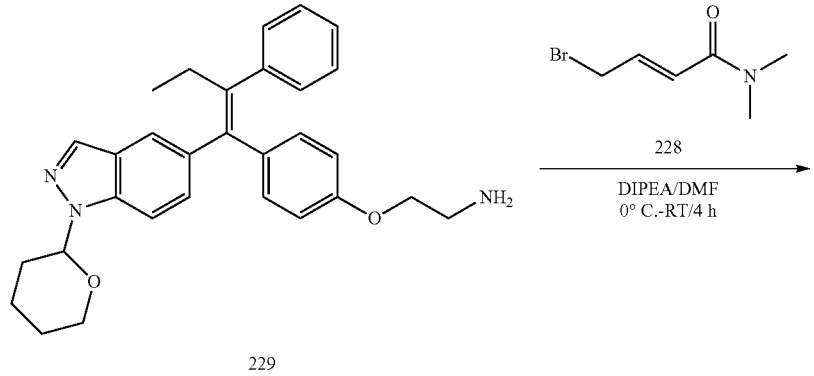

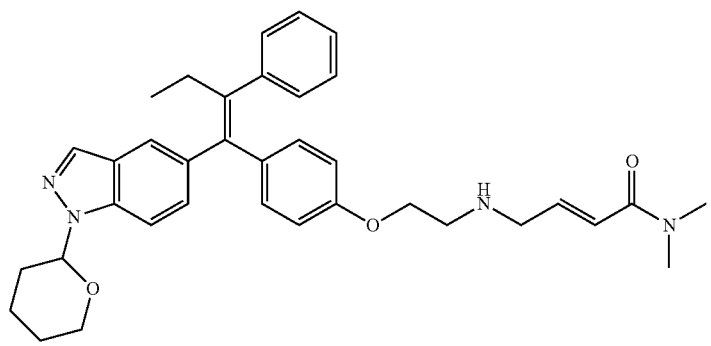

The reaction was carried out according to Scheme 2, Step-3a using 2-(4-(2-phenyl-1-(1-(tetrahydro-2H-pyran-2-yl)-1H-indazol-5-yl)but-1-en-1-yl)phenoxy)ethan-1-amine (0.450 g, 0.96 mmol) for compound 213. The reaction mixture was stirred for 4 h at room temperature, was diluted with cold water (50 mL) and extracted with dichloromethane. The organic layer was washed with water followed by brine, dried over anhydrous sodium sulphate and concentrated under reduced pressure. The crude material was purified by column chromatography over 230-400 mesh silica gel using 1% methanol in dichloromethane to afford the title compound of Ex. 1 Step-8 (0.200 g, 36%) as a gummy solid.

Step-9: Synthesis of (E)-4-((2-(4-((E)-1-(1H-indazol-5-yl)-2-phenylbut-1-en-1-yl)phenoxy)ethyl) amino)-N,N-dimethylbut-2-enamide (Compound 1)

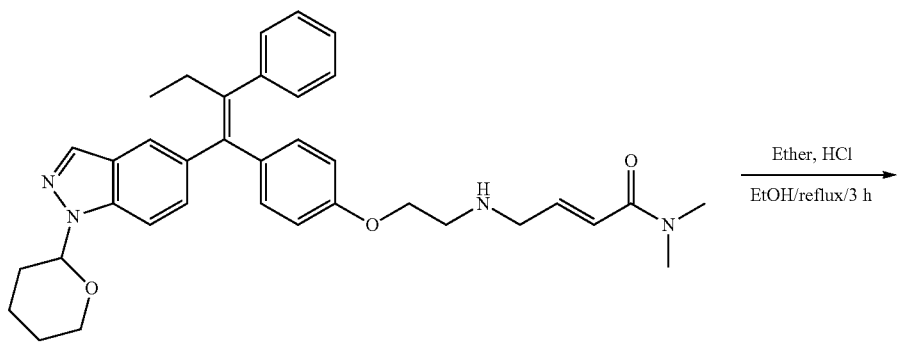

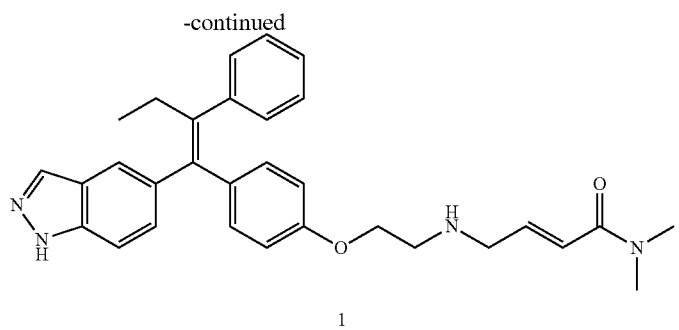

1

To a stirred solution of (E)-N,N-dimethyl-4-((2-(4-((E)-2-phenyl-1-(1-(tetrahydro-2H-pyran-2-yl)-1H-indazol-5-yl)but-1-en-1-yl)phenoxy)ethyl)amino)but-2-enamide (0.180 g, 0.31 mmol) in ethanol (10 mL), at 0° C. was added 2M HCl in ether (10 mL). The reaction mixture was stirred for 3 h at reflux temperature, was diluted with cold water (50 mL) and extracted with ethyl acetate. The organic layer was washed with water followed by brine, dried over anhydrous sodium sulphate and concentrated under reduced pressure. The crude material was purified by column chromatography over 230-400 mesh silica gel using 3-4% methanol in DCM to afford Compound 1 (0.035 g, 23%) as a colourless solid.

Compound 1: $^1$H NMR (400 MHz, CDCl$_3$) δ 10.16 (bs, 1H), 8.07 (s, 1H), 7.66 (s, 1H), 7.5 (d, J=8.8 Hz, 1H), 7.26-7.11 (m, 6H), 6.93-6.87 (m, 1H), 6.78 (d, J=8.8 Hz, 2H), 6.56 (d, J=8.8, 2H), 6.42 (d, J=15.2 Hz, 1H), 3.948 (t, J=4.9 Hz 2H), 3.45 (m, 2H), 3.06 (s, 3H), 2.99 (s, 3H), 2.50-2.45 (m, 2H), 0.95 (t, J=7.2 Hz, 3H). LCMS: 526.3 [M+H]$^+$.

Example 1A—Synthesis of Hydrochloride Salt of Compound 1

Step-1A: Synthesis of 5-bromo-1-(tetrahydro-2H-pyran-2-yl)-1H-indazole)

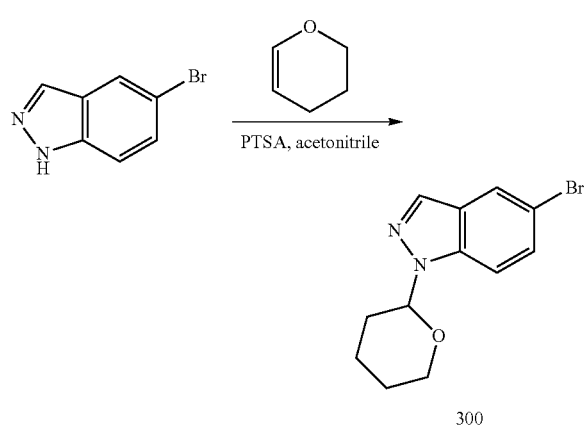

300

In to clean, dry, nitrogen flushed 200l Glass reactor, charged 5-bromo indazole (11.0 Kg, 0.055 mol) actonitrile (110 Lit) and PTSA (1.0 Kg g, 0.055 mol), the reaction mixture were stirred at 28-30° C. for 30 min. To the above solution, dihydropyran (7.03 Kg, 2.55 mol) was added drop wise over a period of 20 min. The resulting mixture was stirred at room temperature for 16 h. Upon completion by TLC, the reaction mixture was quenched with water (500 mL) and acetonitrile was concentrated under reduced pressure. Obtained product was extracted with ethyl acetate (251*3), combined organic extracts were washed with water followed by brine, dried over anhydrous sodium sulphate and concentrated under reduced pressure to get desired compound which was taken as it is for next stage without further purification (14 Kg, 89% Yield, 93.93% HPLC purity) $^1$H NMR (300 MHz, CDCl3): δ 7.95 (s, 1H), 7.85 (s, 1H), 7.45-7.55 (d, 2H), 5.62-5.82 (d, 1H), 3.95-4.05 (d, 1H), 3.75-3.85 (d, 1H), 2.55-2.65 (t, 1H), 2.1-2.2 (m, 2H), 1.65-1.85 (m, 4H), HPLC: 93.93% at 210 nm.

Step-2A: Synthesis of (E)-4-bromobut-2-enoic acid

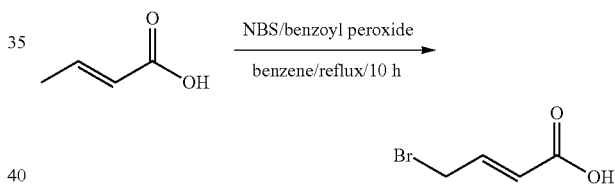

To a stirred solution of (E)-but-2-enoic acid (5.0 Kg, 59.52 mol) in benzene (50.0 Lit) was added N-Bromo succinamide (10.58 Kg, 59.52 mol) followed by benzoyl peroxide (144 g, 0.595 mol) at room temperature. The reaction mixture was heated to reflux for 10 h, which resulted in precipitation of succinamide crystals. The crystals were filtered off and the filtrate was concentrated. The crude was purified by crystallisation using hexane to afford (E)-4-bromobut-2-enoic acid (2.5 Kg, 26.5% Yield) as a white solid. $^1$H NMR (300 MHz, CDCl$_3$): δ 7.07-7.17 (m, 1H), 6.05-6.8 (d, 1H), 4.05-4.1 (d, 2H) HPLC; 84.1% at 210 nm Step-3A: Synthesis of (E)-4-bromo-N,N-dimethylbut-2-enamide

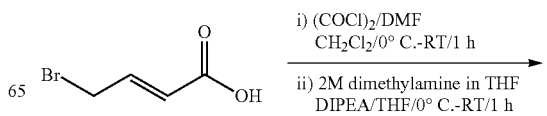

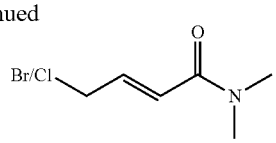

Br/Cl-55:45
301

(E)-4-bromobut-2-enoic acid (5.0 Kg g, 0.030 mol) was taken in dichloromethane (600 mL) and cooled to 0° C. To this solution oxalyl chloride (5.1 Kg, 0.039 mol), catalytic amount DMF (500 mL) were added at the same temperature and stirred for 2 h at room temperature. It was cooled to 0° C. and was basified with sodium carbonate (5.79 Kg, 0.054 mol). To this mixture 2M dimethylamine in THF (15 L, 2M solution) was added slowly (6-8 h) and the contents were stirred at room temperature for 1-2 h. The volatiles were removed by concentration under reduced pressure and the residue was partitioned between water and ethyl acetate. The organic layer was washed with water, brine, dried over sodium sulphate and concentrated. The crude material was purified by column chromatography over 230-400 mesh silica gel using 3-7% ethyl acetate in hexane to afford (E)-4-bromo (chloro)-N,N-dimethylbut-2-enamide (301, 55:45/Br:Cl, 2.5 Kg, 73%) as a brown colour liquid. $^1$H NMR (300 MHz, CDCl$_3$): δ 6.84-6.94 (m, 1H), 6.4-6.5 (m, 1H), 4.15-4.2 (d, 1H), 3.95-4.0 (d, 1H), 2.9-2.95 (s, 3H), 2.95-3.0 (s, 3H), HPLC: 68.23 and 25.7% at 210 nm.

Step-4A: Synthesis of 2-Phenoxyethyl Chloride

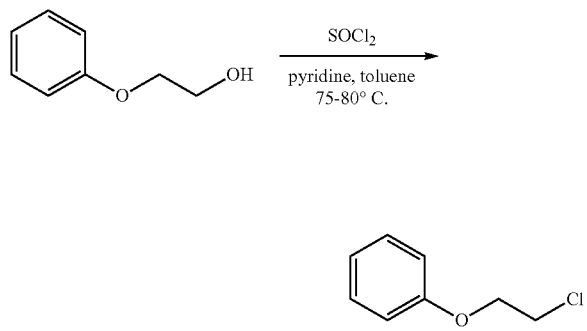

In to clean, dry, nitrogen flushed 7501 GLR, charged toluene (150 L), 2-phenoxyethanol (15 kg, 0.108 mol) and pyridine (1.2 kg, 0.162 mol, 0.15 equiv). reaction mass was cooled to 10-15° C., added thionyl chloride (19.3 kg, 0.162 mol, 1.5 equiv) over 90 min. The reaction mixture was then heated to reflux and maintained for 10-12 h. After the reaction completion, it was cooled to 10-15° C. and quenched with water (500 L). The aqueous phase was separated and discarded. The washing procedure was repeated one more time before the vessel was set for vacuum distillation and heated at less than 60° C. until toluene (500 L) had been removed. The residue was then cooled to 30-35° C. before being transferred to a smaller vessel (16 kg, 94%, 95.89% HPLC purity). $^1$H NMR (400 MHz, DMSO-d6): δ 7.27-7.31 (t, 2H), 6.94-6.96 (t, 3H), 4.22-4.25 (t, 2H), 3.95-4.0 (t, 2H); HPLC: 95.89% at 210 nm.

Step-5A: Synthesis of 1-[4-(2-Chloroethoxy)phenyl]-2-phenyl-1-butanone

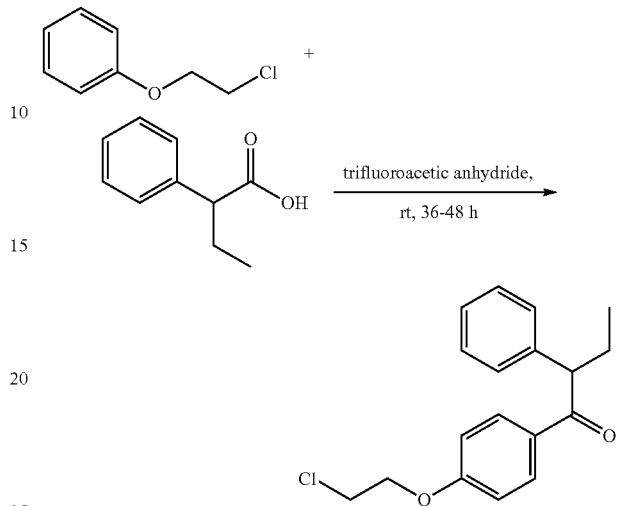

In to clean, dry, nitrogen flushed 2001 Glass reactor, charged 2-Phenoxyethyl chloride (17.0 kg, 69.94 kg at 100%, 1035 mol) and trifluoroacetic anhydride (13 Lt kg) it was stirred for 30 min at 20-25° C. Added 2-Phenylbutyric acid (17.8 kg at 98.7%, 17.9 kg at 100%, 1038 mol). The reaction mixture was maintained at 25-30° C. for 3 days, after completion of the reaction it was quenched with water and basified with potassium carbonate. Obtained product was extracted with DCM (251*3), it was washed with water (251*2) followed by brine (251). Organic layer was dried with sodium sulphate and concentrated under reduced pressure. The solution was cooled to 20° C., and hexane (251) was added. The suspension was cooled to 5° C. and stirred at 0-5° C. for 1 h. The product was isolated by filtration and washed with cold hexane (51). The wet product was air dried to give ketone (24 kg, 78% Yield, 98.82% HPLC purity). $^1$H NMR (400 MHz, CDCl$_3$): δ 7.95-7.97 (d, 2H), 7.286-7.28 (m, 4H), 7.18-7.22 (m, 1H), 6.86-6.88 (d, 2H), 4.38-4.40 (t, 1H), 4.22-4.25 (t, 2H), 3.78-3.85 (t, 2H), 2.18-2.22 (m, 1H), 1.85-1.90 (m, 1H), 0.95-0.98 (t, 3H), HPLC; 98.83% at 210 nm, LCMS: 303[M+H]$^+$.

Step-6A: Synthesis of 1-(4-(2-chloroethoxy)phenyl)-2-phenyl-1-(1-(tetrahydro-2H-pyran-2-yl)-1H-indazol-5-yl)butan-1-ol

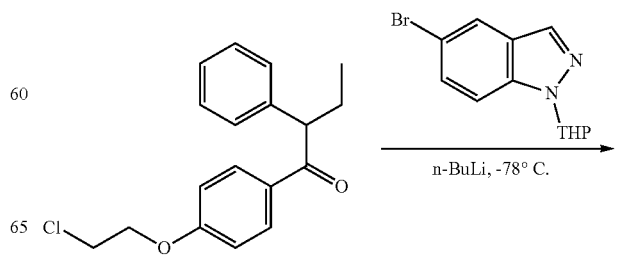

-continued

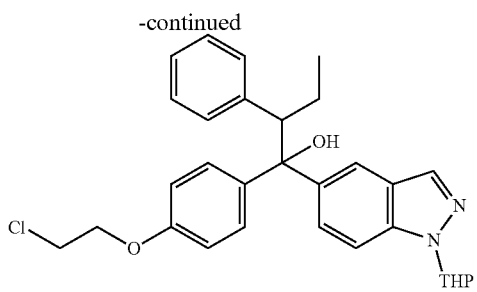

In to clean, dry, nitrogen flushed 200l Glass reactor, charged 1-[4-(2-Chloroethoxy) phenyl]-2-phenyl-1-butanone (compound 3)(11 kg, 0.0364 mol, 1 equiv) Compound 300 (10.2 kg, 0.0364 mol, 1.0 equiv THF (110 L) cooled to −78° C. Added n-BuLi (19 L 2.5 molar 13. equiv) in 6-7 h. reaction mass maintained at −78° C. for 2 hr, after completion of the reaction it was quenched with saturated ammonium chloride (4-5l) at the same time in 2-3 h and the reaction mass was allowed to warm for the room temperature gradually (8-10 h). Added 25l of water and the product was extracted with 25l of ethyl acetate, organic layer was separated and concentrated under reduced vacuum. Obtained crude product was purified through 60-120 silica gel using 0-20ethyl acetate in hexane to get pure compound 4 (6.7 kg, 36.5% Yield, 97.83% HPLC purity) $^1$H NMR (400 MHz, DMSO-d6): δ 8.10 (s, 1H), 7.69-7.72 (d, 1H), 7.65-7.70 (s, 1H), 7.10-7.23 (m, 6H), 6.72-6.74 (d, 2H), 6.55-6.59 (d, 2H), 5.82-5.86 (d, 1H), 3.85-3.90 (s, 1H), 3.75-3.8 (t, 3H), 2.75-2.80 (t, 2H), 1.35-1.40 (m, 3H), 1.95-2.0 (t, 2H), 1.2-2.0 (m, 7H), 0.85-0.90 (t, 3H). HPLC; 97.83% at 210 nm Step-7A: Synthesis of (E)-5-(1-(4-(2-chloroethoxy)phenyl)-2-phenylbut-1-en-1-yl)-1H-indazole

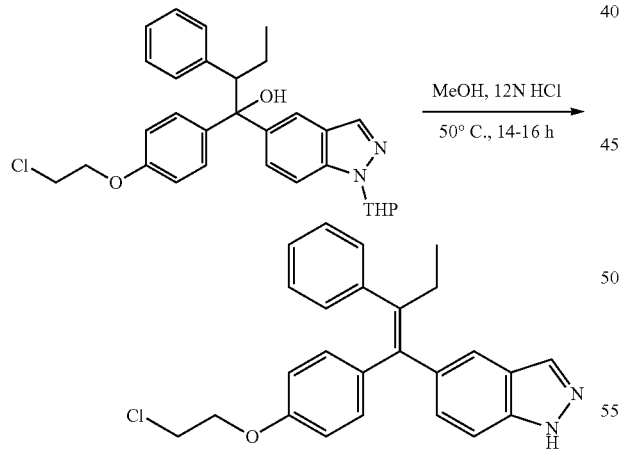

In to clean, 200l Glass reactor, charged compound 4 (6.4 Kg, 12.67 mol), methanol (64 L, 10 Vol), and 11N HCl (13 L, 2.5 Vol), the reaction mixture were maintained at 50° C. for 14-16 h.
After the reaction completion, methanol was concentrated under reduced pressure and the obtained product was extracted with ethyl acetate (25l*3), organic layer was washed with water (25l), dried over anhydrous sodium sulphate and concentrated under reduced pressure. Obtained product was slurry washed with hexane (10l) to get pure compound 5 as off white solid (4.4 kg, 86.37% Yield, 52.92:46.5 isomer ratio)

Step-8A: Synthesis of (E)-5-(1-(4-(2-chloroethoxy)phenyl)-2-phenylbut-1-en-1-yl)-1-(tetrahydro-2H-pyran-2-yl)-1H-indazole

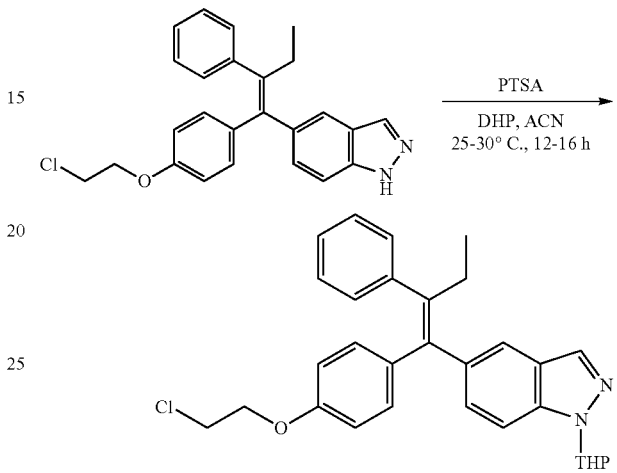

In to clean, dry, nitrogen flushed 200l Glass reactor, charged compound 5 (5.1 Kg, 12.686 mol) actonitrile (5 Lit) and PTSA (241 g, 1.268 mol), the reaction mixture were stirred at 28-30° C. for 30 min. To the above solution, dihydropyran 1.6 Kg, 19.03 mol) was added drop wise over a period of 20 min. The resulting mixture was stirred at room temperature for 16 h. Upon completion by TLC, the reaction mixture was quenched with water (500 mL) and acetonitrile was concentrated under reduced pressure. Obtained product was extracted with ethyl acetate (25l*3), combined organic extracts were washed with water followed by brine, dried over anhydrous sodium sulphate and concentrated under reduced pressure to get the compound 6 (6.Kg, 97% Yield) as a pale yellow gummy material. $^1$H NMR (400 MHz, DMSO-d6): compound is having both geometrical isomers in the ratio 39.2:50.4.

Step-9A: Synthesis of (E)-2-(2-(4-(2-phenyl-1-(1-(tetrahydro-2H-pyran-2-yl)-1H-indazol-5-yl)but-1-en-1-yl)phenoxy)ethyl)isoindoline-1,3-dione

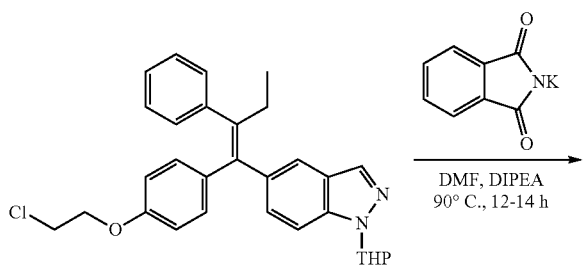

-continued

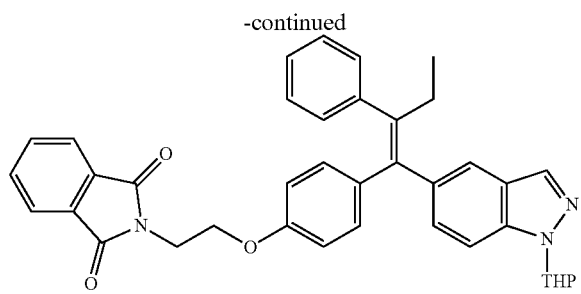

In to clean, dry, nitrogen flushed 200 L Glass reactor, charged compound 6 (5.8 Kg, 11.9 mol, 1.1 equiv), DMF (6 L), potassium phthalamide (2.42 Kg, 13.11 mol), DIPEA (4.6 Kg, 35.7 mol, 3.0 equiv), reaction mass were heated to 90° C. and maintained for 12-14 h. After the reaction completion, it was cooled to 30° C., quenched with 50 L of water and the obtained product was extracted with ethyl acetate, washed with 20 L of water, organic layer was dried over anhydrous sodium sulphate and concentrated under reduced pressure. Obtained solid was stirred with 25 L of 1:1 ethyl acetate and hexane for 5-6 h, filtered the undissolved Z isomer and concentrated the filtrate and the process was repeated till the isomeric purity becomes >80% by HPLC (4.0 kg, 50% Desired isomer).

Step-10A: Synthesis of (E)-2-(4-(2-phenyl-1-(1-(tetrahydro-2H-pyran-2-yl)-1H-indazol-5-yl)but-1-en-1-yl)phenoxy)ethan-1-amine

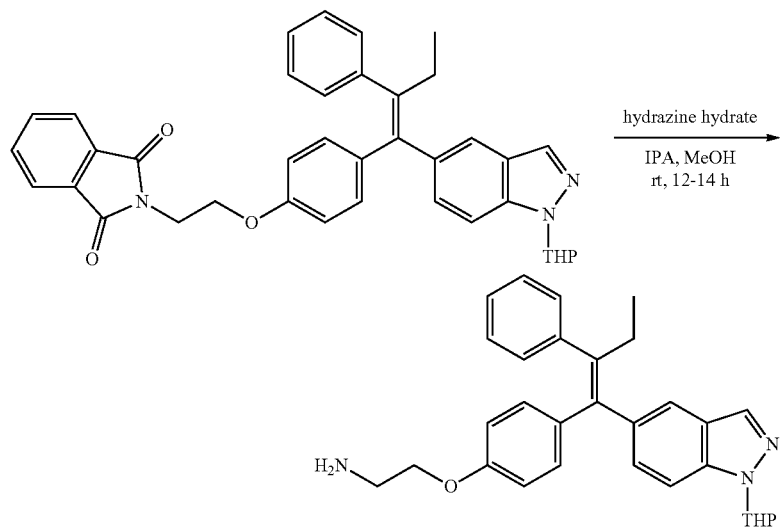

In to clean, dry, nitrogen flushed 2001 Glass reactor, charged compound 7 (6.0 Kg, 10.04 mol), methanol (6 L), IPA (60 L) was cooled to 5-10° C. and added Hydrazine hydrate (10 L, 1.5 vol), After the reaction mass were stirred at 30° C. for 14-16 h. After completion of the reaction, it was filtered to remove succinamide, filtrate was quenched with 10 L of water and the alcohols were concentrated under reduced pressure. Obtained product was extracted with ethyl acetate (25l*2), organic layer was separated washed with water 25l, dried over anhydrous sodium sulphate, concentrated to get compound 8 of (4.5 Kg 59.45% Desired isomer purity. 15% Other isomer).

Step-11A: Synthesis of (E)-2-(4-(2-phenyl-1-(1-(tetrahydro-2H-pyran-2-yl)-1H-indazol-5-yl)but-1-en-1-yl)phenoxy)ethan-1-amine succinate salt

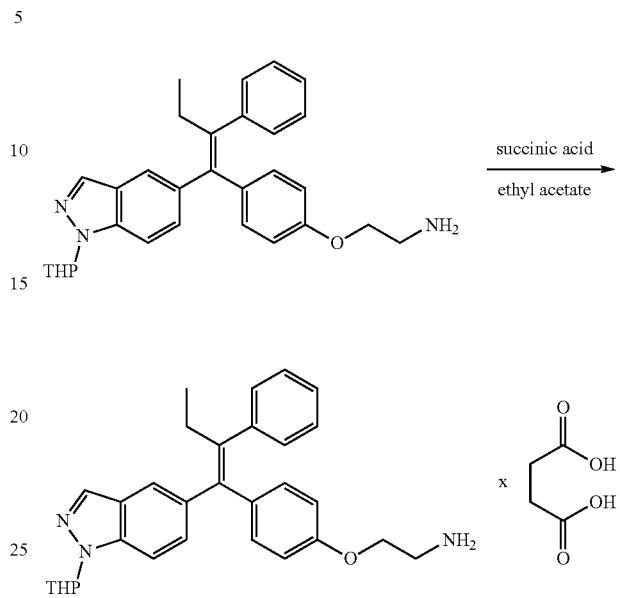

In to clean, dry, nitrogen flushed 2001 Glass reactor, added succinic acid (1.2 Kg, 10.3 mol), ethyl acetate (15 L, 3 vol) and heated to reflux, added compound 8 (4.8 Kg, 10.3 mol) dissolved in (20 L, 4 vol) of ethyl acetate in 20-30 min and continued the reflux for another 30 min. the reaction mass was cooled to 30-40° C. and filtered the solids and washed with (25 L) of ethyl acetate, dried to get 2.1 Kg of desired compound with 93.6% of HPLC purity (2% of undesired geometrical isomer). $^1$H NMR (300 MHz, DMSO-d6): δ 8.10 (s, 1H), 7.65-7.72 (m, 2H), 7.13-7.21 (m, 6H), 6.75-6.78 (d, 2H), 6.62-6.64 (d, 2H), 3.87-4.01 (m, 4H), 3.69-3.73 (m, 4H), 3.04-3.05 (t, 3H), 2.27-2.38 (m, 5H), 1.98-2.0 (d, 1H), 1.6 (s, 1H), 0.85-0.90 (t, 2H). HPLC; 93.6% at 210 nm

91

Step-12A: Synthesis of (E)-2-(4-(2-phenyl-1-(1-(tetrahydro-2H-pyran-2-yl)-1H-indazol-5-yl)but-1-en-1-yl)phenoxy)ethan-1-amine

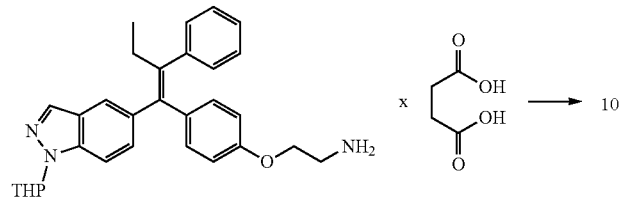

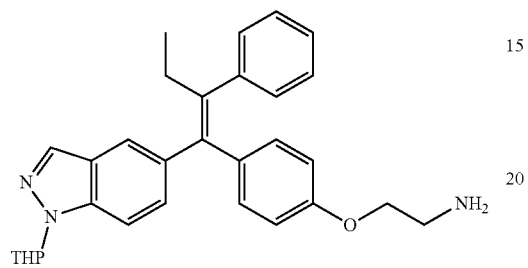

In to a clean 20 l four necked RBF, equipped with mechanical stirrer added water 1, compound 9 (2.1 kg, 3.58 mol) and cooled to 10-15° C., added potassium carbonate solution till the pH becomes 9-10, obtained base was extracted with 5 l*3 of DCM. Combined organic layer was washed with water, dried over anhydrous sodium sulphate, concentrated under reduced pressure to get desired compound (1.5 kg, 89% Yield, 90% HPLC, 2.5% other isomer)

Step-13A: Synthesis of (E)-N,N-dimethyl-4-((2-(4-((E)-2-phenyl-1-(1-(tetrahydro-2H-pyran-2-yl)-1H-indazol-5-yl) but-1-en-1-yl) phenoxy) ethyl) amino) but-2-enamide

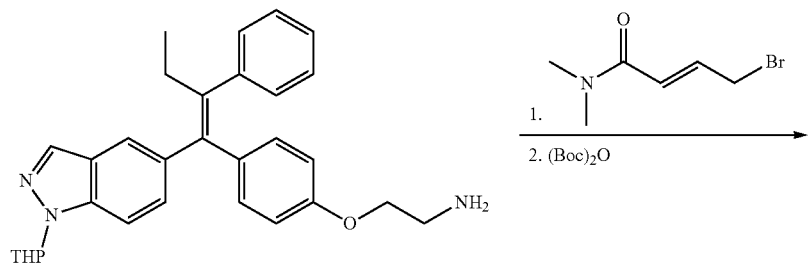

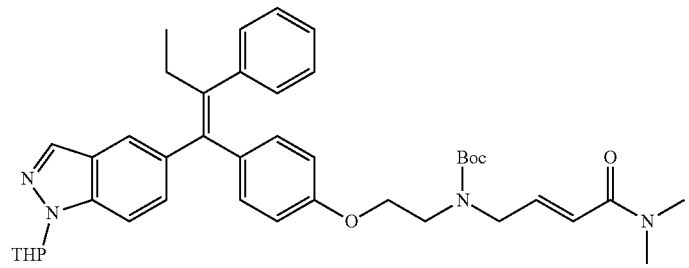

In to a clean, dry, nitrogen flushed 10 l four necked RBF, equipped with mechanical stirrer added compound 10 (1.5 Kg, 3.211 mol) DCM (9 L), DIPEA (1.24 Kg, 9.63 mol, 3.0 equiv) and reaction mixture were cooled to 0-5° C. Added (E)-4-bromo (chloro)-N,N-dimethylbut-2-enamide (0.616 Kg, 3.2 mol) dissolved in DCM (2 L) using dropping funnel in 30-40 min (E)-4-bromo (chloro)-N,N-dimethylbut-2-enamide as prepared in Steps and reaction mass was slowly warmed to rt and kept for 24 hr under stirring. It was cooled to 0-5° C., added Boc anhydride (1.05 Kg, 4.81 mol, 1.5 equiv) in DCM (2 L), and stirred for 4-5 hr. After completion of the reaction, it was quenched with water, DCM layer was separated, washed with brine and dried over anhydrous sodium sulphate and concentrated under reduced pressure to desired crude compound which was purified by 60-120 mesh silica gel using 0-20 ethyl acetate in hexane to get (1.23 Kg, 55.3% Yield, 94.3% HPLC of desired product and 2.1% Other isomer.

Step-14A: Synthesis of tert-butyl ((E)-4-(dimethyl-amino)-4-oxobut-2-en-1-yl)(2-(4-((E)-2-phenyl-1-(1-(tetrahydro-2H-pyran-2-yl)-1H-indazol-5-yl)but-1-en-1-yl)phenoxy)ethyl)carbamate

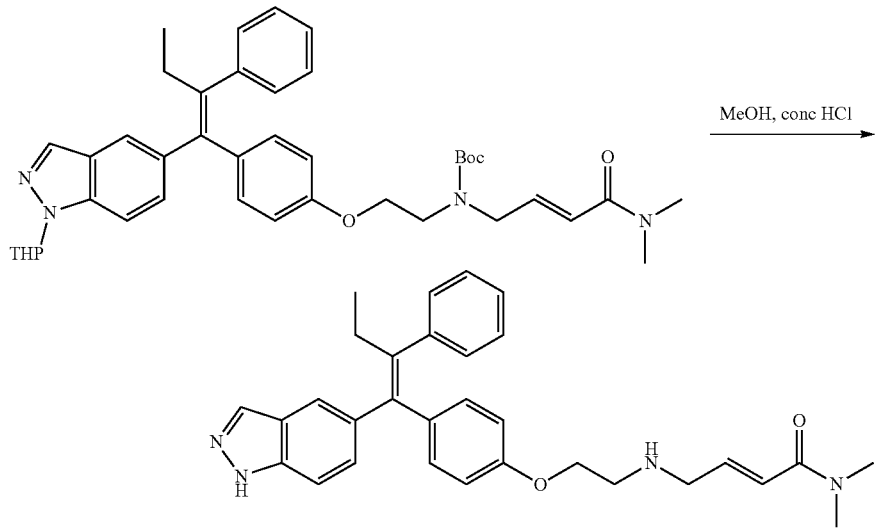

In to a clean, dry, nitrogen flushed 10l four necked RBF, equipped with mechanical stirrer and reflux condenser, added methanol (12 L) and compound 11 (1.2 Kg, 1.76 mol) reaction mixture were cooled to 0-5° C., added concentrated HCl (2.4 L, 2 vol) using dropping funnel in 30 min and the reaction mixture slowly warmed to room temperature followed by 50° C. It was maintained at the same temperature for 4-6 h, after completion of the reaction, methanol was concentrated under reduced pressure. The reaction mixture was basified with sodium carbonate solution at 10-15° C. and the obtained product was extracted with 2l*3 of ethyl acetate, washed with water and dried over anhydrous sodium sulphate and concentrated under reduced to get the desired product (1.0 Kg, 80% Yield, 98.22% HPLC purity)

Step-15A: Synthesis of (E)-4-((2-(4-((E)-1-(1H-indazol-5-yl)-2-phenylbut-1-en-1-yl)phenoxy)ethyl)amino)-N,N-dimethylbut-2-enamide hydrochloride

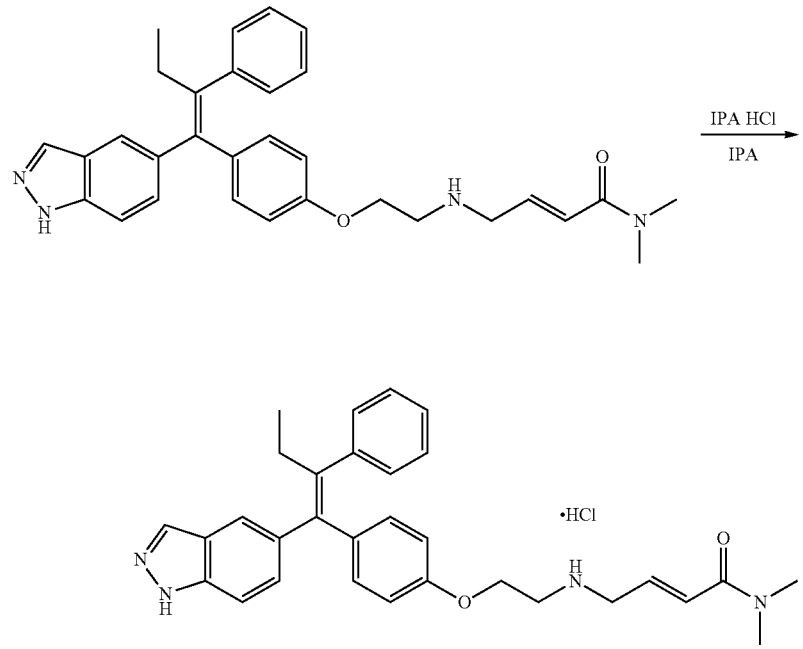 [SMILES: CC/C(=C(/c1ccc(OCCNC/C=C/C(=O)N(C)C)cc1)c1ccc2[nH]ncc2c1)c1ccccc1 ; "IPA HCl" ; CC/C(=C(/c1ccc(OCCNC/C=C/C(=O)N(C)C)cc1)c1ccc2[nH]ncc2c1)c1ccccc1 ; Cl]

In to a clean, dry, nitrogen flushed 5l four necked RBF, equipped with mechanical stirrer, added compound 11 (600 gm, 1.21 mol) dissolved in 9 L of IPA. It was cooled to 5-10° C., added IPA.HCl till the pH becomes 2.5-3 and stirred at the same temperature for 30 min and filtered the solid formed and washed with 3 L of cold IPA and dried well to 550 (85% Yield) of desired compound (98.07% HPLC).

HPLC: 98.07%(210 nm), LCMS (ESI, m/z), 494.5 [M+H]+, Melting point: 220-221° C. Compound 1 (hydrochloride salt): $^1$H NMR (300 MHz, DMSO-d6): δ 13.05 (s, 1H), 9.28 (s, 2H), 8.07 (s, 1H), 7.60 (s, 1H), 7.5-7.52 (d, J=8.8 Hz, 1H), 7.1-7.22 (m, 6H), 6.78-6.84 (m, 3H), 6.52-6.66 (m, 3H), 4.11-4.13 (t, J=4.4 Hz, 2H), 3.76-3.80 (m, 2H), 3.26-3.3 (m, 2H), 3.03 (s, 3H), 2.86 (s, 3H), 2.40-2.41 (m, 2H), 0.86-0.89 (t, J=7.4 Hz, 3H). HPLC; 98.07% at 210 nm.

Example 2: Synthesis of (E)-4-((2-(4-((E)-1-(3-fluoro-1H-indazol-5-yl)-2-phenyl but-1-en-1-yl) phenoxy) ethyl)amino)-N,N-dimethylbut-2-enamide (Compound 2)

Step-1: Synthesis of 5-bromo-3-fluoro-1H-indazole

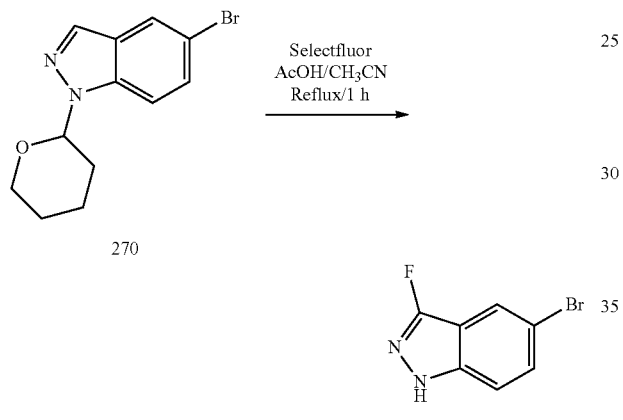

To a stirred solution of 5-bromo-1-(tetrahydro-2H-pyran-2-yl)-1H-indazole (10 g, 35.7 mmol, as prepared in Example 1, Step-1) in 100 mL of acetonitrile, were added acetic acid (4 mL) and selectfluor (25.2 g, 71.4 mmol) at room temperature. Reaction mixture was refluxed for 1 h. Upon completion by TLC, the reaction mixture was diluted with water (100 mL) and extracted with ethyl acetate (200 mL). The combined organic extracts were washed with water, brine, dried over anhydrous sodium sulphate and concentrated under reduced pressure. The crude product was purified over 230-400 mesh silica column chromatography using 1% ethyl acetate in n-hexane to afford 5-bromo-3-fluoro-1H-indazole (6 g, 78%) as a brown oil.

Step-2: Synthesis of 5-bromo-3-fluoro-1-(tetrahydro-2H-pyran-2-yl)-1H-indazole

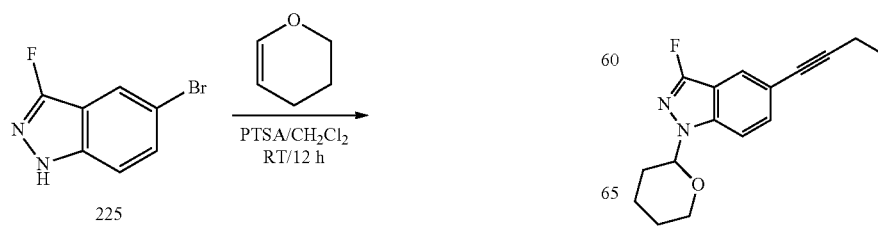

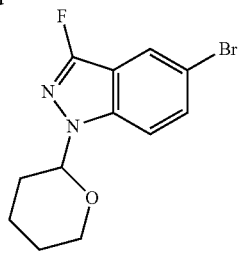

The reaction was carried out according to Scheme 1, Step-1 to give a crude product, which was purified over 230-400 mesh silica column chromatography using 1% ethyl acetate in n-hexane to afford the title compound of Ex. 2 Step-2 (5 g, 60%) as a brown oil.

Step-3: Synthesis of 5-(but-1-yn-1-yl)-3-fluoro-1-(tetrahydro-2H-pyran-2-yl)-1H-indazole

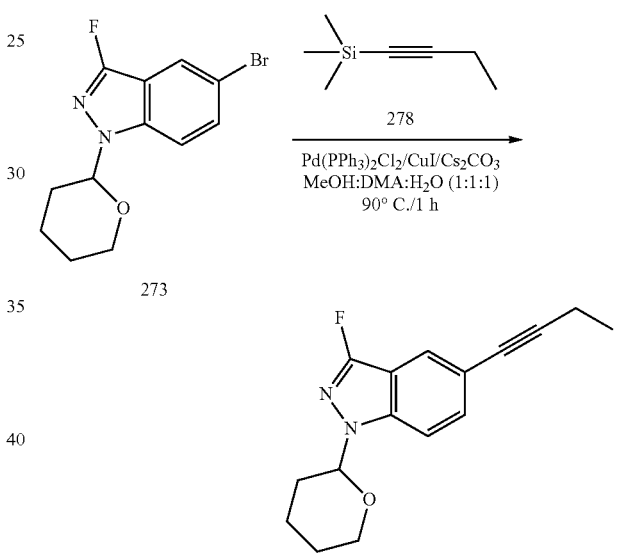

The reaction was carried out according to Scheme 1, Step-2a to afford the title compound of Ex. 2 Step-3 (4.2 g, 99%) as a brown oil.

Step-4: Synthesis of (E)-4-(1-(3-fluoro-1-(tetrahydro-2H-pyran-2-yl)-1H-indazol-5-yl)-2-phenyl-but-1-en-1-yl)phenol

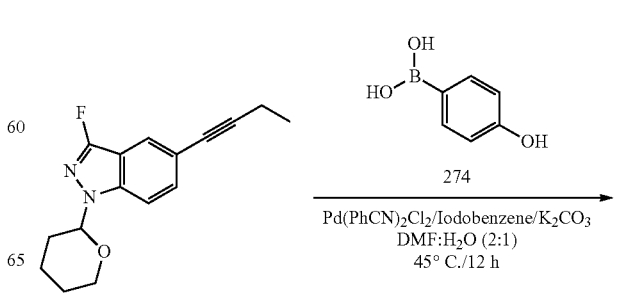

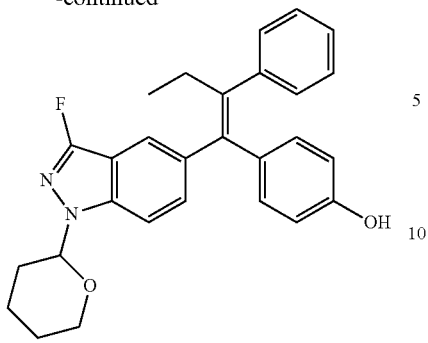

The reaction was carried out according to Scheme 1, Step-6 to afford the title compound of Ex. 2 Step-4 (1 g, 22%).

Step-5: Synthesis of tert-butyl (E)-(2-(4-(1-(3-fluoro-1-(tetrahydro-2H-pyran-2-yl)-1H-indazol-5-yl)-2-phenylbut-1-en-1-yl)phenoxy)ethyl)carbamate

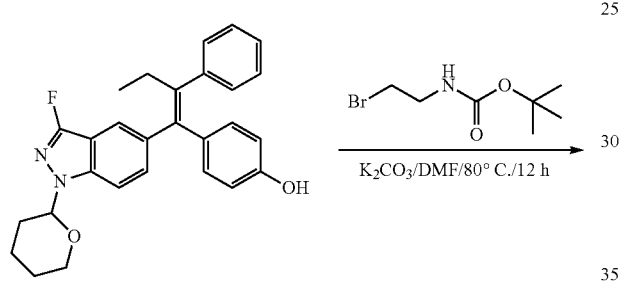

The reaction was carried out according to Scheme 2, Step-1 to give a crude product which was purified by column chromatography over 230-400 mesh silica gel using 10% ethyl acetate in n-hexane to afford the title compound of Ex. 2 Step-5 (1 g, 75%) as a light brown colour gummy mass.

Step-6: Synthesis of (E)-2-(4-(1-(3-fluoro-1H-indazol-5-yl)-2-phenylbut-1-en-1-yl)phenoxy)ethanamine

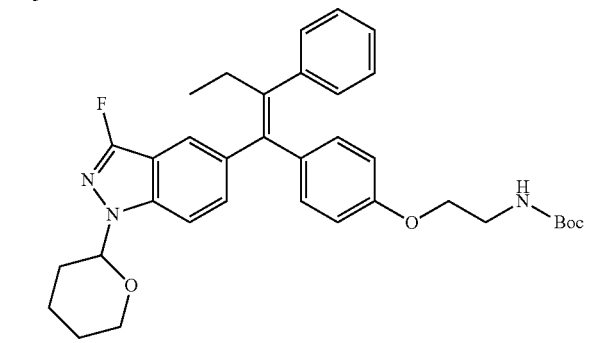

The reaction was carried out according to Scheme 2, Step-2a using (E)-(2-(4-(1-(3-fluoro-1-(tetrahydro-2H-pyran-2-yl)-1H-indazol-5-yl)-2-phenylbut-1-en-1-yl)phenoxy)ethyl)carbamate (0.8 g, 1.61 mmol) for compound 211b. The crude material was purified by silica gel chromatography using (2:98) MeOH in DCM to afford the title compound of Ex. 2 Step-6 (0.23 g) as a white solid.

Step-7: Synthesis of (E)-4-((2-(4-((E)-1-(3-fluoro-1H-indazol-5-yl)-2-phenylbut-1-en-1-yl)phenoxy)ethyl)amino)-N,N-dimethylbut-2-enamide (Compound 2)

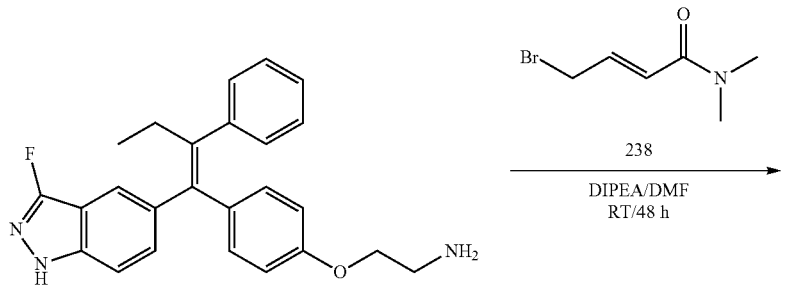

-continued

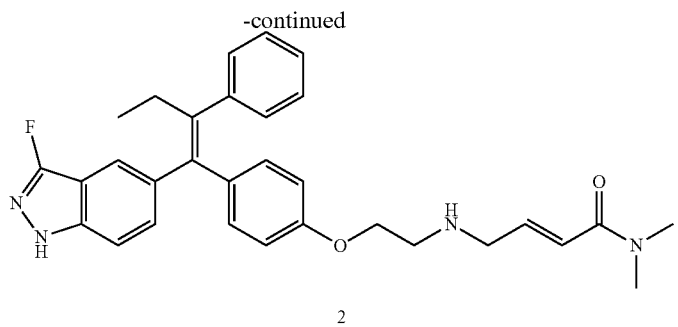

2

The reaction was carried out according to Scheme 2, Step-3a to afford the title compound of Ex. 2 Step-7 (0.13 g, crude), which was purified by HPLC to give a pure isomer (0.07 g, 37%) as an off-white solid.

Compound 2: $^1$H NMR (400 MHz, DMSO-$d_6$) δ 12.57 (s, 1H), 7.50 (s, 1H), 7.47 (dd, J1=8.8 Hz, J2=2.0 Hz, 1H), 7.22-7.19 (m, 6H), 6.77 (s, 1H), 6.74 (s, 1H), 6.74-6.58 (m, 3H), 6.51-6.48 (m, 1H), 3.87 (t, J=5.6 Hz, 2H), 2.98 (s, 3H), 2.79 (s, 3H), 2.73 (t, J=5.6 Hz, 2H), 2.49-2.38 (m, 2H), 0.87 (t, J=7.2 Hz, 3H). ES (MS) 513.2 [M+H]$^+$.

Example 3: Synthesis of (E)-4-((2-(4-((E)-1-(3-fluoro-1H-indazol-5-yl)-2-(3-fluoro-5-(trifluoromethyl) phenyl)but-1-en-1-yl)phenoxy)ethyl)amino)-N,N-dimethylbut-2-enamide (Compound 3)

Step-1: Synthesis of (Z)-5-(1,2-bis(4,4,5,5-tetramethyl-1,3,2-dioxaborolan-2-yl)but-1-en-1-yl)-3-fluoro-1-(tetrahydro-2H-pyran-2-yl)-1H-indazole

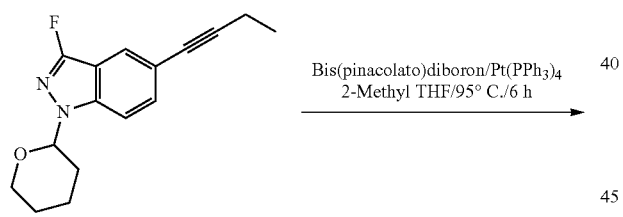

The reaction was carried out according to Scheme 1, Step-3 using 5-(but-1-yn-1-yl)-3-fluoro-1-(tetrahydro-2H-pyran-2-yl)-1H-indazole (2.0 g, 7.29 mmol, as prepared in Example 2, Step-3) for compound 204. The crude material was purified by column chromatography over 230-400 mesh silica gel using 2% EtOAc in n-hexane to afford the title compound of Ex. 3, Step-1 (2.5 g, 65%).

Step-2: Synthesis of tert-butyl (2-(4-iodophenoxy)ethyl)carbamate

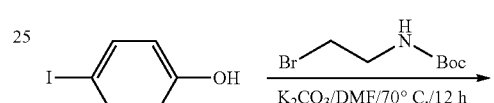

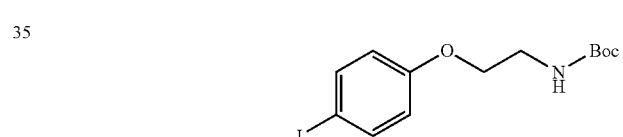

The reaction was carried out according to Scheme 3, Step-1 to obtain the title compound of Ex. 3 Step-2 as an off-white solid (80 g, 97%).

Step-3: Synthesis of tert-butyl (Z)-(2-(4-(1-(3-fluoro-1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)ethyl)carbamate

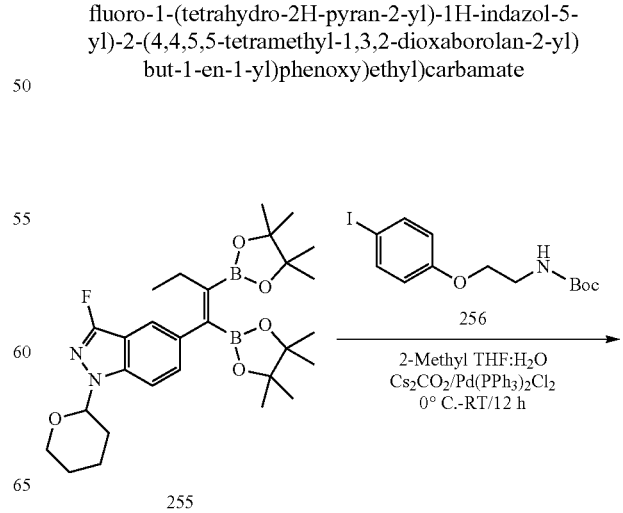

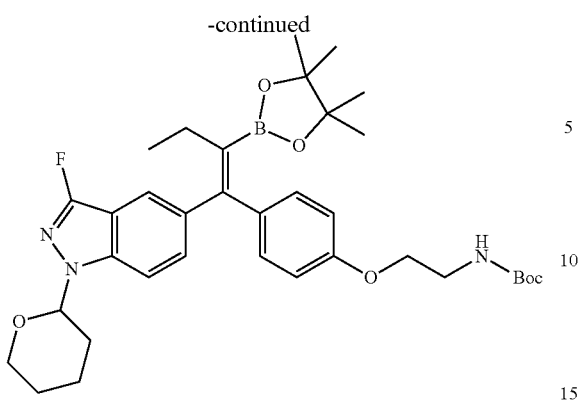

The reaction was carried out according to Scheme 1, Step-4 using (Z)-5-(1,2-bis(4,4,5,5-tetramethyl-1,3,2-dioxaborolan-2-yl)but-1-en-1-yl)-3-fluoro-1-(tetrahydro-2H-pyran-2-yl)-1H-indazole (1.5 g, 2.85 mmol) for compound 206 and tert-butyl (2-(4-iodophenoxy)ethyl)carbamate (1.03 g, 2.85 mmol) for compound 207. The crude product containing the title compound of Ex. 3, Step-3 was used in next step without further purification (2 g).

Step-4: Synthesis of tert-butyl (E)-(2-(4-(1-(3-fluoro-1-(tetrahydro-2H-pyran-2-yl)-1H-indazol-5-yl)-2-(3-fluoro-5-(trifluoromethyl)phenyl)but-1-en-1-yl)phenoxy)ethyl)carbamate The reaction was carried out according to Scheme 1, Step-5, using tert-butyl (Z)-(2-(4-(1-(3-fluoro-1-(tetrahydro-2H-pyran-2-yl)-1H-indazol-5-yl)-2-(4,4,5,5-tetramethyl-1,3,2-dioxaborolan-2-yl)but-1-en-1-yl)-phenoxy)ethyl)carbamate (950 mg, 1.8 mmol) for compound 208 and 1-fluoro-3-iodo-5-(trifluoromethyl)benzene (523 mg, 1.8 mmol) for compound 209. The crude product was purified by silica gel chromatography (2:8 EtOAc in n-hexane) to give the title compound of Ex. 3, Step-4 (0.5 g, 41%).

Step-5: Synthesis of (E)-2-(4-(1-(3-fluoro-1H-indazol-5-yl)-2-(3-fluoro-5-(trifluoro-methyl)phenyl)but-1-en-1-yl)phenoxy)ethan-1-amine

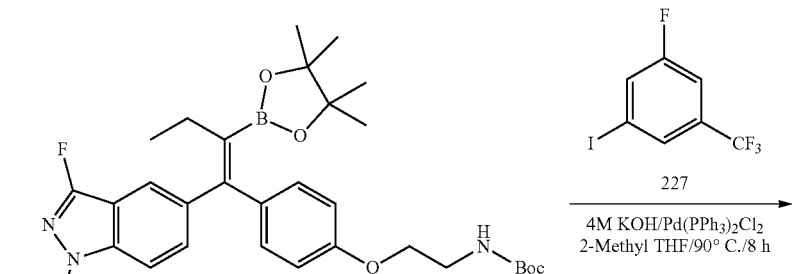

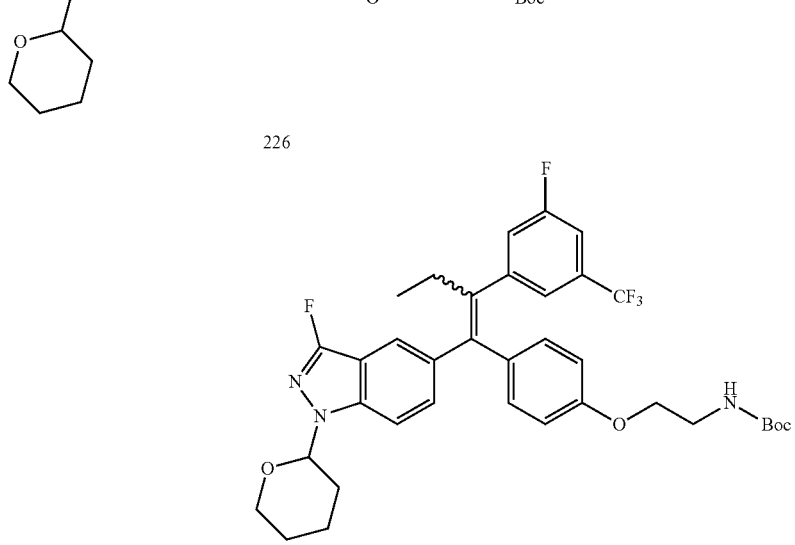

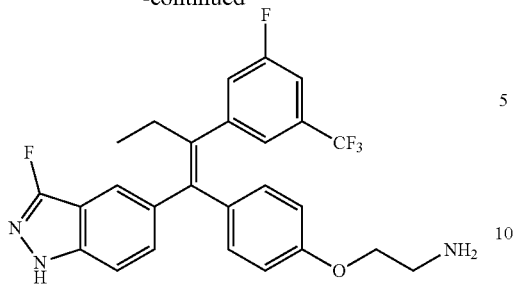

The reaction was carried out according to Scheme 2, Step-2a to afford the title compound of Ex. 3, Step-5 (0.24 g, 66%) as a brown coloured semi solid.

Step-6: Synthesis of (E)-4-((2-(4-((E)-1-(3-fluoro-1H-indazol-5-yl)-2-(3-fluoro-5-(trifluoromethyl)phenyl)but-1-en-1-yl)phenoxy)ethyl)amino)-N,N-dimethylbut-2-enamide (Compound 3)

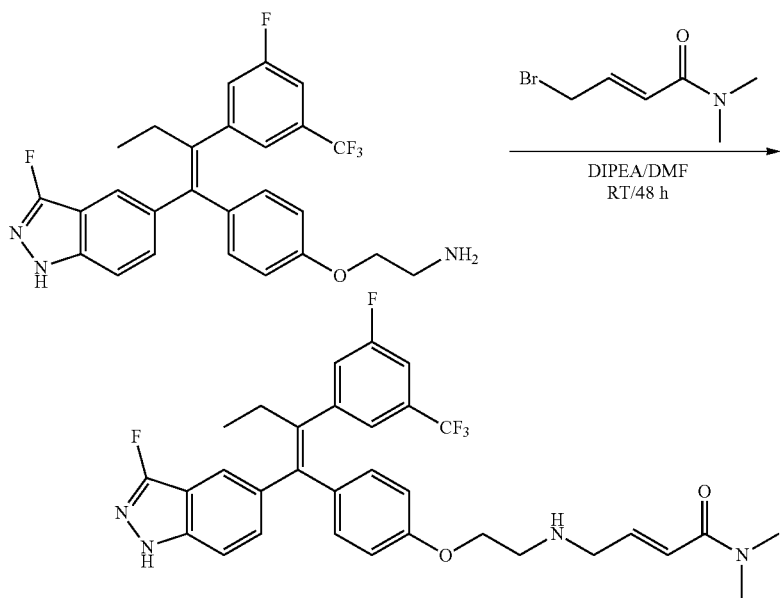

The reaction was carried out according to Scheme 2, Step-3a to afford the title compound of Ex. 3, Step-6 (0.1 g, 29%) as a white solid.

Compound 3: $^1$H NMR (400 MHz, DMSO-$d_6$): δ 12.60 (s, 1H), 7.57 (s, 1H), 7.48 (dd, J1=8.8 Hz, J2=6.8 Hz, 1H), 7.41 (t, J=8.8 Hz, 2H), 7.27 (s, 1H), 7.23 (dd, J1=8.4 Hz, J2=0.8 Hz, 1H), 6.80 (d, J=8.8 Hz, 2H), 6.68-6.47 (m, 4H), 3.89 (t, J=5.2 Hz, 2H), 2.99 (s, 3H), 2.84 (s, 3H), 2.77 (t, J=5.6 Hz, 2H), 2.49-2.42 (m, 2H), 0.89 (t, J=7.2 Hz, 3H). ES (MS): 599.3 [M+H]$^+$.

Example 4: Synthesis of (E)-4-((2-(4-((E)-1-(4-fluoro-1H-indazol-5-yl)-2-phenyl but-1-en-1-yl)phenoxy) ethyl)amino)-N,N-dimethylbut-2-enamide. (Compound 4)

The compound was synthesized following the approach as outlined in Example 2 by substituting into Step-2 5-bromo-4-fluoro-1H-indazole (preparation shown below in Ex. 4 Steps 1-2) for compound 225 to afford Compound 4 (0.03 g, 5%) as a white solid.

Step-1: Synthesis of 4-bromo-3-fluoro-2-methylaniline

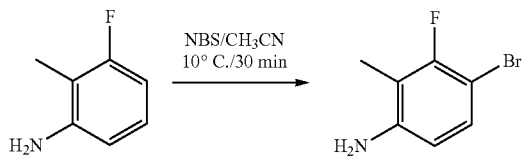

To a stirred solution of 3-fluoro-2-methylaniline (15 g, 0.1199 mol) in acetonitrile (300 mL) was added N-bromo succinamide (23.5 g, 0.131 mol) at 0° C. The reaction mixture was stirred for 30 min at 10° C., after completion of reaction (monitored by TLC), the reaction mixture was diluted with EtOAc. Organic layer was washed with water followed by brine, dried over anhydrous sodium sulphate, filtered and concentrated under reduced pressure. The crude product was used in next step without further purification to afford 4-bromo-3-fluoro-2-methylaniline (25 g, crude) as a white solid.

Step-2: Synthesis of 5-bromo-4-fluoro-1H-indazole

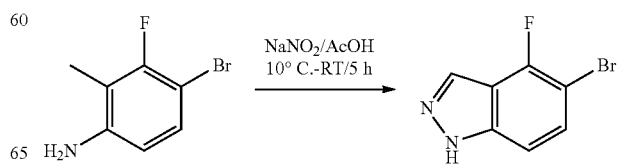

To a stirred solution of 4-bromo-3-fluoro-2-methylaniline (20 g, 98 mmol) in acetic acid was added sodium nitrite (8.1 g, 117 mmol) at 10° C., and the contents were stirred at room temperature for 5 h. After completion of reaction (monitored by TLC), the reaction mixture was cooled to 0° C., 50% NaOH solution was added drop wise till the pH of the solution becomes 9. Reaction mixture was diluted with ethyl acetate and the organic layer was washed with water followed by brine. The organic layer was dried over anhydrous $Na_2SO_4$ and concentrated under reduced pressure. The crude compound was purified by column chromatography over 230-400 mesh silica gel using (10-15%) ethyl acetate in n-hexane as an eluent to obtain title compound of Ex. 4 Step-2 (6.1 g, 29%) as a yellow solid.

Compound 4: $^1$H NMR (400 MHz, DMSO-$d_6$): δ 13.39 (s, 1H), 8.17 (s, 1H), 7.39 (d, J=8.4 Hz, 1H), 7.24-7.2 (m, 2H), 7.18-7.15 (m, 4H), 6.77 (d, J=8.4 Hz, 2H), 6.62-6.57 (m, 3H), 6.51-6.47 (m, 1H), 3.86 (t, J=5.6 Hz, 2H), 3.31 (m, 2H), 2.98 (s, 3H), 2.83 (s, 3H), 2.77 (t, J=5.4 Hz, 2H), 2.33-2.30 (m, 2H), 0.89 (t, J=7.4 Hz, 3H). ES (MS): 513.3 [M+H]$^+$.

Example 5: Synthesis of (E)-4-((2-(4-((E)-2-(3,5-difluorophenyl)-1-(1H-indazol-5-yl)but-1-en-1-yl)phenoxy)ethyl)amino)-N,N-dimethylbut-2-enamide (Compound 5)

Step-1: Synthesis of tert-butyl (E)-(2-(4-(2-(3,5-difluorophenyl)-1-(1-(tetrahydro-2H-pyran-2-yl)-1H-indazol-5-yl)but-1-en-1-yl)phenoxy)ethyl)carbamate

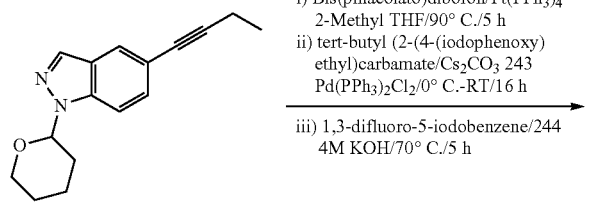

242 i) Bis(pinacolato)diboron/Pt(PPh$_3$)$_4$
2-Methyl THF/90° C./5 h
ii) tert-butyl (2-(4-(iodophenoxy)ethyl)carbamate/Cs$_2$CO$_3$ 243
Pd(PPh$_3$)$_2$Cl$_2$/0° C.-RT/16 h
iii) 1,3-difluoro-5-iodobenzene/244
4M KOH/70° C./5 h

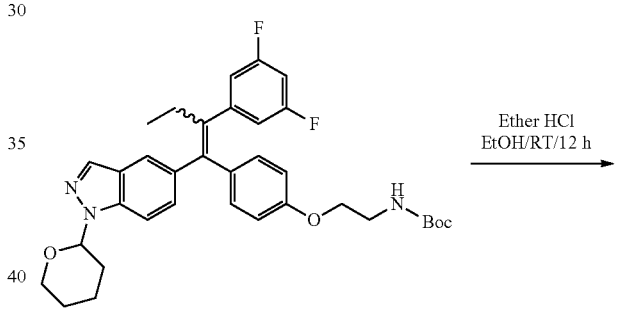

Ether HCl
EtOH/RT/12 h

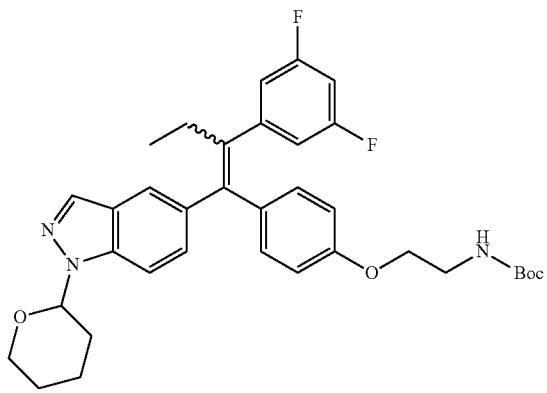

To a stirred solution of 5-(but-1-yn-1-yl)-1-(tetrahydro-2H-pyran-2-yl)-1H-indazole (0.4 g, 1.574 mmol, Example 1, Step-3) in 2-methyl THF (5 mL), was added bis(pinacolato)diboron (0.44 g, 1.732 mmol), tetrakis(triphenylphosphine)platinum(0) (14.6 mg, 0.0118 mmol) under nitrogen atmosphere, reaction mixture was heated at 90° C. for 5 h. After completion of reaction (monitored by TLC), reaction mixture was allowed to cool to 4° C. and tert-butyl (2-(4-iodophenoxy)ethyl)carbamate (571 mg, 1.574 mmol, Example 3, Step-2), bis(triphenylphosphine)palladium(II) dichloride (55 mg, 0.078 mmol), cesium carbonate (1.023 g, 3.140 mmol) and 2-methyl THF (5 mL) were added. This mixture was degassed with nitrogen and water (1.2 mL) was added. Reaction mixture was stirred at room temperature for 16 h. After completion of reaction (monitored by TLC), 1,3-difluoro-5-iodobenzene (528 mg, 2.20 mmol) and 4M aqueous KOH (3 mL) were added and the mixture was degassed with nitrogen and heated at 70° C. for 5 h. Upon completion, the reaction mixture was filtered through a celite/silicagel pad and washed with EtOAc. The filtrate was washed with water, brine, dried over anhydrous sodium sulphate, filtered and concentrated under reduced pressure. The crude product was purified by silica gel chromatography (2:8 EtOAc in n-hexane) to give title compound of Ex. 5 Step-1 (500 mg, 54%).

Step-2: Synthesis of (E)-2-(4-(2-(3,5-difluorophenyl)-1-(1H-indazol-5-yl)but-1-en-1-yl)phenoxy)ethan-1-amine The reaction was carried out according to Scheme 2, Step-2a by substituting in tert-butyl (E)-(2-(4-(2-(3,5-difluorophenyl)-1-(1-(tetrahydro-2H-pyran-2-yl)-1H-indazol-5-yl)but-1-en-1-yl)phenoxy)ethyl)carbamate for compound 211b to afford title compound of Ex. 5 Step-2 (0.340 g, 97%) as a white solid.

Step-3: Synthesis of (E)-4-((2-(4-((E)-2-(3,5-difluorophenyl)-1-(1H-indazol-5-yl)but-1-en-1-yl)phenoxy) ethyl)amino)-N,N-dimethylbut-2-enamide (Compound 5)

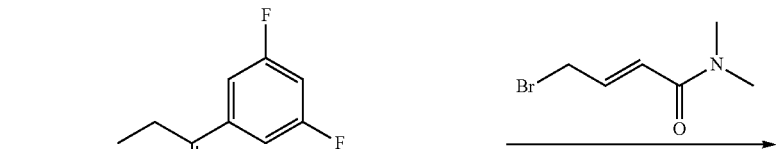

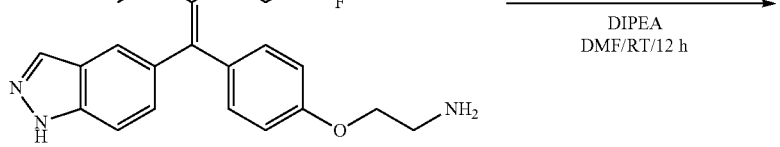

5

The compound was made according to Scheme 2, Step-3a by substituting in (E)-2-(4-(2-(3,5-difluorophenyl)-1-(1H-indazol-5-yl)but-1-en-1-yl)phenoxy)ethan-1-amine for compound 213 to afford Compound 5 (60 mg, 14%) as a white solid.

Compound 5: $^1$H NMR (400 MHz, DMSO-$d_6$): δ 13.08 (s, 1H), 8.07 (s, 1H), 7.61 (s, 1H), 7.52 (d, J=8.8 Hz, 1H), 7.12 (d, J=8.4 Hz, 1H), 6.99 (m, 1H), 6.868 (m, 1H), 6.795 (d, J=8.8 Hz, 2H), 6.67 (d, J=8.8 Hz, 2H), 6.63-6.58 (m, 1H), 3.9 (t, J=5.6 Hz, 2H), 3.31 (m, 2H), 2.99 (s, 3H), 2.84 (s, 3H), 2.79 (t, J=5.6 Hz, 2H), 2.39 (q, J=7.2 Hz, 2H), 0.89 (t, J=7.4 Hz, 3H). LCMS: 531.3 [M+H]$^+$.

Example 6: Synthesis of (E)-4-((2-(4-((E)-2-(3,4-difluorophenyl)-1-(1H-indazol-5-yl)but-1-en-1-yl)phenoxy)ethyl)amino)-N,N-dimethylbut-2-enamide (Compound 6)

The compound was synthesized following the approach as outlined in Example 3 substituting into Step-4 tert-butyl (E)-(2-(4-(2-(3,4-difluorophenyl)-1-(1-(tetrahydro-2H-pyran-2-yl)-1H-indazol-5-yl)but-1-en-1-yl)phenoxy)ethyl) carbamate for compound 226 (preparation shown below in Example 6, Step-1) and 1,2-difluoro-5-iodobenzene for compound 227 to afford Compound 6 (50 mg, 8%) as a white solid.

Step-1: Synthesis of tert-butyl (E)-(2-(4-(2-(3,4-difluorophenyl)-1-(1-(tetrahydro-2H-pyran-2-yl)-1H-indazol-5-yl)but-1-en-1-yl)phenoxy)ethyl)carbamate

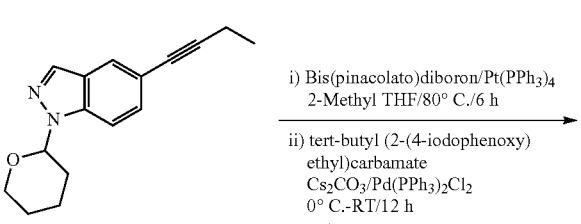

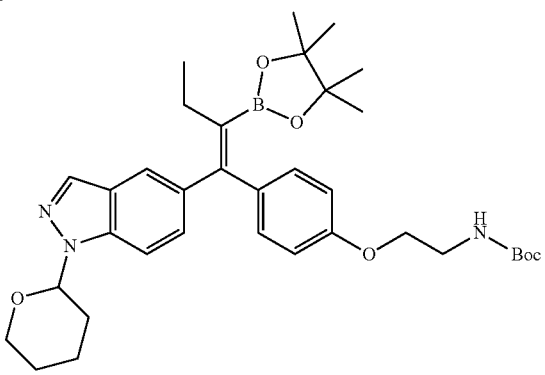

To a stirred solution of 5-(but-1-yn-1-yl)-1-(tetrahydro-2H-pyran-2-yl)-1H-indazole (2.5 g, 9.84 mmol, as prepared in Example 1, Step-3) in 2-methyl THF (20 mL), was added bis(pinacolato)diboron (2.52 g, 9.94 mmol), tetrakis(triphenylphosphine)platinum(0) (93 mg, 0.0748 mmol) under nitrogen atmosphere, reaction mixture was heated at 80° C. for 6 h. The solution was allowed to cool to 4° C., and tert-butyl (2-(4-iodophenoxy)ethyl)carbamate (3.57 g, 9.84 mmol, as prepared in Example 3, Step-2), bis(triphenylphosphine)palladium(II) dichloride (345 mg, 0.492 mmol), cesium carbonate (6.4 g, 19.68 mmol) and 2-methyl THF (10 mL) were added. This mixture was degassed with nitrogen and water (6 mL) was added. This mixture was stirred at room temperature for 12 h. After completion of reaction, reaction mixture was diluted with water and extracted with EtOAc. The Organic layer was dried over anhydrous sodium sulphate and concentrated under reduced pressure. The crude material was purified by column chromatography over 230-400 mesh silica gel using EtOAc in n-hexane (3:7) to afford the title compound of Ex. 6 Step-1 (3.85 g, 64%) as a gummy solid.

Compound 6: $^1$H NMR (400 MHz, DMSO-$d_6$): δ 13.09 (s, 1H), 8.07 (s, 1H), 7.60 (s, 1H), 7.51 (d, J=8.0 Hz, 1H), 7.29-7.20 (m, 2H), 7.11 (d, J=8.8 Hz, 1H), 6.94 (bs, 1H), 6.77 (d, J=8.80 Hz, 2H), 6.65 (d, J=8.8 Hz, 2H), 6.63-6.48 (m, 2H), 3.71 (t, J=5.6 Hz, 2H), 2.99 (s, 3H), 2.84 (s, 3H), 2.78 (t, J=5.2 Hz, 2H), 2.43-2.32 (m, 2H), 0.89 (t, J=7.2 Hz, 3H). LCMS: 531.3 [M+H]$^+$.

Example 7: Synthesis of (E)-4-((2-(4-((E)-2-(3-chloro-5-fluorophenyl)-1-(1H-indazol-5-yl)but-1-en-1-yl) phenoxy)ethyl)amino)-N,N-dimethylbut-2-enamide The compound was synthesized following the approach as outlined in Example 3 by substituting into Step-4 tert-butyl (Z)-(2-(4-(1-(1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)-ethyl)carbamate (1.5 g, 2.43 mmol, as prepared in Example 6, Step-1) for compound 226 and 1-chloro-3-fluoro-5-iodobenzene for compound 227 in step-4 to afford the title compound (50 mg, 9%) as a white solid.

Compound 7: $^1$H NMR (400 MHz, DMSO-$d_6$): δ 13.10 (s, 1H), 8.08 (s, 1H), 7.61 (s, 1H), 7.52 (d, J=8.8 Hz, 1H), 7.19 (d, J=8.8 Hz, 1H), 7.12 (d, J=8.6 Hz, 1H), 7.05 (s, 2H), 7.00 (d, J=8.8 Hz, 2H), 6.68 (d, J=8.8 Hz, 2H), 6.63-6.58 (m, 1H), 6.52-6.48 (m, 1H), 3.9 (t, J=5.6 Hz, 2H), 3.33-3.31 (m, 2H), 2.99 (s, 3H), 2.84 (s, 3H), 2.79 (t, J=5.6 Hz, 2H), 2.44-2.32 (m, 2H), 0.89 (t, J=7.4 Hz, 3H). ESMS: 547.3 [M+H]$^+$.

Example 8: Synthesis of (E)-4-((2-(4-((E)-1-(1H-indazol-5-yl)-2-phenylbut-1-en-1-yl)phenoxy) ethyl) amino)-N-methyl-N-(prop-2-yn-1-yl)but-2-enamide (Compound 8)

The compound was synthesized following the approach as outlined in Example 1 by substituting into Step-8 (E)-4-bromo-N-methyl-N-(prop-2-yn-1-yl)but-2-enamide (preparation shown below in Ex. 8 Step-1) for compound 228 and 2-(4-(1-(1H-indazol-5-yl)-2-phenylbut-1-en-1-yl)phenoxy) ethan-1-amine (preparation shown below in Ex. 9, Step 4-5) for compound 229 to afford Compound 8 (4 mg, yield: 5%) as a light green solid.

Step-1: Synthesis of (E)-4-bromo-N-methyl-N-(prop-2-yn-1-yl)but-2-enamide

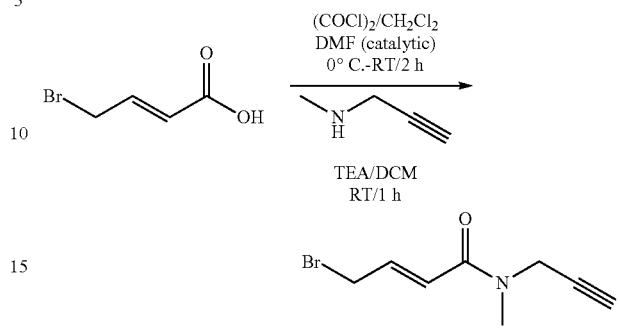

The reaction was carried out according to Scheme 4, Step-2, using N-methylprop-2-yn-1-amine for compound 221 to afford a mixture of (E)-4-bromo-N-methyl-N-(prop-2-yn-1-yl)but-2-enamide (0.5 g, 19%) as a brown colour liquid.

Compound 8: $^1$H NMR (400 MHz, DMSO-$d_6$): δ 13.06 (s, 1H), 8.06 (s, 1H), 7.61 (s, 1H), 7.51 (d, J=7.2 Hz, 1H), 7.22-7.10 (m, 6H), 6.74 (d, J=8.8 Hz, 2H), 6.60-6.52 (m, 4H), 4.22-4.16 (m, 2H), 3.87 (t, J=5.2 Hz, 2H), 3.02 (s, 2H), 2.87 (bs, 1H), 2.78 (t, J=5.6 Hz, 2H), 2.43-2.37 (m, 2H), 0.87 (t, J=7.6 Hz, 3H). ESMS: 519.2 [M+H]$^+$.

Example 9: Synthesis of (E)-4-((2-(4-((E)-1-(1H-indazol-5-yl)-2-phenylbut-1-en-1-yl)phenoxy)ethyl) amino)-N-(but-3-yn-1-yl)-N-methylbut-2-enamide (Compound 9)

Step-1: Synthesis of but-3-yn-1-yl 4-methylbenzenesulfonate

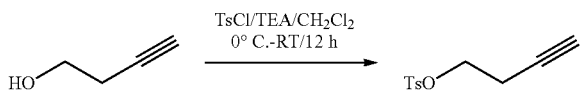

To a stirred solution of but-3-yn-1-ol (5 g, 0.0714 mmol) in dichloromethane (50 mL) at 0° C. was added triethylamine (10.82 g, 0.107 mmol) and tosyl chloride (13.61 g, 0.0714 mmol). The reaction mixture was stirred at room temperature for 12 h, after completion of reaction (monitored by TLC), reaction mixture was diluted with dichloromethane. The organic layer was washed with water, brine and dried over anhydrous Na$_2$SO$_4$ and concentrated under reduced pressure to afford but-3-yn-1-yl 4-methylbenzenesulfonate (13 g, 81%).

Step-2: Synthesis of N-methylbut-3-yn-1-amine

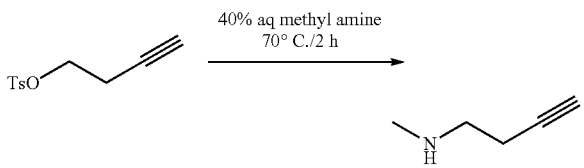

But-3-yn-1-yl 4-methylbenzenesulfonate (10 g, 44.6 mmol) was added to 40% aqueous methylamine (30 mL). The contents were heated at 70° C. under nitrogen for 2 h. After completion of reaction, reaction mixture was cooled to room temperature, the volatiles removed under vacuum and extracted with dichloromethane (250 mL). The organic layer was washed with water, brine and dried over anhydrous sodium sulphate. Organic layer was dried under reduced pressure to give N-methylbut-3-yn-1-amine (3.7 g, crude).

Step-3: Synthesis of (E)-4-bromo-N-(but-3-yn-1-yl)-N-methylbut-2-enamide

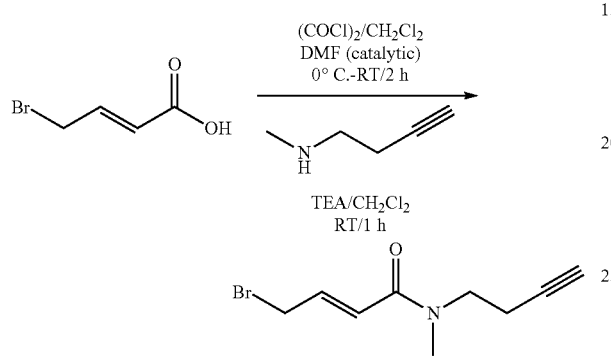

The reaction was carried out according to Scheme 4, Step-2, using N-methylbut-3-yn-1-amine for compound 221, to afford a mixture of (E)-4-bromo-N-(but-3-yn-1-yl)-N-methylbut-2-enamide (1.8 g, crude) as a brown colour liquid.

Step-4: Synthesis of tert-butyl (2-(4-(2-phenyl-1-(1-(tetrahydro-2H-pyran-2-yl)-1H-indazol-5-yl)but-1-en-1-yl)phenoxy)ethyl)carbamate

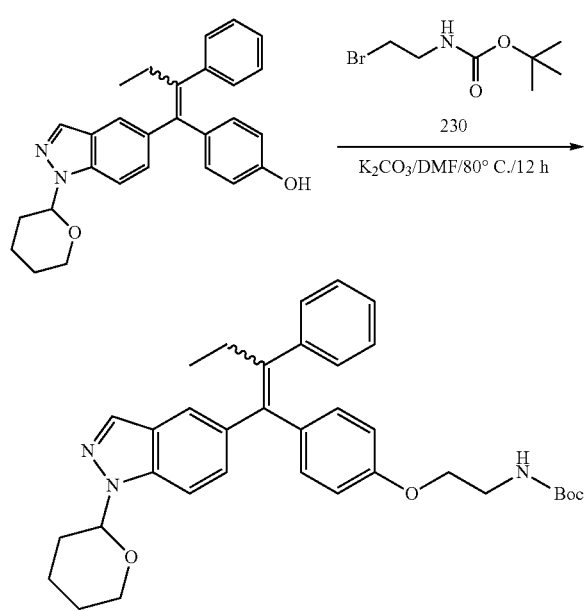

To a solution of (E)-4-(2-phenyl-1-(1-(tetrahydro-2H-pyran-2-yl)-1H-indazol-5-yl)but-1-en-1-yl)phenol (3 g, 7.0 mmol, as prepared in Example 1, Step-4) in DMF (30 mL), were added sequentially potassium carbonate (4.8 g, 35.3 mmol) and tert-butyl (2-bromoethyl)carbamate (3.16 g, 14.1 mmol). The reaction mixture was stirred at 80° C. for 12 h, after completion of reaction, reaction mixture was poured on ice cold water. The solid separated was filtered and dried under reduced pressure to afford the title compound of Ex. 9 Step-4 (2.5 g, 64%) as an off-white solid.

Step-5: Synthesis of 2-(4-(1-(1H-indazol-5-yl)-2-phenylbut-1-en-1-yl)phenoxy)ethan-1-amine

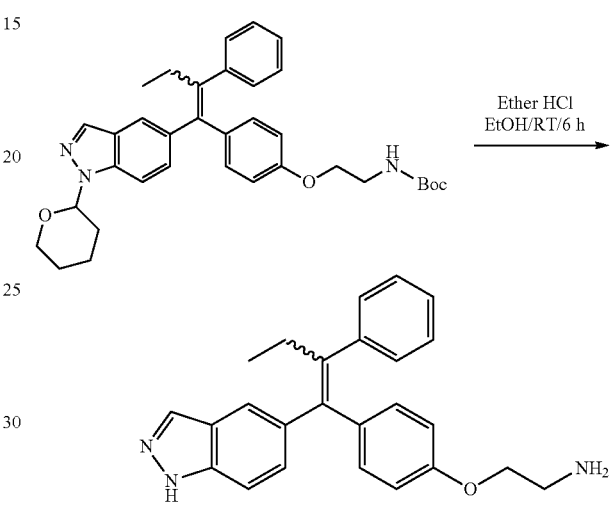

The reaction was carried out according to Scheme 2, Step-2a using tert-butyl (2-(4-(2-phenyl-1-(1-(tetrahydro-2H-pyran-2-yl)-1H-indazol-5-yl)but-1-en-1-yl)phenoxy)ethyl)carbamate (2.5 g, 4.4 mmol) for compound 211b to afford the title compound of Ex 9. Step-5 (0.8 g, 47%) as an off-white solid.

Compound 9: $^1$H NMR (400 MHz, DMSO-d$_6$): δ 13.07 (s, 1H), 8.06 (s, 1H), 7.61 (s, 1H), 7.51 (d, J=8.8 Hz, 1H), 7.20-7.11 (m, 6H), 6.74 (d, J=8.8 Hz, 2H), 6.60-6.57 (m, 4H), 3.86 (t, J=4.8 Hz, 2H), 3.49-3.38 (m, 3H), 3.03 (s, 2H), 2.86-2.84 (m, 3H), 2.77 (t, J=6.40 Hz, 2H), 2.43-2.32 (m, 4H), 0.87 (t, J=7.2 Hz, 3H). LCMS: 533.4 [M+H]$^+$.

Example 10: Synthesis of (E)-4-((2-(4-((E)-1-(1H-indazol-5-yl)-2-phenylbut-1-en-1-yl)phenoxy)ethyl)amino)-1-(azetidin-1-yl)but-2-en-1-one (Compound 10)

The compound was synthesized following the approach as outlined in Example 9 by substituting into Step-4 (E)-1-(azetidin-1-yl)-4-bromobut-2-en-1-one (preparation shown below in Ex. 10 Step-1) for compound 230 to afford compound 10 (22 mg, 4.1%) as a white solid.

Step-1: Synthesis of (E)-1-(azetidin-1-yl)-4-bromobut-2-en-1-one

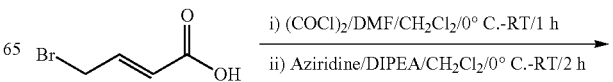

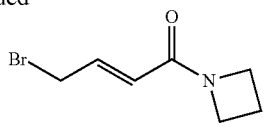

The reaction was carried out according to Scheme 4, Step-2, using aziridine for compound 221, to afford (E)-1-(azetidin-1-yl)-4-bromobut-2-en-1-one (1 g, 27%) as a brown colour liquid.

Compound 10: $^1$H NMR (400 MHz, DMSO-d$_6$): δ 13.08 (s, 1H), 8.07 (s, 1H), 7.6 (s, 1H), 7.51 (d, J=8.4 Hz, 1H), 7.2 (d, J=7.6 Hz, 2H), 7.15-7.11 (m, 4H), 6.75 (d, J=8.8 Hz, 2H), 6.61-6.57 (m, 3H), 6.04 (d, J=16 Hz, 1H), 4.12 (t, J=7.6 Hz, 2H), 3.88-3.84 (m, 4H), 3.32-3.3 (m, 2H), 2.77 (t, J=5.6 Hz, 2H), 2.42-2.4 (m, 2H), 2.19-2.15 (m, 2H), 0.88 (t, J=7.6 Hz, 3H). LCMS: 507.1 [M+H]$^+$.

Example 11: Synthesis of (E)-4-((2-(4-((E)-1-(1H-indazol-5-yl)-2-phenylbut-1-en-1-yl)phenoxy)ethyl)amino)-1-(pyrrolidin-1-yl)but-2-en-1-one (Compound 11)

The compound was synthesized following the approach as outlined in Example 9 by substituting into Step-4 (E)-4-bromo-1-(pyrrolidin-1-yl)but-2-en-1-one (preparation shown below in Ex. 9 Step-1) for compound 230 to afford title compound 11 (7.5 mg, 6.6%) as a white solid.

Step-1: Synthesis of (E)-4-bromo-1-(pyrrolidin-1-yl)but-2-en-1-one

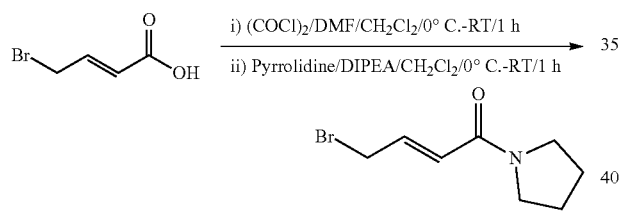

The reaction was carried out according to Scheme 4, Step-2, using pyrrolidine to afford (E)-4-bromo-1-(pyrrolidin-1-yl)but-2-en-1-one (0.31 g, 6%) as a brown colour liquid.

Compound 11: $^1$H NMR (400 MHz, DMSO-d$_6$): δ 13.06 (s, 1H), 8.07 (s, 1H), 7.61 (s, 1H), 7.51 (d, J=8.8 Hz, 1H), 7.22-7.11 (m, 6H), 6.75 (d, J=8.8 Hz, 2H), 6.65-6.58 (m, 3H), 6.31 (d, J=15.2 Hz, 1H), 3.86 (t, J=5.6 Hz, 2H), 3.45 (t, J=6.8 Hz, 2H), 2.77 (t, J=5.6 Hz, 2H), 2.43-2.38 (m, 2H), 1.9-1.73 (m, 6H), 0.88 (t, J=7.2 Hz, 5H). LCMS: 521.3 [M+H]$^+$.

Example 12: Synthesis of (E)-4-((2-(4-((E)-1-(1H-indazol-5-yl)-2-phenylbut-1-en-1-yl)phenoxy)ethyl)amino)-1-(piperidin-1-yl)but-2-en-1-one (Compound 12)

Step-1: Synthesis of (E)-4-bromo-1-(piperidin-1-yl)but-2-en-1-one

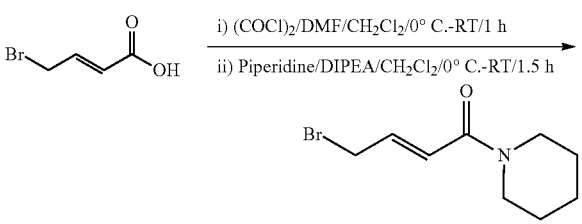

The reaction was carried out according to Scheme 4, Step-2, using piperidine, for compound 221 to afford (E)-4-bromo-1-(piperidin-1-yl)but-2-en-1-one (3.9 g, 55%) as a brown colour liquid.

Step-2: Synthesis of (2E)-4-((2-(4-(1-(1H-indazol-5-yl)-2-phenylbut-1-en-1-yl)phenoxy)ethyl)amino)-1-(piperidin-1-yl)but-2-en-1-one

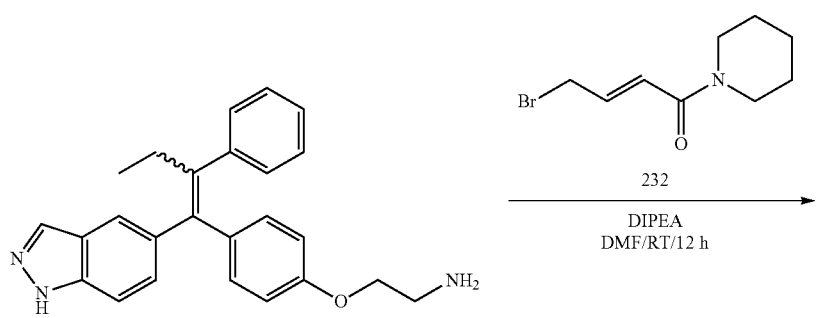

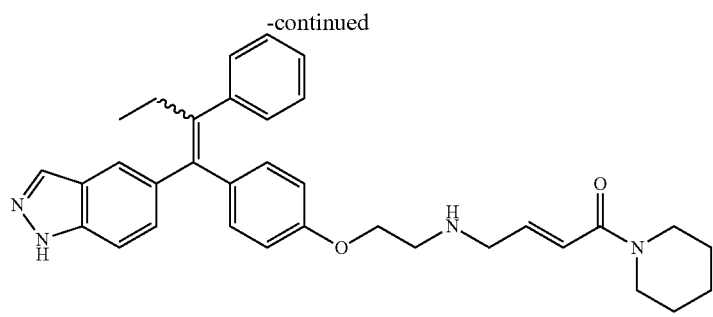

The reaction was carried out according to Scheme 2, Step-3a, using 2-(4-(1-(1H-indazol-5-yl)-2-phenylbut-1-en-1-yl)phenoxy)-ethan-1-amine (as prepared in Example 9, Step 4-5) for compound 213 to give a crude material which was used in next step without further purification (716 mg, crude).

Step-3: Synthesis of tert-butyl (2-(4-(1-(1H-indazol-5-yl)-2-phenylbut-1-en-1-yl)phenoxy)ethyl) ((E)-4-oxo-4-(piperidin-1-yl)but-2-en-1-yl)carbamate

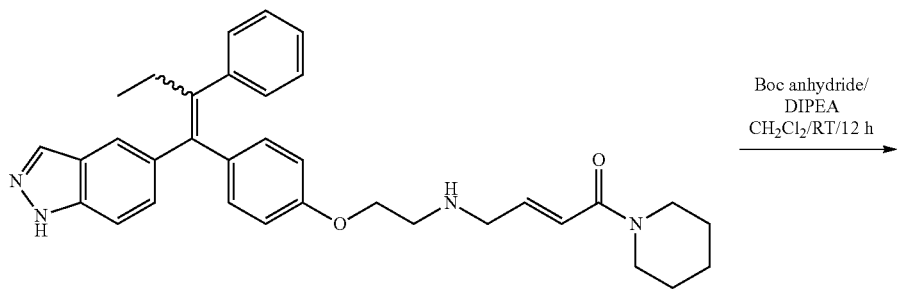

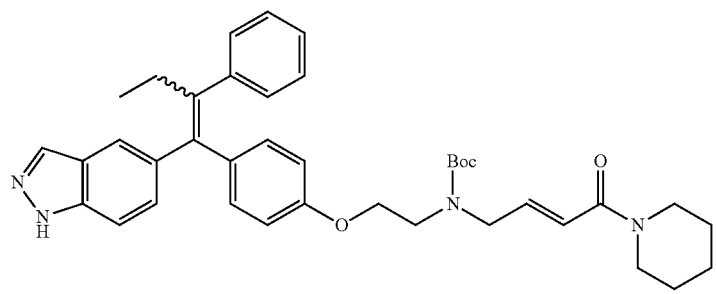

The reaction was carried out according to Scheme 2, Step-5, using (2E)-4-((2-(4-(1-(1H-indazol-5-yl)-2-phenyl-but-1-en-1-yl)phenoxy)ethyl)amino)-1-(piperidin-1-yl)but-2-en-1-one (0.716 g, 1.34 mmol) for compound 215. The crude compound was purified by column chromatography using 4% MeOH in dichloromethane to afford the title compound of Ex. 12 Step-3 (0.32 g, 37%).

Step-4: Synthesis of (E)-4-((2-(4-((E)-1-(1H-inda-zol-5-yl)-2-phenylbut-1-en-1-yl)phenoxy)ethyl) amino)-1-(piperidin-1-yl)but-2-en-1-one (Compound 12)

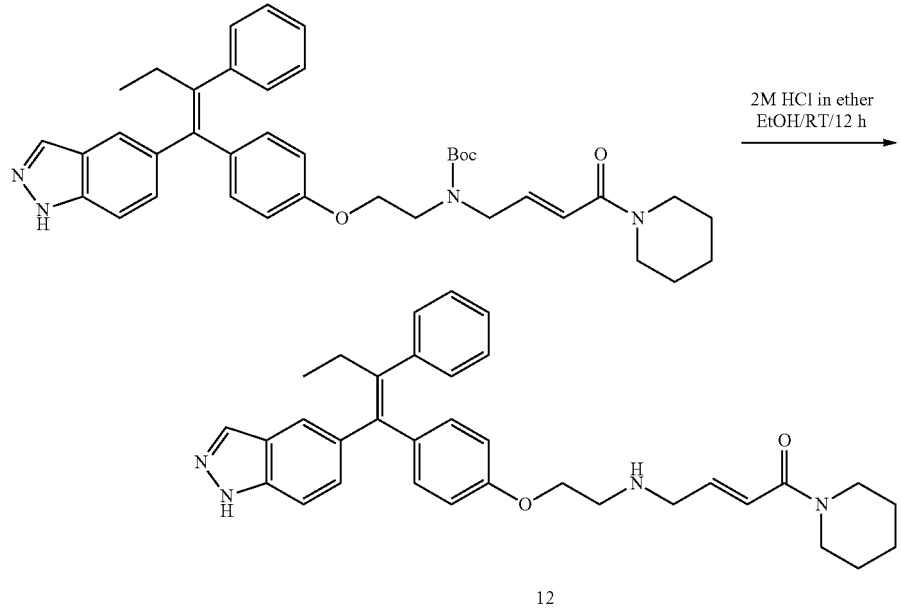

12

The reaction was carried out according to Scheme 2, Step-6c, using tert-butyl (2-(4-(1-(1H-indazol-5-yl)-2-phenylbut-1-en-1-yl)phenoxy)ethyl)((E)-4-oxo-4-(piperidin-1-yl)but-2-en-1-yl)carbamate (0.32 g, 0.504 mmol) for compound 211c to deliver crude compound, which was purified by preparative TLC to afford compound 12 (74 mg, 27%).

Compound 12: $^1$H NMR (400 MHz, DMSO-$d_6$): δ 13.06 (s, 1H), 8.06 (s, 1H), 7.61 (s, 1H), 7.51 (d, J=8.8 Hz, 1H), 7.2 (d, J=7.6 Hz, 2H), 7.15-7.1 (m, 4H), 6.75 (d, J=8.4 Hz, 2H), 6.6-6.5 (m, 4H), 3.86 (t, J=6 Hz, 2H), 3.42 (t, J=5.6 Hz, 4H), 2.77 (t, J=5.6 Hz, 2H), 2.5 (m, 3H), 2.43-2.38 (m, 2H), 1.58-1.53 (m, 2H), 1.42 (d, J=3.6 Hz, 4H), 0.87 (t, J=7.2 Hz, 3H). LCMS: 535.3 [M+H]$^+$.

Example 13: Synthesis of (E)-4-((2-(4-((E)-2-cyclobutyl-1-(1H-indazol-5-yl)-2-phenylvinyl)phenoxy) ethyl)amino)-N,N-dimethylbut-2-enamide (Compound 13)

Step-1: Synthesis of (6-chlorohex-1-yn-1-yl)trimethylsilane

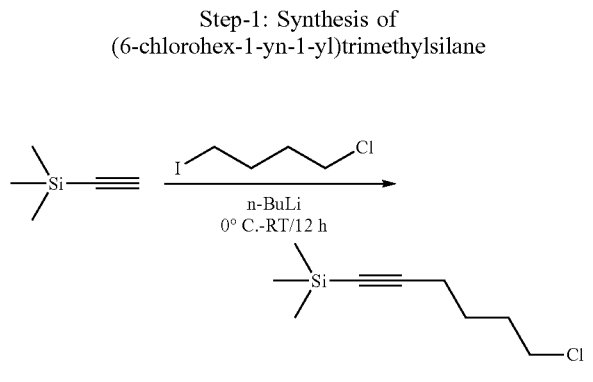

A solution of trimethylsilylacetylene (10 g, 101 mmol) in dry tetrahydrofuran (90 mL) was stirred at 0° C. under nitrogen atmosphere; n-BuLi (44.5 mL of 2.6M solution in hexane, 111.2 mmol) was added drop wise. The solution was stirred for 30 minutes, a solution of 1-chloro-4-iodobutane (13.6 mL, 111.2 mmol) in dry tetrahydrofuran (30 mL) was added. The reaction mixture was allowed to warm to 20° C. and stirred for 12 h. The reaction mixture was poured into water, the aqueous mixture was extracted with diethyl ether. The ethereal extracts were washed with water and dried over anhydrous sodium sulphate. The solvent was removed under reduced pressure to obtain 6-chloro-1-trimethylsilylhex-1-yne (18 g) as a yellow liquid and was used in next step without further purification.

Step-2: Synthesis of (cyclobutylethynyl)trimethylsilane

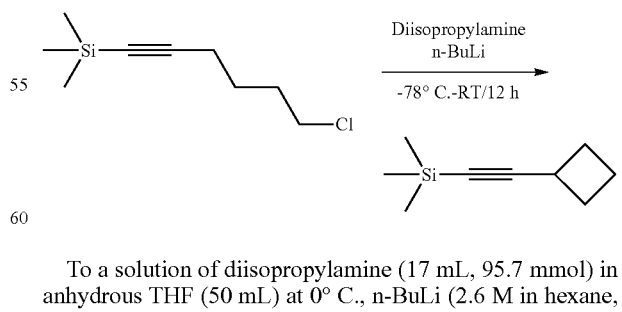

To a solution of diisopropylamine (17 mL, 95.7 mmol) in anhydrous THF (50 mL) at 0° C., n-BuLi (2.6 M in hexane, 36.8 mL, 95.7 mmol) was added dropwise. The mixture was stirred for 20 minutes at 0° C. and then cooled to −78° C. To this mixture, a solution of (6-chlorohex-1-yn-1-yl)trimethylsilane (9 g, 47 mmol) in anhydrous THF (50 mL) was added drop wise. The resulting mixture was allowed to warm to room temperature and stirred for 12 h. The reaction mixture was carefully quenched at room temperature with saturated aqueous NH₄Cl (100 mL), extracted with pentane (200 mL). The combined organic layers were washed with brine and dried over anhydrous Na₂SO₄. The solvent was evaporated under reduced pressure. The residue was distilled at 160-162° C./760 Torr to afford the title compound as a colourless liquid (4 g, 55%).

Step-3: Synthesis of 5-(cyclobutylethynyl)-1-(tetrahydro-2H-pyran-2-yl)-1H-indazole

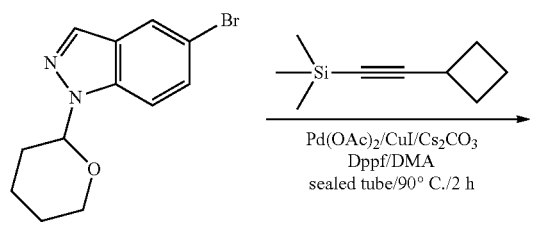

Pd(OAc)₂/CuI/Cs₂CO₃
Dppf/DMA
sealed tube/90° C./2 h

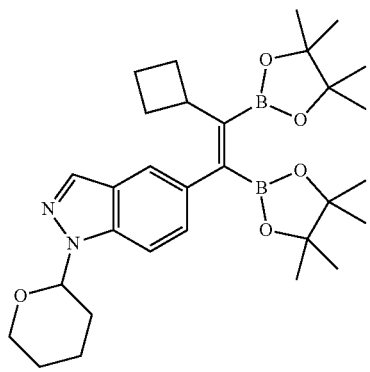

The reaction was carried out according to Scheme 1, Step-3 to afford the title compound of Ex. 13 Step-4 (0.5 g, 66%).

Step-5: Synthesis of tert-butyl (Z)-(2-(4-(2-cyclobutyl-1-(1-(tetrahydro-2H-pyran-2-yl)-1H-indazol-5-yl)-2-(4,4,5,5-tetramethyl-1,3,2-dioxaborolan-2-yl)vinyl)phenoxy)-ethyl)carbamate

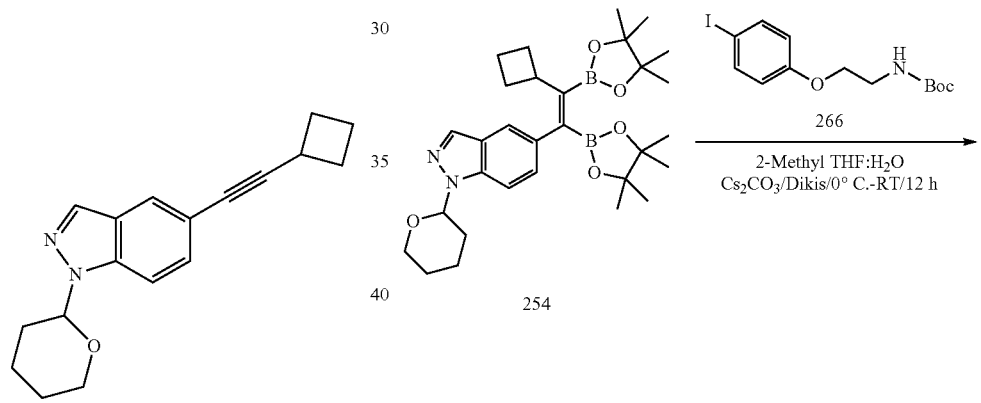

254

2-Methyl THF:H₂O
Cs₂CO₃/Dikis/0° C.-RT/12 h

The reaction was carried out according to Scheme 1, Step-2, using cyclobutylethynyl)trimethylsilane for compound 203, to afford the title compound of Ex. 13 Step-3 (450 mg, 84%) as a brown oil.

Step-4: Synthesis of (Z)-5-(2-cyclobutyl-1,2-bis(4,4,5,5-tetramethyl-1,3,2-dioxaborolan-2-yl)vinyl)-1-(tetrahydro-2H-pyran-2-yl)-1H-indazole

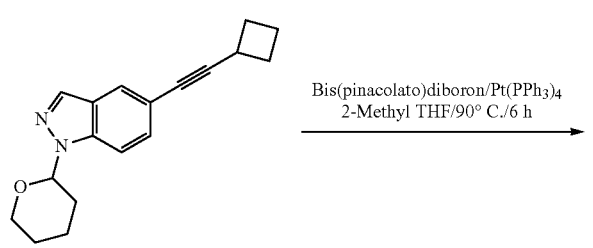

Bis(pinacolato)diboron/Pt(PPh₃)₄
2-Methyl THF/90° C./6 h

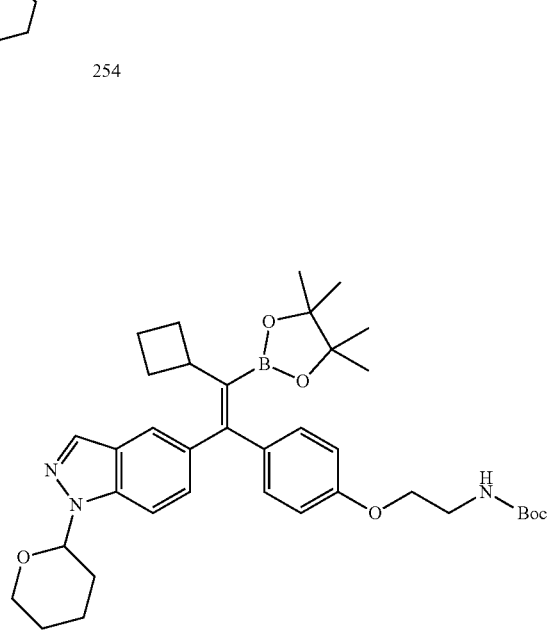

The reaction was carried out according to Scheme 1, Step-4, using tert-butyl (2-(4-iodophenoxy)ethyl)carbamate (as prepared in Example 3, Step-2) for compound 207 to afford the title compound of Ex. 13 Step-5 (0.36 g, 50%).

Step-6: Synthesis of tert-butyl (E)-(2-(4-(2-cyclobutyl-2-phenyl-1-(1-(tetrahydro-2H-pyran-2-yl)-1H-indazol-5-yl)vinyl)phenoxy)ethyl)carbamate

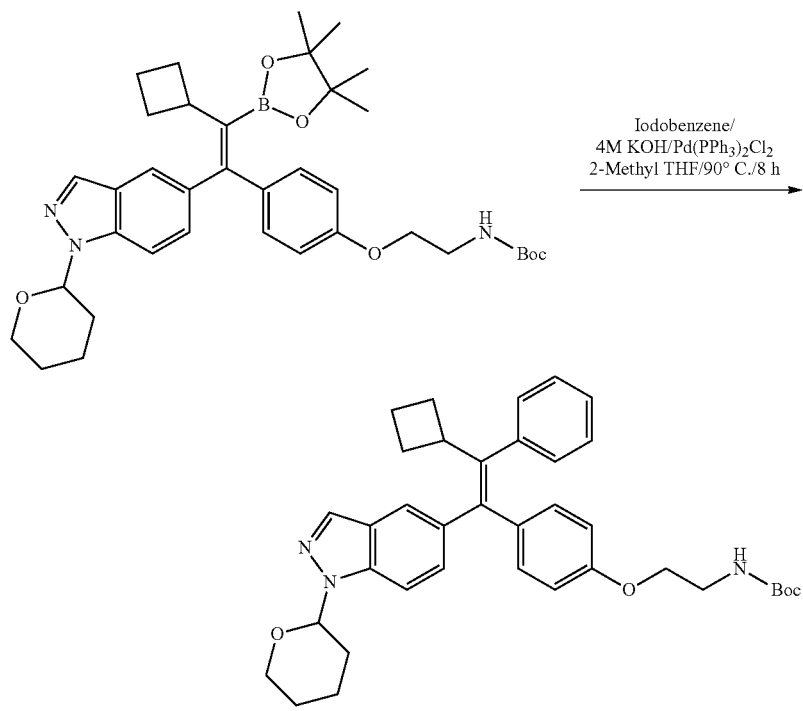

The reaction was carried out according to Scheme 1, Step-5, using iodobenzene for compound 209 to give the title compound of Ex. 13 Step-6 (0.17 g, 51%).

Step-7: Synthesis of (E)-2-(4-(2-cyclobutyl-1-(1H-indazol-5-yl)-2-phenylvinyl) phenoxy)ethan-1-amine

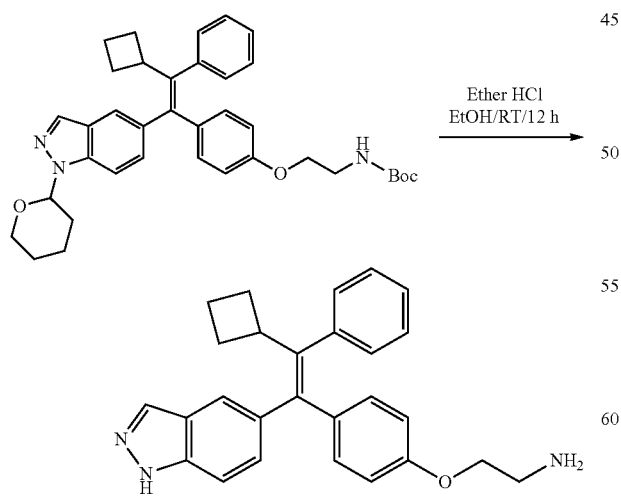

The reaction was carried out according to Scheme 2, Step-2a to afford the title compound of Ex. 13 Step-7 (0.04 g, 34%) as a brown coloured semi solid.

Step-8: Synthesis of (E)-4-((2-(4-((E)-2-cyclobutyl-1-(1H-indazol-5-yl)-2-phenylvinyl)phenoxy) ethyl) amino)-N,N-dimethylbut-2-enamide (Compound 13)

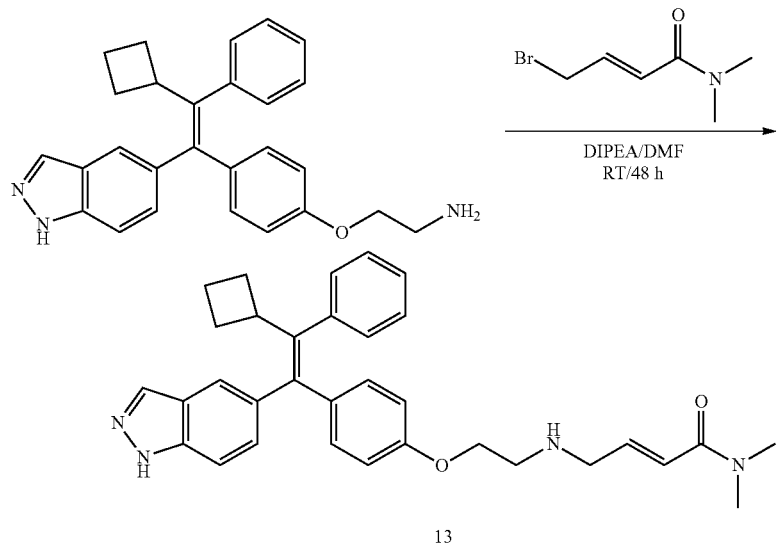

The reaction was carried out according to Scheme 2, Step-3a, using (E)-4-bromo-N,N-dimethylbut-2-enamide (as prepared in Example 1, Step-7) for compound 214 to afford compound 13 (0.2 g, 40%) as a white solid.

Compound 13: $^1$H NMR (400 MHz, DMSO-$d_6$): δ 13.06 (s, 1H), 8.07 (s, 1H), 7.58 (s, 1H), 7.51 (d, J=6.8 Hz, 1H), 7.24 (d, J=5.2 Hz, 2H), 7.17-7.09 (m, 4H), 6.78 (d, J=6.8 Hz, 2H), 6.60-6.46 (m, 4H), 3.83 (t, J=4.4 Hz, 2H), 3.50-3.39 (m, 2H), 2.97 (s, 3H), 2.83 (s, 3H), 2.75 (t, J=4.4 Hz, 2H), 1.8-1.77 (m, 4H), 1.57-1.55 (m, 1H), 1.36-1.24 (m, 2H). LC (MS) 521.3 [M+H]$^+$.

Example 14: Synthesis of (E)-4-((2-(4-((E)-2-cyclobutyl-1-(3-fluoro-1H-indazol-5-yl)-2-phenylvinyl) phenoxy)ethyl)amino)-N,N-dimethylbut-2-enamide 2,2,2-trifluoro acetate (Compound 14)

Step-1: Synthesis of 5-(cyclobutylethynyl)-3-fluoro-1-(tetrahydro-2H-pyran-2-yl)-1H-indazole

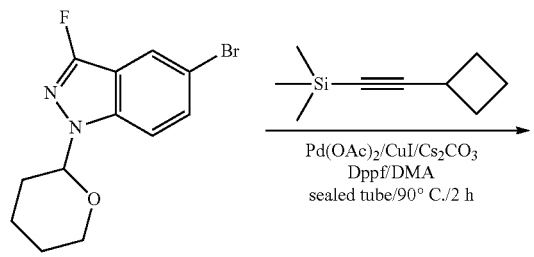

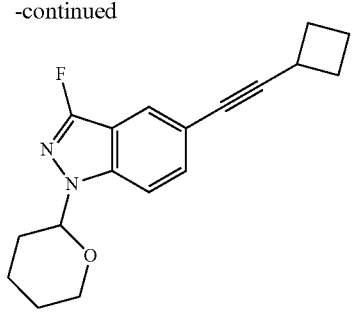

The reaction was carried out according to Scheme 1, Step-2b, using 5-bromo-3-fluoro-1-(tetrahydro-2H-pyran-2-yl)-1H-indazole (as prepared in Example 2, Step-2) for compound 202 and cyclobutylethynyl)trimethylsilane (as prepared in Example 13, Step-3) for compound 203 to afford the title compound in Ex. 14 Step-1 (2.15 g, 86%).

Step-2: Synthesis of (Z)-5-(2-cyclobutyl-1,2-bis(4,4,5,5-tetramethyl-1,3,2-dioxaborolan-2-yl) vinyl)-3-fluoro-1-(tetrahydro-2H-pyran-2-yl)-1H-indazole

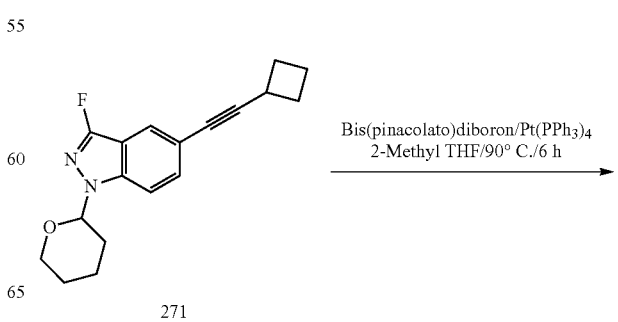

-continued

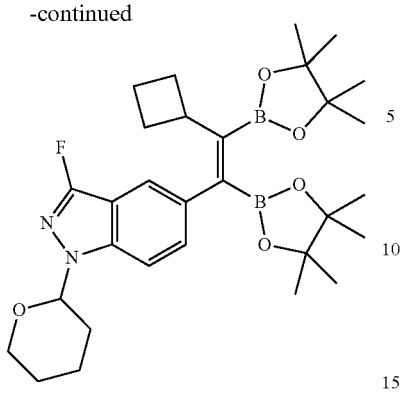

The reaction was carried out according to Scheme 1, Step-3 to afford the title compound of Ex. 14 Step-2 (4.3 g, 51.8%).

Step-3: Synthesis of tert-butyl (E)-(4-(dimethyl-amino)-4-oxobut-2-en-1-yl)(2-(4-iodophenoxy) ethyl)carbamate

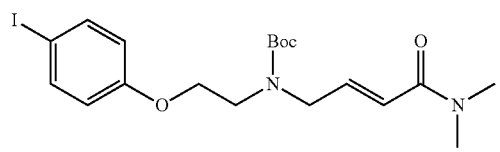 [SMILES: CN(C)C(=O)/C=C/CN(CCOc1ccc(I)cc1)C(=O)OC(C)(C)C]

Step-3.1: Synthesis of 2-(4-iodophenoxy)ethan-1-amine

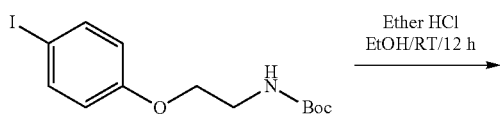

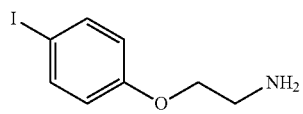

To a stirred solution of tert-butyl (2-(4-iodophenoxy) ethyl)carbamate (25 g, 68.6 mmol, Example 3, Step-2) in ethanol (50 mL) was added at 0° C., 2M HCl in ether (250 mL). The reaction mixture was stirred for 12 h at room temperature. After completion of reaction, reaction mixture was basified with saturated NaHCO₃, extracted with 10% MeOH in DCM. Organic layer was concentrated under reduced pressure and the crude material was used in next step without further purification (16 g, 88%).

Step-3.2: Synthesis of (E)-4-((2-(4-iodophenoxy) ethyl)amino)-N,N-dimethylbut-2-enamide

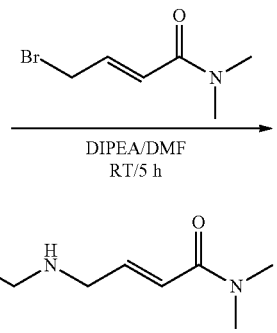

The reaction was carried out according to Scheme 2, Step-3a, using (E)-4-bromo-N,N-dimethylbut-2-enamide (Example 1, Step-7) for compound 214 to give a crude product which was used in next step without further purification (18.8 g, crude).

Step-3.3: Synthesis of tert-butyl (E)-(4-(dimethyl-amino)-4-oxobut-2-en-1-yl)(2-(4-iodophenoxy) ethyl)carbamate

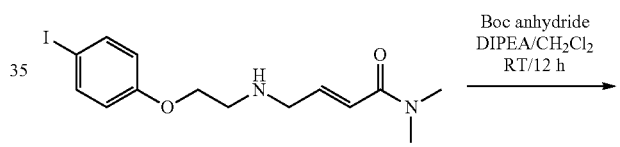

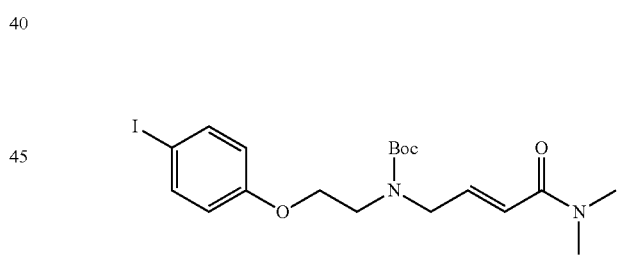

To a stirred solution of (E)-4-((2-(4-iodophenoxy)ethyl) amino)-N,N-dimethylbut-2-enamide (18.8 g, 50.26 mmol) in dry dichloromethane (150 mL) was added DIPEA (6.4 g, 50.2 mmol) at 0° C., stirred for 15 min at 0° C. To the above reaction mixture, was added boc anhydride (13.1 g, 60.3 mmol), resulting mixture was stirred at room temperature for 12 h. Upon completion by TLC, the reaction mixture was cooled to 0° C., quenched with ice cold water (500 mL) and extracted with dichloromethane (500 mL). The combined organic extracts were washed with water, followed by brine, dried over anhydrous sodium sulphate and concentrated under reduced pressure. The crude material was purified by column chromatography over 230-400 mesh silica using 3% MeOH in dichloromethane as an eluent to afford tert-butyl (E)-(4-(dimethylamino)-4-oxobut-2-en-1-yl)(2-(4-iodophenoxy)ethyl)carbamate (9 g, 37.8%).

Step-4: Synthesis of tert-butyl (2-(4-((E)-2-cyclobutyl-1-(3-fluoro-1-(tetrahydro-2H-pyran-2-yl)-1H-indazol-5-yl)-2-phenylvinyl)phenoxy)ethyl) ((E)-4-(dimethylamino)-4-oxobut-2-en-1-yl)carbamate

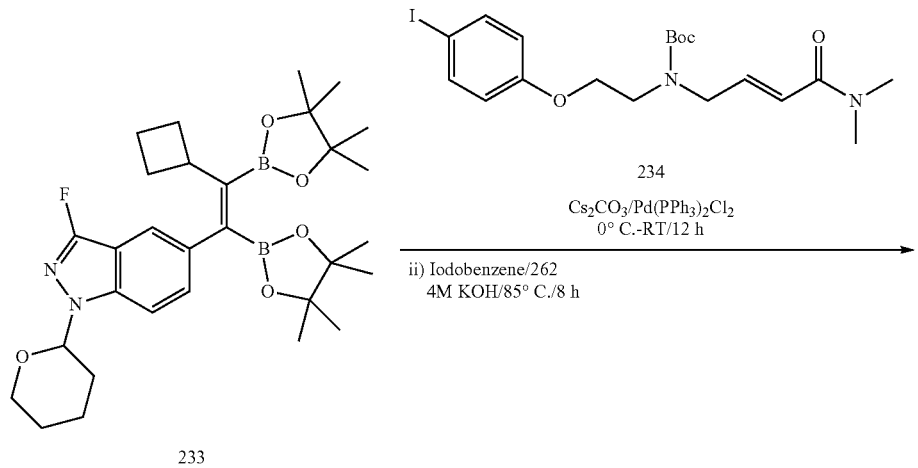

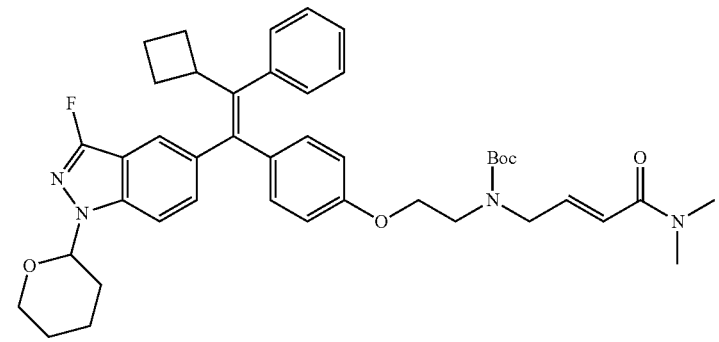

The reaction was carried out according to Scheme 1, Step-4 and Step-5 to give a crude product. The crude product containing the title compound of Ex. 14 Step-4, which was used in next step without further purification (340 mg, crude).

Step-5: Synthesis of (E)-4-((2-(4-((E)-2-cyclobutyl-1-(3-fluoro-1H-indazol-5-yl)-2-phenylvinyl)phenoxy) ethyl)amino)-N,N-dimethylbut-2-enamide 2,2,2-trifluoroacetate (Compound 14)

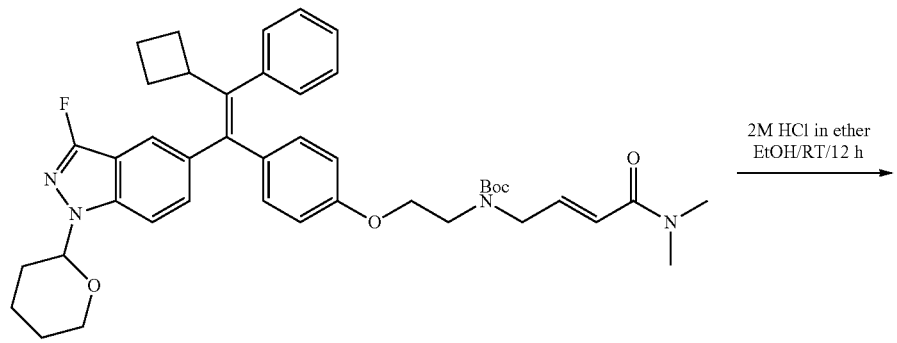

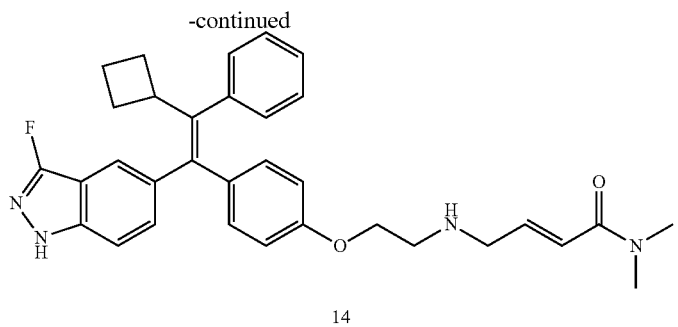

14

The reaction was carried out according to Scheme 2, Step-6c to provide a crude compound, which was purified by preparative HPLC to afford compound 14 (15 mg, 7%) as an off-white solid.

Compound 14: $^1$H NMR (400 MHz, DMSO-d$_6$): δ 12.59 (s, 1H), 8.08 (s, 1H), 7.49-7.27 (m, 2H), 7.26-7.21 (m, 3H), 7.2-7.16 (m, 1H), 7.1 (d, J=6.8 Hz, 2H), 6.78 (d, J=14.8 Hz, 1H), 6.63 (d, J=8.8 Hz, 2H), 6.57-6.52 (m, 2H), 4.05 (t, J=4.8 Hz, 2H), 3.78 (d, J=6.0 Hz, 2H), 3.38-3.36 (m, 1H), 3.24 (s, 2H), 3.02 (s, 3H), 2.87 (s, 3H), 1.8-1.76 (m, 4H), 1.6-1.5 (m, 1H), 1.35 (m, 1H). LCMS: 539.3 [M+H]$^+$.

Example 15: Synthesis of (E)-4-((2-(4-((E)-1-(1H-indazol-5-yl)-2-phenylbut-1-en-1-yl)phenoxy)ethyl)amino)-1-morpholinobut-2-en-1-one (Compound 15)

The compound was synthesized following the approach as outlined in Example 9 by substituting into Step-4 (E)-4-bromo-1-morpholinobut-2-en-1-one (preparation shown below in Ex. 15 Step-1) for compound 230 to afford compound 15 (15 mg, 3.2%) as a white solid.

Step-1: Synthesis of (E)-4-bromo-1-morpholinobut-2-en-1-one

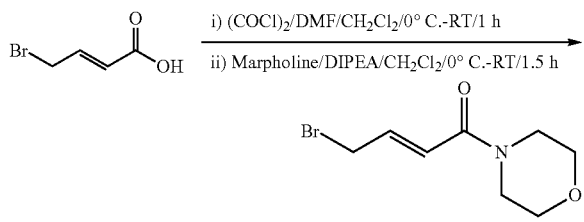

The reaction was carried out according to Scheme 4, Step-2, using morphorline for compound 221, to afford (E)-4-bromo-1-(piperidin-1-yl)but-2-en-1-one (2.1 g, 29.6%) as a brown colour liquid.

Compound 15: $^1$H NMR (400 MHz, DMSO-d$_6$) δ 13.08 (s, 1H), 8.07 (s, 1H), 7.61 (s, 1H), 7.51 (d, J=6.8 Hz, 1H), 7.21-7.11 (m, 6H), 6.74 (d, J=8.8 Hz, 2H), 6.7-6.62 (m, 1H), 6.59 (d, J=8.4 Hz, 2H), 6.51 (d, J=15.2 Hz, 1H), 3.86 (t, J=5.2 Hz, 2H), 3.58-3.4 (m, 10H), 2.77 (t, J=5.2 Hz, 2H), 2.41-2.39 (m, 2H), 0.88 (t, J=7.2 Hz, 3H). LCMS: 537.1 [M+H]$^+$.

Example 16: Synthesis of (E)-4-((2-(4-((E)-1-(1H-indazol-5-yl)-2-phenylbut-1-en-1-yl)phenoxy)ethyl)amino)-N-ethyl-N-methylbut-2-enamide (Compound 16)

The compound was synthesized following the approach as outlined in Example 12 by substituting into Step-2 (E)-4-bromo-N-ethyl-N-methylbut-2-enamide (preparation shown below in Ex. 16 Step-1) for compound 232 to afford compound 16 (0.147 g, 96%).

Step-1: Synthesis of (E)-4-bromo-N-ethyl-N-methylbut-2-enamide

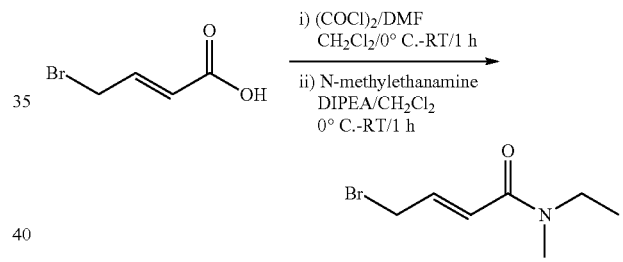

The reaction was carried out according to Scheme 4, Step-2, using (E)-4-bromobut-2-enoic acid (Example 1, Step-7) and N-methylethylamine, to give a crude material, which was purified by column chromatography over 230-400 mesh silica gel using 15% ethyl acetate in n-hexane to afford (E)-4-bromo-N-ethyl-N-methylbut-2-enamide (2.8 g, 44%).

Compound 16: $^1$H NMR (400 MHz, DMSO-d$_6$): δ 13.06 (s, 1H), 8.06 (s, 1H), 7.61 (s, 1H), 7.51 (d, J=8.8 Hz, 1H), 7.22-7.1 (m, 6H), 6.74 (d, J=8.8 Hz, 2H), 6.6-6.65 (m, 3H), 6.46 (d, J=15.2 Hz, 1H), 3.87 (t, J=5.6 Hz, 2H), 3.36-3.35 (m, 3H), 2.96 (s, 2H), 2.82 (s, 2H), 2.79-2.76 (t, J=5.6 Hz, 2H), 2.43-2.38 (m, 2H), 1.06-0.97 (m, 3H), 0.88 (t, J=7.2 Hz, 3H). LCMS: 509.4 [M+H]$^+$.

Example 17: Synthesis of (E)-4-((2-(4-((E)-1-(1H-indazol-5-yl)-2-phenylbut-1-en-1-yl)phenoxy)ethyl)amino)-N-methyl-N-propylbut-2-enamide (Compound 17)

The compound was synthesized following the approach as outlined in Example 9 by substituting into Step-4 (E)-4-bromo-N-methyl-N-propylbut-2-enamide (preparation shown below in Ex. 17 Step-2) for compound 230 to afford compound 17 (0.015 g, 3.1%).

Step-1: Synthesis of (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole

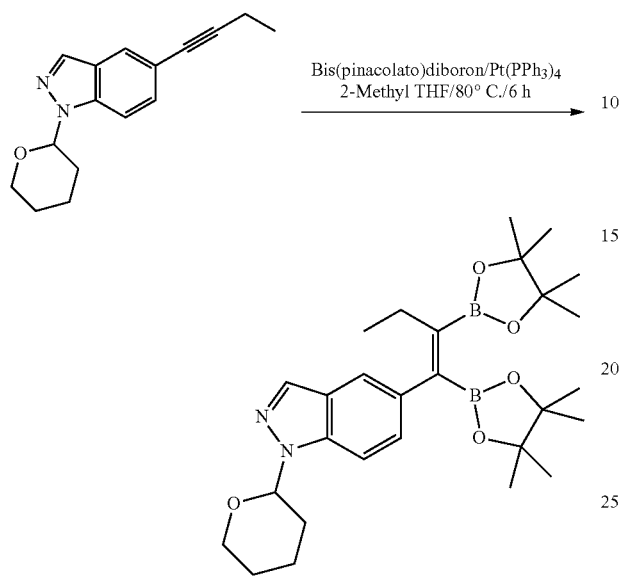

The reaction was carried out according to Scheme 1, Step-3 using 5-(but-1-yn-1-yl)-1-(tetrahydro-2H-pyran-2-yl)-1H-indazole (as prepared in Ex. 1, Step-3) for compound 204. The crude material containing the title compound of Ex. 17 Step-1 was used in next step without further purification (20 g) as brown color oil.

Step-2: Synthesis of (E)-4-bromo-N-methyl-N-propylbut-2-enamide

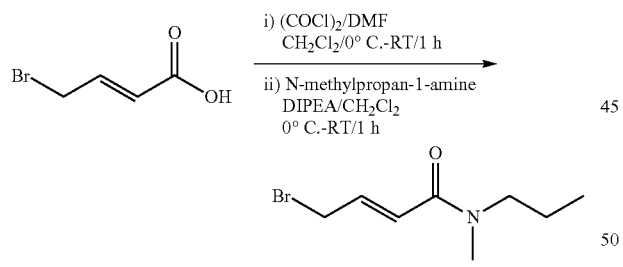

The reaction was carried out according to Scheme 4, Step-2, using (E)-4-bromobut-2-enoic acid (as prepared in Example 1, Step-7.1) for compound 204 and N-methylpropylamine, to give a crude material, which was purified by column chromatography over 230-400 mesh silica gel using 15% ethyl acetate in n-hexane to afford (E)-4-bromo-N-methyl-N-propylbut-2-enamide (0.536 g, 23%).

Compound 17: $^1$H NMR (400 MHz, DMSO-d$_6$): δ 13.08 (s, 1H), 8.07 (s, 1H), 7.61 (s, 1H), 7.51 (d, J=8.4 Hz, 1H), 7.22-7.19 (m, 2H), 7.18-7.11 (m, 4H), 6.75 (d, J=8.8 Hz, 2H), 6.59 (d, J=8.8 Hz, 3H), 7.5-7.44 (d, J=15.2 Hz, 1H), 3.86 (t, J=5.6 Hz, 2H), 3.32-3.30 (m, 4H), 2.96 (s, 1H), 2.83 (s, 2H), 2.67 (d, J=2.0 Hz, 2H), 2.44-2.38 (m, 2H), 1.49-1.45 (m, 2H), 0.88 (t, J=7.2 Hz, 3H), 0.80 (t, 7.2 Hz, 3H). LCMS: 523.2 [M+H]$^+$.

Example 18: Synthesis of (E)-4-((2-(4-((E)-1-(1H-indazol-5-yl)-2-phenylbut-1-en-1-yl)phenoxy)ethyl)amino)-N-(2-hydroxyethyl)-N-methylbut-2-enamide (Compound 18)

The compound was synthesized following the approach as outlined in Example 9 by substituting into Step-4 (E)-4-bromo-N-(2-hydroxyethyl)-N-methylbut-2-enamide (preparation shown below in Ex. 18 Step-1) for compound 230 to afford compound 18 (0.017 g, 3.1%).

Step-1: Synthesis of (E)-4-bromo-N-(2-hydroxyethyl)-N-methylbut-2-enamide

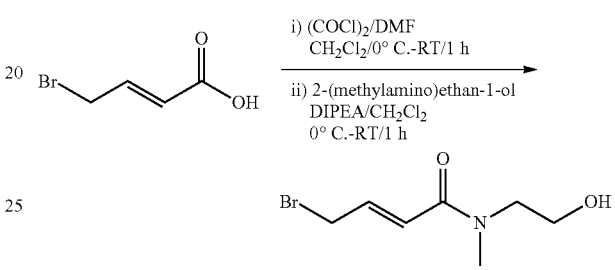

The reaction was carried out according to Scheme 4, Step-2, using (E)-4-bromobut-2-enoic acid (Example 1, Step-7) for compound 220 and 2-(methylamino)ethan-1-ol for compound 221, to give a crude material, which was purified by column chromatography over 230-400 mesh silica gel using 30% ethyl acetate in n-hexane to afford (E)-4-bromo-N-(2-hydroxyethyl)-N-methylbut-2-enamide (1 g, 25%).

Compound 18: $^1$H NMR (400 MHz, DMSO-d$_6$): δ 13.08 (s, 1H), 8.06 (s, 1H), 7.61 (s, 1H), 7.51 (d, J=8.3 Hz, 1H), 7.21 (d, J=7.3 Hz, 2H), 7.19-7.11 (m, 4H), 6.74 (d, J=8.8 Hz, 2H), 6.59 (d, J=8.8 Hz, 3H), 6.53-6.51 (m, 1H), 4.79-4.66 (m, 1H), 3.86 (t, J=5.1 Hz, 2H), 3.49 (d, J=8.8 Hz, 2H), 3.39-3.35 (m, 2H), 3.03 (s, 1H), 2.86 (s, 2H), 2.77 (s, 2H), 2.40 (d, J=7.4 Hz, 2H), 0.87 (t, J=7.3 Hz, 3H). LCMS: 525.2 [M+H]$^+$.

Example 19: Synthesis of (E)-4-((2-(4-((E)-2-(2-chloro-4-fluorophenyl)-1-(3-fluoro-1H-indazol-5-yl)but-1-en-1-yl)phenoxy)ethyl)amino)-N,N-dimethylbut-2-enamide (Example 19)

The compound was synthesized following the approach as outlined in Example 14 by substituting into Step-4 (Z)-5-(1,2-bis(4,4,5,5-tetramethyl-1,3,2-dioxaborolan-2-yl)but-1-en-1-yl)-3-fluoro-1-(tetrahydro-2H-pyran-2-yl)-1H-indazole (as prepared in Example 3, Step-1) for compound 233 and 2-chloro-4-fluoro-1-iodobenzene to afford compound 19 (0.11 g, 12%) as an off-white solid.

Compound 19: $^1$H NMR (400 MHz, DMSO-d$_6$): δ 12.6 (s, 1H), 7.6 (s, 1H), 7.5 (d, J=6.0 Hz, 1H), 7.35-7.31 (m, 2H), 7.25 (d, J=1.2 Hz, 1H), 7.14-7.10 (m, 1H), 6.83 (d, J=6.8 Hz, 2H), 6.63 (d, J=7.4 Hz, 2H), 6.59 (t, J=4 Hz, 1H), 6.5 (d, J=8.8 Hz, 1H), 3.87 (t, J=4.4 Hz, 2H), 2.99 (s, 3H), 2.84 (s, 3H), 2.77 (t, J=4.4 Hz, 2H), 3.3 (m, 2H), 2.4 (q, J=6 Hz, 2H), 0.88 (t, J=6.0 Hz, 3H). LCMS: 565.3 [M+H]$^+$.

Example 20: There is no Example 20

Example 21: Synthesis of (E)-4-((2-(4-((E)-1-(1H-indazol-5-yl)-2-phenylbut-1-en-1-yl)phenoxy)ethyl)amino)-N,N,3-trimethylbut-2-enamide (Compound 21)

The compound was synthesized following the approach as outlined in Example 14 by substituting into Step-4 (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole (as prepared in Example 17, Step-1) for compound 233 and tert-butyl (E)-(4-(dimethylamino)-2-methyl-4-oxobut-2-en-1-yl)(2-(4-iodophenoxy) ethyl)carbamate (preparation shown below in Steps 1-6) for compound 234 to afford compound 21 (35 mg, 10%).

Step-1: synthesis of ethyl (E)-4-hydroxy-3-methylbut-2-enoate

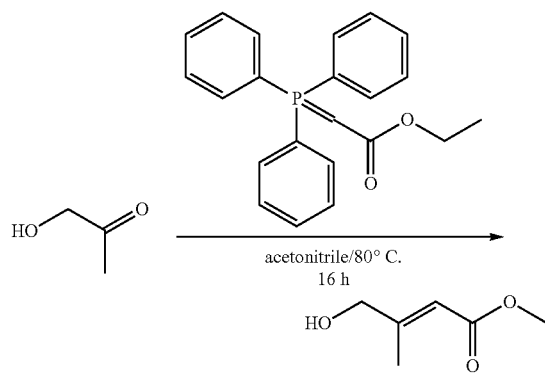

To a stirred solution of 1-hydroxypropan-2-one (10 g, 134 mmol) in acetonitrile (300 mL), was added ethyl 2-(triphenylphosphoranylidene)acetate (56 g, 161 mmol) and the reaction was heated to 80° C. for 16 h. Reaction mixture was evaporated under reduced pressure, diluted with diethyl ether (200 mL) then filtered by using buckner funnel, solid was washed with diethyl ether (2×100 mL), filtrate was evaporated to get the crude product which was purified through column chromatography over silica gel and the column eluting with 15% EtoAc in n-hexane as an eluent to afford the title compound of Ex. 21 Step-1 as a colourless waxy liquid (13.8 g, 71%).

Step-2: Synthesis of ethyl (E)-4-bromo-3-methylbut-2-enoate

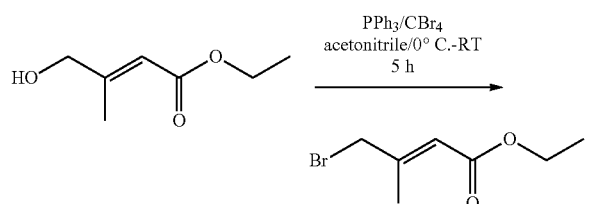

To an ice cooled solution of ethyl (E)-4-hydroxy-3-methylbut-2-enoate (10 g, 6.9 mmol) in acetonitrile (20 mL), were added triphenyl phosphine (18.2 g, 6.9 mmol) and carbon tetra bromide (23 g, 6.9 mmol) and the reaction was allowed to room temperature for 5 h. Reaction mixture was concentrated to get the crude product, which was purified through column chromatography over silica gel and the column eluting with 10% EtoAc in n-hexane as a eluent to afford the title compound of Ex. 21 Step-2 as a colourless oil (8.5 g, 59%).

Step-3: Synthesis of ethyl (E)-4-((2-(4-iodophenoxy)ethyl)amino)-3-methylbut-2-enoate

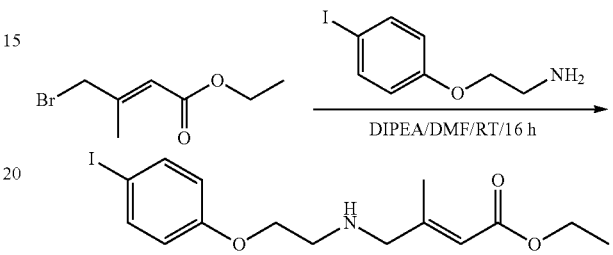

The reaction was carried out according to Scheme 3, Step-3 to give a crude product, which was purified through column chromatography over silica gel, and the column was eluting with 30% EtoAc in n-hexane as a eluent to get the title compound of Ex. 21 Step-3 (3.1 g, 42%).

Step-4: Synthesis of ethyl (E)-4-((tert-butoxycarbonyl) (2-(4-iodophenoxy)-ethyl)amino)but-2-enoate

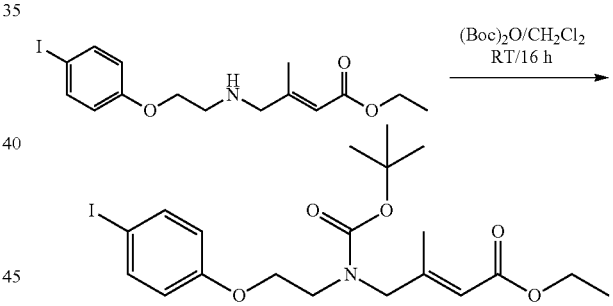

The reaction was carried out according to Scheme 3, Step-4 to give a crude product which was purified through column chromatography over silica gel and the column eluting with 20% EtoAc in n-hexane as an eluent to get the title compound of Ex. 21 Step-4 as colourless oil (3.8 g, 97%).

Step-5: Synthesis of (E)-4-((tert-butoxycarbonyl) (2-(4-iodophenoxy)ethyl)amino)-3-methylbut-2-enoic acid

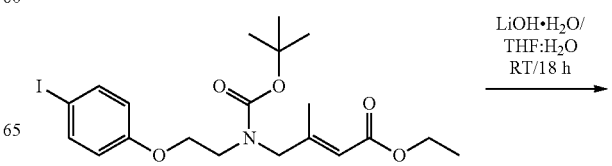

-continued

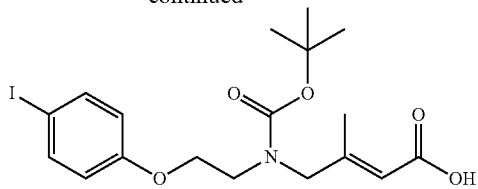

To a stirred solution ethyl (E)-4-((tert-butoxycarbonyl)(2-(4-iodophenoxy) ethyl)amino)but-2-enoate (3.8 g, 7.7 mmol) in THF:H$_2$O (40:10 mL), was added lithium hydroxide monohydrate (0.65 g, 15.5 mmol) and the reaction was stirred for 18 h at room temperature. Water was added to the reaction mixture, washed with diethyl ether (100 mL) aqueous layer was adjusted to pH 2-3 by using 10% citric acid then extracted with dichloromethane (2×100 mL), organic layer was dried over anhydrous sodium sulphate, concentrated to get the title compound of Ex. 21 Step-5 (1.7 g, 48%).

Step-6: Synthesis of tert-butyl (E)-(4-(dimethylamino)-2-methyl-4-oxobut-2-en-1-yl)(2-(4-iodophenoxy) ethyl)carbamate

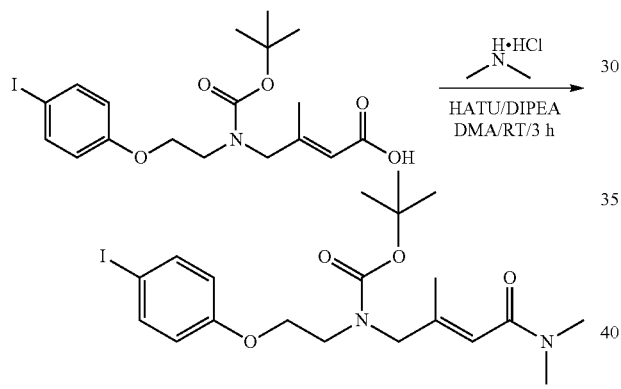

The reaction was carried out as described in Example 1 by substituting into Step-7.2 (E)-4-((tert-butoxycarbonyl)(2-(4-iodophenoxy)ethyl)amino)-3-methylbut-2-enoic acid for compound 235 and substituting DMA for CH$_2$Cl$_2$ as the solvent to afford the title compound of Ex. 21 Step-6 (2.5 g, crude).

Compound 21: $^1$H NMR (400 MHz, DMSO-d$_6$): δ 13.08 (s, 1H), 8.07 (s, 1H), 7.61 (s, 1H), 7.51 (d, J=8.8 Hz, 1H), 7.22-7.21 (m, 2H), 7.19-7.11 (m, 4H), 6.74 (d, J=8.4 Hz, 2H), 6.59 (d, J=8.8 Hz, 2H), 6.04 (s, 1H), 3.87 (t, J=5.2 Hz, 2H), 3.14 (s, 2H), 2.9 (s, 3H), 2.8 (s, 3H), 2.74 (t, J=5.2 Hz, 2H), 2.43-2.38 (m, 2H), 1.75 (s, 3H), 0.88 (t, J=6.8 Hz, 3H). LCMS: 509.3[M+H]$^+$.

Example 22: Synthesis of (Z)-4-((2-(4-((E)-1-(1H-indazol-5-yl)-2-phenylbut-1-en-1-yl)phenoxy)ethyl) amino)-N,N-dimethylbut-2-enamide (Compound 22)

The compound was synthesized following the approach as outlined in Example 14 by substituting into Step-4 (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole (as prepared in Example 17, Step-1) for compound 233 and tert-butyl (Z)-(4-(dimethylamino)-4-oxobut-2-en-1-yl)(2-(4-iodophenoxy) ethyl)carbamate (preparation shown below in Ex. 22 Steps 1-7) for compound 234 to afford compound 22 (0.27 g, 38%).

Step-1: Synthesis of 1-(2-bromoethoxy)-4-iodobenzene

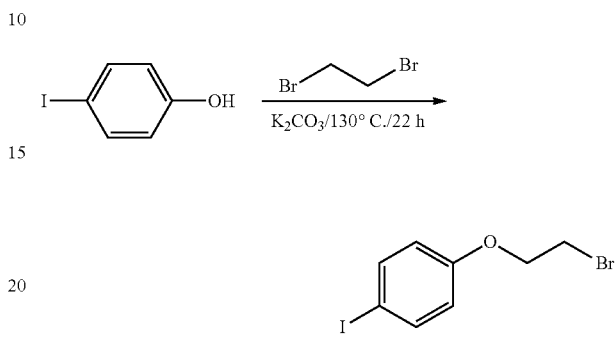

To a stirred solution of 4-iodophenol (20 g, 90 mmol) was added potassium carbonate (9.4 g, 136 mmol) and stirred for 10 min at 0° C., to the above mixture 1,2-dibromoethane (145 g, 772 mmol) was added. The contents were stirred at 130° C. for 22 h. After completion of reaction, reaction mixture was poured onto ice cold water, and extracted with ethyl acetate. The combined organic layers were washed with water followed by saturated NaCl solution, dried over anhydrous Na$_2$SO$_4$ and concentrated under reduced pressure. The crude material was purified by column chromatography over 230-400 mesh silica using 3% EtOAc in n-hexane as an eluent to obtain desired compound 1-(2-bromoethoxy)-4-iodobenzene (20.1 g, 67.6%).

Step-2: Synthesis of 2-((2-(4-iodophenoxy)ethyl) amino)ethan-1-ol

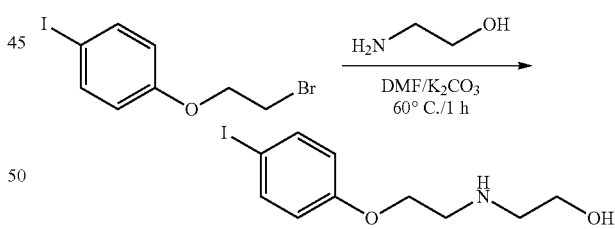

To a stirred solution of 1-(2-bromoethoxy)-4-iodobenzene (20 g, 61 mmol) in DMF (100 mL) was 2-aminoethan-1-ol (37.36 g, 610 mmol). The reaction mixture was stirred for 1 h at 60° C., after completion of reaction (monitored by TLC), reaction mixture was diluted with cold water (50 mL) and extracted with ethyl acetate. The combined organic layers were washed with water followed by saturated NaCl solution, dried over anhydrous Na$_2$SO$_4$ and concentrated under reduced pressure. The crude material was purified by column chromatography over 230-400 mesh silica using 20% MeOH in dichloromethane as an eluent to obtain desired compound 2-((2-(4-iodophenoxy)ethyl)amino) ethan-1-ol (13.2 g, 70.58%).

Step-3: Synthesis of tert-butyl (2-hydroxyethyl)(2-(4-iodophenoxy)ethyl)carbamate

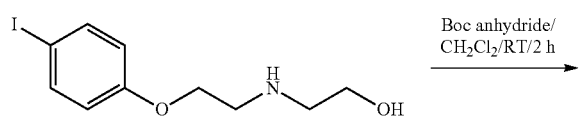

The reaction was carried out according to Scheme 4, Step-4 to give a crude material, which was purified by column chromatography over 230-400 mesh silica using 7% MeOH in dichloromethane as an eluent to obtain desired compound tert-butyl (2-hydroxyethyl)(2-(4-iodophenoxy) ethyl)carbamate (16.7 g, 95.9%).

Step-4: Synthesis of tert-butyl (2-(4-iodophenoxy) ethyl) (2-oxoethyl)carbamate

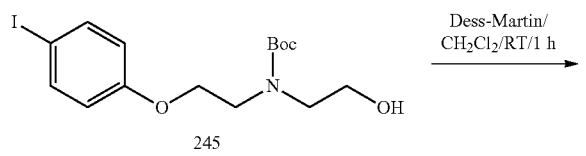

To a stirred solution of tert-butyl (2-hydroxyethyl)(2-(4-iodophenoxy)ethyl)carbamate (6.7 g, 16.4 mmol) in dichloromethane (150 mL) was added Dess-Martin periodinane (10.46 g, 24.6 mmol). The reaction mixture was stirred for 1 h at room temperature, after completion of reaction (monitored by TLC), reaction mixture was diluted with 1:1 mixture of hypo and $NaHCO_3$ solution and extracted with dichloromethane (100 mL). The organic layer was washed with water followed by saturated NaCl solution, dried over anhydrous $Na_2SO_4$ and concentrated under reduced pressure. The crude product was used in next step without further purification (5.9 g, 89.9%).

Step-5: Synthesis of ethyl ethyl (Z)-4-((tert-butoxycarbonyl) (2-(4-iodophenoxy)ethyl)amino)but-2-enoate

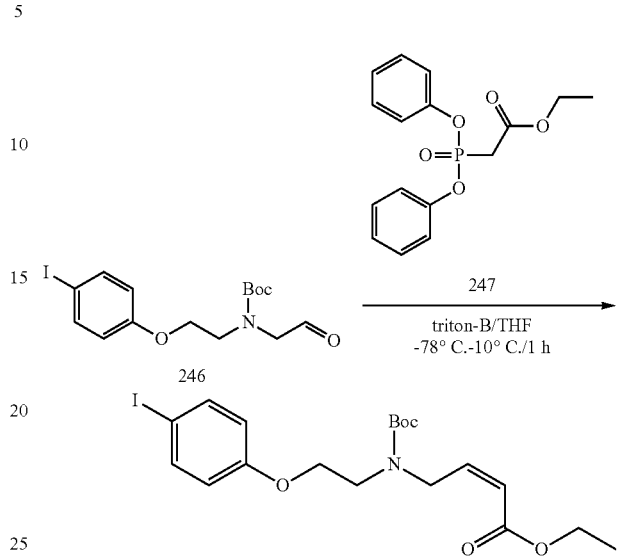

To a stirred solution of ethyl 2-(diphenoxyphosphoryl) acetate (4.71 g, 14.7 mmol) and triton-B (9.39 mL, 17.7 mmol) in THF (70 mL) at −78° C., tert-butyl (2-(4-iodophenoxy)ethyl)(2-oxoethyl)carbamate (5.97 g, 14.7 mmol) in THF (30 mL) was added was added dropwise. The reaction mixture was stirred for 1 h at 10° C., after completion of reaction (monitored by TLC), reaction mixture was diluted with ammonium chloride solution and extracted with EtOAc (100 mL). The organic layer was washed with water followed by saturated NaCl solution, dried over anhydrous $Na_2SO_4$ and concentrated under reduced pressure. The crude product was purified by column chromatography over 230-400 mesh silica-gel by eluting with 9% EtOAc in n-hexane to afford title compound of Ex. 22 Step-5 (0.82 g, 11.7%).

Step-6: Synthesis of (Z)-4-((tert-butoxycarbonyl) (2-(4-iodophenoxy)ethyl)amino) but-2-enoic acid

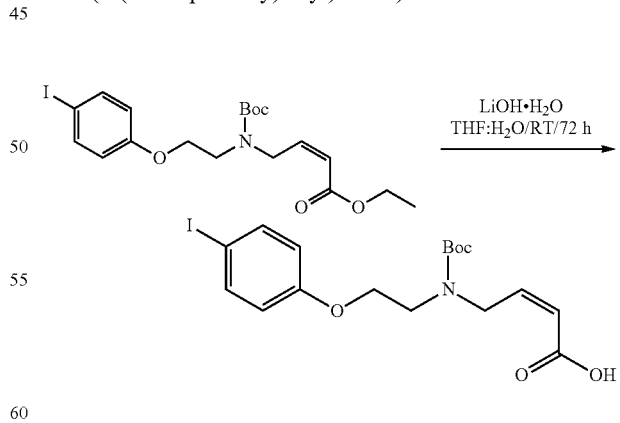

To a stirred solution of ethyl (Z)-4-((tert-butoxycarbonyl) (2-(4-iodophenoxy)ethyl) amino)but-2-enoate (0.8 g, 1.6 mmol) in THE (10 mL) was added $LiOH.H_2O$ (0.353 g, 8.4 mmol) and water (5 mL). The reaction mixture was stirred for 72 h at room temperature, after completion of reaction (monitored by TLC), reaction mixture was diluted with water and extracted with dichloromethane (100 mL). The organic layer was washed with water followed by saturated NaCl solution, dried over anhydrous Na$_2$SO$_4$ and concentrated under reduced pressure. The crude product was used in next step without further purification (0.705 g, 93.7%).

Step-7: Synthesis of tert-butyl (Z)-(4-(dimethylamino)-4-oxobut-2-en-1-yl) (2-(4-iodophenoxy) ethyl)carbamate

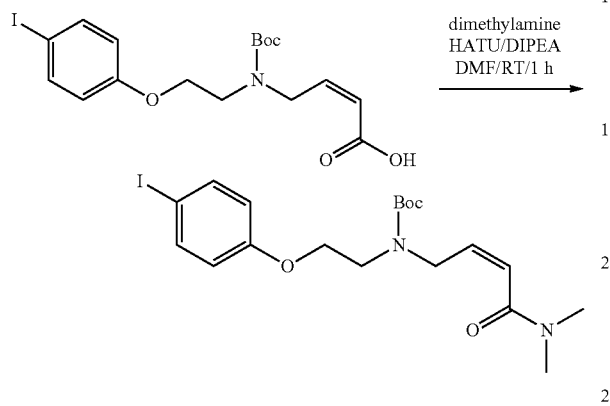

The reaction was carried out as described in Example 1, Step-7.2 by substituting (Z)-4-((tert-butoxycarbonyl)(2-(4-iodophenoxy)ethyl)amino) but-2-enoic acid for compound 235 and substituting DMF for CH$_2$Cl$_2$ as the solvent to give a crude product, which was purified by column chromatography over 230-400 mesh silica-gel by eluting with 40-70% EtOAc in n-hexane to afford title compound of Ex. 22 Step-7 (0.97 g, 70.8%).

Compound 22: $^1$H NMR (400 MHz, DMSO-d$_6$): δ 13.06 (s, 1H), 8.06 (s, 1H), 7.61 (s, 1H), 7.51 (d, J=8.8 Hz, 2H), 7.12-7.10 (m, 4H), 674 (d, J=8.8 Hz, 2H), 6.58 (d, J=8.8 Hz, 2H), 6.15 (d, J=11.6 Hz, 2H), 5.93-5.86 (m, 1H), 3.84 (t, J=5.4 Hz, 2H), 3.40 (dd, J$_1$=6.4 Hz, J$_2$=1.6 Hz, 2H), 2.93 (s, 3H), 2.80 (s, 3H), 2.77 (t, J=5.6 Hz, 2H), 2.40 (q, J=7.3 Hz, 2H), 0.88 (t, J=7.2 Hz, 3H). LCMS: 495.3 [M+H]$^+$.

Example 23: Synthesis of (E)-4-((2-(4-((E)-2-cyclobutyl-1-(1H-indazol-5-yl)-2-phenylvinyl)phenoxy) ethyl)amino)-1-morpholinobut-2-en-1-one (Compound 23)

The reaction was carried out following the approach as outlined by Example 2, Step-7, by substituting into Ex. 2, Step-7 (E)-2-(4-(2-cyclobutyl-1-(1H-indazol-5-yl)-2-phenylvinyl)phenoxy)ethanamine (as prepared in Example 13, Step-7) for compound 237 and (E)-4-bromo-1-morpholinobut-2-en-1-one (as prepared in Example 15, Step-1) for compound 238 to afford Compound 23 (0.045 g, 5%).

Compound 23: $^1$H NMR (400 MHz, DMSO-d$_6$): δ 13.06 (s, 1H), 8.07 (s, 1H), 7.58 (s, 1H), 7.51 (d, J=8.8 Hz, 1H), 7.27-7.23 (m, 2H), 7.17-7.13 (m, 2H), 7.11-7.08 (m, 2H), 6.77 (d, J=8.8 Hz, 2H), 6.66-6.61 (m, 1H), 6.53 (d, J=8.8 Hz, 3H), 3.82 (t, J=5.6 Hz, 2H), 3.51-3.49 (m, 8H), 3.40 (t, J=8.5 Hz, 1H), 3.29 (s, 2H), 2.74 (t, J=5.7 Hz, 2H), 1.82-1.76 (m, 4H), 1.57-1.54 (m, 1H), 1.23 (m, 1H). LCMS: 563.3 [M+H]$^+$.

Example 24: Synthesis of (E)-4-((2-(4-((E)-2-cyclobutyl-1-(4-fluoro-1H-indazol-5-yl)-2-phenylvinyl) phenoxy)ethyl)amino)-N,N-dimethylbut-2-enamide (Compound 24)

The compound was synthesized following the approach as outlined in Example 14 by substituting into Step-1 5-bromo-4-fluoro-1-(tetrahydro-2H-pyran-2-yl)-1H-indazole (preparation shown below in Ex. 24 Step-1) for compound 240 to afford Compound 24 (0.03 g, 5%).

Step-1: Synthesis of 5-bromo-4-fluoro-1-(tetrahydro-2H-pyran-2-yl)-1H-indazole

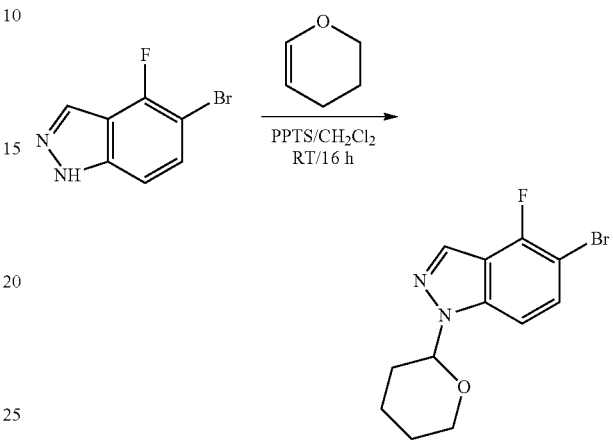

The reaction was carried out according to Scheme 1, Step-1 to give a crude material which was purified by column chromatography over 230-400 mesh silica using 3-4% ethyl acetate in n-hexane to afford 5-bromo-4-fluoro-1-(tetrahydro-2H-pyran-2-yl)-1H-indazole (5 g, 72%) as a brown oil.

Compound 24: $^1$H NMR (400 MHz, DMSO-d$_6$): δ 13.4 (s, 1H), 8.2 (s, 1H), 7.39 (d, J=8.8 Hz, 1H), 7.29-2.26 (m 2H), 7.2-7.16 (m, 2H), 7.11 (d, J=7.2 Hz, 2H), 6.8 (d, J=8.8 Hz, 2H), 6.6-6.54 (m, 3H), 6.52 (d, J=16.0 Hz, 1H), 3.84 (t, J=5.6 Hz, 2H), 3.3-3.26 (m, 3H), 2.97 (s, 3H), 2.83 (s, 3H), 2.76 (t, J=5.6 Hz, 2H), 1.8-1.7 (m, 4H), 1.56-1.5 (m, 1H), 1.34-1.3 (m, 1H). LCMS: 539.3 [M+H]$^+$.

Example 25: Synthesis of (E)-4-((2-((5-((Z)-1-(1H-indazol-5-yl)-2-phenylbut-1-en-1-yl)pyridin-2-yl) oxy) ethyl) amino)-N,N-dimethylbut-2-enamide The compound was synthesized following the approach as outlined in Example 14 by substituting into Step-4 (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole (as prepared in Example 17, Step-1) for compound 233 and tert-butyl (E)-(4-(dimethylamino)-4-oxobut-2-en-1-yl)(2-((5-iodopyridin-2-yl)oxy) ethyl)carbamate (preparation shown below in Ex. 25 Steps 1-2) for compound 234 to afford Compound 25 (80 mg, 18%) as an off-white solid.

Step-1: Synthesis of tert-butyl (2-((5-iodopyridin-2-yl)oxy)ethyl)carbamate

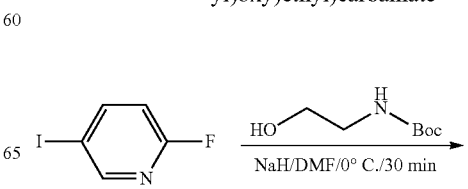

141
-continued

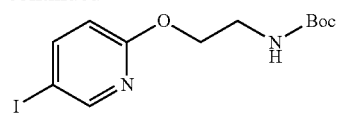

To a stirred solution of 2-fluoro-5-iodopyridine (5 g, 22.4 mmol) in DMF (25 mL) was added sodium hydride (0.7 g, 33.5 mmol) and stirred for 10 min at 0° C., to the above mixture tert-butyl (2-hydroxyethyl)carbamate (1.8 g, 11.2 mmol) was added. The contents were stirred at 0° C. for 30 min. After completion of reaction, reaction mixture was poured onto ice cold water, and extracted with ethyl acetate. The combined organic layers were washed with water followed by saturated NaCl solution, dried over anhydrous Na$_2$SO$_4$ and concentrated under reduced pressure. The crude material was purified by column chromatography over 230-400 mesh silica using 15% EtOAc in n-hexane as an eluent to obtain desired compound tert-butyl (2-((5-iodopyridin-2-yl)oxy)ethyl)carbamate as an off-white solid (3.5 g, 43%).

Step-2: Synthesis of tert-butyl (E)-(4-(dimethylamino)-4-oxobut-2-en-1-yl) (2-((5-iodopyridin-2-yl)oxy)ethyl)carbamate

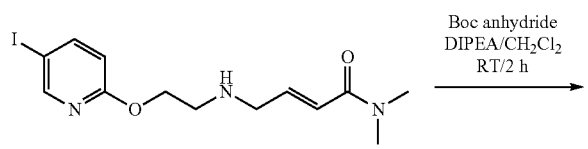

The reaction was carried out following the approach as outlined by Example 14, Step-3.1, by substituting into Ex. 14, Step-3.1 tert-butyl (2-((5-iodopyridin-2-yl)oxy)ethyl)carbamate for compound 241 to deliver the title compound of Ex. 25 Step-2 (3.6 g, 47%).

Compound 25: $^1$H NMR (400 MHz, DMSO-d$_6$): δ 13.1 (s, 1H), 8.1 (s, 1H), 7.65 (s, 1H), 7.58 (d, J=2.0 Hz, 1H), 7.54 (d, J=8.0 Hz, 1H), 7.23 (d, J=6.8 Hz, 2H), 7.17-7.12 (m, 5H), 6.6-6.5 (m, 1H), 6.5-6.47 (m, 2H), 4.1 (t, J=5.6 Hz, 2H), 3.3 (m, 2H), 2.98 (s, 3H), 2.84 (s, 3H), 2.75 (t, J=5.6 Hz, 2H), 2.46-2.40 (m, 2H), 0.89 (t, J=7.2 Hz, 3H). LCMS: 496.3 [M+H]$^+$.

142

Example 26: Synthesis of (E)-4-((2-(4-((E)-1-(1H-indazol-5-yl)-2-(o-tolyl)but-1-en-1-yl)phenoxy)ethyl)amino)-N-(2-hydroxyethyl)-N-methylbut-2-enamide (Compound 26)

Step-1: Synthesis of (E)-5-(1-(4-(2-chloroethoxy)phenyl)-2-(o-tolyl)but-1-en-1-yl)-1-(tetrahydro-2H-pyran-2-yl)-1H-indazole

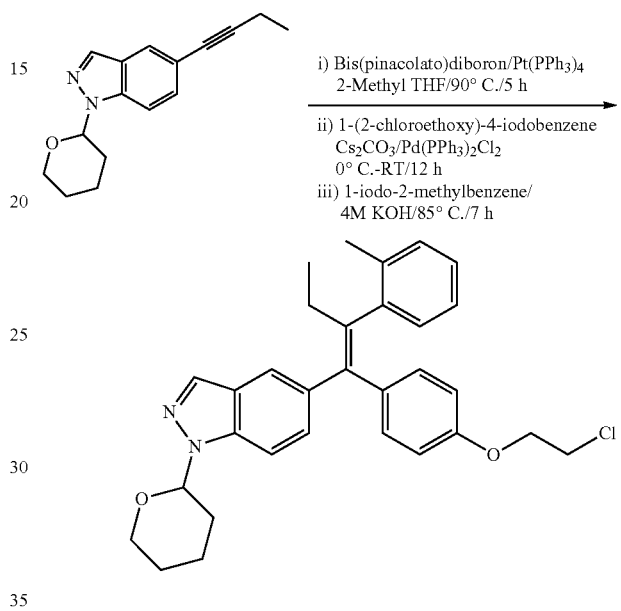

The same procedures as described in Example 5 by substituting into Step-1 (i) 5-(but-1-yn-1-yl)-1-(tetrahydro-2H-pyran-2-yl)-1H-indazole (as prepared in Example 1, Step-3) for compound 242, (ii) 1-(2-chloro-ethoxy)-4-iodobenzene for compound 243, and (iii) 1-iodo-2-methylbenzene for compound 244, to give crude material, which was purified by column chromatography over 230-400 mesh silica gel using 5% EtOAc in n-hexane to afford the title compound of Ex. 26 Step-1 (2.9 g, 29.8%) as an off-white solid.

Step-2: Synthesis of (E)-2-((2-(4-(1-(1-(tetrahydro-2H-pyran-2-yl)-1H-indazol-5-yl)-2-(o-tolyl)but-1-en-1-yl)phenoxy)ethyl)amino)ethan-1-ol

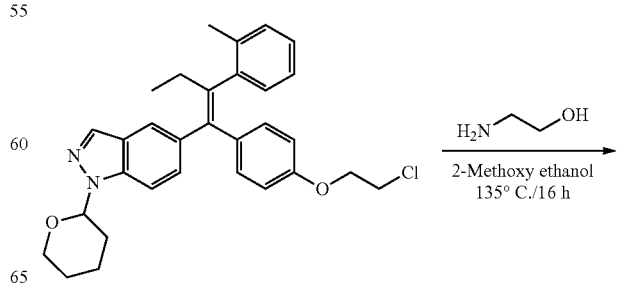

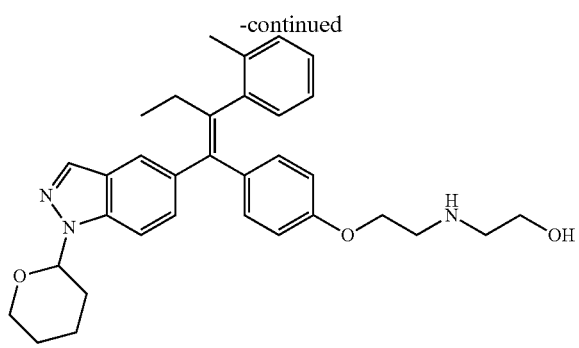

To a stirred solution of (E)-5-(1-(4-(2-chloroethoxy)phenyl)-2-(o-tolyl)but-1-en-1-yl)-1-(tetrahydro-2H-pyran-2-yl)-1H-indazole (2.8 g, 5.6 mmol) in 2-methoxy ethanol (28 mL) was 2-aminoethan-1-ol (3.3 mL, 56 mmol). The reaction mixture was stirred for 16 h at 135° C., after completion of reaction (monitored by TLC), reaction mixture was diluted with cold water (50 mL) and extracted with ethyl acetate. The combined organic layers were washed with water followed by saturated NaCl solution, dried over anhydrous $Na_2SO_4$ and concentrated under reduced pressure. The crude product was used in next step without further purification (3.2 g, crude).

Step-3: Synthesis of tert-butyl (E)-(2-hydroxyethyl)(2-(4-(1-(1-(tetrahydro-2H-pyran-2-yl)-1H-indazol-5-yl)-2-(o-tolyl)but-1-en-1-yl)phenoxy)ethyl)carbamate

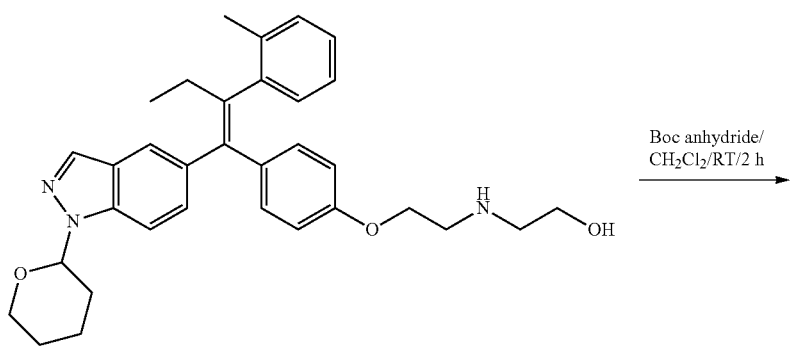

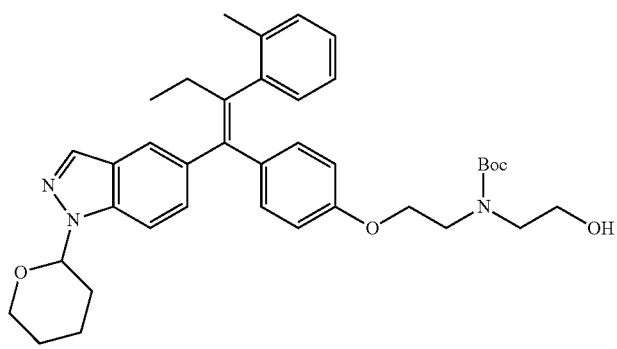

The reaction was carried out according to Scheme 3, Step-4 to give a crude product which was used in next step without further purification (3.8 g, crude).

Step-4: Synthesis of tert-butyl (E)-(2-oxoethyl)(2-(4-(1-(1-(tetrahydro-2H-pyran-2-yl)-1H-indazol-5-yl)-2-(o-tolyl)but-1-en-1-yl)phenoxy)ethyl)carbamate

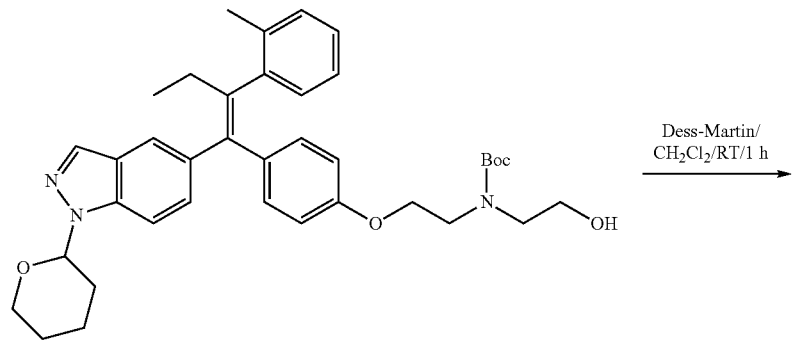

306

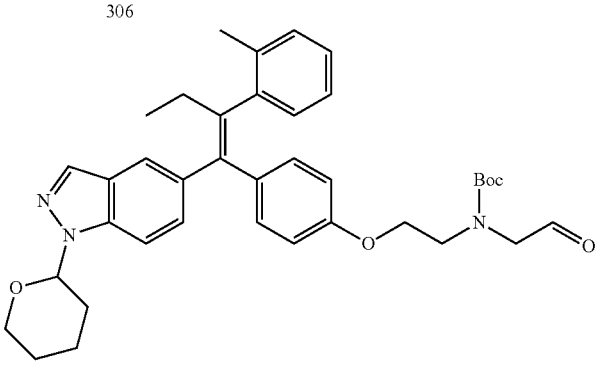

307

The reaction was carried out as described in Example 22, Step-4, substituting compound 306 for compound 245 to give a crude product which was purified by column chromatography over 100-200 mesh silica-gel by eluting with 30% EtOAc in n-hexane to afford the title compound of Ex. 26 Step-4 (1.5 g, 40%).

Step-5: Synthesis of ethyl (E)-4-((tert-butoxycarbonyl) (2-(4-((E)-1-(1-(tetrahydro-2H-pyran-2-yl)-1H-indazol-5-yl)-2-(o-tolyl)but-1-en-1-yl)phenoxy) ethyl)amino)but-2-enoate

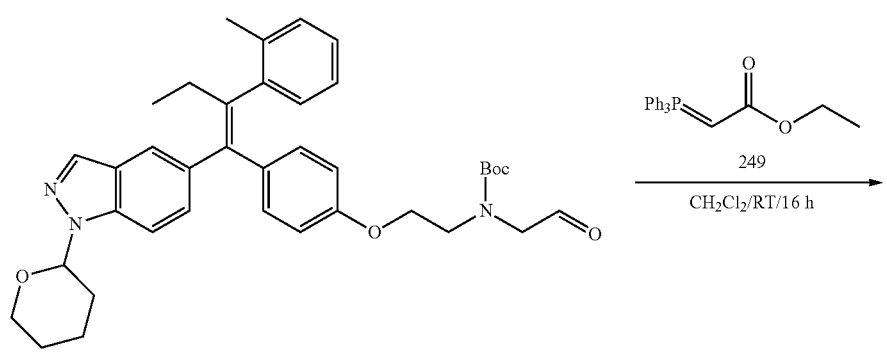

248

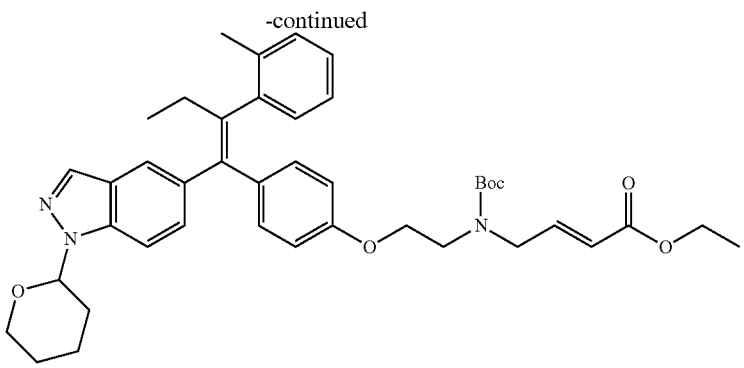

The reaction was carried out as described in Example 22, Step-5, substituting compound 248 for compound 246 and substituting compound 249 for compound 247 to give a crude product which was purified by column chromatography over 230-400 mesh silica-gel by eluting with 20% EtOAc in n-hexane to afford title compound of Ex. 26 Step-5 (1.37 g, 82%).

Step-6: Synthesis of (E)-4-((tert-butoxycarbonyl)(2-(4-((E)-1-(1-(tetrahydro-2H-pyran-2-yl)-1H-indazol-5-yl)-2-(o-tolyl)but-1-en-1-yl)phenoxy)ethyl)amino)but-2-enoic acid To a stirred solution of ethyl (E)-4-((tert-butoxycarbonyl)(2-(4-((E)-1-(1-(tetrahydro-2H-pyran-2-yl)-1H-indazol-5-yl)-2-(o-tolyl)but-1-en-1-yl)phenoxy)ethyl)amino)but-2-enoate (0.38 g, 0.54 mmol) in THF (16 mL) was added LiOH.H$_2$O (0.15 g, 3.78 mmol) and water (4 mL). The reaction mixture was stirred for 60 h at room temperature, after completion of reaction (monitored by TLC), reaction mixture was diluted with water and extracted with dichloromethane (100 mL). The organic layer was washed with water followed by saturated NaCl solution, dried over anhydrous Na$_2$SO$_4$ and concentrated under reduced pressure. The crude product was purified by combi-flash to afford title compound of Ex. 26 Step-7 (0.33 g, 91%).

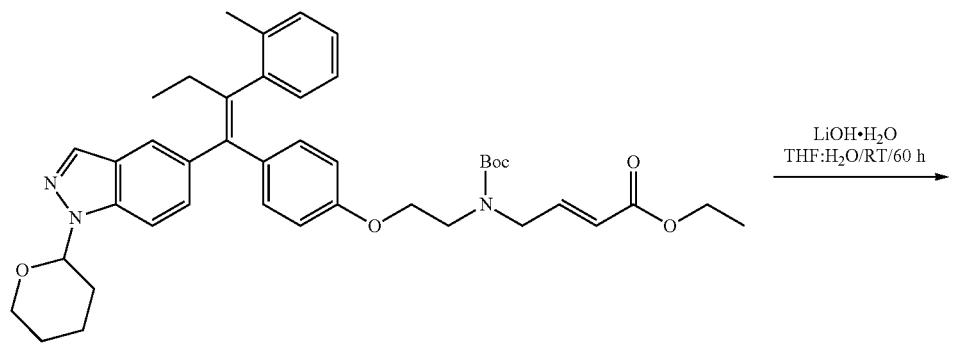

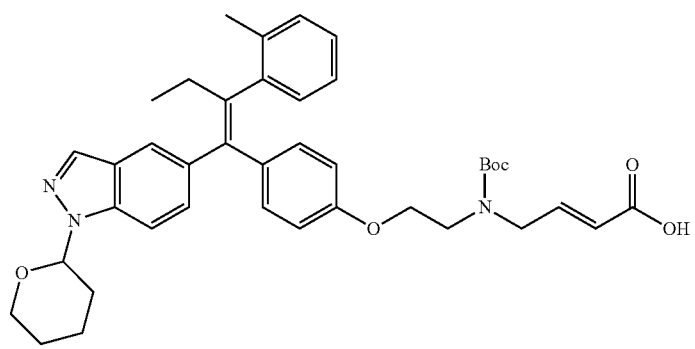

Step-8: Synthesis of tert-butyl ((E)-4-((2-hydroxy-ethyl)(methyl)amino)-4-oxobut-2-en-1-yl) (2-(4-((E)-1-(1-(tetrahydro-2H-pyran-2-yl)-1H-indazol-5-yl)-2-(o-tolyl)but-1-en-1-yl)phenoxy)ethyl) carbamate

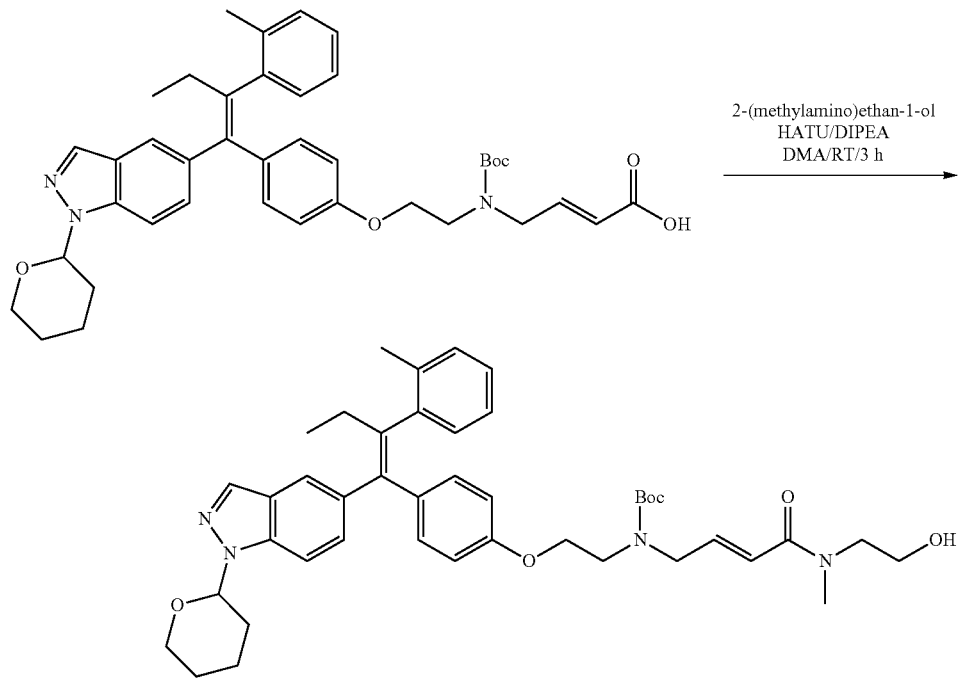

To a stirred solution of (E)-4-((tert-butoxycarbonyl)(2-(4-((E)-1-(1-(tetrahydro-2H-pyran-2-yl)-1H-indazol-5-yl)-2-(o-tolyl)but-1-en-1-yl)phenoxy)ethyl)amino)but-2-enoic acid (0.33 g, 0.49 mmol) in DMA (14 mL) was added DIPEA (0.25 mL, 1.47 mmol), HATU (0.18 g, 0.49 mmol) and 2-(methylamino)ethan-1-ol (0.036 g, 0.49 mmol). The reaction mixture was stirred for 3 h at room temperature, after completion of reaction (monitored by TLC), reaction mixture was diluted with water and extracted with dichloromethane (100 mL). The organic layer was washed with water followed by saturated NaCl solution, dried over anhydrous Na$_2$SO$_4$ and concentrated under reduced pressure. The crude product was purified by column chromatography over 230-400 mesh silica-gel by eluting with 3% MeOH in dichloromethane to afford title compound of Ex. 26 Step-8 (0.4 g, crude).

Step-9: Synthesis of (E)-4-((2-(4-((E)-1-(1H-indazol-5-yl)-2-(o-tolyl)but-1-en-1-yl)phenoxy)ethyl)amino)-N-(2-hydroxyethyl)-N-methylbut-2-enamide (Compound 26)

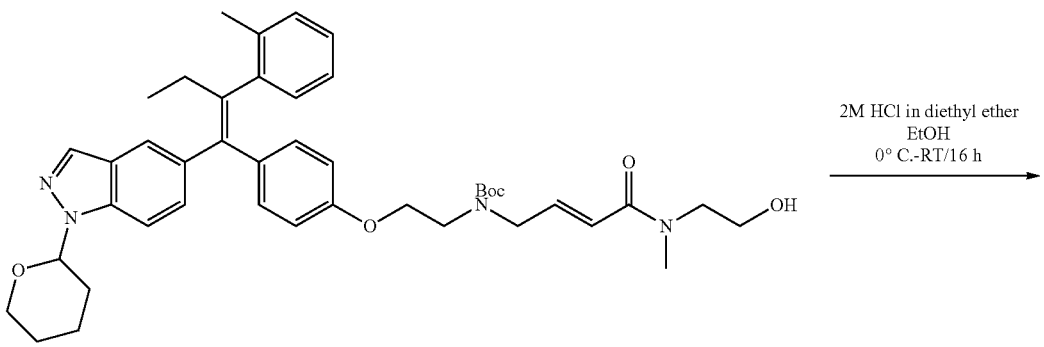

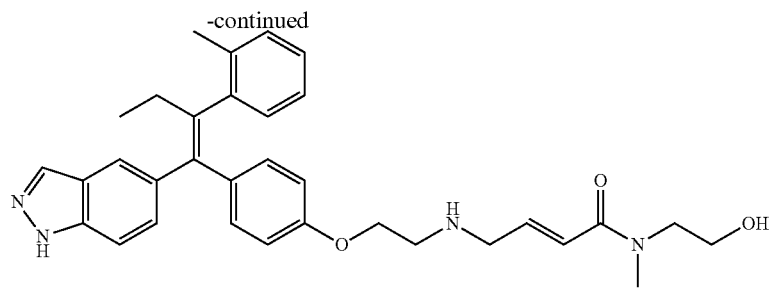

26

The reaction was carried out according to Scheme 2, Step-6c, substituting compound 250 for compound 211c to give a crude product which was purified by preparative HPLC to afford the Compound 26 (20 mg).

Compound 26: $^1$H NMR (400 MHz, DMSO-d$_6$): δ 13.07 (s, 1H), 8.08 (s, 1H), 7.65 (s, 1H), 7.53 (d, J=8.4 Hz, 1H), 7.23 (d, J=8.8 Hz, 1H), 7.16-7.12 (m, 2H), 7.09-7.03 (m, 3H), 6.74 (d, J=8.8 Hz, 2H), 6.63-6.46 (m, 4H), 4.76-4.64 (m, 1H), 3.84 (t, J=5.2 Hz, 2H), 3.50-3.47 (m, 2H), 3.39-3.36 (m, 2H), 3.02 (s, 4H), 2.86 (s, 1H), 2.75-2.67 (m, 1H), 2.33-2.30 (m, 2H), 2.10 (s, 3H), 2.0 (bs, 1H), 0.86 (t, J=7.4 Hz, 3H). LCMS: 539.4 [M+H]$^+$.

Example 27: There is no Example 27

Example 28: Synthesis of (E)-4-((2-(4-((E)-2-(2-chloro-4-fluorophenyl)-1-(3-fluoro-(3-fluoro-1H-indazol-5-yl)but-1-en-1-yl)phenoxy)ethyl)amino)-N-(2-hydroxyethyl)-N-methylbut-2-enamide (Compound 28)

Step-1: Synthesis of (E)-4-((2-(4-((E)-2-(2-chloro-4-fluorophenyl)-1-(3-fluoro-1H-indazol-5-yl)but-1-en-1-yl)phenoxy)ethyl)amino)-N-(2-hydroxyethyl)-N-methylbut-2-enamide

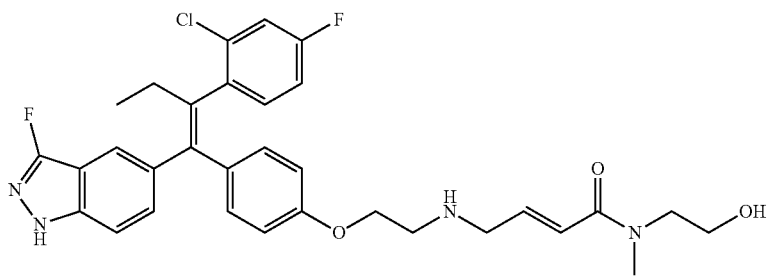 [SMILES: CC/C(=C(/c1ccc(OCCNC/C=C/C(=O)N(C)CCO)cc1)c1ccc2[nH]nc(F)c2c1)c1ccc(F)cc1Cl]

The compound was synthesized by following the approach as outlined in Example 3 by (i) substituting into Step-4 2-chloro-4-fluoro-1-iodobenzene for compound 227 and (ii) substituting into Step-6 of Ex. 3 (E)-4-bromo-N-(2-hydroxyethyl)-N-methylbut-2-enamide (as prepared in Example 18, Step-1) for compound 251 to afford the title compound as a crude (0.5 g) and used without further purification.

Step-2: Synthesis of tert-butyl (2-(4-((E)-2-(2-chloro-4-fluorophenyl)-1-(3-fluoro-1H-indazol-5-yl)but-1-en-1-yl)phenoxy)ethyl) ((E)-4-((2-hydroxy-ethyl)(methyl)-amino)-4-oxobut-2-en-1-yl) carbamate

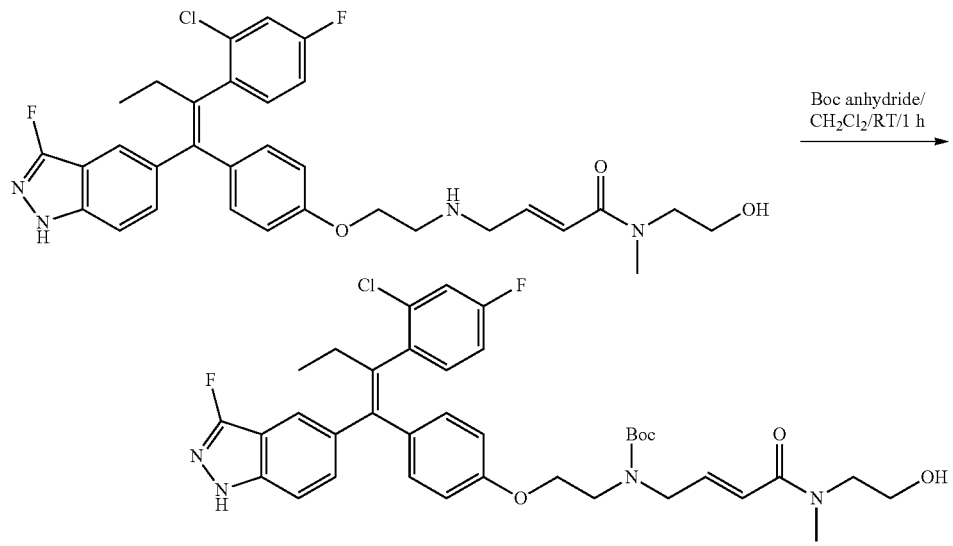

The reaction was carried out according to Scheme 2, Step-5 to give a crude product which was purified by preparative HPLC to obtain pure title compound of Step-2 Ex. 28 (0.28 g, 48%).

Step-3: Synthesis of (E)-4-((2-(4-((E)-2-(2-chloro-4-fluorophenyl)-1-(3-fluoro-1H-indazol-5-yl)but-1-en-1-yl)phenoxy)ethyl)amino)-N-(2-hydroxyethyl)-N-methylbut-2-enamide (Compound 28)

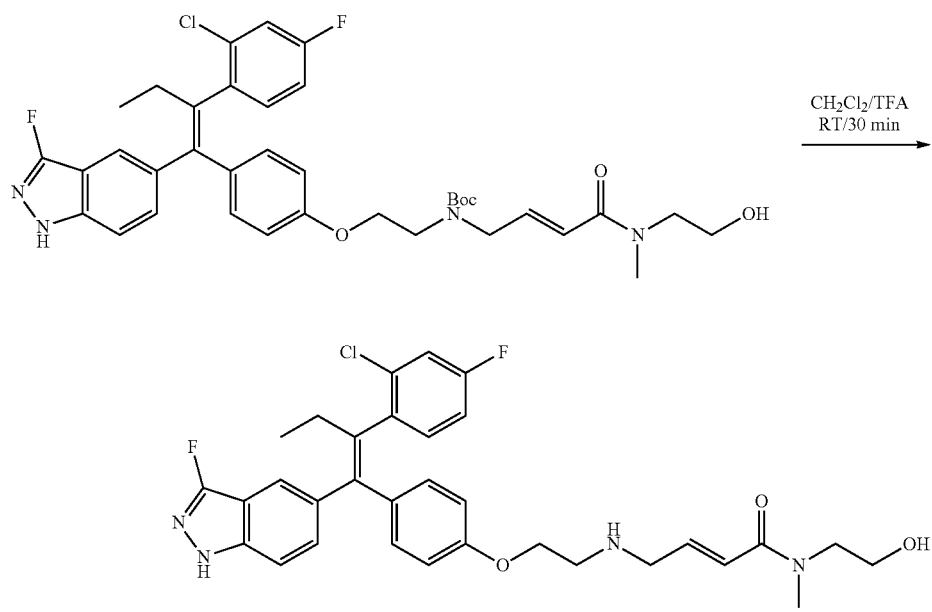

The reaction was carried out according to Scheme 2, Step-6b to give a crude product, which was purified by preparative HPLC to obtain compound 28 (0.025 g, 11%).

Compound 28: $^1$H NMR (400 MHz, DMSO-d$_6$): δ 12.59 (s, 1H), 7.54 (s, 1H), 7.49 (d, J=8.8 Hz, 1H), 7.34-7.31 (m, 2H), 7.24 (d, J=8.8 Hz, 1H), 7.14-7.11 (m, 1H), 6.83 (d, J=8.4 Hz, 2H), 6.63 (d, J=8.3 Hz, 2H), 6.59-6.52 (m, 2H), 4.76-4.64 (m, 1H), 3.87 (t, J=4.7 Hz, 2H), 3.50-3.46 (m, 2H), 3.40-3.38 (m, 4H), 3.03 (s, 1H), 2.86-2.81 (m, 4H), 2.36-2.33 (m, 2H), 0.88 (t, J=7.3 Hz, 3H). LCMS: 595.2 [M+H]$^+$.

Example 29: Synthesis of (E)-4-((2-(4-((E)-1-(1H-indazol-5-yl)-2-(4-isopropyl phenyl)but-1-en-1-yl)phenoxy)ethyl)amino)-N,N-dimethylbut-2-enamide (Compound 29)

Step-1: Synthesis of tert-butyl (2-(4-((E)-1-(1H-indazol-5-yl)-2-(4-isopropylphenyl)but-1-en-1-yl)phenoxy) ethyl) ((E)-4-(dimethylamino)-4-oxobut-2-en-1-yl)carbamate The compound was synthesized following the approach as outlined in Example 3 by substituting (i) into Step-1 5-(but-1-yn-1-yl)-1-(tetrahydro-2H-pyran-2-yl)-1H-indazole (prepared in Example 1, Step-3) for compound 252 and (ii) into Step-4 4-isopropyliodobenzene for compound 227. The resulting intermediate was subjected to the reaction conditions described in Scheme 2, Step-5 to give a crude product which was purified through column chromatography over 230-400 mesh silica-gel, column was eluted with 2% MeOH in dichloromethane as an eluent to afford the title compound of Ex. 29 Step-1 (0.096 g, 29%).

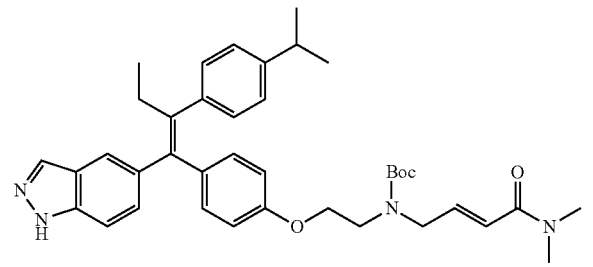 [SMILES: CC/C(=C(/c1ccc(OCCN(C/C=C/C(=O)N(C)C)C(=O)OC(C)(C)C)cc1)c1ccc2[nH]ncc2c1)c1ccc(C(C)C)cc1]

Step-2: Synthesis of (E)-4-((2-(4-((E)-1-(1H-indazol-5-yl)-2-(4-isopropylphenyl)but-1-en-1-yl)phenoxy)ethyl)amino)-N,N-dimethylbut-2-enamide (Compound 29)

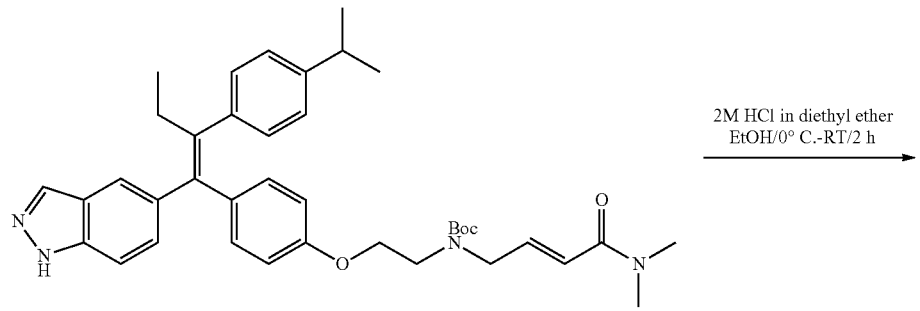

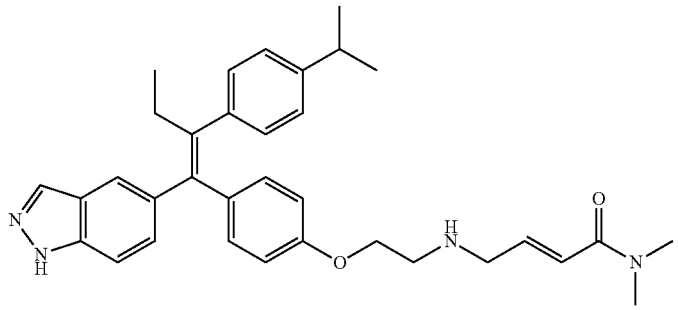

The reaction was carried out according to Scheme 2, Step-6c to give a crude compound was purified by preparative HPLC to afford Compound 29 (0.010 g, 12%).

Compound 29: $^1$H NMR (400 MHz, DMSO-d$_6$): δ 13.05 (s, 1H), 8.06 (s, 1H), 7.6 (s, 1H), 7.5 (d, J=8.8 Hz, 1H), 7.1-7.05 (m, 5H), 6.74 (d, J=8.8 Hz, 2H), 6.63-6.58 (m, 3H), 6.5 (d, J=15.2 Hz, 1H), 3.66 (t, J=5.6 Hz, 2H), 3.31 (m, 2H), 2.98 (s, 3H), 2.84 (s, 3H), 2.82-2.76 (m, 3H), 2.4-2.35 (m, 2H), 1.16 (d, J=6.8 Hz, 6H), 0.88 (t, J=7.3 Hz, 3H). LCMS: 537.4 [M+H]$^+$.

Example 30: Synthesis of (E)-4-((2-(4-((E)-4-chloro-1-(1H-indazol-5-yl)-2-phenyl but-1-en-1-yl) phenoxy) ethyl)amino)-N,N-dimethylbut-2-enamide (Compound 30)

The compound was synthesized following the approach as outlined in Example 5 by substituting into Step-1 5-(4-chlorobut-1-yn-1-yl)-1-(tetrahydro-2H-pyran-2-yl)-1H-indazole (preparation shown below in Ex. 30 Steps 1-2) for compound 242, tert-butyl (E)-(4-(dimethylamino)-4-oxobut-2-en-1-yl)(2-(4-iodophenoxy)ethyl)carbamate (as prepared in Example 14, Step-3) for compound 243, and iodobenzene for compound 244 and continuing with Ex. 5 Step-2 to afford Compound 30 (0.04 g, 6%).

Step-1: Synthesis of 4-(1-(tetrahydro-2H-pyran-2-yl)-1H-indazol-5-yl)but-3-yn-1-ol

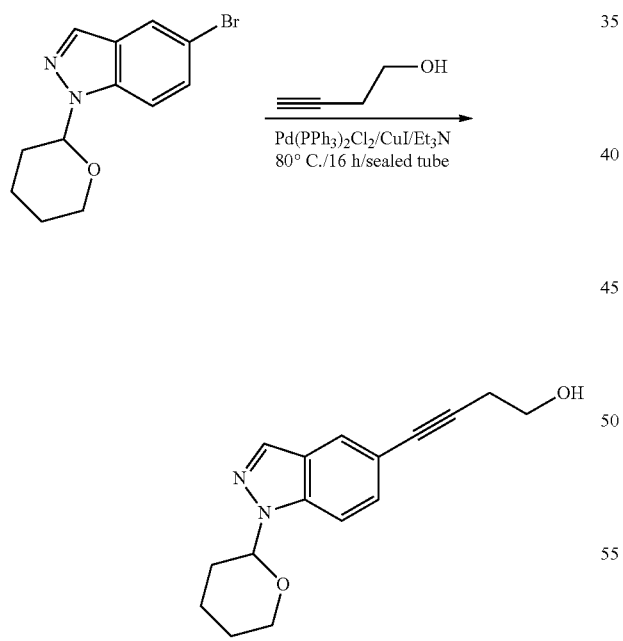

The reaction was carried out according to Scheme 1, Step-2, using 5-bromo-1-(tetrahydro-2H-pyran-2-yl)-1H-indazole (Example 1, Step-3) for compound 202 and but-3-yn-1-ol for compound 203, to give a crude product which was purified over silica-gel column chromatography using 15% ethyl acetate in n-hexane to afford the title compound of Ex. 30 Step-1 (1.3 g, 54%).

Step-2: Synthesis of 5-(4-chlorobut-1-yn-1-yl)-1-(tetrahydro-2H-pyran-2-yl)-1H-indazole

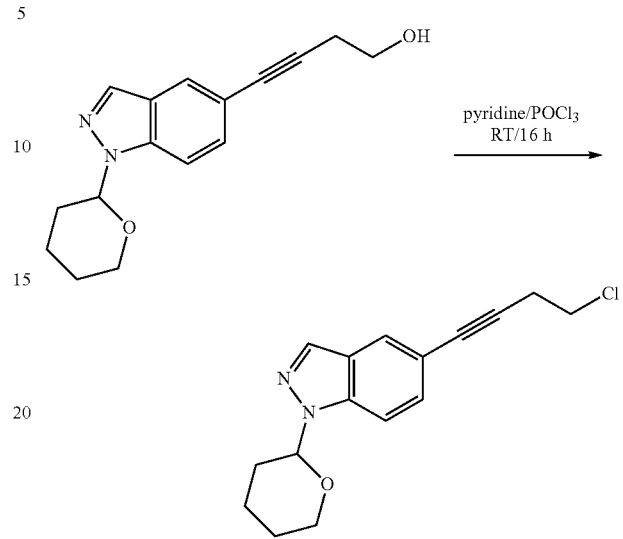

To an ice cold solution of 4-(1-(tetrahydro-2H-pyran-2-yl)-1H-indazol-5-yl)but-3-yn-1-ol (2.6 g, 9.6 mmol) in pyridine (36 mL), was added POCl$_3$. Reaction mixture was allowed to room temperature for 16 h. Upon completion of reaction, excess of POCl$_3$ was removed under vacuum, basified with sodium bicarbonate solution, extracted with ethyl acetate (2×100 mL), combined organic layers were washed with brine solution and dried over anhydrous sodium sulphate. Organic layer was concentrated to dryness to afford the crude product, which was purified by column chromatography over silica-gel, column was eluting with 10% EtOAc in n-hexane to obtain the title compound of Ex. 30 Step-2 (1.5 g, 54%).

Compound 30: $^1$H NMR (400 MHz, DMSO-d$_6$): δ 13.1 (s, 1H), 8.08 (s, 1H), 7.7 (s, 1H), 7.53 (d, J=8.8 Hz, 1H), 7.26-7.16 (m, 6H), 6.77 (d, J=8.8 Hz, 2H), 6.6 (d, J=8.0 Hz, 3H), 6.5 (t, J=5.2 Hz, 1H), 3.87 (d, J=5.6 Hz, 2H), 3.46 (t, J=6.8 Hz, 2H), 3.3 (m, 2H), 2.98 (s, 3H), 2.89 (t, J=7.2 Hz, 2H), 2.84 (s, 3H), 2.77 (t, J=5.2 Hz, 2H). LCMS: 529.3 [M+H]$^+$.

Example 31: Synthesis of (E)-4-((2-(4-((E)-1-(1H-indazol-5-yl)-2-(4-isopropyl phenyl)but-1-en-1-yl) phenoxy)ethyl)amino)-N,N-dimethylbut-2-enamide (Compound 31)

The compound was synthesized following the approach as outlined in Example 3 by substituting into Step-4 (Z)-tert-butyl (2-(4-(1-(1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)ethyl)carbamate (as prepared in Example 6, Step-1) for compound 226 and 2-iodo-1-methoxybenzene for compound 227 to afford Compound 31 (0.014 g, 3%).

Compound 31: $^1$H NMR (400 MHz, DMSO-d$_6$): δ 13.05 (s, 1H), 8.07 (s, 1H), 7.6 (s, 1H), 7.5 (d, J=8.4 Hz, 1H), 7.15-7.11 (m, 2H), 6.94 (d, J=8.4 Hz, 1H), 6.87 (d, J=7.2 Hz, 1H), 6.78-6.72 (m, 3H), 6.58-6.54 (m, 3H), 6.5 (d, J=15.2 Hz, 1H), 3.85 (t, J=5.6 Hz, 2H), 3.77 (s, 3H), 3.31 (m, 2H), 2.98 (s, 3H), 2.84 (s, 3H), 2.76 (t, J=5.6 Hz, 2H), 2.33 (s, 2H), 0.88 (t, J=7.2 Hz, 3H). LCMS: 525.3 [M+H]$^+$.

Example 32: Synthesis of (E)-4-((2-(4-((E)-2-(2-(difluoromethoxy)phenyl)-1-(1H-indazol-5-yl)but-1-en-1-yl)phenoxy)ethyl)amino)-N,N-dimethylbut-2-enamide (Compound 32)

The compound was synthesized following the approach as outlined in Example 3 by substituting into Step-4 (Z)-tert-butyl (2-(4-(1-(1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)ethyl)carbamate (as prepared in Example 6, Step-1) for compound 226 and 2-iodo-1-difluromethoxy-benzene for compound 227 to afford Compound 32 (0.022 g, 4%).

Compound 32: $^1$H-NMR (400 MHz, DMSO-$d_6$): δ 13.08 (s, 1H), 8.09 (s, 1H), 7.62 (s, 1H), 7.53 (d, J=8.8 Hz, 1H), 7.25-7.23 (m, 1H), 7.22-7.08 (m, 5H), 6.78 (d, J=8.8 Hz, 2H), 6.62-6.57 (m, 3H), 6.5 (d, J=15.2 Hz, 1H), 3.85 (t, J=5.2 Hz, 2H), 3.32-3.3 (m, 2H), 2.98 (s, 3H), 2.84 (s, 3H), 2.77 (t, J=5.2 Hz, 2H), 2.33 (m, 2H), 0.87 (t, J=7.2 Hz, 3H), LC-MS: 561.3 [M+H]$^+$.

Example 33: Synthesis of (E)-4-((2-(4-((E)-1-(1H-indazol-5-yl)-2-(2-(trifluoro-methoxy)phenyl)but-1-en-1-yl)phenoxy)ethyl)amino)-N,N-dimethylbut-2-enamide (Compound 33)

The compound was synthesized following the approach as outlined in Example 3 by substituting into Step-4 tert-butyl ((E)-4-(dimethylamino)-4-oxobut-2-en-1-yl)(2-(4-((Z)-1-(1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)ethyl)carbamate (preparation shown below in Ex. 33 Step-1) for compound 226 and 2-iodo-1-trifluromethoxy-benzene for compound 227 and continuing with Ex. 3 Step-5 to afford Compound 33 (0.030 g, 26%).

Step-1: Synthesis of tert-butyl ((E)-4-(dimethylamino)-4-oxobut-2-en-1-yl)(2-(4-((Z)-1-(1-(tetrahydro-2H-pyran-2-yl)-1H-indazol-5-yl)-2-(4, 5, 5-tetramethyl-1,3,2-dioxaborolan-2-yl)but-1-en-1-yl)phenoxy)ethyl)carbamate

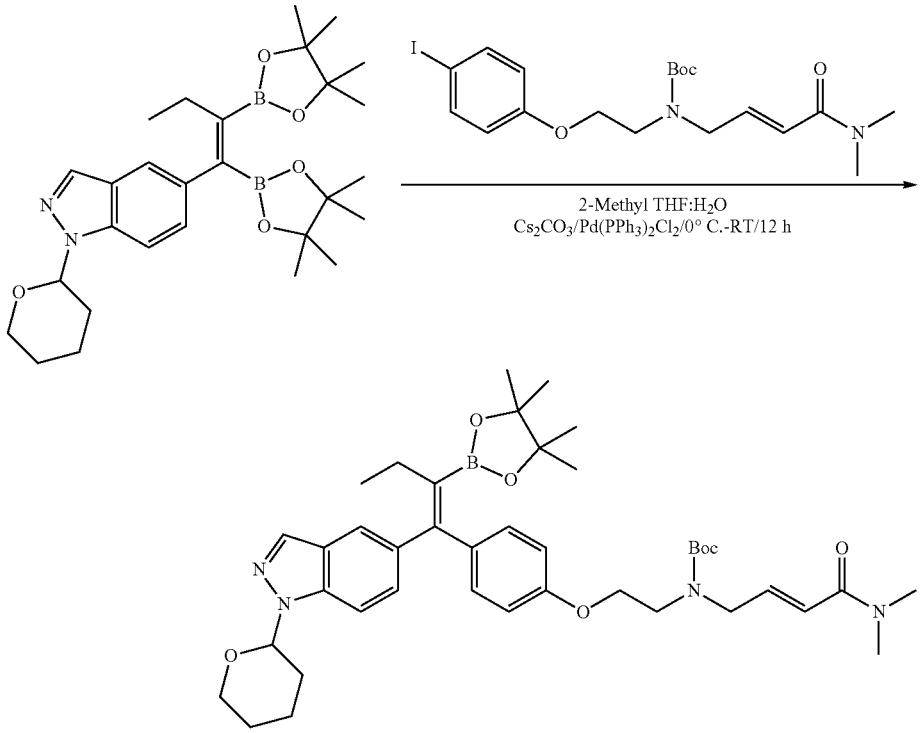

The reaction was carried out according to Scheme 1, Step-4, using (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole (as prepared in Example 17, Step-1) for compound 206 and tert-butyl (E)-(4-(dimethylamino)-4-oxobut-2-en-1-yl)(2-(4-iodophenoxy)ethyl)carbamate (as prepared in Example 14, Step-3) for compound 207, to give a crude material which was purified by column chromatography over 230-400 mesh silica gel using MeOH in dichloromethane (1.6:98.4) to afford the title compound of Ex. 33 Step-1 (4.04 g, 43%).

Compound 33: $^1$H-NMR (400 MHz, DMSO-$d_6$): δ 13.10 (s, 1H), 8.1 (s, 1H), 7.6 (s, 1H), 7.5 (d, J=8.8 Hz, 1H), 7.42-7.39 (m, 1H), 7.38-7.26 (m, 2H), 7.22-7.18 (m, 1H), 7.13-7.11 (m, 1H), 6.74 (d, J=8.80 Hz, 2H), 6.62-6.58 (m, 3H), 6.51-6.48 (d, J=15.2 Hz, 1H), 3.86 (t, J=5.6 Hz, 2H), 3.31-3.3 (m, 2H), 2.98 (s, 3H), 2.84 (s, 3H), 2.76 (t, J=5.6 Hz, 2H), 2.43-2.42 (m, 2H), 0.86 (t, J=7.60 Hz, 3H). LCMS: 579.0 [M+H]$^+$.

Example 34: Synthesis of (E)-4-((2-(4-((E)-1-(1H-indazol-5-yl)-2-(2-isopropyl phenyl)but-1-en-1-yl)phenoxy)ethyl)amino)-N,N-dimethylbut-2-enamide (Compound 34)

The compound was synthesized following the approach as outlined in Example 12 by substituting into Step-2 (E)-2-(4-(1-(1H-indazol-5-yl)-2-(2-isopropylphenyl)but-1-en-1- yl)phenoxy)ethan-1-amine (preparation shown below in Ex. 34 Step-1) for compound 253 and (E)-4-bromo-N,N-dimethylbut-2-enamide (as prepared in Example 1, Step-7) for compound 232 to afford Compound 34 (0.010 g, 6%).

Step-1: Synthesis of tert-butyl (E)-(2-(4-(2-(2-isopropylphenyl)-1-(1-(tetrahydro-2H-pyran-2-yl)-1H-indazol-5-yl)but-1-en-1-yl)phenoxy)ethyl)carbamate

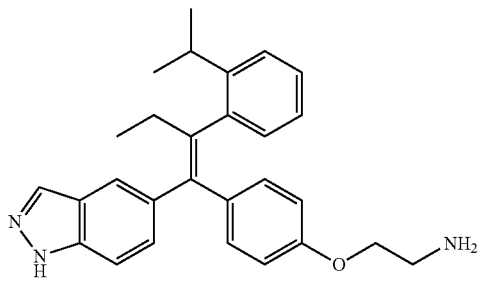 [SMILES: CC/C(=C(/c1ccc(OCCN)cc1)c1ccc2[nH]ncc2c1)c1ccccc1C(C)C]

The compound was synthesized following the approach as outlined in Example 7 by substituting 2-iodo-1-iospropylbenzene in Step-1, continuing with Step-2, and proceeding directly to Step 4 to obtain the title compound (0.5 g, 98%).

Compound 34: $^1$H-NMR (400 MHz, DMSO-$d_6$): δ 13.07 (s, 1H), 8.10 (s, 1H), 7.64 (s, 1H), 7.53 (d, J=8.8 Hz, 1H), 7.24 (d, J=6.8 Hz, 1H), 7.19-7.14 (m, 4H), 6.72 (d, J=8.8 Hz, 2H), 6.6-6.46 (m, 4H), 3.84 (t, J=5.6 Hz, 2H), 3.30 (m, 2H), 3.17 (t, J=6.80 Hz, 1H), 2.98 (s, 3H), 2.84 (s, 3H), 2.75 (t, J=5.6 Hz, 1H), 2.67 (t, J=6.0 Hz, 1H), 2.36-2.30 (m, 2H), 1.13 (d, J=6.8 Hz, 3H), 0.86 (t, J=7.60 Hz, 3H), 0.61 (d, J=6.80 Hz, 3H), LC-MS: 537.3 [M+H]$^+$.

Example 35: Synthesis of (E)-4-((2-(4-((E)-2-(2-ethylphenyl)-1-(1H-indazol-5-yl)but-1-en-1-yl)phenoxy) ethyl)amino)-N,N-dimethylbut-2-enamide (Compound 35)

The compound was synthesized following the approach as outlined in Example 5 by substituting into Step-1 tert-butyl (E)-(4-(dimethylamino)-4-oxobut-2-en-1-yl)(2-(4-iodophenoxy) ethyl) carbamate (as prepared in Example 14, Step-3) for compound 243 and 2-iodo-1-methylbenzene for compound 244 and continuing with Step-2 to deliver Compound 35 (0.079 g, 10%).

Compound 35: $^1$H NMR (400 MHz, DMSO-$d_6$): δ 13.06 (s, 1H), 8.08 (s, 1H), 7.64 (s, 1H), 7.53 (d, J=8.4 Hz, 1H), 7.2-7.13 (m, 5H), 6.73 (d, J=8.8 Hz, 2H), 6.6-6.47 (m, 4H), 3.84 (t, J=5.6 Hz, 2H), 3.3-3.29 (m, 2H), 2.98 (s, 3H), 2.84 (s, 3H), 2.75 (t, J=5.6 Hz, 2H), 2.67-2.63 (m, 1H), 2.41-2.26 (m, 3H), 1.02 (t, J=7.6 Hz, 3H), 0.86 (t, J=7.6 Hz, 3H) LCMS: 523.3 [M+H]$^+$.

Example 36: Synthesis of (E)-4-((2-(4-((E)-1-(1H-indazol-5-yl)-2-(o-tolyl)but-1-en-1-yl)phenoxy) ethyl) amino)-N,N-dimethylbut-2-enamide (Compound 36)

Step-1: Synthesis of tert-butyl (2-(4-((E)-1-(1H-indazol-5-yl)-2-(o-tolyl)but-1-en-1-yl)phenoxy) ethyl) ((E)-4-(dimethylamino)-4-oxobut-2-en-1-yl) carbamate

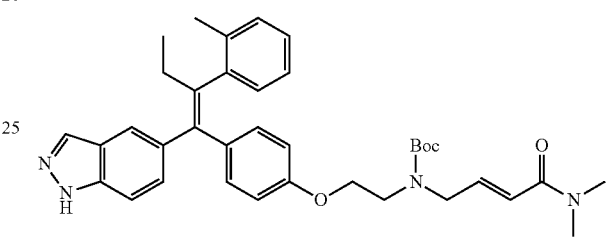

The compound was synthesized following the approach as outlined in Example 3 by substituting into Step-4 (Z)-tert-butyl (2-(4-(1-(1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)ethyl)carbamate (as prepared in Example 6, Step-1) for compound 226 and 2-iodo-1-methylbenzene for compound 227. The resulting intermediate was subjected to the reaction conditions described in Scheme 2, Step-5 to give a crude product, which was purified through silica gel chromatography with 2% MeOH in dichloromethane as an eluent to afford the title compound of Ex. 36 Step-1 (0.12 g, 27%).

Step-2: Synthesis of (E)-4-((2-(4-((E)-1-(1H-indazol-5-yl)-2-(o-tolyl)but-1-en-1-yl)phenoxy)ethyl) amino)-N,N-dimethylbut-2-enamide (Compound 36)

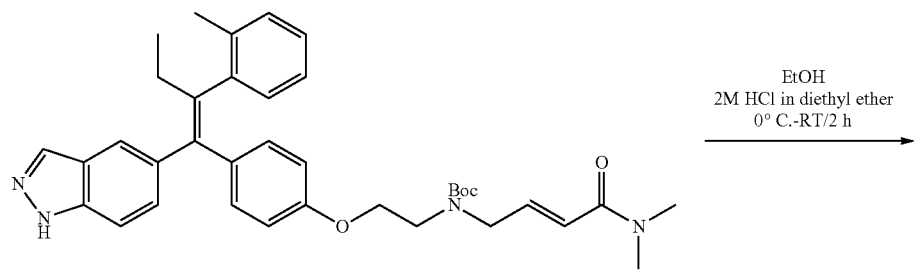

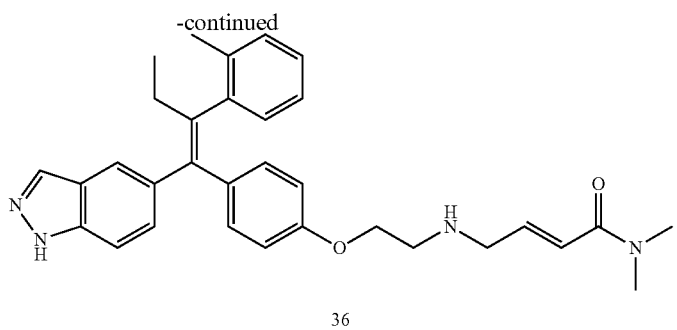

36

The reaction was carried out according to Scheme 2, Step-6c, to afford the crude product, which was purified by preparative TLC to afford the title compound of Ex. 36 Step-2 (0.015 g, 15%).

Compound 36: $^1$H NMR (400 MHz, DMSO-d$_6$): δ 13.08 (s, 1H), 8.08 (s, 1H), 7.65 (s, 1H), 7.53 (d, J=8.8 Hz, 1H), 7.4 (d, J=7.2 Hz, 1H), 7.16-7.13 (m, 2H), 7.1-7.03 (m, 2H), 6.74 (d, J=8.8 Hz, 2H), 6.6-6.47 (m, 4H), 3.84 (t, J=5.6 Hz, 2H), 3.29-3.1 (m, 2H), 2.98 (s, 3H), 2.84 (s, 3H), 2.76 (t, J=5.6 Hz, 2H), 2.33-2.31 (m, 2H), 2.1 (s, 3H), 0.86 (t, J=7.6 Hz, 3H). LCMS: 509.3 [M+H]$^+$.

Example 37: There is no Example 37

Example 38: Synthesis of (E)-4-((2-((5-((Z)-1-(1H-indazol-5-yl)-2-phenylbut-1-en-1-yl)pyrimidin-2-yl)oxy)ethyl)amino)-N,N-dimethylbut-2-enamide (Compound 38)

The compound was synthesized following the approach as outlined in Example 12 by substituting into Step-2 (E)-4-((2-((5-((Z)-1-(1H-indazol-5-yl)-2-phenylbut-1-en-1-yl)pyrimidin-2-yl)oxy) ethyl)amino)-N,N-dimethylbut-2-enamide (preparation shown below in Ex. 38 Steps 1-4) for compound 253 and (E)-4-bromo-N,N-dimethylbut-2-enamide (as prepared in Example 1, Step-7) for compound 232 to afford Compound 38 (0.11 g, 13%).

Step-1: Synthesis of tert-butyl (2-((5-bromopyrimidin-2-yl)oxy)ethyl)carbamate

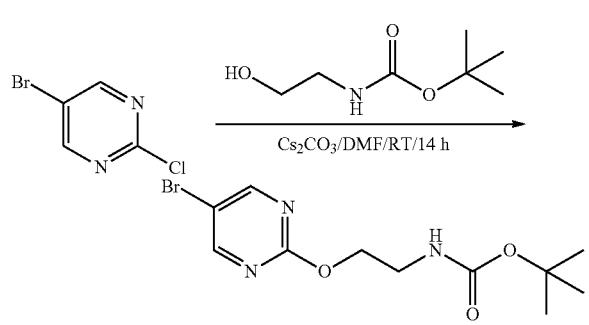

To a stirred solution of tert-butyl (2-hydroxyethyl)carbamate (3.25 g, 20.2 mmol) in DMF (90 mL), was added cesium carbonate (7.57 g, 23.3 mmol). Reaction mixture was stirred for about 15 min at room temperature, 5-Bromo-2-chloropyrimidine (3.0 g, 15.5 mmol) was added to the reaction mixture and stirred for 14 h. Upon completion, reaction mixture was diluted with water, extracted with ethyl acetate, the combined organic layers were washed with water followed by brine. The organic layer was dried over anhydrous sodium sulphate, concentrated to dryness under reduced pressure. The crude product was purified through column chromatography over silica gel, eluting with 15-20% EtoAc in n-hexane to afford the title compound (4.5 g, 55%).

Step-2: Synthesis of tert-butyl (2-((5-iodopyrimidin-2-yl)oxy)ethyl)carbamate

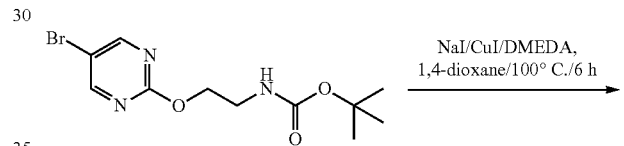

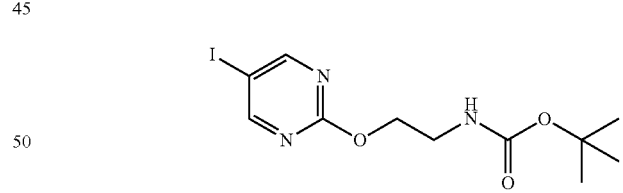

To a stirred solution of tert-butyl (2-((5-bromopyrimidin-2-yl)oxy)ethyl)carbamate (4.0 g, 12.6 mmol) in 1,4-dioxane (80 mL), were added NaI (3.78 g, 25.2 mmol), CuI (2.4 g, 12.6 mmol) and N,N'-dimethylethylenediamine (2.2 g, 25.2 mmol). The reaction mixture was heated to 100° C. for 6 h. Upon completion, reaction mixture was cooled to room temperature, filtered through celite pad and the celite pad was washed with ethyl acetate (200 mL). The obtained filtrate was washed with water, brine and dried over anhydrous sodium sulphate and concentrated to dryness. The crude product was purified through column chromatography over silica gel, eluting with 15% EtOAc in n-hexane to afford the title compound of Ex. 38 Step-1 (3.2 g, 69%).

Step-3: Synthesis of tert-butyl (Z)-(2-((5-(2-phenyl-1-(1-(tetrahydro-2H-pyran-2-yl)-1H-indazol-5-yl)but-1-en-1-yl)pyrimidin-2-yl)oxy)ethyl)carbamate

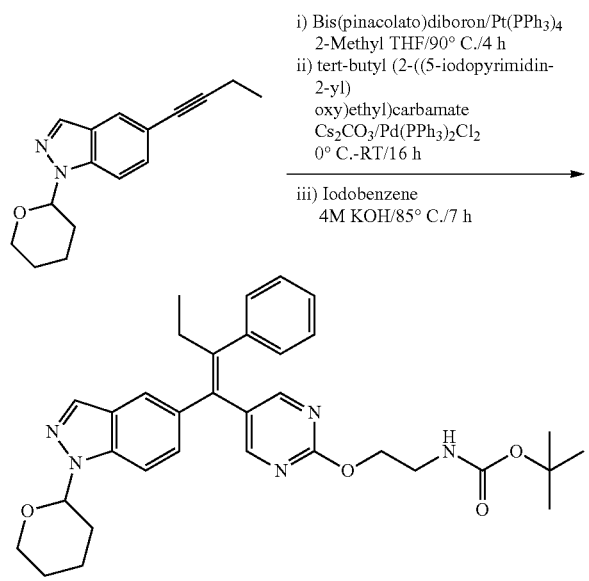

The reactions were carried out as described in Example 5, Step-1, using 5-(but-1-yn-1-yl)-1-(tetrahydro-2H-pyran-2-yl)-1H-indazole (Example 1, Step-3) and substituting Iodobenzene for compound 244 to give a crude product which was purified by silica gel chromatography, eluting with 25-30% EtOAc in n-hexane to obtain the title compound of Ex. 38 Step-3 (2.9 g, crude).

Step-4: Synthesis of (Z)-2-((5-(1-(1H-indazol-5-yl)-2-phenylbut-1-en-1-yl)pyrimidin-2-yl)oxy)ethan-1-amine

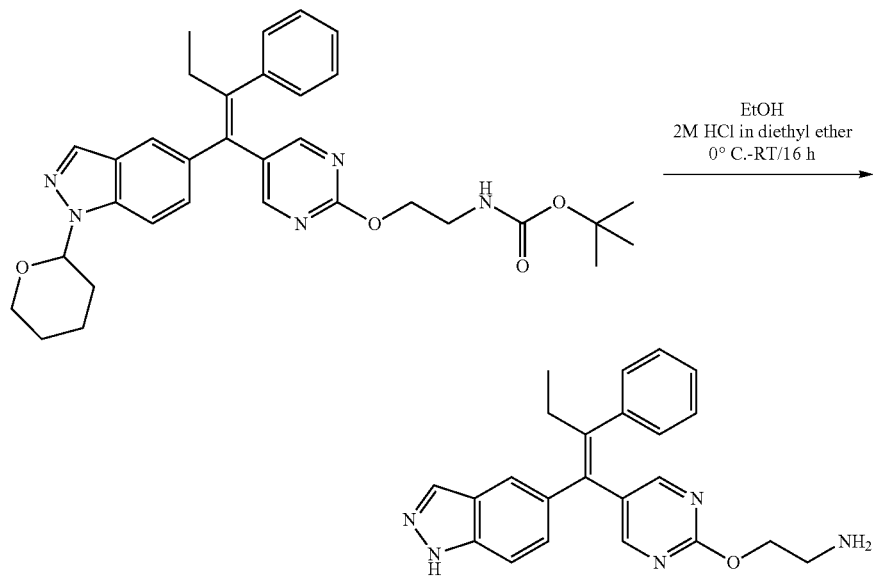

The reaction was carried out according to Scheme 2, Step-2b to afford the title compound of Ex. 38 Step-4 (1.6 g, 85%).

Compound 38: $^1$H NMR (400 MHz, DMSO-$d_6$): δ 13.12 (s, 1H), 8.09 (s, 1H), 7.99 (s, 2H), 7.69 (s, 1H), 7.56 (d, J=8.4 Hz, 1H), 7.3-7.17 (m, 6H), 6.62-6.47 (m, 2H), 4.18 (t, J=6 Hz, 2H), 3.30-3.28 (m, 2H), 2.98 (s, 3H), 2.83 (s, 3H), 2.68 (t, J=6 Hz, 2H), 2.46-2.42 (m, 2H), 0.90 (t, J=7.2 Hz, 3H). LCMS: 497.3 [M+H]$^+$.

Example 39: Synthesis of (E)-1-(azetidin-1-yl)-4-((2-(4-((E)-2-cyclobutyl-1-(1H-indazol-5-yl)-2-phenylvinyl) phenoxy)ethyl)amino)but-2-en-1-one (Compound 39)

The compound was synthesized following the approach as outlined in Example 12 by substituting into Step-2 (E)-2-(4-(2-cyclobutyl-1-(1H-indazol-5-yl)-2-phenylvinyl) phenoxy)ethan-1-amine (as prepared in Example 13, Step-7) for compound 253 and (E)-1-(azetidin-1-yl)-4-bromobut-2-en-1-one (as prepared in Example 10, Step-1) for compound 232 to afford Compound 39 (0.030 g, 4%).

Compound 39: $^1$H NMR (400 MHz, DMSO-$d_6$): δ 13.06 (s, 1H), 8.07 (s, 1H), 7.58 (s, 1H), 7.51 (d, J=8.8 Hz, 1H), 7.27-7.23 (m, 2H), 7.17-7.08 (m, 5H), 6.79-6.76 (m, 2H), 6.59 (t, J=5.2 Hz, 1H), 6.57-6.53 (m, 2H), 6.04-5.75 (m, 1H), 4.11 (t, J=7.6 Hz, 2H), 3.87-3.80 (m, 4H), 3.41 (t, J=8.8 Hz, 1H), 3.29-3.27 (m, 2H), 2.74 (t, J=5.6 Hz, 2H), 2.17 (t, J=7.6 Hz, 2H), 1.82-1.76 (m, 4H), 1.59-1.55 (m, 1H), 1.36-1.32 (m, 1H). LCMS: 533.3 [M+H]$^+$.

Example 40: Synthesis of (E)-1-(azetidin-1-yl)-4-((2-(4-((E)-2-cyclobutyl-1-(3-fluoro-1H-indazol-5-yl)-2-phenylvinyl)phenoxy)ethyl)amino)but-2-en-1-one (Compound 40)

The compound was synthesized following the approach as outlined in Example 3 by (i) substituting into Step-4 (Z)-5-(1,2-bis(4,4,5,5-tetramethyl-1,3,2-dioxaborolan-2-yl)but-1-en-1-yl)-3-fluoro-1-(tetrahydro-2H-pyran-2-yl)-1H-indazole (as prepared in Example 3, Step-1) for compound 226 and iodobenzene for compound 227 and (ii) substituting into Step-6 (E)-1-(azetidin-1-yl)-4-bromobut-2-en-1-one (as prepared in Example 10, Step-1) for compound 251 to deliver the title compound (0.007 g, 3%).

Compound 40: $^1$H NMR (400 MHz, DMSO-d$_6$): δ 12.57 (s, 1H), 7.49 (s, 1H), 7.46 (d, J=8.0 Hz, 1H), 7.27-7.1 (m, 6H), 6.8 (d, J=8.8 Hz, 2H), 6.6 (t, J=5.2 Hz, 1H), 6.55 (d, J=8.8 Hz, 2H), 6.02 (d, J=15.6 Hz, 1H), 4.12 (t, J=7.4 Hz, 2H), 3.87-3.83 (m, 4H), 3.4-3.37 (m, 1H), 3.29-3.27 (m, 2H), 2.74 (t, J=5.6 Hz, 2H), 2.2-2.1 (m, 2H), 1.83-1.75 (m, 4H), 1.6-1.56 (m, 1H), 1.34-1.24 (m, 1H). LCMS: 551.3 [M+H]$^+$.

Example 41: Synthesis of (E)-4-((2-(4-((E)-2-cyclobutyl-1-(1H-indazol-5-yl)-2-phenylvinyl) phenoxy) ethyl)amino)-N-(2-hydroxyethyl)-N-methylbut-2-enamide (Compound 41)

The compound was synthesized following the approach as outlined in Example 12 by substituting into Step-2 (E)-2-(4-(2-cyclobutyl-1-(1H-indazol-5-yl)-2-phenylvinyl) phenoxy)ethan-1-amine (as prepared in Example 13, Step-7) for compound 253 and (E)-4-bromo-N-(2-hydroxyethyl)-N-methylbut-2-enamide (as prepared in Example 18, Step-1) for compound 232 to afford Compound 41 (0.012 g, 9%).

Compound 41: $^1$H NMR (400 MHz, DMSO-d$_6$): δ 13.06 (s, 1H), 8.08 (s, 1H), 7.58 (s, 1H), 7.51 (d, J=8.0 Hz, 1H), 7.27-7.24 (m, 2H), 7.17-7.09 (m, 4H), 7.78 (d, J=7.6 Hz, 2H), 6.58-6.52 (m, 4H), 4.77-4.64 (m, 1H), 3.85 (t, J=5.2 Hz, 2H), 3.51-3.41 (m, 2H), 3.39-3.34 (m, 5H), 3.03 (s, 1H), 2.86 (s, 2H), 2.80-2.79 (m, 2H), 1.82-1.76 (m, 4H), 1.57-1.55 (m, 1H), 1.35-1.32 (m, 1H), LCMS: 551.3 [M+H]$^+$.

Example 42: Synthesis of (E)-1-(azetidin-1-yl)-4-((2-(4-((E)-2-cyclobutyl-1-(1H-indazol-5-yl)-2-(o-tolyl) vinyl)phenoxy)ethyl)amino)but-2-en-1-one (Compound 42)

The compound was synthesized following the approach as outlined in Example 3 by (i) substituting into Step-4 (Z)-tert-butyl (2-(4-(2-cyclobutyl-1-(1-(tetrahydro-2H-pyran-2-yl)-1H-indazol-5-yl)-2-(4,4,5,5-tetramethyl-1,3,2-dioxaborolan-2-yl)vinyl)phenoxy)ethyl)carbamate (as prepared in Example 13, Step-5) for compound 226 and 1-iodo-2-methylbenzene for compound 227 and (ii) substituting into Step-6 (E)-1-(azetidin-1-yl)-4-bromobut-2-en-1-one (as prepared in Example 10, Step-1) for compound 251 to afford Compound 42 (0.05 g, 4.5%).

Compound 42: $^1$H NMR (400 MHz, DMSO-d$_6$): δ 13.07 (s, 1H), 8.09 (s, 1H), 7.60 (s, 1H), 7.53 (d, J=2.0 Hz, 1H), 7.16-7.08 (m, 5H), 6.77 (d, J=8.8 Hz, 2H), 6.61-6.57 (m, 1H), 6.54 (d, J=8.8 Hz, 2H), 6.03 (d, J=15.6 Hz, 1H), 4.11 (t, J=7.6 Hz, 2H), 3.87-3.82 (m, 4H), 3.43-3.39 (m, 1H), 3.31 (s, 2H), 2.77 (t, J=5.6 Hz, 2H), 2.19-2.15 (m, 2H), 2.12 (s, 3H), 1.89-1.73 (m, 3H), 1.61-1.53 (m, 2H), 1.36-1.32 (m, 1H). LCMS: 547.3 [M+H]$^+$.

Example 43: Synthesis of (E)-4-((2-(4-((E)-1-(3-fluoro-1H-indazol-5-yl)-2-(2-fluoro phenyl)but-1-en-1-yl)phenoxy)ethyl)amino)-N,N-dimethylbut-2-enamide (Compound 43)

The compound was synthesized following the approach as outlined in Example 3 by substituting into Step-4 1-iodo-2-fluorobenzene for compound 227 to afford Compound 43 (0.025 g, 10%).

Compound 43: $^1$H NMR (400 MHz, DMSO-d$_6$): δ 12.59 (s, 1H), 7.52 (s, 1H), 7.48 (dd, J$_1$=8.8 Hz, J$_2$=2.0 Hz, 1H), 7.24-7.18 (m, 3H), 7.08-7.03 (m, 2H), 6.80 (d, J=8.4 Hz, 2H), 6.63-6.57 (m, 3H), 6.49 (d, J=5.2 Hz, 1H), 3.86 (t, J=5.6 Hz, 2H), 3.33-3.31 (m, 2H), 2.98 (s, 3H), 2.84 (s, 3H), 2.77 (t, J=5.6 Hz, 2H), 2.37-2.32 (m, 2H), 0.88 (t, J=7.2 Hz, 3H). LCMS: 531.3 [M+H]$^+$.

Example 44: Synthesis of (E)-4-((2-(4-((E)-1-(3-fluoro-1H-indazol-5-yl)-2-(3-fluoro phenyl)but-1-en-1-yl) phenoxy)ethyl)amino)-N,N-dimethylbut-2-enamide (Compound 44)

The compound was synthesized following the approach as outlined in Example 3 by substituting into Step-4 1-iodo-3-fluorobenzene for compound 227 to afford Compound 44 (0.010 g, 4%).

Compound 44: $^1$H NMR (400 MHz, DMSO-d$_6$): δ 12.60 (s, 1H), 7.52 (s, 1H), 7.47 (d, J=8.8 Hz, 1H), 7.25-7.19 (m, 2H), 6.99-6.94 (m, 3H), 6.78 (d, J=8.8 Hz, 2H), 6.64 (d, J=8.8 Hz, 2H), 6.59 (t, J=5.2 Hz, 1H), 6.50 (d, J=15.2 Hz, 1H), 3.88 (d, J=5.6 Hz, 2H), 3.33-3.31 (m, 2H), 2.99 (s, 3H), 2.84 (s, 3H), 2.78 (t, J=5.2 Hz, 2H), 2.42-2.38 (m, 2H), 0.88 (t, J=7.6 Hz, 3H). LCMS: 531.3 [M+H]$^+$.

Example 45: Synthesis of (E)-4-((2-(4-((E)-1-(3-fluoro-1H-indazol-5-yl)-2-(3-fluorophenyl)but-1-en-1-yl) phenoxy)ethyl)amino)-N,N-dimethylbut-2-enamide (Compound 45)

The compound was synthesized following the approach as outlined in Example 3 by substituting into Step-4 1-iodo-4-fluorobenzene for compound 227 to afford Compound 45 (0.008 g, 3.8%).

Compound 45: $^1$H NMR (400 MHz, DMSO-d$_6$): δ 12.60 (s, 1H), 7.51 (s, 1H), 7.47 (dd, J$_1$=8.8 Hz, J$_2$ 1.6 Hz, 1H), 7.21-7.19 (m, 3H), 7.18-7.02 (m, 2H), 6.75 (d, J=8.8 Hz, 2H), 6.64-6.58 (m, 3H), 6.51 (d, J=15.2 Hz, 1H), 3.88 (t, J=5.6 Hz, 2H), 3.31 (d, J=4.4 Hz, 2H), 2.99 (s, 3H), 2.84 (s, 3H), 2.78 (t, J=5.2 Hz, 2H), 2.39-2.37 (m, 2H), 0.87 (t, J=7.2 Hz, 3H). LCMS: 531.3 [M+H]$^+$.

Example 46: Synthesis of (E)-4-((2-(4-((E)-2-(2-chloro-4-fluorophenyl)-2-cyclobutyl-1-(3-fluoro-1H-indazol-5-yl)vinyl)phenoxy)ethyl)amino)-N,N-dimethylbut-2-enamide (Compound 46)

The compound was synthesized following the approach as outlined in Example 3 by (i) substituting into Step-3 (Z)-5-(2-cyclobutyl-1,2-bis(4,4,5,5-tetramethyl-1,3,2-dioxaborolan-2-yl)vinyl)-3-fluoro-1-(tetrahydro-2H-pyran-2-yl)-1H-indazole (as prepared in Example 14, Step-2) for compound 255 and (E)-tert-butyl (4-(dimethylamino)-4-oxobut-2-en-1-yl)(2-(4-iodophenoxy)ethyl)-carbamate (as prepared in Example 14, Step-3) for compound 256 and (ii) substituting into Step-4 2-chloro-4-fluoro-1-iodobenzene for compound 227 and (iii) continuing with Step-5 to afford Compound 46 (0.02 g, 10%).

Compound 46: $^1$H NMR (400 MHz, DMSO-d$_6$): δ 12.6 (s, 1H), 7.49 (d, J=5.2 Hz 2H), 7.37-7.31 (m, 2H), 7.23 (d, J=8.8 Hz, 1H), 7.18-7.15 (m, 1H), 6.87 (d, J=8.8 Hz, 2H), 6.63-6.57 (m, 3H), 6.5 (d, J=15.2 Hz, 1H), 3.87 (t, J=5.6 Hz, 2H), 3.51 (s, 1H), 3.39-3.33 (m, 2H), 2.98 (s, 3H), 2.84 (s, 3H), 2.79 (t, J=5.4 Hz, 2H), 1.87-1.78 (m, 3H), 1.68-1.58 (m, 2H), 1.38-1.36 (m, 1H). LCMS: 591.2 [M+H]$^+$.

Example 47: There is no Example 47

Example 48: There is no Example 48

Example 49: Synthesis of (E)-4-((2-(2-fluoro-4-((Z)-1-(3-fluoro-1H-indazol-5-yl)-2-phenylbut-1-en-1-yl)phenoxy)ethyl)amino)-N,N-dimethylbut-2-enamide (Compound 49)

The compound was synthesized following the approach as outlined in Example 12 by substituting into Step-2 (Z)-2-(2-fluoro-4-(1-(3-fluoro-1H-indazol-5-yl)-2-phenylbut-1-en-1-yl)phenoxy)ethan-1-amine (preparation shown below in Ex. 49 Steps 1-3) for compound 253 and (E)-4-bromo-N,N-dimethylbut-2-enamide and (E)-4-chloro-N,N-dimethylbut-2-enamide mixture (preparation shown below in Ex. 49 Step 4) for compound 232 to afford Compound 49 (0.03 g, 7%).

Step-1: Synthesis of 2-fluoro-4-iodophenol

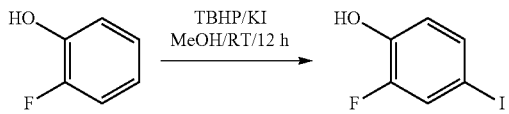 [SMILES: Oc1ccccc1F ; Oc1ccc(I)cc1F]

A mixture of 2-fluorophenol (5 g, 44 mmol) and potassium iodide (8.14 g, 49 mmol) in methanol (150 mL) was added tert-butyl hydroperoxide (6.43 mL, 66.9 mmol) and stirred at room temperature for 12 h. After completion of reaction, reaction mixture was quenched with sodium thiosulphate and extracted with EtOAc. Organic layer was washed water followed by brine, concentrated under reduced pressure to obtain the crude compound. Crude material was purified by column chromatography over 230-400 mesh silica gel using 15% EtOAc in n-hexane to give the title compound (5.7 g).

Step-2: Synthesis of tert-butyl (2-(2-fluoro-4-iodophenoxy)ethyl)carbamate

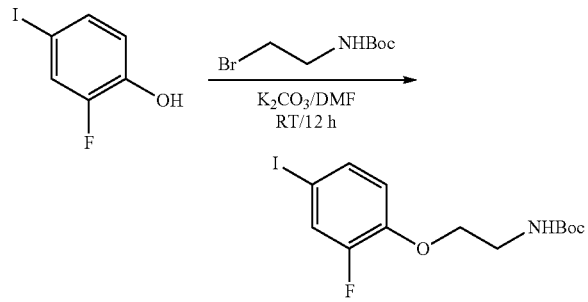

To a solution of 2-fluoro-4-iodophenol (4.6 g, 21 mmol) in DMF (40 mL) was added potassium carbonate (16 g, 116 mmol) and tert-butyl (2-bromoethyl)carbamate (8.62 g, 38.6 mmol). The reaction mixture was stirred at room temperature for 12 h. The reaction mixture was quenched with water and extracted with ethyl acetate (250 mL×2). The combined organic layers were washed with water, brine, dried over anhydrous sodium sulphate and concentrated under reduced pressure. The crude material was purified by column chromatography over 230-400 mesh silica gel using 30% ethyl acetate in n-hexane to afford tert-butyl (2-(2-fluoro-4-iodophenoxy)ethyl)carbamate (4.53 g, 61%).

Step-3: Synthesis of (Z)-2-(2-fluoro-4-(1-(3-fluoro-1H-indazol-5-yl)-2-phenylbut-1-en-1-yl)phenoxy)ethan-1-amine

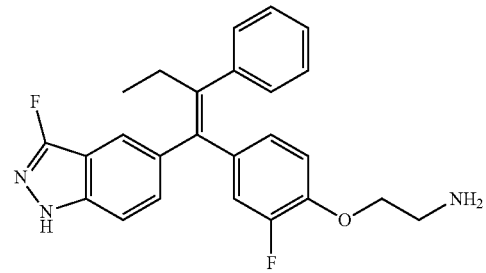 [SMILES: CC/C(=C(/c1ccc(OCCN)c(F)c1)c1ccc2[nH]nc(F)c2c1)c1ccccc1]

The compound was synthesized following the approach as outlined in Example 3 by substituting tert-butyl (2-(2-fluoro-4-iodophenoxy)ethyl)carbamate for compound 256 in Step-3, and substituting iodobenzene for compound 227 in Step-4. The crude material was used in next step without further purification (2.1 g).

Step-4: Synthesis of (E)-4-bromo-N,N-dimethylbut-2-enamide and (E)-4-chloro-N,N-dimethylbut-2-enamide mixture

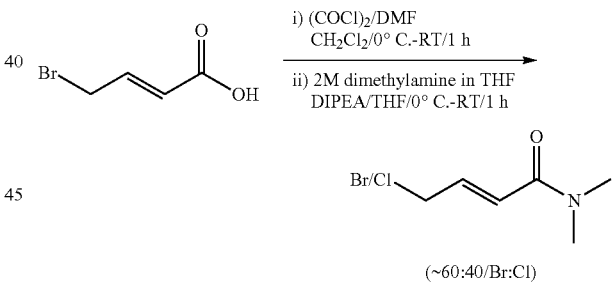

(~60:40/Br:Cl)

The reaction was carried out according to Scheme 4, Step-2 using (E)-4-bromobut-2-enoic acid (Example 1, Step-7.1) and dimethylamine to give crude material, which was purified by silica column chromatography to afford (E)-4-bromo-N,N-dimethylbut-2-enamide and (E)-4-chloro-N,N-dimethylbut-2-enamide mixture (~60:40/Br:Cl, 18 g, 51%) as a brown colour liquid. $^1$H NMR (400 MHz, DMSO-$d_6$): δ 6.95-6.86 (m, 1H), 6.57-6.46 (m, 1H), 4.19-4.18 (m, 1H), 4.05-4.03 (m, 1H), 3.09-3.05 (m, 3H), 3.0-2.98 (m, 3H). LCMS: 194.0 and 148.1 [M+H]$^+$ Compound 49: $^1$H NMR (400 MHz, DMSO-$d_6$): 12.59 (s, 1H), 7.54 (s, 1H), 7.48 (d, J=7.2 Hz, 1H), 7.25-7.22 (m, 3H), 7.17-7.15 (m, 3H), 6.84 (t, J=8.6 Hz, 1H), 6.64-6.47 (m, 4H), 3.94 (t, J=5.4 Hz, 2H), 3.31-3.20 (m, 2H), 2.98 (s, 3H), 2.84 (s, 3H), 2.79 (t, J=5.8 Hz, 2H), 2.41 (q, J=6.8 Hz, 2H), 0.86 (t, J=7.6 Hz, 3H). LCMS: 531.3 [M+H]$^+$ Example 50: Synthesis of (E)-4-((2-(4-((E)-2-(2,6-difluorophenyl)-1-(3-fluoro-1H-indazol-5-yl)but-1-en-1-yl)phenoxy)ethyl)amino)-N,N-dimethylbut-2-enamide (Compound 50)

Step-1: Synthesis of tert-butyl (E)-(2-(4-(2-(2,6-difluorophenyl)-1-(3-fluoro-1-(tetrahydro-2H-pyran-2-yl)-1H-indazol-5-yl)but-1-en-1-yl)phenoxy)ethyl)carbamate

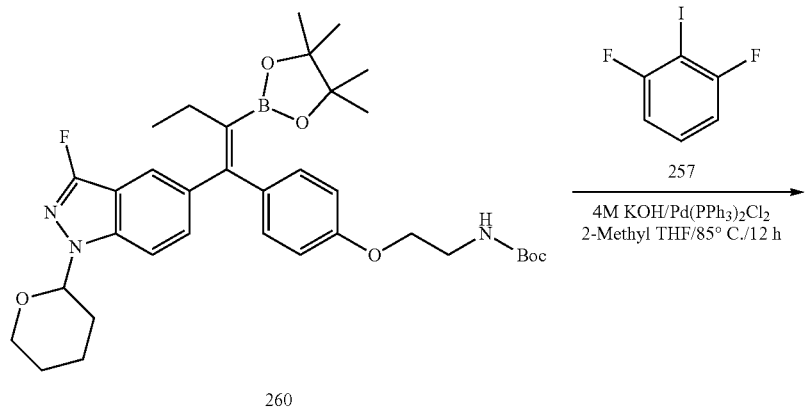

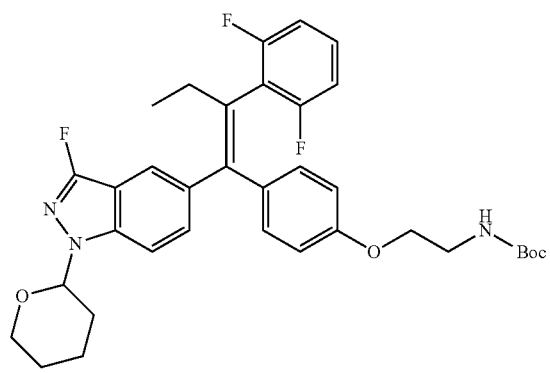

The reaction was carried out according to Scheme 1, Step-5, using tert-butyl (Z)-(2-(4-(1-(3-fluoro-1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)ethyl)carbamate (2.79 g, 4.39 mmol, as prepared in Example 3, Step-3) for compound 208. The crude product was purified by silica gel chromatography using 5-15% EtOAc in n-hexane to give title compound of Ex. 50 Step-1 (2.1 g, 77.2%).

Step-2: Synthesis of (E)-2-(4-(2-(2, 6-difluorophenyl)-1-(3-fluoro-1H-indazol-5-yl)but-1-en-1-yl)phenoxy)ethan-1-amine

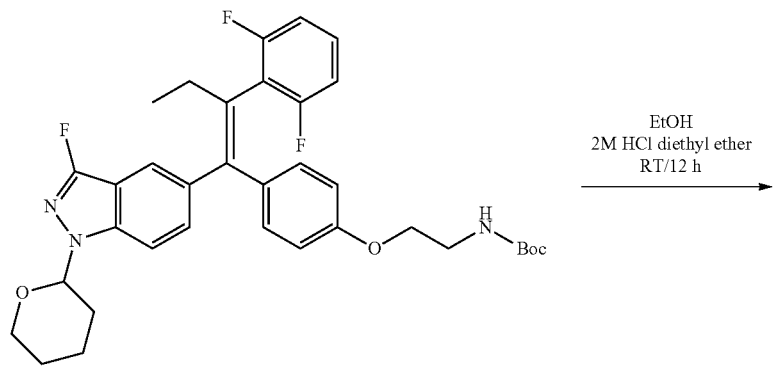

The reaction was carried out according to Scheme 2, Step-2b, using tert-butyl (E)-(2-(4-(2-(2,6-difluorophenyl)-1-(3-fluoro-1-(tetrahydro-2H-pyran-2-yl)-1H-indazol-5-yl)but-1-en-1-yl)phenoxy)ethyl)carbamate (2.1 g, 3.38 mmol, as prepared in Example 50, Step 1). The crude material was used in next step without further purification (1.2 g, crude).

Step-3: Synthesis of (E)-4-((2-(4-((E)-2-(2, 6-difluorophenyl)-1-(3-fluoro-1H-indazol-5-yl)but-1-en-1-yl)phenoxy)ethyl)amino)-N,N-dimethylbut-2-enamide

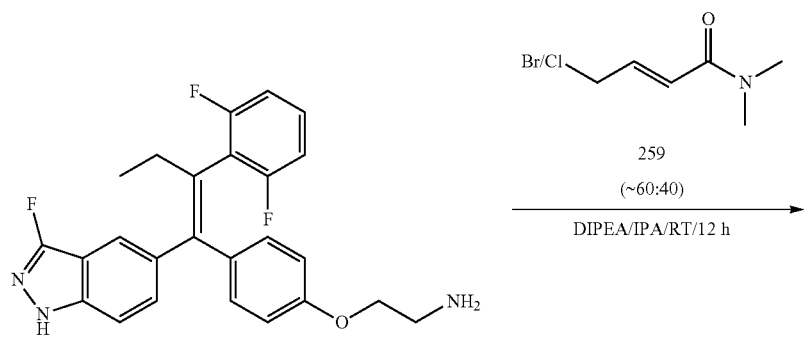

-continued

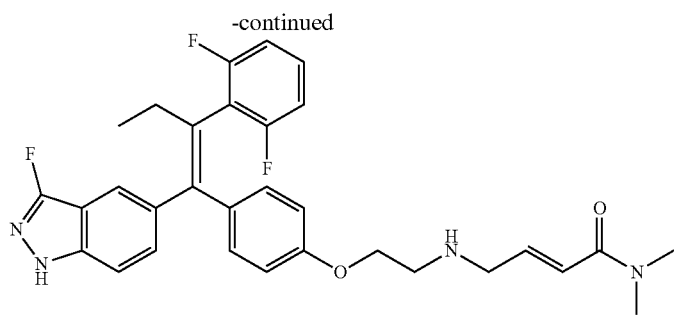

The reaction was carried out according to Scheme 2, Step-3b using (E)-2-(4-(2-(2,6-difluorophenyl)-1-(3-fluoro-1H-indazol-5-yl)but-1-en-1-yl)phenoxy)ethan-1-amine (1.2 g, 2.7 mmol) and (E)-4-bromo-N,N-dimethylbut-2-enamide for compound 213 and (E)-4-chloro-N,N-dimethylbut-2-enamide mixture (as prepared in Example 49, Step-4) for compound 214 to obtain crude product, which was used in next step without further purification (1.15 g, crude).

Step-4: Synthesis of tert-butyl (2-(4-((E)-2-(2,6-difluorophenyl)-1-(3-fluoro-1H-indazol-5-yl)but-1-en-1-yl)phenoxy)ethyl)((E)-4-(dimethylamino)-4-oxobut-2-en-1-yl)carbamate

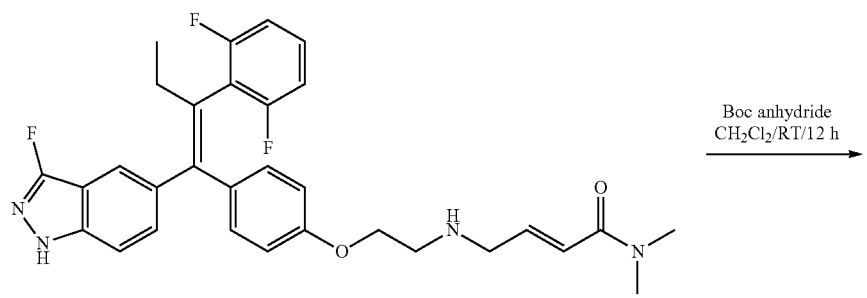

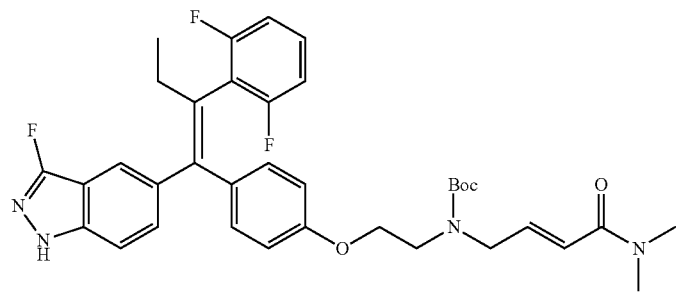

The reaction was carried out according to Scheme 2, Step-5 using (E)-4-((2-(4-((E)-2-(2,6-difluorophenyl)-1-(3-fluoro-1H-indazol-5-yl)but-1-en-1-yl)phenoxy)ethyl)amino)-N,N-dimethylbut-2-enamide (1.15 g, 2.13 mmol) for compound 215. Crude material was purified by column chromatography over 230-400 mesh silica gel using (2.5%) MeOH in dichloromethane to obtain the title compound of Ex. 50 Step-4 (0.3 g, 22.2%).

Step-5: Synthesis of (E)-4-((2-(4-((E)-2-(2, 6-difluorophenyl)-1-(3-fluoro-1H-indazol-5-yl)but-1-en-1-yl)phenoxy)ethyl)amino)-N,N-dimethylbut-2-enamide

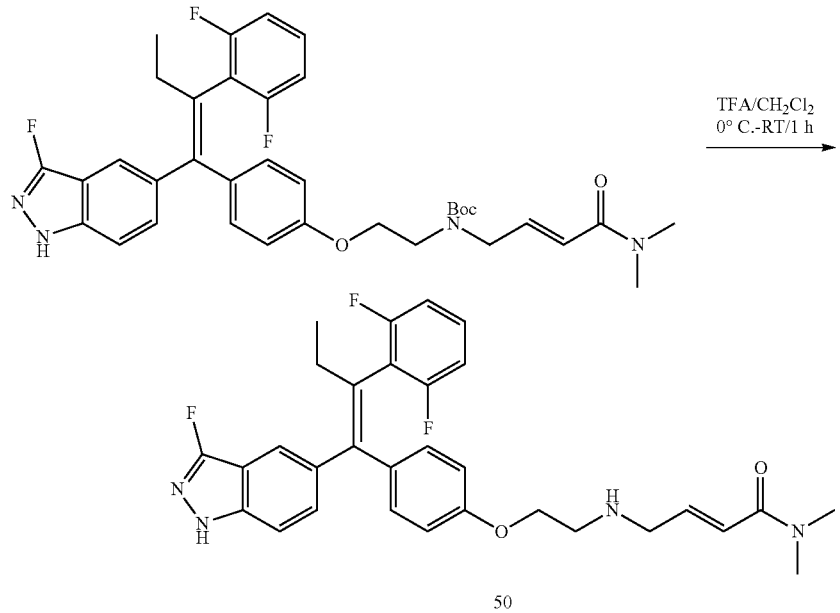

The reaction was carried out according to Scheme 2, Step-6b, using tert-butyl (2-(4-((E)-2-(2,6-difluorophenyl)-1-(3-fluoro-1H-indazol-5-yl)but-1-en-1-yl)phenoxy)ethyl)((E)-4-(dimethylamino)-4-oxobut-2-en-1-yl)carbamate (0.3 g, 0.462 mmol) for compound 211c. Crude compound was purified by preparative HPLC to afford Compound 50 (0.065 g, 25.6%).

Compound 50: $^1$H NMR (400 MHz, DMSO-$d_6$): δ 12.60 (s, 1H), 7.52 (s, 1H), 7.49 (dd, $J_1$=8.8 Hz, $J_2$=1.2 Hz, 1H), 7.23-7.12 (m, 1H), 7.11-7.02 (m, 3H), 6.83 (d, J=8.4 Hz, 2H), 6.65 (d, J=8.4 Hz, 2H), 6.62-6.48 (m, 2H), 3.88 (t, J=5.6 Hz, 2H), 3.32-3.31 (m, 2H), 2.99 (s, 3H), 2.84 (s, 3H), 2.79 (t, J=5.4 Hz, 2H), 2.35 (q, J=7.0 Hz, 2H), 0.91 (t, J=7.4 Hz, 3H). LCMS: 549.3 [M+H]$^+$ Example 51: Synthesis of (E)-4-((2-(4-((E)-1-(3-fluoro-1H-indazol-5-yl)-2-(pyridin-3-yl)but-1-en-1-yl)phenoxy)ethyl)amino)-N,N-dimethylbut-2-enamide (Compound 51)

The compound was synthesized following the approach as outlined in Example 50 by substituting into Step-1 3-iodopyridine for compound 257 to afford Compound 51 (0.02 g, 10%).

Compound 51: $^1$H NMR (400 MHz, DMSO-$d_6$): δ 12.59 (s, 1H), 8.31-8.30 (m, 1H), 8.26 (d, J=2 Hz, 1H), 7.62 (dd, $J_1$=6.0 Hz, $J_2$=2.0 Hz, 1H), 7.54 (s, 1H), 7.48 (dd, $J_1$=8.0 Hz, $J_2$=2.0 Hz, 1H), 7.28-7.24 (m, 1H), 7.22 (dd, J=8.8 Hz, $J_2$=1.2 Hz, 1H), 6.79-6.77 (m, 2H), 6.65-6.60 (m, 3H), 6.58-6.48 (m, 1H), 3.89 (t, J=5.4 Hz, 2H), 3.32-3.31 (m, 2H), 2.99 (s, 3H), 2.84 (s, 3H), 2.79 (t, J=5.4 Hz, 2H), 2.42 (q, J=7.4 Hz, 2H), 0.88 (t, J=7.4 Hz, 3H). LCMS: 514.3 [M+H]$^+$ Example 52: Synthesis of (E)-4-((2-(4-((E)-1-(3-fluoro-1H-indazol-5-yl)-2-(pyridin-4-yl)but-1-en-1-yl)phenoxy)ethyl)amino)-N,N-dimethylbut-2-enamide (Compound 52)

The compound was synthesized following the approach as outlined in Example 50 by substituting into Step-1 4-iodopyridine for compound 257 to afford the title Compound 52 (0.05 g, 19.9%).

Compound 52: $^1$H NMR (400 MHz, DMS-$d_6$): δ 12.60 (s, 1H), 8.39-8.37 (m, 2H), 7.53 (s, 1H), 7.50-7.47 (m, 1H), 7.21 (dd, $J_1$=8.6 Hz, $J_2$=1.4 Hz, 1H), 7.14-7.13 (m, 2H), 6.80-6.78 (m, 2H), 6.66-6.60 (m, 2H), 6.59-6.48 (m, 2H), 3.89 (t, J=5.4 Hz, 2H), 3.33-3.31 (m, 2H), 2.99 (s, 3H), 2.84 (s, 3H), 2.79 (t, J=5.8 Hz, 2H), 2.42 (q, J=7.4 Hz, 2H), 0.87 (t, J=7.2 Hz, 3H). LCMS: 514.3 [M+H]$^+$ Example 53: Synthesis of (E)-4-((2-(4-((E)-2-cyclobutyl-1-(3-fluoro-1H-indazol-5-yl)-2-phenylvinyl)phenoxy)ethyl)amino)-N-(2-hydroxyethyl)-N-methylbut-2-enamide (Compound 53)

The compound was synthesized following the approach as outlined in Example 50 by substituting into Step-3 (E)-2-(4-(2-cyclobutyl-1-(3-fluoro-1H-indazol-5-yl)-2-phenylvinyl)phenoxy)ethan-1-amine (preparation shown below in Ex. 53 Step-1) for compound 258 and (E)-4-bromo-N-(2-hydroxyethyl)-N-methylbut-2-enamide (as prepared in Example 18, Step-1) for compound 259 to afford Compound 53 (0.011 g, 5%).

Step-1: Synthesis of (E)-2-(4-(2-cyclobutyl-1-(3-fluoro-1H-indazol-5-yl)-2-phenylvinyl)phenoxy)ethan-1-amine

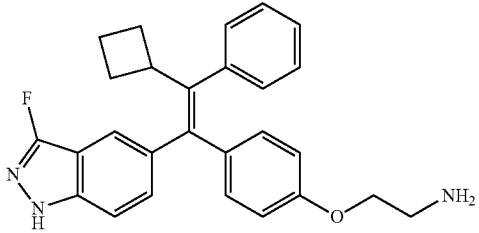 [SMILES: NCCOc1ccc(/C(=C(\c2ccccc2)C2CCC2)c2ccc3[nH]nc(F)c3c2)cc1]

The compound was synthesized following the approach as outlined in Example 3 substituting tert-butyl (Z)-(2-(4-(2-cyclobutyl-1-(1-(tetrahydro-2H-pyran-2-yl)-1H-indazol-5-yl)-2-(4,4,5,5-tetramethyl-1,3,2-dioxaborolan-2-yl)vinyl)phenoxy)-ethyl)carbamate (as prepared in Example 13, Step-5) for compound 226 and iodobenzene for compound 227 in Step-4 and following Step-5 to deliver the title compound (0.85, crude).

Compound 53: $^1$H NMR (400 MHz, DMSO-$d_6$): δ 12.56 (s, 1H), 7.48 (s, 2H), 7.46-7.23 (m, 4H), 7.21 (dd, $J_1$=8.8 Hz, $J_2$=1.6 Hz, 2H), 6.80-6.78 (m, 2H), 6.60-6.47 (m, 4H), 4.77-4.64 (m, 1H), 3.85 (t, J=5.2 Hz, 2H), 3.51-3.41 (m, 2H), 3.39-3.34 (m, 4H), 3.03 (s, 1H), 2.86 (s, 2H), 2.80-2.79 (m, 2H), 1.82-1.76 (m, 4H), 1.57-1.55 (m, 1H), 1.35-1.32 (m, 1H). LCMS: 569.3 [M+H]$^+$

Example 54: Synthesis of (E)-4-((2-(4-((E)-1-(1H-indazol-5-yl)-2-phenylprop-1-en-1-yl)phenoxy)ethyl)amino)-N,N-dimethylbut-2-enamide (Compound 54)

The title compound was synthesized following the approach as outlined in Example 1. Without wishing to be bound by theory, it is believed that Compound 54 resulted due to inclusion of methyl iodide in the ethyl iodide used in Step-2 of Example 1.

Compound 54: $^1$H NMR (400 MHz, DMSO-$d_6$): δ 13.05 (s, 1H), 8.05 (s, 1H), 7.6 (s, 1H), 7.50 (d, J=8.4 Hz, 1H), 7.21-7.09 (m, 6H), 6.75 (d, J=8.8 Hz, 2H), 6.62-6.48 (m, 4H), 3.88 (t, J=5.2 Hz, 2H), 3.31 (d, J=4.8 Hz, 2H), 2.99 (s, 3H), 2.84 (s, 3H), 2.79-2.77 (m, 2H), 2.07 (s, 3H). LCMS: 481.3 [M+H]$^+$

Example 55: There is no Example 55

Example 56: Synthesis of (E)-4-((2-(4-((E)-2-cyclopropyl-1-(1H-indazol-5-yl)-2-phenylvinyl)phenoxy)ethyl)amino)-N,N-dimethylbut-2-enamide (Compound 56)

The compound was synthesized following the approach as outlined in Example 50 by substituting into Step-1 tert-butyl (Z)-(2-(4-(2-cyclopropyl-1-(1-(tetrahydro-2H-pyran-2-yl)-1H-indazol-5-yl)-2-(4,4,5,5-tetramethyl-1,3,2-dioxaborolan-2-yl)vinyl)phenoxy)ethyl)carbamate (preparation shown below in Step 1-2) for compound 260 and iodobenzene for compound 257 to afford Compound 56 (0.12 g).

Step-1: Synthesis of 5-(cyclopropylethynyl)-1-(tetrahydro-2H-pyran-2-yl)-1H-indazole

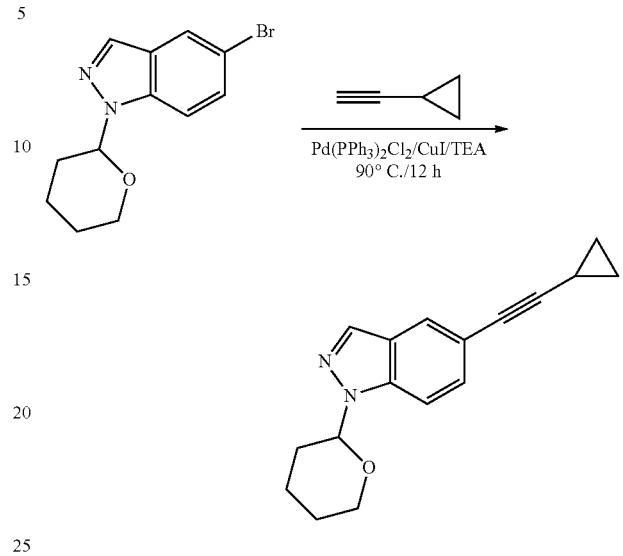

The reaction was carried out according to Scheme 1, Step-2 substituting 5-bromo-1-(tetrahydro-2H-pyran-2-yl)-1H-indazole (5.5 g, 19.57 mmol) in 88 mL of triethyl amine and ethynylcyclopropane (2.5 g, 39.14 mmol) and heated at 90° C. for 12 h. Upon completion by TLC, the reaction mixture was quenched with water (10 mL) and extracted with ethyl acetate (2×50 mL). The combined organic extracts were washed with water, brine, dried over sodium sulphate and concentrated. The crude product was purified over 230-400 mesh silica column chromatography using 5% ethyl acetate in n-hexane to afford 5-(cyclopropylethynyl)-1-(tetrahydro-2H-pyran-2-yl)-1H-indazole (4.5 g, 86%).

Step-2: Synthesis of tert-butyl (Z)-(2-(4-(2-cyclopropyl-1-(1-(tetrahydro-2H-pyran-2-yl)-1H-indazol-5-yl)-2-(4,4,5,5-tetramethyl-1,3,2-dioxaborolan-2-yl)vinyl)phenoxy)ethyl)carbamate

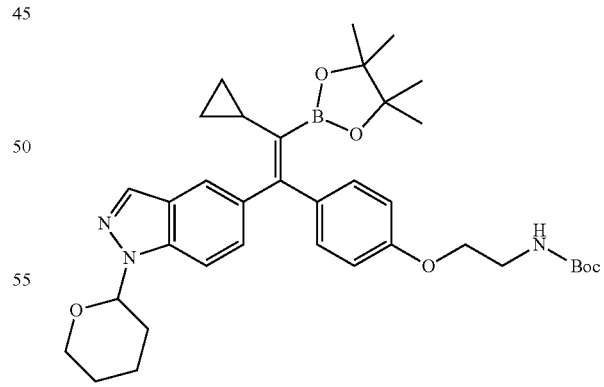

The compound was synthesized following the approach as outlined in Example 3 by substituting into Step-1 5-(cyclopropylethynyl)-1-(tetrahydro-2H-pyran-2-yl)-1H-indazole for compound 252, and continuing with Steps 2-3 to afford the crude material containing the title compound of Ex. 56 Step-2, which was used in next step without further purification (6 g, crude).

Compound 56: ¹H NMR (400 MHz, DMSO-d₆): δ 13.04 (s, 1H), 8.06 (s, 1H), 7.73 (s, 1H), 7.51 (d, J=8.8 Hz, 1H), 7.27 (d, J=8.4 Hz, 1H), 7.21-7.04 (m, 5H), 6.72 (d, J=8.4 Hz, 2H), 6.61-6.46 (m, 4H), 3.83 (t, J=5.6 Hz, 2H), 3.31-3.29 (m, 2H), 2.98 (s, 3H), 2.83 (s, 3H), 2.75 (t, J=5.2 Hz, 2H), 2.0-2.30 (m, 1H), 1.74-1.71 (m, 1H), 0.58-0.56 (m, 2H), 0.21-0.20 (m, 2H). LCMS: 507.4 [M+H]⁺

Example 57: Synthesis of (E)-4-((2-(4-((E)-2-(2-chloro-4-fluorophenyl)-1-(4-fluoro-1H-indazol-5-yl)but-1-en-1-yl)phenoxy)ethyl)amino)-N,N-dimethyl-but-2-enamide (Compound 57)

The compound was synthesized following the approach as outlined in Example 50 by substituting into Step-2 tert-butyl (E)-(2-(4-(2-(2-chloro-4-fluorophenyl)-1-(4-fluoro-1-(tetrahydro-2H-pyran-2-yl)-1H-indazol-5-yl)but-1-en-1-yl)phenoxy)ethyl)carbamate (preparation shown below in Step-1) for compound 261 to afford Compound 57 (0.04 g, 15.7%).

Step-1: Synthesis of tert-butyl (E)-(2-(4-(2-(2-chloro-4-fluorophenyl)-1-(4-fluoro-1-(tetrahydro-2H-pyran-2-yl)-1H-indazol-5-yl)but-1-en-1-yl)phenoxy)ethyl)carbamate

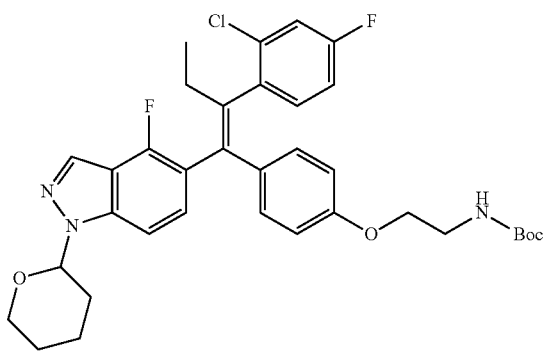 [SMILES: CC/C(=C(/c1ccc(OCCNC(=O)OC(C)(C)C)cc1)c1ccc2c(cnn2C2CCCCO2)c1F)c1ccc(F)cc1Cl]

The compound was synthesized following the approach as outlined in Example 3 by substituting 5-(but-1-yn-1-yl)-4-fluoro-1-(tetrahydro-2H-pyran-2-yl)-1H-indazole (Example 4, Step-4) for compound 252 in Step-1, proceeding directly to Step-3, and substituting 2-chloro-4-fluoro-1-iodobenzene for compound 227 in Step-4 to afford the title compound of this step. The crude product was purified by silica gel column chromatography, eluting with 2% MeOH in dichloromethane to afford the title compound (1.3 g, 16%).

Compound 57: ¹H NMR (400 MHz, DMSO-d₆): δ 13.42 (s, 1H), 8.18 (s, 1H), 7.42 (d, J=6.4 Hz, 1H), 7.36 (dd, J₁=7.2 Hz, J₂=2.0 Hz, 1H), 7.31 (dd, J₁=6.8 Hz, J₂=5.2 Hz, 1H), 7.25-7.22 (m, 1H), 7.14 (dt, J=6.8 Hz, J₂=5.2 Hz, 1H), 6.84 (d, J=7.2 Hz, 2H), 6.63 (d, J=7.2 Hz, 2H), 6.61-6.57 (m, 1H), 6.49 (d, J=12.4 Hz, 1H), 3.87 (t, J=4.4 Hz, 2H), 3.33-3.31 (m, 2H), 2.97 (s, 3H), 2.84 (s, 3H), 2.78 (t, J=4.4 Hz, 2H), 2.30-2.25 (m, 2H), 0.82 (t, J=6.2 Hz, 3H). LCMS: 565.3 [M+H]⁺

Example 58: Synthesis of (E)-4-((2-((5-((Z)-2-(2-chloro-4-fluorophenyl)-1-(3-fluoro-1H-indazol-5-yl)but-1-en-1-yl)pyridin-2-yl)oxy)ethyl)amino)-N,N-dimethylbut-2-enamide (Compound 58)

The compound was synthesized following the approach as outlined in Example 14 by substituting into Step-4 (i) (Z)-5-(1,2-bis(4,4,5,5-tetramethyl-1,3,2-dioxaborolan-2-yl)but-1-en-1-yl)-3-fluoro-1-(tetrahydro-2H-pyran-2-yl)-1H-indazole (as prepared in Example 3, Step-1) for compound 233, (ii) tert-butyl (E)-(4-(dimethylamino)-4-oxobut-2-en-1-yl)(2-((5-iodopyridin-2-yl)oxy)ethyl)carbamate (as prepared in Example 25, Step-2) for compound 234, and (iii) 2-chloro-4-fluoro-1-iodobenzene for compound 262 to deliver Compound 58 (0.115 g, 10%).

Compound 58: ¹H NMR (400 MHz, DMSO-d₆): δ 12.63 (s, 1H), 7.69 (d, J=2.0 Hz, 1H), 7.59 (s, 1H), 7.51 (dd, J=8.6 Hz, J₂=1.8 Hz, 1H), 7.43-7.35 (m, 2H), 7.29 (d, J=1.4 Hz, 1H), 7.27-7.15 (m, 2H), 6.62-6.47 (m, 3H), 4.14 (t, J=5.9 Hz, 2H), 2.93 (s, 3H), 2.84 (s, 3H), 2.78 (t, J=5.8 Hz, 2H), 2.37 (q, J=7.3 Hz, 2H), 0.89 (t, J=7.3 Hz, 3H). LCMS: 566.3 [M+H]⁺.

Example 59: Synthesis of (E)-4-((2-((5-((Z)-2-(2-chloro-4-fluorophenyl)-4,4,4-trifluoro-1-(3-fluoro-1H-indazol-5-yl)but-1-en-1-yl)pyridin-2-yl)oxy)ethyl)amino)-N,N-dimethylbut-2-enamide (Compound 59)

Step-1: Synthesis of 3-fluoro-1-(tetrahydro-2H-pyran-2-yl)-5-((trimethylsilyl)ethynyl)-1H-indazole

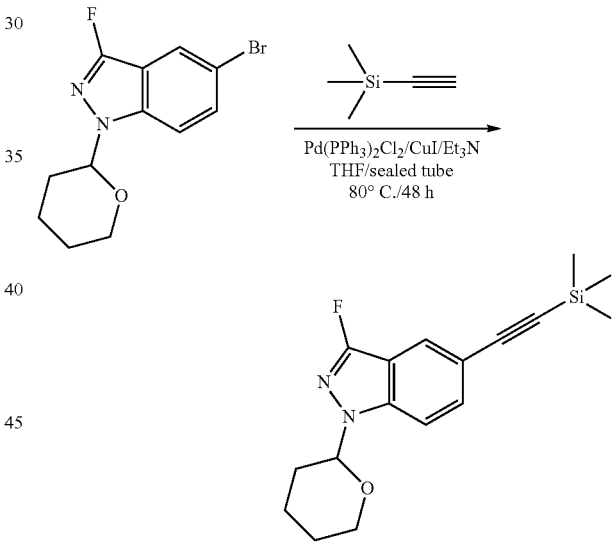

To a stirred solution of 5-bromo-3-fluoro-1-(tetrahydro-2H-pyran-2-yl)-1H-indazole (4.5 g, 15 mmol, as prepared in Example 2, Step-2) in 35 mL of THF:Et₃N (5:1) in a sealed tube, were added copper iodide (0.288 g, 1.5 mmol) at room temperature. This mixture was degassed with three vacuum/N₂ cycles, and were added ethynyltrimethylsilane (2.22 g, 22 mmol) followed by Pd(PPh₃)₂Cl₂ (0.5 g, 0.7 mmol). The pressure tube was sealed and heated at 80° C. for 48 h. Upon completion by TLC, the reaction mixture was diluted with water (250 mL) and extracted with EtOAc (2×100 mL). The combined organic extracts were washed with water, brine, dried over anhydrous sodium sulphate and concentrated under reduced pressure. The crude product was purified by combo-flash using 5% EtOAc in n-hexane to afford 3-fluoro-1-(tetrahydro-2H-pyran-2-yl)-5-((trimethylsilyl)ethynyl)-1H-indazole (3.2 g, 72%).

183

Step-1A: Alternative Synthesis of 3-fluoro-1-(tetrahydro-2H-pyran-2-yl)-5-((trimethylsilyl) ethynyl)-1H-indazole

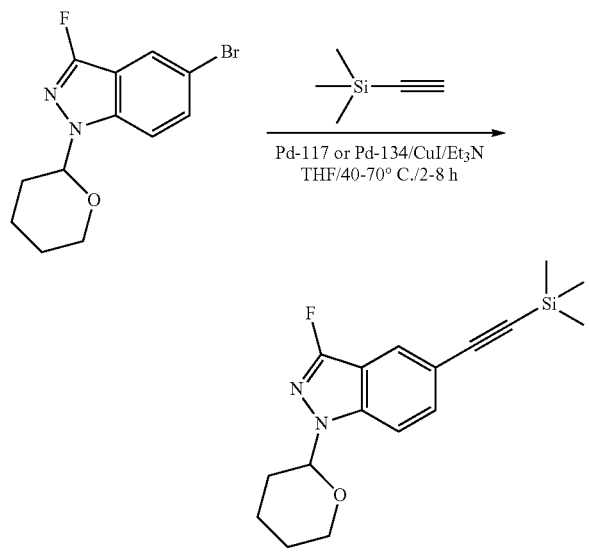

Pd-117 = PdCl2 (DPEPhos) Pd-134 = PdCl2 (Xant-Phos)

Step-1A presents a proposed alternative to Step-1 of Example 59, for the possible preparation of 3-fluoro-1-(tetrahydro-2H-pyran-2-yl)-5-((trimethylsilyl)ethynyl)-1H-indazole, which may be used as intermediate for further synthetic routes that include that compound. To a stirred solution of 5-bromo-3-fluoro-1-(tetrahydro-2H-pyran-2-yl)-1H-indazole (5 g, 16.71 mmol) in 30 mL of 2-Methyl THF(6V) in a 100 ml RBF, were added triethylamine (5.07 g, 50 mmol), copper iodide (0.16 g, 0.84 mmol) at room temperature. This mixture was degassed with three vacuum/N₂ cycles, and were added ethynyltrimethylsilane (4.10 g, 41.74 mmol) followed by Pd-134 (0.31 g, 0.41 mmol) or Pd-117. The reaction mixture heated at 40° C.-75° C. for 3-8 h. Upon completion by TLC, the reaction mixture was filtered through celite bed and washed with 30 ml 2-Methyl THF. Filtrate washed with brine and concentrated under reduced pressure to afford 3-fluoro-1-(tetrahydro-2H-pyran-2-yl)-5-((trimethylsilyl)ethynyl)-1H-indazole crude (6.1 g) and used for next stage as considering 100% yield.

Step-2: Synthesis of 5-ethynyl-3-fluoro-1-(tetrahydro-2H-pyran-2-yl)-1H-indazole

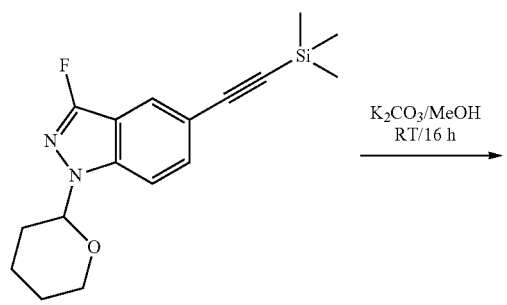

184

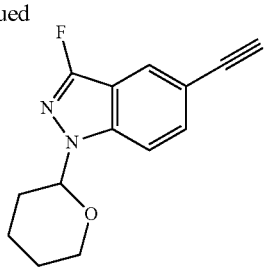

To a stirred solution of 3-fluoro-1-(tetrahydro-2H-pyran-2-yl)-5-((trimethylsilyl)ethynyl)-1H-indazole (3.2 g, 10 mmol) in methanol 32 mL was added potassium carbonate (0.151 g, mmol), reaction mixture was stirred for 16 h at room temperature. After completion of reaction, reaction mixture was diluted with ethyl acetate and the organic layer was washed with water followed by brine. The organic layer was dried over anhydrous Na₂SO₄ and concentrated under reduced pressure to obtain title compound of Ex. 59 Step-2 (2.8 g, crude).

Step-3: Synthesis of 3-fluoro-1-(tetrahydro-2H-pyran-2-yl)-5-(4,4,4-trifluorobut-1-yn-1-yl)-1H-indazole

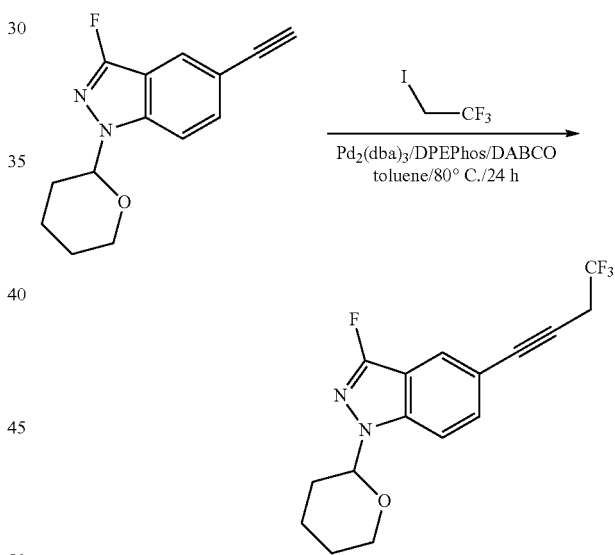

To a stirred solution of 5-ethynyl-3-fluoro-1-(tetrahydro-2H-pyran-2-yl)-1H-indazole (2.6 g, 10.6 mmol) in 20 mL of toluene, were added 1,1,1-trifluoro-2-iodoethane (4.47 g, 21.3 mmol) at room temperature. This mixture was degassed with three vacuum/N₂ cycles, and were added Pd₂(dba)₃ (0.487 g, 0.5 mmol) followed by DPEphos (1.14 g, 2.1 mmol) and DABCO (2.39 g, 21.3 mmol). Reaction mixture was heated at 80° C. for 24 h. Upon completion by TLC, the reaction mixture was diluted with water (250 mL) and extracted with EtOAc (2×100 mL). The combined organic extracts were washed with water, brine, dried over anhydrous sodium sulphate and concentrated under reduced pressure. The crude product was purified by column chromatography using 5% EtOAc in n-hexane to afford 3-fluoro-1-(tetrahydro-2H-pyran-2-yl)-5-(4,4,4-trifluorobut-1-yn-1-yl)-1H-indazole (1.6 g, 46%).

Step-4: Synthesis of tert-butyl ((E)-4-(dimethyl-amino)-4-oxobut-2-en-1-yl)(2-((5-((E)-4,4,4-trifluoro-1-(3-fluoro-1-(tetrahydro-2H-pyran-2-yl)-1H-indazol-5-yl)-2-(4,4,5,5-tetramethyl-1,3,2-dioxaborolan-2-yl)but-1-en-1-yl)pyridin-2-yl)oxy)ethyl)carbamate

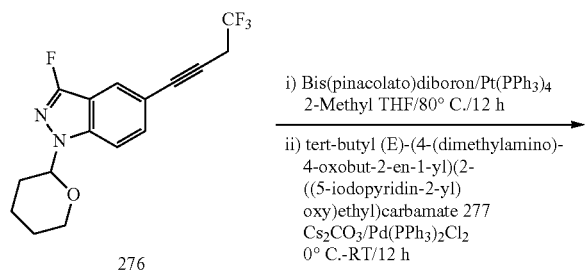

To a stirred solution of 3-fluoro-1-(tetrahydro-2H-pyran-2-yl)-5-(4,4,4-trifluorobut-1-yn-1-yl)-1H-indazole (1 g, 3.06 mmol) in 2-methyl THF (20 mL), was added bis(pinacolato)diboron (0.934 g, 3.68 mmol), tetrakis(triphenylphosphine)platinum (0) (0.026 g, 0.02 mmol) under nitrogen atmosphere, reaction mixture was stirred at 80° C. for 12 h. The solution was allowed to cool to room temperature and tert-butyl (E)-(4-(dimethylamino)-4-oxobut-2-en-1-yl)(2-((5-iodopyridin-2-yl)oxy)ethyl)carbamate (1.12 g, 2.37 mmol), bis(triphenylphosphine)palladium (II) dichloride (0.092 g, 0.13 mmol), cesium carbonate (1.7 g, 5.26 mmol) and 2-methyl THF (20 mL) were added. This mixture was degassed with nitrogen and water (0.3 mL) was added. This mixture was stirred at room temperature for 12 h. After completion of reaction, reaction mixture was diluted with water followed by extracted with ethyl acetate, organic layer was dried over anhydrous sodium sulphate and concentrated under reduced pressure to afford the crude compound. Crude compound was purified by combi-flash using 3% MeOH in dichloromethane to afford the title compound of Ex. 59 Step-4 (1.2 g).

Step-5: Synthesis of tert-butyl (2-((5-((Z)-2-(2-chloro-4-fluorophenyl)-4,4,4-trifluoro-1-(3-fluoro-1-(tetrahydro-2H-pyran-2-yl)-1H-indazol-5-yl)but-1-en-1-yl)pyridin-2-yl)oxy)ethyl) ((E)-4-(dimethylamino)-4-oxobut-2-en-1-yl)carbamate

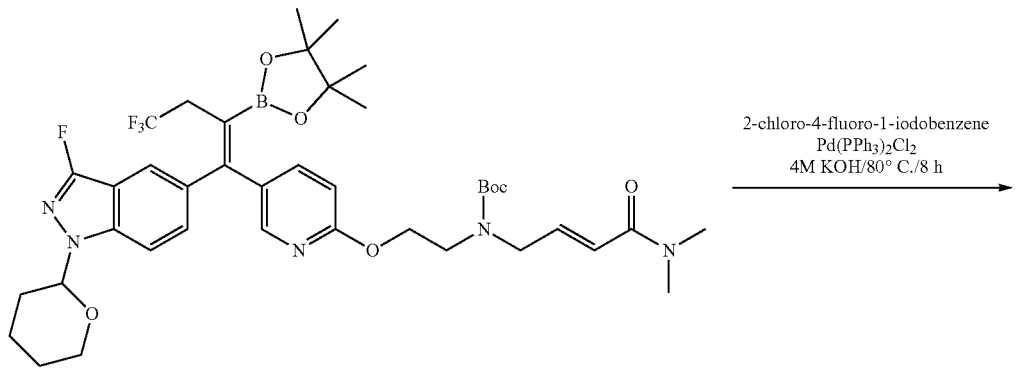

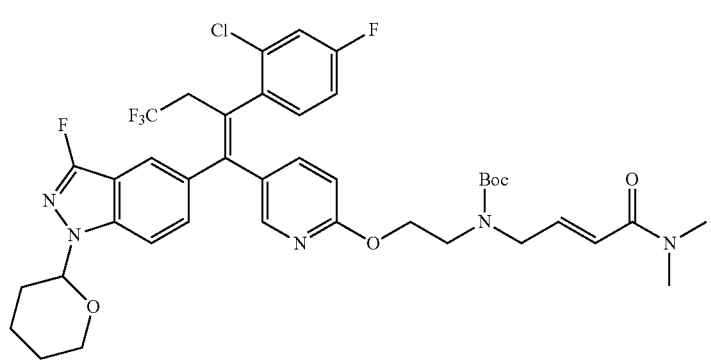

The reaction was carried out according to Scheme 1, Step-5 using tert-butyl ((E)-4-(dimethylamino)-4-oxobut-2-en-1-yl)(2-((5-((E)-4,4,4-trifluoro-1-(3-fluoro-1-(tetrahydro-2H-pyran-2-yl)-1H-indazol-5-yl)-2-(4,4,5,5-tetramethyl-1,3,2-dioxaborolan-2-yl)but-1-en-1-yl)pyridin-2-yl)oxy)ethyl)carbamate (1.2 g, 1.49 mmol) for compound 208 in 2-m and 2-chloro-4-fluoro-1-iodobenzene (0.383 g, 1.49 mmol) for compound 209. Reaction mixture was stirred at 80° C. for 8 h. The crude material was purified by combiflash using 3% MeOH in dichloromethane to afford the title compound of Ex. 59 Step-5 (0.92 g, 76%).

Step-6: Synthesis of (E)-4-((2-((5-((Z)-2-(2-chloro-4-fluorophenyl)-4,4,4-trifluoro-1-(3-fluoro-1H-indazol-5-yl)but-1-en-1-yl)pyridin-2-yl)oxy)ethyl)amino)-N,N-dimethylbut-2-enamide

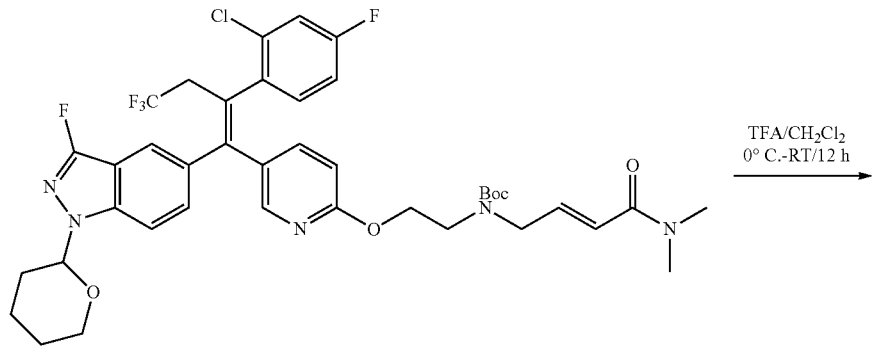

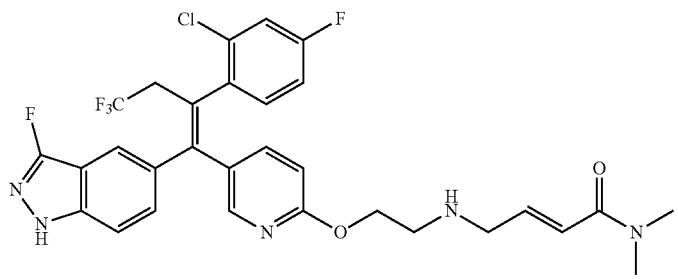

59

The reaction was carried out according to Scheme 2, Step-6b using tert-butyl (2-((5-((Z)-2-(2-chloro-4-fluorophenyl)-4,4,4-trifluoro-1-(3-fluoro-1-(tetrahydro-2H-pyran-2-yl)-1H-indazol-5-yl)but-1-en-1-yl)pyridin-2-yl)oxy)ethyl)((E)-4-(dimethylamino)-4-oxobut-2-en-1-yl)carbamate (0.92 g, 1.14 mmol) for compound 211c to afford crude compound, which was purified by preparative HPLC to afford Compound 59 (0.27 g, 38%) as a free base.

Compound 59: $^1$H NMR (400 MHz, DMSO-$d_6$): δ 12.71 (s, 1H), 7.71 (d, J=2 Hz, 2H), 7.65 (m, 2H), 7.57-7.52 (m, 2H), 7.37 (dd, $J_1$=8.8 Hz, $J_2$=2.4 Hz, 1H), 7.28-7.19 (m, 3H), 6.62-6.46 (m, 3H), 4.15 (t, J=4.1 Hz, 2H), 3.54-3.40 (m, 2H), 3.37-3.28 (m, 2H), 2.98 (s, 3H), 2.84 (s, 3H), 2.76 (t, J=4.1 Hz, 2H). LCMS: 620.2 [M+H]$^+$.

Example 60: Synthesis of (E)-N,N-dimethyl-4-((2-((5-((Z)-4,4-trifluoro-1-(3-fluoro-1H-indazol-5-yl)-2-phenylbut-1-en-1-yl)pyridin-2-yl)oxy)ethyl)amino)but-2-enamide (Compound 60)

Step-1: Synthesis of tert-butyl ((E)-4-(dimethylamino)-4-oxobut-2-en-1-yl)(2-((5-((Z)-4,4-trifluoro-1-(3-fluoro-1-(tetrahydro-2H-pyran-2-yl)-1H-indazol-5-yl)-2-phenylbut-1-en-1-yl)pyridin-2-yl)oxy)ethyl)carbamate

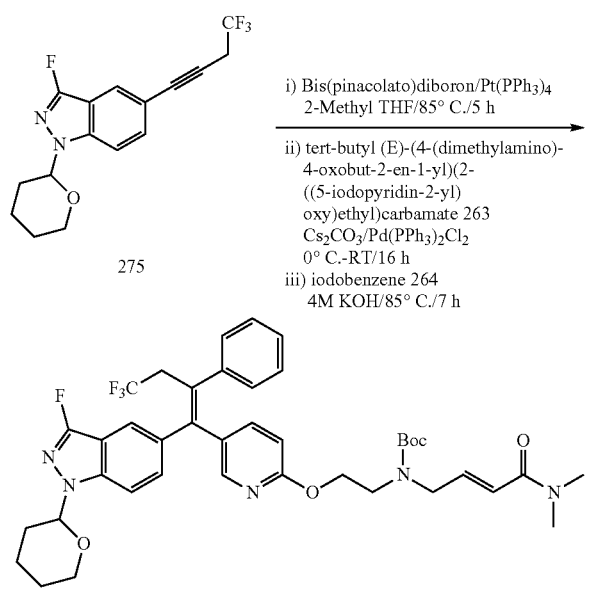

To a stirred solution of 3-fluoro-1-(tetrahydro-2H-pyran-2-yl)-5-(4,4,4-trifluorobut-1-yn-1-yl)-1H-indazole (0.66 g, 2.02 mmol, prepared as outlined in Example 59, Step-1 through Step-3) in 2-methyl THF (10 mL), was added bis(pinacolato)diboron (0.566 g, 2.22 mmol), tetrakis(triphenylphosphine)platinum (0) (0.025 g, 0.02 mmol) under nitrogen atmosphere, reaction mixture was stirred at 85° C. for 5 h. The solution was allowed to cool to room temperature and tert-butyl (E)-(4-(dimethylamino)-4-oxobut-2-en-1-yl)(2-((5-iodopyridin-2-yl)oxy)ethyl)carbamate (0.72 g, 1.51 mmol, as prepared in Example 25, Step-2), bis(triphenylphosphine)palladium (II) dichloride (0.071 g, 0.1 mmol), cesium carbonate (1.3 g, 4.04 mmol) and 2-methyl THF (10 mL) were added. This mixture was degassed with nitrogen and water (0.12 mL) was added. This mixture was stirred at room temperature for 16 h. After completion of reaction, to the above reaction mixture 4M KOH (2.78 mL, 11.13 mmol) and iodobenzene (0.33 g, 1.61 mmol) were added. Reaction mixture was stirred at 85° C. for 7 h. After completion of reaction, reaction mixture was cooled to room temperature, diluted with water and extracted with EtOAc. The organic layer was dried over anhydrous sodium sulphate and concentrated under reduced pressure. The crude material was purified by combi-flash using 100% ethyl acetate as an eluent to afford tert-butyl ((E)-4-(dimethylamino)-4-oxobut-2-en-1-yl)(2-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)ethyl)carbamate (0.35 g, 23%).

Step-2: Synthesis of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy) ethyl)amino)but-2-enamide

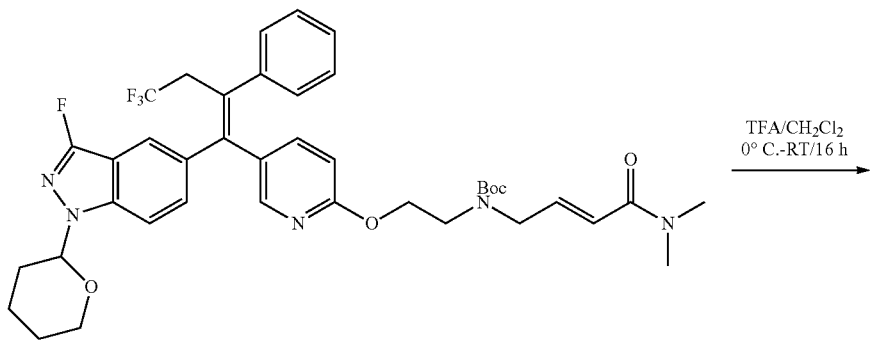

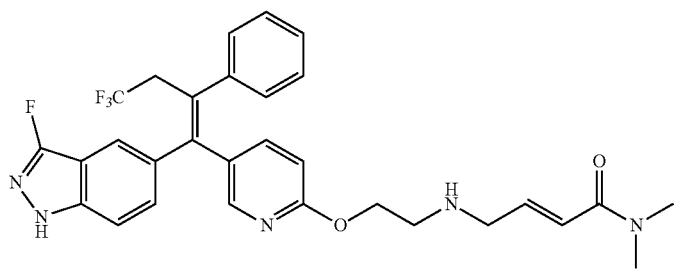

To a stirred solution of tert-butyl ((E)-4-(dimethylamino)-4-oxobut-2-en-1-yl)(2-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)ethyl)carbamate (0.35 g, 0.46 mmol) in dichloromethane (10 mL) was added at 0° C., TFA (1 mL). The reaction mixture was stirred for 16 h at room temperature. After completion of reaction, reaction mixture was basified with saturated NaHCO₃, extracted with ethyl acetate. Organic layer was concentrated under reduced pressure to afford crude compound, which was purified by preparative HPLC to afford desired compound (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide (0.03 g, 11%).

Compound 60: ¹H NMR (400 MHz, DMSO-d₆): δ 12.71 (s, 1H), 7.63 (s, 2H), 7.54 (m, 1H), 7.26-7.18 (m, 7H), 6.62-6.46 (m, 3H), 4.13 (t, J=5.8 Hz, 2H), 3.51-3.43 (m, 2H), 3.34-3.28 (m, 2H), 2.98 (s, 3H), 2.83 (s, 3H), 2.75 (t, J=5.8 Hz, 2H). LCMS: 568.2 [M+H]⁺.

Example 60A: Synthesis of Hydrochloride Salt of Compound 60

Step-1: Synthesis of (E)-N,N-dimethyl-4-((2-((5-((Z)-4,4,4-trifluoro-1-(3-fluoro-1H-indazol-5-yl)-2-phenylbut-1-yl)pyridin-2-yl)oxy)ethyl)amino)but-2-enamide hydrochloride

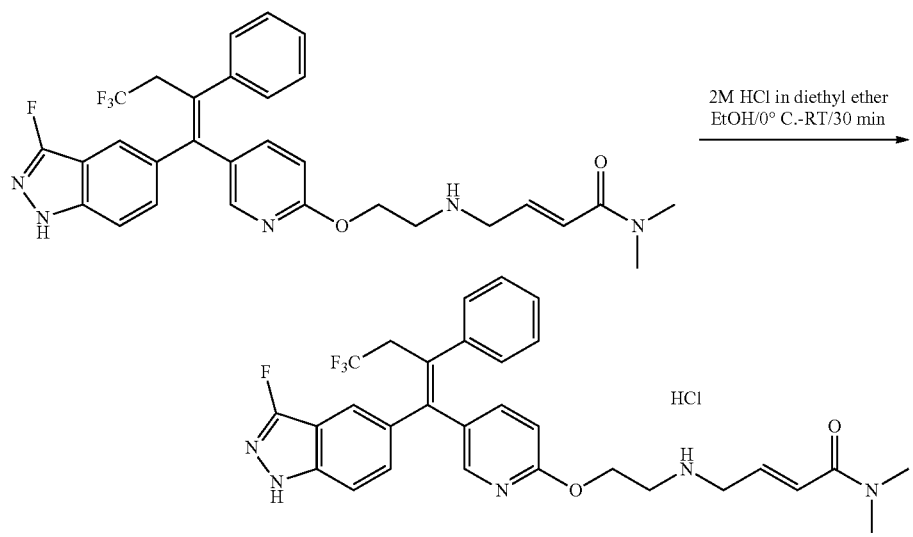

To a stirred solution of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide (4.1 g, 7.23 mmol) in ethanol (24 mL) was added 2M HCl in diethyl ether (7.5 mL) at 0° C. A white solid was observed in the reaction mixture after stirring for 30 min at room temperature. Reaction mixture was concentrated under vacuum at 35° C. and the solid obtained was co-distilled with dichloromethane under vacuum at 45° C. The solid obtained was washed with n-pentane and dried under vacuum at 50° C. for 4 h to obtain the title compound (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide hydrochloride (4.3 g, 98%). ¹H NMR (400 MHz, DMSO-d₆): δ 12.74 (s, 1H), 9.26 (bs, 2H), 7.69-7.34 (m, 3H), 7.28-7.17 (m, 7H), 6.81 (d, J=15.2 Hz, 1H), 6.62-6.53 (m, 2H), 4.37 (t, J=4.4 Hz, 2H), 3.77-3.76 (m, 2H), 3.51-3.43 (m, 2H), 3.23 (bs, 2H), 3.03 (s, 3H), 2.86 (s, 3H). LCMS: 568.3 [M+H]⁺

Example 60B: Synthesis of Hydrochloride Salt of Compound 60

To a stirred solution of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide (0.200 g, 0.35 mmol) in ethanol (0.6 mL) was added 2M HCl in diethyl ether (0.88 mL) at 0° C. A white solid was observed in the reaction mixture after stirring for 30 min at room temperature. Reaction mixture was concentrated under vacuum at 35° C. and the solid obtained was co-distilled with dichloromethane under vacuum at 45° C. The solid obtained was washed with n-pentane and dried under vacuum at 50° C. for 4 h to obtain the title compound (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide hydrochloride (0.150 g, 67%). ¹H NMR (400 MHz, DMSO-d₆): δ 12.71 (s, 1H), 9.07 (bs, 2H), 7.69-7.54 (m, 3H), 7.26-7.18 (m, 7H), 6.80 (d, J=15.2 Hz, 1H), 6.62-6.46 (m, 2H), 4.35 (m, 2H), 3.75 (m, 2H), 3.51-3.43 (m, 2H), 3.34-3.28 (m, 2H), 2.98 (s, 3H), 2.83 (s, 3H). LCMS: 568.2 [M+H]⁺.

Example 61: Synthesis of (E)-N,N-dimethyl-4-((2-(4-((E)-4,4,4-trifluoro-1-(3-fluoro-1H-indazol-5-yl)-2-(3-fluoropyridin-4-yl)but-1-en-1-yl)phenoxy)ethyl)amino)but-2-enamide (Compound 61)

The compound was synthesized following the approach as outlined in Example 60 by substituting into Step-1 tert-butyl (E)-(4-(dimethylamino)-4-oxobut-2-en-1-yl)(2-(4-iodophenoxy)ethyl)carbamate (as prepared in Example 14, Step-3) for compound 263 and 3-fluoro-4-iodopyridine for compound 264 to afford Compound 61 (0.02 g, 5.8%).

Compound 61: ¹H NMR (400 MHz, DMSO-d₆): δ 12.71 (s, 1H), 8.39 (s, 1H), 8.34 (d, J=2 Hz, 1H), 7.59 (s, 1H), 7.56-7.49 (m, 2H), 7.20 (d, J=2.4 Hz, 1H), 6.85 (d, J=8.9 Hz, 2H), 6.85 (d, 1H), 6.68 (d, J=8.9 Hz, 2H), 6.63-6.47 (m, 1H), 4.15 (m, 2H), 3.79 (t, J=5.7 Hz, 2H), 3.45 (q, J=10.8 Hz, 2H), 3.25 (m, 2H), 2.98 (s, 3H), 2.84 (s, 3H). LCMS: 586.2 [M+H]⁺.

Example 62: Synthesis of (E)-N,N-dimethyl-4-((2-((5-((Z)-4,4,4-trifluoro-1-(3-fluoro-1H-indazol-5-yl)-2-(3-fluoropyridin-4-yl)but-1-en-1-yl)pyridin-2-yl)oxy)ethyl)amino)but-2-enamide (Compound 62)

The compound was synthesized following the approach as outlined in Example 59 by substituting into Step-5 3-fluoro-4-iodopyridine for compound 265 to afford Compound 62 (0.07 g, 12%).
Compound 62: ¹H NMR (400 MHz, DMSO-d₆): δ 12.76 (s, 1H), 8.43-8.39 (m, 2H), 7.72-7.56 (m, 4H), 7.28-7.24 (m, 2H), 6.62-6.48 (m, 3H), 4.15 (t, J=5.8 Hz, 2H), 4.15 (m, 2H), 3.51-3.46 (m, 2H), 3.38-3.31 (m, 2H), 2.98 (s, 3H), 2.84 (s, 3H). LCMS: 587.2 [M+H]⁺

Example 63: Synthesis of (E)-N,N-dimethyl-4-((2-(4-((E)-2-phenyl-1-(1H-pyrazolo[4,3-b]pyridin-5-yl)but-1-en-1-yl)phenoxy)ethyl)amino)but-2-enamide (Compound 63)

The compound was synthesized following the approach as outlined in Example 50 by substituting into Step-2 tert-butyl (E)-(2-(4-(2-phenyl-1-(1-(tetrahydro-2H-pyran-2-yl)-1H-pyrazolo[4,3-b]pyridin-5-yl)but-1-en-1-yl)phenoxy)ethyl)carbamate (preparation shown below in Ex. 63 Step 1-6) for compound 261 to afford Compound 63 (0.013 g, 5.2%).

Step-1: Synthesis of 6-bromo-2-methylpyridin-3-amine

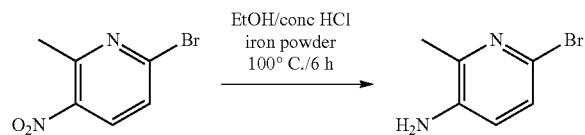

To a stirred solution of 6-bromo-2-methyl-3-nitropyridine (15 g, 69.12 mmol) in ethanol (280 mL) was added iron powder (57.9 g, 1036 mmol) followed by conc HCl (30 mL). The reaction mixture was stirred for 6 h at 100° C., after completion of reaction (monitored by TLC), reaction mixture was cooled to room temperature, filtered through celite. Filtrate was basified with saturated NaHCO₃ solution, extracted with EtOAc. Organic layer was washed with water followed by brine, dried over anhydrous sodium sulphate, filtered and concentrated under reduced pressure. The crude product was used in next step without further purification to afford desired compound (5.6 g, 65%) as an off-white solid.

Step-2: Synthesis of 5-bromo-1H-pyrazolo[4,3-b]pyridine

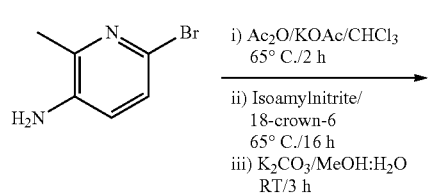

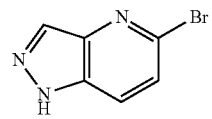

To a stirred solution of 6-bromo-2-methyl-3-nitropyridine (5 g, 26.73 mmol) in chloroform was added potassium acetate (3.14 g, 32.08 mmol) and acetic anhydride (10.9 g, 106 mmol) at 10° C., the contents were stirred at 65° C. temperature for 2 h. After completion of reaction (monitored by TLC), the reaction mixture was cooled to room temperature, isoamylnitrite (3.75 g, 32.06 mmol) was added drop wise over a period of 15 min, followed by 18-crown-6 (0.7 g, 2.67 mmol) was added, reaction mixture was stirred at 65° C. for 16 h. After completion of reaction (monitored by TLC), the reaction mixture was cooled to room temperature, methanol and water mixture 120 mL (1:1) was added to the reaction mixture followed by potassium carbonate (34.48 g, 24.99 mmol) and KOH (4.2 g, 74.97 mmol), reaction mixture was stirred for 3 h at room temperature. After completion of reaction, reaction mixture was added diluted with ethyl acetate and the organic layer was washed with water followed by brine. The organic layer was dried over anhydrous Na₂SO₄ and concentrated under reduced pressure to obtain this title compound (5 g) as an off-white solid.

Step-3: Synthesis of 5-bromo-1-(tetrahydro-2H-pyran-2-yl)-1H-pyrazolo[4,3-b]pyridine

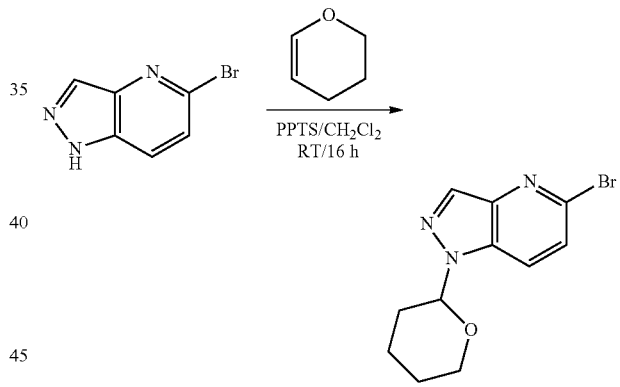

The reaction was carried out according to Scheme 1, Step-1 to give crude material, which was purified by column chromatography over 230-400 mesh silica using 10-15% ethyl acetate in n-hexane to afford 5-bromo-1-(tetrahydro-2H-pyran-2-yl)-1H-pyrazolo[4,3-b]pyridine (5 g, 78%).

Step-4: Synthesis of 5-(but-1-yn-1-yl)-1-(tetrahydro-2H-pyran-2-yl)-1H-pyrazolo[4,3-b]pyridine

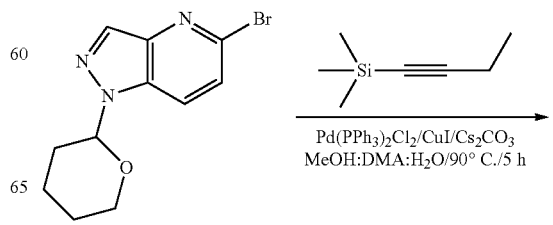

-continued

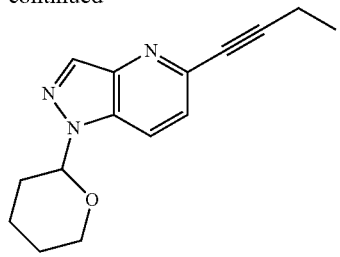

The reaction was carried out according to Scheme 1, Step-2 to give crude material, which was purified over 230-400 mesh silica column chromatography using 10-15% ethyl acetate in n-hexane to afford the title compound of Ex. 63 Step-4 (3.5 g, 77.7%) as a brown oil.

Step-5: Synthesis of tert-butyl (2-(4-(4,4,5,5-tetramethyl-1,3,2-dioxaborolan-2-yl)phenoxy)ethyl)carbamate

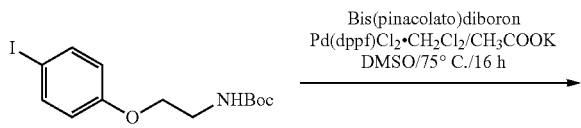

-continued

To a solution of tert-butyl (2-(4-iodophenoxy)ethyl)carbamate (25 g, 68.87 mmol) in DMSO (200 mL) was added potassium acetate (20.24 g, 206.6 mmol) and bis(pinacolato)diboron (34.98 g, 137.74 mmol). The contents were degassed with three vacuum/$N_2$ cycles, Pd(dppf)$Cl_2$.$CH_2Cl_2$ (2.8 g, 3.44 mmol) was added and the resulting mixture was stirred at 75° C. for 16 h. Upon completion by TLC, the reaction mixture was quenched with water (500 mL) and extracted with ethyl acetate (2×250 mL). The combined organic extracts were washed with water, brine, dried over anhydrous sodium sulphate and concentrated under reduced pressure. The crude material was purified by column chromatography, eluted with 10-15% ethyl acetate in n-hexane to afford the title compound of Ex. 63 Step-5 (50 g, mixture with bis(pinacolato)diboron).

Step-6: Synthesis of tert-butyl (E)-(2-(4-(2-phenyl-1-(1-(tetrahydro-2H-pyran-2-yl)-1H-pyrazolo[4,3-b]pyridin-5-yl)but-1-en-1-yl)phenoxy)ethyl)carbamate

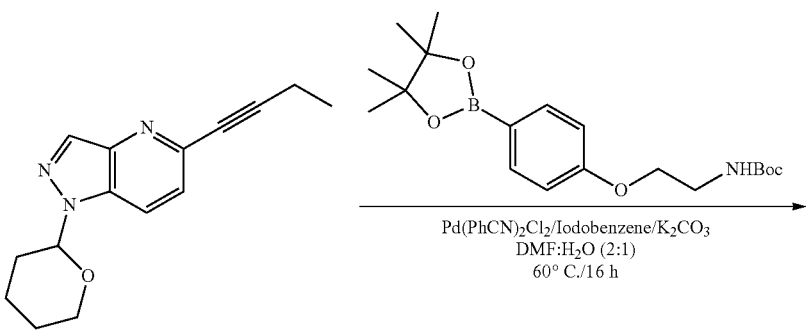

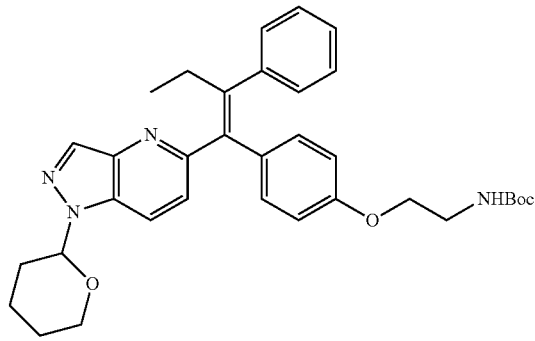

The reaction was carried according to Scheme 1, Step-6 using 5-(but-1-yn-1-yl)-1-(tetrahydro-2H-pyran-2-yl)-1H-pyrazolo[4,3-b]pyridine for compound 204, iodobenzene for compound 209, tert-butyl (2-(4-(4,4,5,5-tetramethyl-1,3,2-dioxaborolan-2-yl)phenoxy)ethyl)carbamate for compound 210 to obtain crude material, which was purified by silica column chromatography to afford the title compound of Ex. 63 Step-6 (4 g, crude).

Compound 63: $^1$H NMR (400 MHz, DMSO-d$_6$): δ 13.29 (s, 1H), 8.26 (s, 1H), 7.97 (s, J=8.8 Hz, 1H), 7.24-7.13 (m, 6H), 6.75 (d, J=8.8 Hz, 2H), 6.62-6.57 (m, 3H), 6.50 (d, J=15.2 Hz, 1H), 3.87 (t, J=5.6 Hz, 2H), 3.3-3.29 (m, 2H), 2.98 (s, 3H), 2.84 (s, 3H), 2.78 (t, J=5.4 Hz, 2H), 2.37-2.30 (m, 2H), 0.86 (t, J=7.6 Hz, 3H). LCMS: 496.4 [M+H]$^+$.

Example 64: Synthesis of (E)-4-((2-(3-fluoro-4-((Z)-1-(3-fluoro-1H-indazol-5-yl)-2-phenylbut-1-en-1-yl)phenoxy)ethyl)amino)-N,N-dimethylbut-2-enamide (Compound 64)

The compound was synthesized following the approach as outlined in Example 50 by substituting into Step-2 tert-butyl (Z)-(2-(3-fluoro-4-(1-(3-fluoro-1-(tetrahydro-2H-pyran-2-yl)-1H-indazol-5-yl)-2-phenylbut-1-en-1-yl)phenoxy)ethyl)carbamate (preparation shown below in Step 1-4) for compound 261 to afford Compound 64 (0.16 g, 17.4%).

Step-1: Synthesis of 4-amino-3-fluorophenol

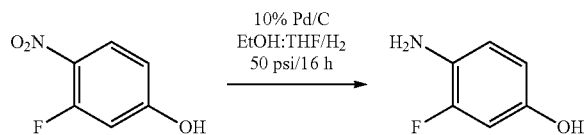 [SMILES: O=[N+]([O-])c1ccc(O)cc1F ; Nc1ccc(O)cc1F]

A mixture of 3-fluoro-4-nitrophenol (6 g, 38.4 mmol) and 10% Pd/C (1.8 g) in EtOH (60 mL) and THF (36 mL) was stirred under H$_2$ (1 atm) for 16 h. After filtration, the filtrate was concentrated to yield 4.68 g (96.5%) of 4-amino-3-fluorophenol.

Step-2: Synthesis of 3-fluoro-4-iodophenol

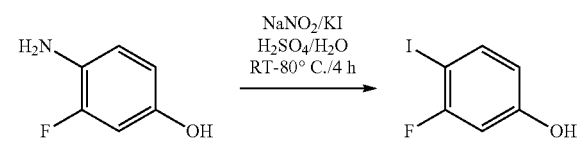 [SMILES: Nc1ccc(O)cc1F ; Oc1ccc(I)c(F)c1]

4-Amino-3-fluorophenol (5 g, 39.4 mmol) was suspended in 15 mL water and H$_2$SO$_4$ (4.62 g), mixture was cooled in an ice-salt bath to −5° C. To this mixture was added, dropwise, a solution of sodium nitrite (2.71 g, 39.4 mmol) in 15 mL water. The internal temperature was kept below +2° C. The resulting brown solution was stirred for a further 15 min at −5° C., then a solution of potassium iodide (7.87 g, 47.2 mmol) in 30 mL water was slowly added dropwise. After complete addition, the reaction was stirred at room temperature for 4 h. Upon completion, the reaction mixture was diluted with EtOAc. Organic layer was washed with water followed by brine, dried over anhydrous sodium sulphate, filtered and concentrated to give the title compound of Ex. 64 Step-2 (5 g, 53.3%).

Step-3: Synthesis of tert-butyl (2-(3-fluoro-4-iodophenoxy)ethyl)carbamate

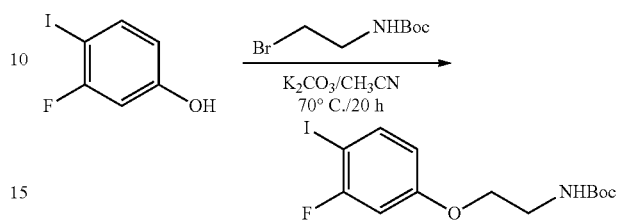

The reaction was carried out according to Scheme 3, Step-1 using 3-fluoro-4-iodophenol and tert-butyl (2-bromoethyl)carbamate to obtain crude material, which was purified by silica gel column chromatography to afford tert-butyl (2-(3-fluoro-4-iodophenoxy)ethyl)carbamate (5 g).

Step-4: Synthesis of tert-butyl (Z)-(2-(3-fluoro-4-(1-(3-fluoro-1-(tetrahydro-2H-pyran-2-yl)-1H-indazol-5-yl)-2-phenylbut-1-en-1-yl)phenoxy)ethyl)carbamate

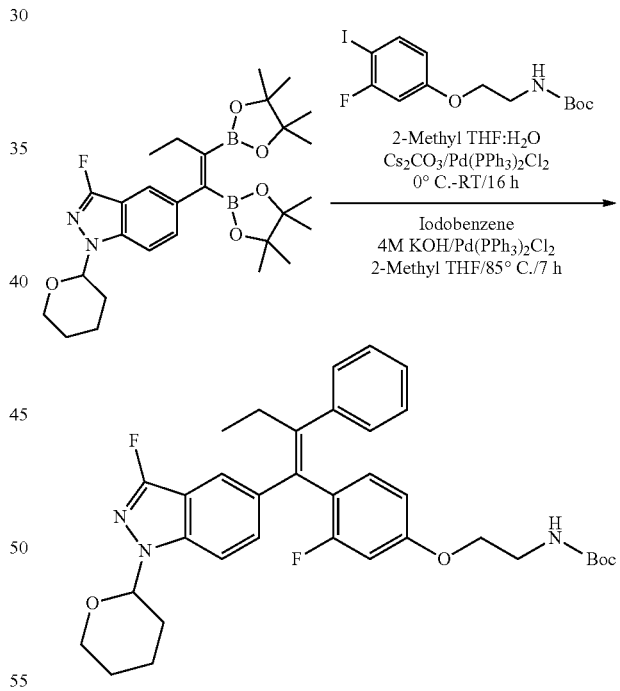

The reaction was carried out following the approach as outlined by Example 50, Step-1, by substituting (Z)-5-(1,2-bis(4,4,5,5-tetramethyl-1,3,2-dioxaborolan-2-yl)but-1-en-1-yl)-3-fluoro-1-(tetrahydro-2H-pyran-2-yl)-1H-indazole (8 g, 15.19 mmol) for compound 260 and tert-butyl (2-(3-fluoro-4-iodophenoxy)ethyl)carbamate (5.4 g, 14.43 mmol) for compound 257 to afford crude material. It was purified by silica gel chromatography using 15% EtOAc in n-hexane to give the title compound of Ex. 64 Step-4 (3.5 g, 38%).

Compound 64: $^1$H NMR (400 MHz, DMSO-d$_6$): δ 12.57 (s, 1H), 7.49 (s, 1H), 7.46 (d, J=2.0 Hz, 1H), 7.27 (dd, J=8.5

Hz, $J_2$=1.2 Hz, 1H), 7.21-7.09 (m, 3H), 6.92 (t, J=8.6 Hz, 1H), 6.62-6.47 (m, 4H), 3.88 (t, J=5.6 Hz, 2H), 3.30 (s, 2H), 2.98 (s, 3H), 2.83 (s, 3H), 2.76 (t, J=5.6 Hz, 2H), 2.44 (q, J=7.8 Hz, 2H), 2.10 (bs, 1H), 0.89 (t, J=7.3 Hz, 3H). LCMS: 531.3 [M+H]$^+$.

Example 65: Synthesis of (E)-4-((2-(4-((E)-2-(2,4-difluorophenyl)-1-(3-fluoro-1H-indazol-5-yl)but-1-en-1-yl)phenoxy)ethyl)amino)-N,N-dimethylbut-2-enamide (Compound 65)

The compound was synthesized following the approach as outlined in Example 50 by substituting into Step-1 2,4-difluoro-1-iodobenzene to afford Compound 65 (0.06 g, 23.7%).

Compound 65: $^1$H NMR (400 MHz, DMSO-d$_6$): δ 12.59 (s, 1H), 7.52 (s, 1H), 7.49 (dd, $J_1$=8.8 Hz, $J_2$=1.2 Hz, 1H), 7.28-7.21 (m, 2H), 7.09 (dd, J=10 Hz, $J_2$=2.4 Hz, 1H), 6.97 (dd, J=8.4 Hz, $J_2$=2.4 Hz, 1H), 6.80 (d, J=8.4 Hz, 2H), 6.64 (d, J=8.8 Hz, 2H), 6.63-6.58 (m, 1H), 6.50 (d, J=15.2 Hz, 1H), 3.88 (t, J=5.6 Hz, 2H), 3.32-3.31 (m, 2H), 2.98 (s, 3H), 2.84 (s, 3H), 2.78 (t, J=5.4 Hz, 2H) 2.34 (q, J=7.6 Hz, 2H), 0.89 (t, J=7.6 Hz, 3H). LCMS: 549.3 [M+H]$^+$ Example 66: Synthesis of (E)-4-((2-(4-((E)-1-(3,6-difluoro-1H-indazol-5-yl)-2-phenylbut-1-en-1-yl)phenoxy)ethyl)amino)-N,N-dimethylbut-2-enamide (Compound 66)

The compound was synthesized following the approach as outlined in Example 50 by (i) substituting into Step-1 tert-butyl (Z)-(2-(4-(1-(3,6-difluoro-1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)ethyl)carbamate (preparation shown below in Ex. 66 Steps 1-7) for compound 260 and iodobenzene for compound 251, and (ii) conducting Step-5 of Ex. 50 by following the reaction conditions described in Scheme 2, Step-6b to deliver Compound 66 (0.012 g).

Step-1: Synthesis of N-(5-fluoro-2-methylphenyl)acetamide

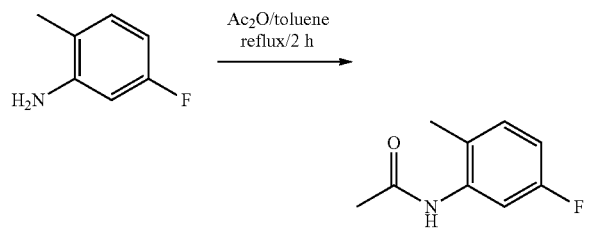

To a stirred solution of 5-fluoro-2-methylaniline (25 g, 200 mmol) in toluene was added acetic anhydride (25 mL) at 10° C., the contents were stirred at reflux temperature for 2 h. After completion of reaction (monitored by TLC), the reaction mixture was cooled to room temperature, solid obtained was filtered and washed with diethyl ether and hexane to obtain desired compound (28 g, 84%).

Step-2: Synthesis of N-(4-bromo-5-fluoro-2-methylphenyl)acetamide

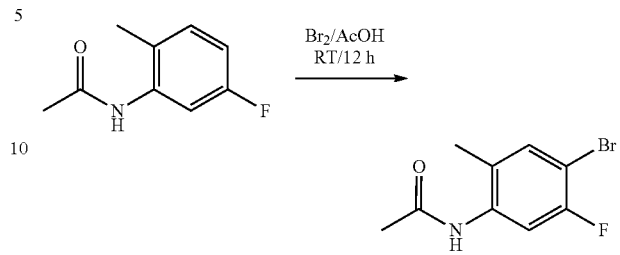

To a stirred solution of N-(5-fluoro-2-methylphenyl)acetamide (28 g, 167 mmol) in acetic acid (150 mL) was added bromine (9.6 mL, 186 mmol) at 10° C. The reaction mixture was stirred for 12 h at room temperature, after completion of reaction (monitored by TLC), solid separated was filtered and dried under reduced pressure. The crude product was used in next step without further purification to afford N-(4-bromo-5-fluoro-2-methylphenyl)acetamide (40 g, 97%).

Step-3: Synthesis of 1-(5-bromo-6-fluoro-1H-indazol-1-yl)ethan-1-one

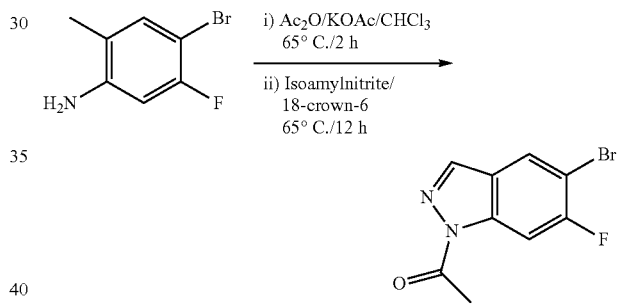

To a stirred solution of 4-bromo-5-fluoro-2-methylaniline (40 g, 163 mmol) in chloroform (400 mL) was added potassium acetate (32 g, 326 mmol) and acetic anhydride (45 mL) at 10° C., the contents were stirred at 65° C. temperature for 2 h. After completion of reaction (monitored by TLC), the reaction mixture was cooled to room temperature, isoamylnitrite (50 mL, 371 mmol) was added drop wise over a period of 15 min, followed by 18-crown-6 (2.16 g, 8.18 mmol) was added, reaction mixture was stirred at 65° C. for 12 h. After completion of reaction (monitored by TLC), the reaction mixture was cooled to room temperature, diluted with ethyl acetate. Organic layer was washed with water followed by brine. The organic layer was dried over anhydrous Na$_2$SO$_4$ and concentrated under reduced pressure to obtain title compound of Ex. 66 Step-3 (38.3 g, 44%).

Step-4: Synthesis of 5-bromo-6-fluoro-1H-indazole

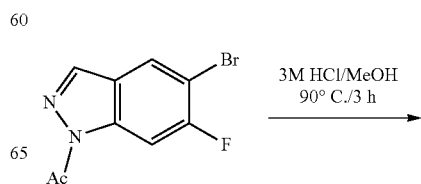

-continued

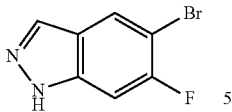

To a stirred solution of 1-(5-bromo-6-fluoro-1H-indazol-1-yl)ethan-1-one (20 g, 78.43 mmol) in 3M HCl (400 mL) was added methanol (80 mL), reaction mixture was stirred at 90° C. for 3 h. After completion of reaction (monitored by TLC), the reaction mixture was cooled to room temperature and basified with 1M NaOH, solid separated was filtered and dried under reduced pressure to obtain title compound of Ex. 66 Step-4 (7.6 g, 45%).

Step-5: Synthesis of 5-bromo-6-fluoro-1-(tetrahydro-2H-pyran-2-yl)-1H-indazole

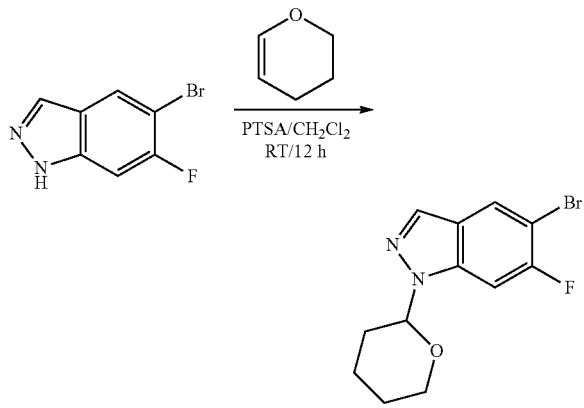

The reaction was run according to Scheme 1, Step-1 using 5-bromo-6-fluoro-1H-indazole (7.6 g, 35.34 mmol) for compound 201. The crude material from the reaction was purified by silica gel chromatography using 4% ethyl acetate in n-hexane to afford 5-bromo-6-fluoro-1-(tetrahydro-2H-pyran-2-yl)-1H-indazole (8.83 g, 84%).

Step-6: Synthesis of 5-(but-1-yn-1-yl)-3,6-difluoro-1-(tetrahydro-2H-pyran-2-yl)-1H-indazole

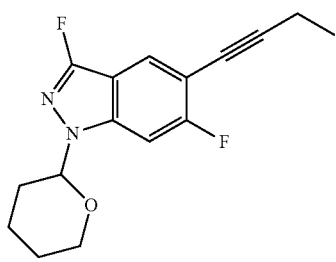 [SMILES: CCC#Cc1cc2c(F)nn(C3CCCCO3)c2cc1F]

The compound was synthesized following the approach as outlined in Example 2 by (i) substituting into Step-1 5-bromo-6-fluoro-1-(tetrahydro-2H-pyran-2-yl)-1H-indazole for compound 270 and (ii) following the reaction conditions of Steps 2 and 3 of Ex. 2. to afford the title compound of Ex. 66 Step-6 (12.19 g, 87%).

Step-7: Synthesis of tert-butyl (Z)-(2-(4-(1-(3,6-difluoro-1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)ethyl)carbamate

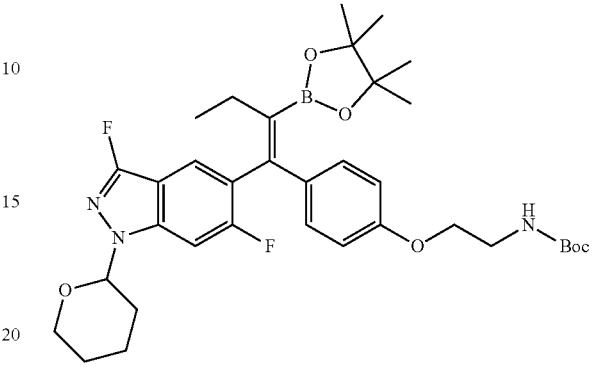

The compound was synthesized following the approach as outlined in Example 14 by (i) substituting into Step-2 5-(but-1-yn-1-yl)-3,6-difluoro-1-(tetrahydro-2H-pyran-2-yl)-1H-indazole for compound 271 and (ii) substituting into Step-4 tert-butyl (2-(4-iodophenoxy)ethyl)carbamate (as prepared in Example 3, Step-2) for compound 234 to deliver the title compound in Ex. 66 Step-7.

Compound 66: $^1$H NMR (400 MHz, DMSO-$d_6$): δ 12.65 (s, 1H), 7.69 (d, J=6.8 Hz, 1H), 7.34 (dd, $J_1$=6.0 Hz, $J_2$=2.0 Hz, 1H), 7.25-7.21 (m, 2H), 7.17-7.14 (m, 3H), 6.79 (d, J=8.8 Hz, 2H), 6.64-6.57 (m, 3H), 6.49 (d, J=15.2 Hz, 1H), 3.87 (t, J=5.6 Hz, 2H), 2.98 (s, 3H), 2.84 (s, 3H), 2.77 (t, J=5.6 Hz, 2H), 2.33-2.31 (m, 2H), 0.81 (t, J=7.6 Hz, 3H). LCMS: 531.3 [M+H]$^+$.

Example 67: Synthesis of (E)-4-((2-(4-((E)-1-(3-fluoro-1H-indazol-5-yl)-2-(pyridin-2-yl)but-1-en-1-yl)phenoxy)ethyl)amino)-N,N-dimethylbut-2-enamide (Compound 67)

The compound was synthesized following the approach as outlined in Example 14 by substituting into Step-4 (Z)-5-(1,2-bis(4,4,5,5-tetramethyl-1,3,2-dioxaborolan-2-yl)but-1-en-1-yl)-3-fluoro-1-(tetrahydro-2H-pyran-2-yl)-1H-indazole (as prepared in Example 3, Step-1) for compound 233 and 2-iodopyridine for compound 262 to deliver Compound 67 (0.010 g) as an off-white solid.

Compound 67: $^1$H NMR (400 MHz, DMSO-$d_6$): δ 12.6 (s, 1H), 8.56 (d, J=4.4 Hz, 1H), 7.53 (s, 1H), 7.50-7.45 (m, 2H), 7.21 (dd, $J_1$=8.8 Hz, $J_2$=1.4 Hz, 1H), 7.13 (dd, $J_1$=4.9 Hz, $J_2$=6.9 Hz, 1H), 6.87 (d, J=7.8 Hz, 1H), 6.72 (d, J=8.8 Hz, 2H), 6.64-6.57 (m, 3H), 6.50 (d, J=15.1 Hz, 1H), 3.88 (t, J=5.7 Hz, 2H), 3.32-3.21 (m, 2H), 299 (s, 3H), 2.84 (s, 3H), 2.78 (t, J=5.6 Hz, 2H), 2.54-2.52 (m, 2H), 0.86 (t, J=7.3 Hz, 3H). LCMS: 514.3 [M+H]$^+$.

Example 68: Synthesis of (E)-4-((2-((5-((Z)-1-(3-fluoro-1H-indazol-5-yl)-2-phenylbut-1-en-1-yl)pyridin-2-yl)oxy)ethyl)amino)-N,N-dimethylbut-2-enamide (Compound 68)

The compound was synthesized following the approach as outlined in Example 14 by substituting into Step-4 (Z)-5-(1,2-bis(4,4,5,5-tetramethyl-1,3,2-dioxaborolan-2-yl)but-1-en-1-yl)-3-fluoro-1-(tetrahydro-2H-pyran-2-yl)-1H-indazole (as prepared in Example 3, Step-1) for compound 233 and tert-butyl (E)-(4-(dimethylamino)-4-oxobut-2-en-1-yl)(2-((5-iodopyridin-2-yl)oxy)ethyl)carbamate (as prepared in Example 25, Step-2) for compound 234 to deliver Compound 68 (0.165 g, 11%).

Compound 68: $^1$H NMR (400 MHz, DMSO-d$_6$): δ 12.6 (s, 1H), 7.59 (d, J=2.0 Hz, 1H), 7.56 (s, 1H), 7.50 (dd, J$_1$=8.8 Hz, J$_2$=2.0 Hz, 1H), 7.26-7.22 (m, 3H), 7.18-7.14 (m, 4H), 6.61-6.56 (m, 1H), 6.51-6.46 (m, 2H), 4.13 (t, J=5.6 Hz, 2H), 3.30-3.29 (m, 2H), 3.29 (s, 3H), 2.84 (s, 3H), 2.76 (t, J=5.9 Hz, 2H), 2.42 (q, J=7.4 Hz, 2H), 2.1-2.0 (bs, 1H), 0.88 (t, J=7.3 Hz, 3H). LCMS: 514.3 [M+H]$^+$.

Example 69: Synthesis of (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide (Compound 69)

Step-1: Synthesis of tert-butyl (E)-(2-(4-(4-(4,4,4-trifluoro-1-(3-fluoro-1-(tetrahydro-2H-pyran-2-yl)-1H-indazol-5-yl)-2-phenylbut-1-en-1-yl)phenoxy)ethyl)carbamate

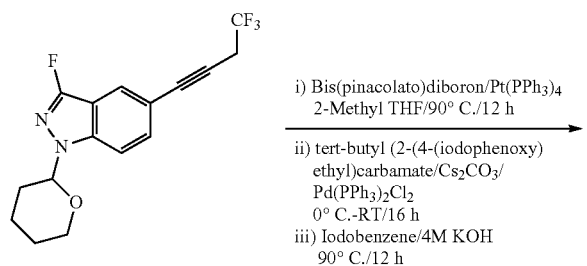

i) Bis(pinacolato)diboron/Pt(PPh$_3$)$_4$
2-Methyl THF/90° C./12 h ii) tert-butyl (2-(4-(iodophenoxy)ethyl)carbamate/Cs$_2$CO$_3$/
Pd(PPh$_3$)$_2$Cl$_2$
0° C.-RT/16 h iii) Iodobenzene/4M KOH
90° C./12 h -continued

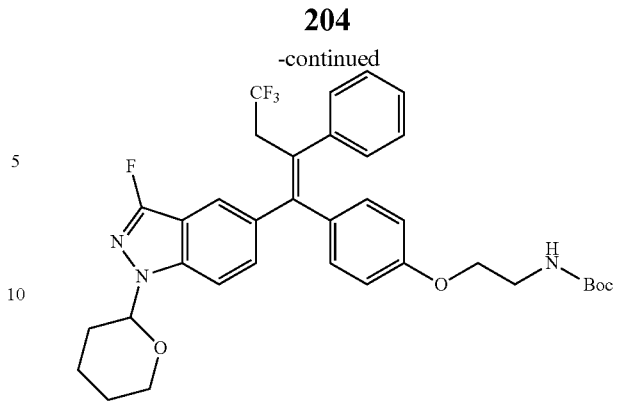

To a stirred solution of 3-fluoro-1-(tetrahydro-2H-pyran-2-yl)-5-(4,4,4-trifluorobut-1-yn-1-yl)-1H-indazole (1.6 g, 4 mmol, Example 59, Step-3) in 2-methyl THF (30 mL), was added bis(pinacolato)diboron (1.24 g, 4 mmol), tetrakis(triphenylphosphine)platinum (0) (0.06 g, 0.04 mmol) under nitrogen atmosphere, reaction mixture was stirred at 90° C. for 12 h. The solution was allowed to cool to room temperature and tert-butyl (2-(4-iodophenoxy)ethyl)carbamate (1.78 g, 4 mmol, Example 3, Step-2), bis(triphenylphosphine)palladium (II) dichloride (0.172 g, 0.2 mmol), cesium carbonate (3.19 g, 9 mmol) and 2-methyl THF (30 mL) were added. This mixture was degassed with nitrogen and water (0.3 mL) was added. This mixture was stirred at room temperature for 16 h. After completion of reaction, to the above reaction mixture 4M KOH (1.47 g, 26 mmol) and iodobenzene (1.95 g, 9 mmol) were added. Reaction mixture was stirred at 90° C. for 12 h. After completion of reaction, reaction mixture was cooled to room temperature, diluted with water and extracted with EtOAc. The organic layer was dried over anhydrous sodium sulphate and concentrated under reduced pressure. The crude material was purified by column chromatography over 230-400 mesh silica gel using 15% EtOAc in n-hexane to afford tert-butyl (E)-(2-(4-(4,4,4-trifluoro-1-(3-fluoro-1-(tetrahydro-2H-pyran-2-yl)-1H-indazol-5-yl)-2-phenylbut-1-en-1-yl)phenoxy)ethyl)carbamate (1.5 g, 50%).

Step-2: Synthesis of (E)-2-(4-(4,4,4-trifluoro-1-(3-fluoro-1H-indazol-5-yl)-2-phenylbut-1-en-1-yl)phenoxy)ethan-1-amine

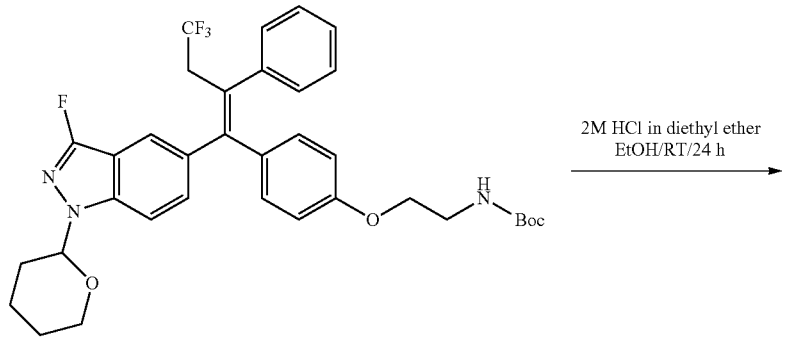

2M HCl in diethyl ether
EtOH/RT/24 h

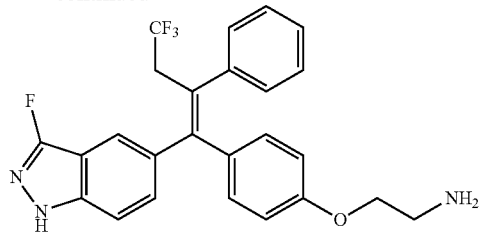

The reaction was carried out according to Scheme 2, Step-2 using tert-butyl (E)-(2-(4-(4,4,4-trifluoro-1-(3-fluoro-1-(tetrahydro-2H-pyran-2-yl)-1H-indazol-5-yl)-2-phenylbut-1-en-1-yl)phenoxy)ethyl)carbamate (1.5 g, 2.3 mmol) to afford crude title compound (1.1 g crude).

Step-3: Synthesis of (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide

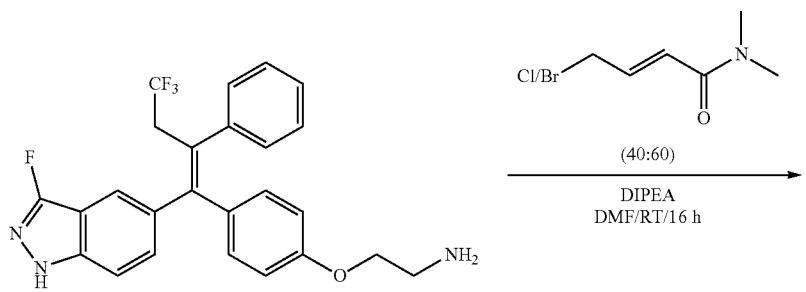

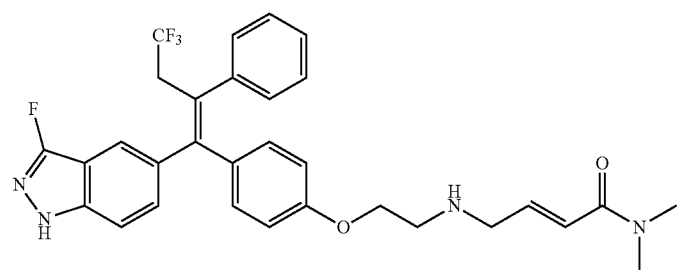

The reaction was carried out according to Scheme 2, Step-3 using (E)-2-(4-(4,4,4-trifluoro-1-(3-fluoro-1H-indazol-5-yl)-2-phenylbut-1-en-1-yl)phenoxy)ethan-1-amine (1.1 g, 2 mmol) and (E)-4-bromo-N,N-dimethylbut-2-enamide and (E)-4-chloro-N,N-dimethylbut-2-enamide mixture (0.41 g, 2 mmol, Example 63, Step-8). The crude material was used in next step without further purification (1.8 g, crude).

Step-4: Synthesis of tert-butyl ((E)-4-(dimethyl-amino)-4-oxobut-2-en-1-yl)(2-(4-((E)-4,4-trifluoro-1-(3-fluoro-1H-indazol-5-yl)-2-phenylbut-1-en-1-yl)phenoxy)ethyl)carbamate

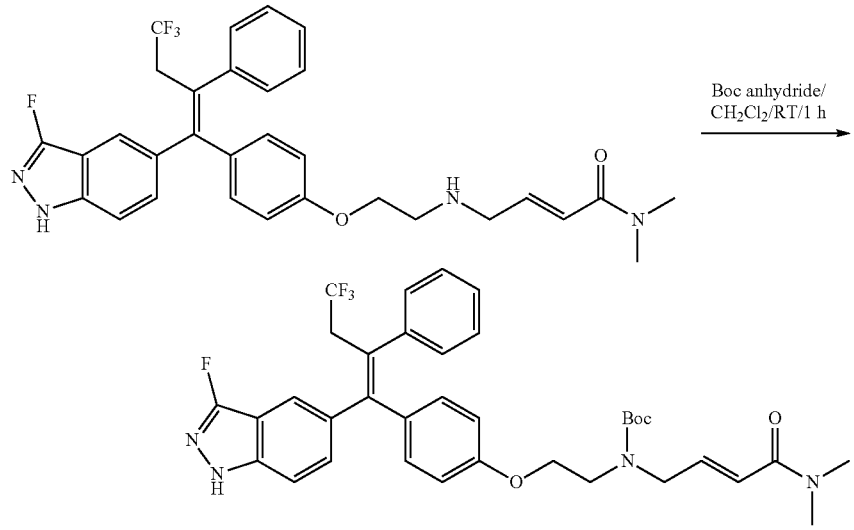

The procedure described in Scheme 2, Step-5 was used with (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide (1.8 g, 3.18 mmol) to provide crude material, which was purified by silica gel chromatography using (2%) MeOH in dichloromethane to afford tert-butyl ((E)-4-(dimethylamino)-4-oxobut-2-en-1-yl)(2-(4-((E)-4,4,4-trifluoro-1-(3-fluoro-1H-indazol-5-yl)-2-phenylbut-1-en-1-yl)phenoxy)ethyl)carbamate (0.2 g).

Step-5: Synthesis of (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide

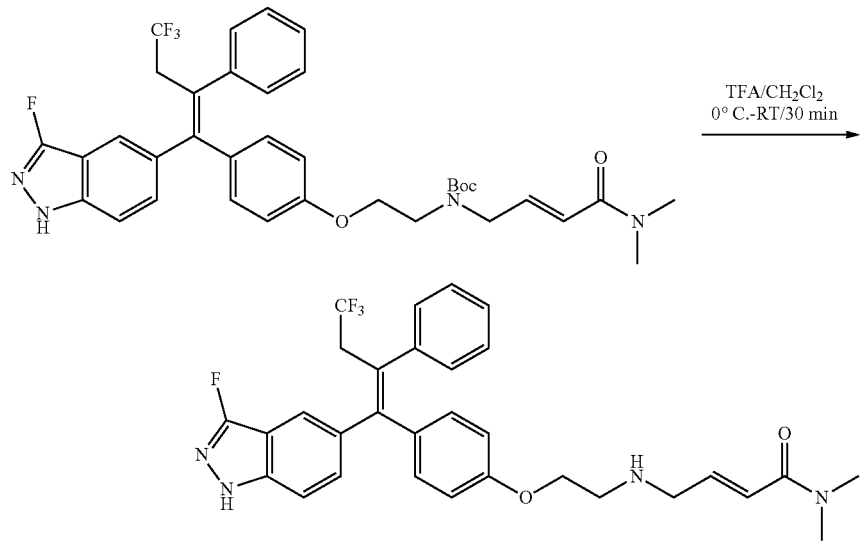

The reaction was carried out according to Scheme 2, Step-6b using tert-butyl ((E)-4-(dimethylamino)-4-oxobut-2-en-1-yl)(2-(4-((E)-4,4,4-trifluoro-1-(3-fluoro-1H-indazol-5-yl)-2-phenylbut-1-en-1-yl)phenoxy)ethyl)carbamate (0.2 g, 0.3 mmol) to afford crude compound, which was purified by preparative TLC to afford desired compound (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide (0.05 g, 29%).

Compound 69: $^1$H NMR (400 MHz, CDCl$_3$): δ 9.40 (s, 1H), 7.66 (s, 1H), 7.39-7.15 (m, 7H), 6.91-6.86 (m, 1H), 6.79 (d, J=8.8 Hz, 2H), 6.56 (d, J=8.8 Hz, 2H), 6.44 (d, J=15.1 Hz, 1H), 3.95 (t, J=5.7 Hz, 2H), 3.46 (q, J=10.8 Hz, 2H), 3.32-3.29 (m, 2H), 3.06 (s, 3H), 3.00 (s, 3H), 2.95 (t, J=5.4 Hz, 2H). LCMS: 567.3 [M+H]$^+$.

Example 69A: Synthesis of (E)-N,N-dimethyl-4-((2-(4-((E)-4,4,4-trifluoro-1-(3-fluoro-1H-indazol-5-yl)-2-phenylbut-1-en-ylbut-1-en-1-yl)phenoxy)ethyl)amino)but-2-enamide hydrochloride Step-1A: Synthesis of 3-fluoro-1-(tetrahydro-2H-pyran-2-yl)-5-((trimethylsilyl)ethynyl)-1H-indazole

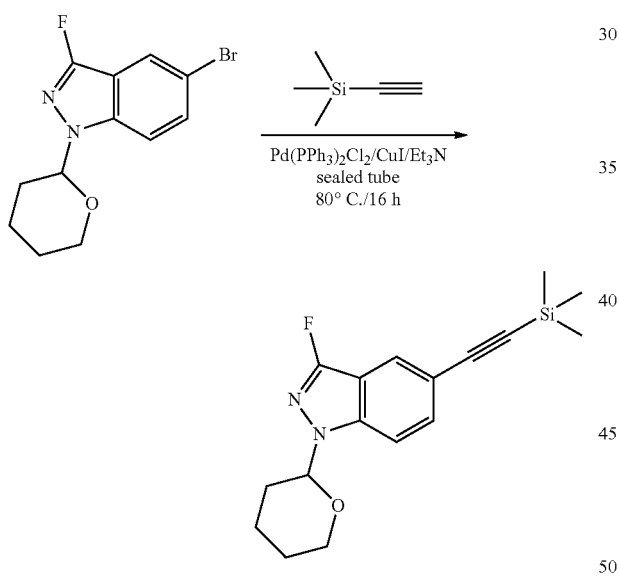

To a stirred solution of 5-bromo-3-fluoro-1-(tetrahydro-2H-pyran-2-yl)-1H-indazole (1.5 Kg, 5.014 mol) in Et$_3$N (10 L) in a sealed tube, was added copper iodide (95.5 g, 0.501 mol) at room temperature. This mixture was degassed with three vacuum/N$_2$ cycles, were added ethynyltrimethylsilane (0.73 Kg, 7.52 mol) followed by Pd(PPh$_3$)$_2$Cl$_2$ (175 g, 0.25 mol). The pressure tube was sealed and heated at 80° C. for 16 h. Upon completion by TLC, the reaction mixture was diluted with EtOAc (10 L), washed with water. The combined organic extracts were washed with brine, dried over anhydrous sodium sulphate and concentrated under reduced pressure to afford the crude product 3-fluoro-1-(tetrahydro-2H-pyran-2-yl)-5-((trimethylsilyl)ethynyl)-1H-indazole as dark brown oil (1.71 Kg, crude) 65.7% purity by HPLC.

Step-2A: Synthesis of 5-ethynyl-3-fluoro-1-(tetrahydro-2H-pyran-2-yl)-1H-indazole

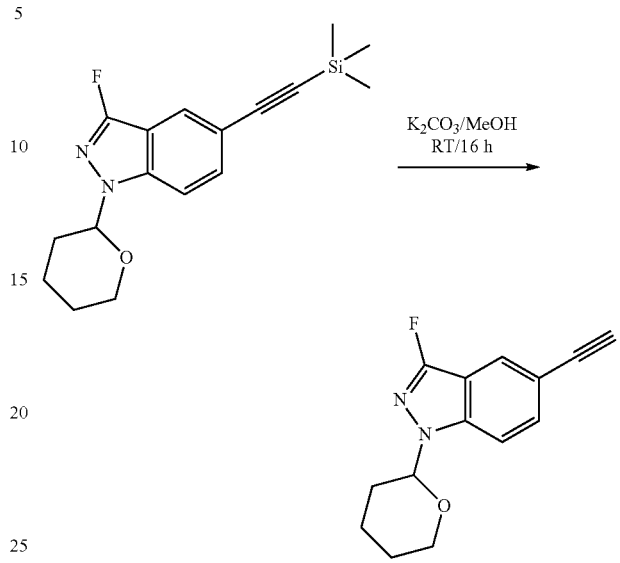

To a stirred solution of 3-fluoro-1-(tetrahydro-2H-pyran-2-yl)-5-((trimethylsilyl)ethynyl)-1H-indazole (1.7 Kg, 5.37 mol) in Methanol 12 L was added potassium carbonate (74.6 g, 0.53 mol), reaction mixture was stirred for 16 h at room temperature. After completion of reaction, methanol was evaporated, residue was diluted with ethyl acetate (6 L) and organic layer was washed with water followed by brine. The combined organic layer was dried over anhydrous Na$_2$SO$_4$ and concentrated under reduced pressure to obtain title compound (1.5 Kg crude) 72.3% purity by HPLC.

Step-3A: Synthesis of 3-fluoro-1-(tetrahydro-2H-pyran-2-yl)-5-(4,4,4-trifluorobut-1-yn-1-yl)-1H-indazole

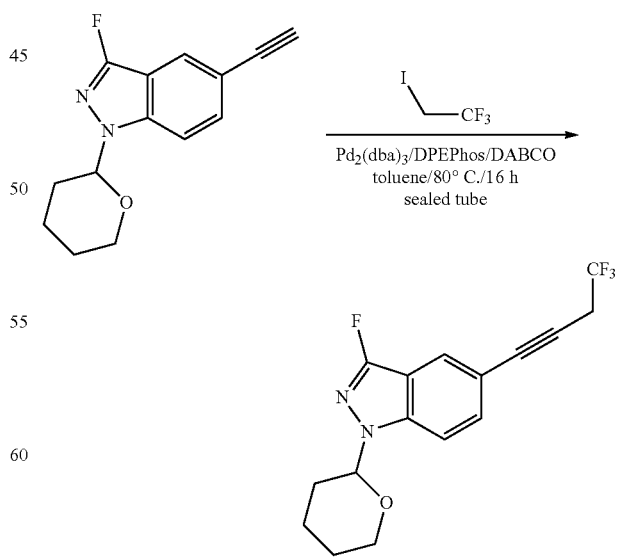

A mixture of Pd$_2$(dba)$_3$ (0.187 Kg, 0.204 mol), DPEphos (0.44 Kg, 0.818 mol) and DABCO (0.91 Kg, 0.818 mol)

under nitrogen atmosphere in toluene (5 L) was added a solution of 5-ethynyl-3-fluoro-1-(tetrahydro-2H-pyran-2-yl)-1H-indazole (1 Kg, 4.093 mol) in toluene (5 L). Reaction mixture was degassed with nitrogen for 10 min, to the above mixture 1,1,1-trifluoro-2-iodoethane (1.71 Kg, 8.187 mol) was added. This mixture was again degassed with three vacuum/$N_2$ cycles, heated at 80° C. for 16 h. Upon completion by TLC, reaction mixture was cooled to room temperature, filtered through celite. Filtrate was diluted with water and extracted with EtOAc (2×3 L). The organic layer was dried over anhydrous sodium sulphate and concentrated under reduced pressure. The crude material was purified by column chromatography over 60-120 mesh silica-gel using 6% ethyl acetate in n-hexane as an eluent to afford 3-fluoro-1-(tetrahydro-2H-pyran-2-yl)-5-(4,4,4-trifluorobut-1-yn-1-yl)-1H-indazole (1.1 Kg, 82% yield, 78% purity by HPLC).

Step-4A: Synthesis of tert-butyl ((E)-4-(dimethylamino)-4-oxobut-2-en-1-yl) (2-(4-((Z)-4,4,4-trifluoro-1-(3-fluoro-1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)ethyl)carbamate

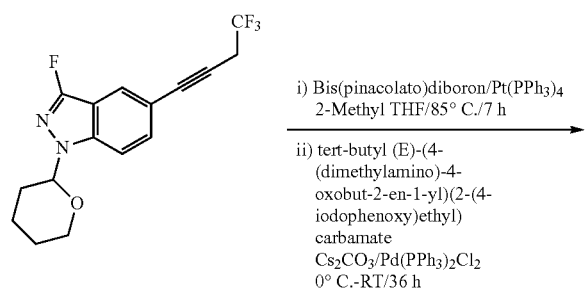

i) Bis(pinacolato)diboron/Pt(PPh$_3$)$_4$
2-Methyl THF/85° C./7 h ii) tert-butyl (E)-(4-(dimethylamino)-4-oxobut-2-en-1-yl)(2-(4-iodophenoxy)ethyl)carbamate
Cs$_2$CO$_3$/Pd(PPh$_3$)$_2$Cl$_2$
0° C.-RT/36 h

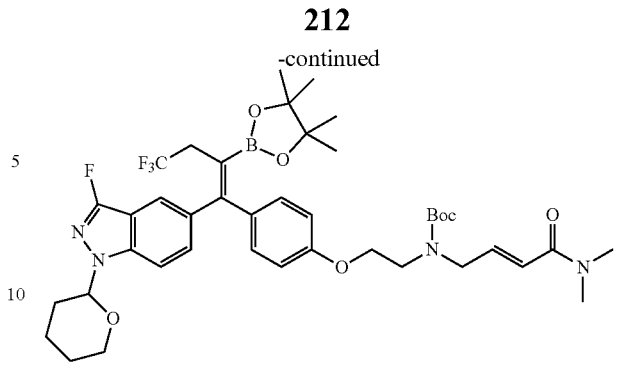

To a stirred solution of 3-fluoro-1-(tetrahydro-2H-pyran-2-yl)-5-(4,4,4-trifluorobut-1-yn-1-yl)-1H-indazole (500 g, 1.532 mol) in 2-methyl THF (2.5 L), was added bis(pinacolato)diboron (0.39 Kg, 1.532 mol), tetrakis(triphenylphosphine)platinum (0) (19 g, 0.0153 mol) under nitrogen atmosphere, reaction mixture was stirred at 85° C. for 7 h. The reaction mixture was allowed to cool to room temperature, tert-butyl (E)-(4-(dimethylamino)-4-oxobut-2-en-1-yl)(2-(4-iodophenoxy)ethyl)carbamate (0.62 Kg, 1.072 mol), bis(triphenylphosphine)palladium (II) dichloride (53.7 g, 0.076 mol), cesium carbonate (0.6 Kg, 3.064 mol), 2-methyl THF (5 L) and water (250 mL) were added. This mixture was degassed with nitrogen for 15 min, stirred at room temperature for 36 h. After completion of reaction, reaction mixture was cooled to room temperature, filtered through celite. Filtrate was diluted with water and extracted with EtOAc (2×3 L). The organic layer was dried over anhydrous sodium sulphate and concentrated under reduced pressure. The crude material was purified by column chromatography over 60-120 mesh silica-gel using 5% MeOH in dichloromethane as an eluent to afford tert-butyl ((E)-4-(dimethylamino)-4-oxobut-2-en-1-yl)(2-(4-((Z)-4,4,4-trifluoro-1-(3-fluoro-1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)ethyl)carbamate (600 g, 49%), purity by HPLC 58%.

Step-5A: Synthesis of tert-butyl ((E)-4-(dimethylamino)-4-oxobut-2-en-1-yl) (2-(4-((E)-4,4,4-trifluoro-1-(3-fluoro-1-(tetrahydro-2H-pyran-2-yl)-1H-indazol-5-yl)-2-phenylbut-1-en-1-yl)phenoxy)ethyl)carbamate

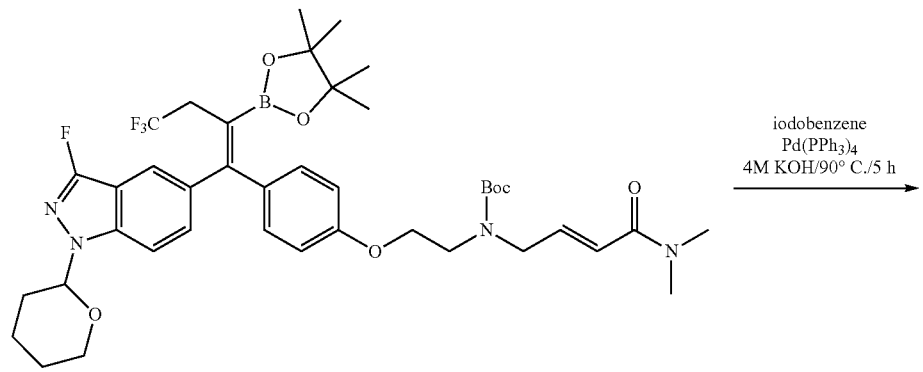

iodobenzene
Pd(PPh$_3$)$_4$
4M KOH/90° C./5 h

-continued

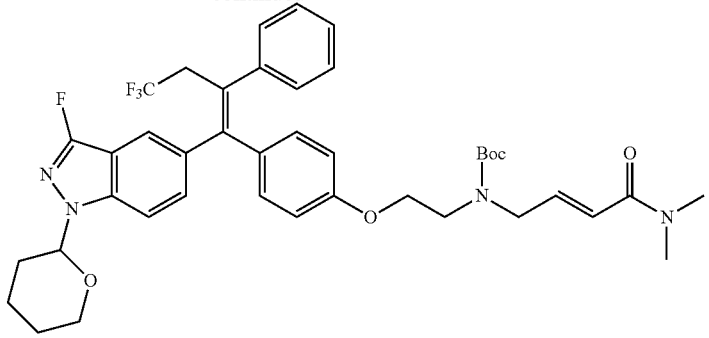

6

To a stirred solution of tert-butyl ((E)-4-(dimethylamino)-4-oxobut-2-en-1-yl)(2-(4-((Z)-4,4,4-trifluoro-1-(3-fluoro-1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)ethyl)carbamate (600 g, 0.74 mol) in 2-methyl THF (6 L), was added to the above reaction mixture 4M KOH (1.2 L, 2 vol), tetrakis(triphenylphosphine)palladium(0) (43 g, 0.037 mol) and iodobenzene (128 g, 0.62 mol) were added. Reaction mixture was stirred at 90° C. for 5 h. After completion of reaction, reaction mixture was cooled to room temperature followed by filtered through celite. Filtrate was diluted with water and extracted with EtOAc (2×2 L). The organic layer was dried over anhydrous sodium sulphate and concentrated under reduced pressure to afford title compound tert-butyl ((E)-4-(dimethyl amino)-4-oxobut-2-en-1-yl)(2-(4-((E)-4,4,4-trifluoro-1-(3-fluoro-1-(tetrahydro-2H-pyran-2-yl)-1H-indazol-5-yl)-2-phenylbut-1-en-1-yl)phenoxy)ethyl)carbamate (700 g, crude) 48% purity by HPLC.

Step-6A: Synthesis of (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide

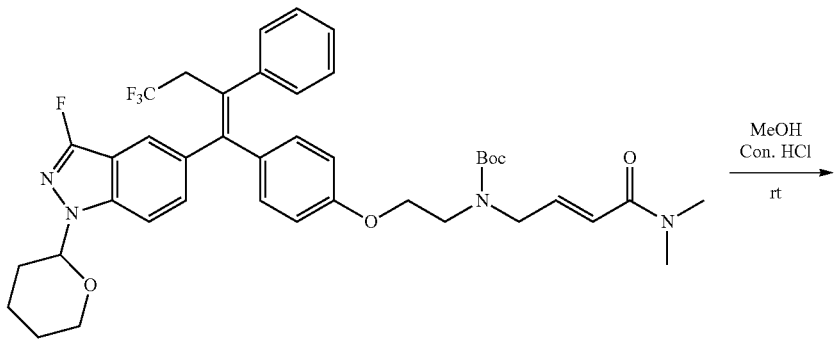

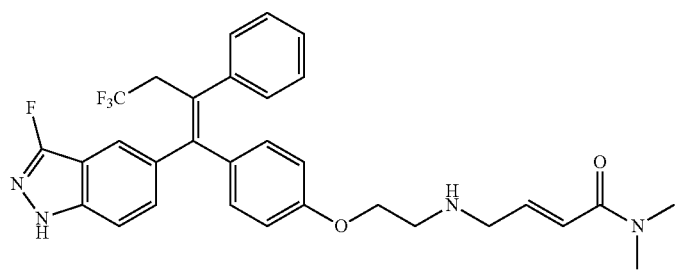

To a stirred solution of tert-butyl ((E)-4-(dimethylamino)-4-oxobut-2-en-1-yl)(2-(4-((E)-4,4,4-trifluoro-1-(3-fluoro-1-(tetrahydro-2H-pyran-2-yl)-1H-indazol-5-yl)-2-phenylbut-1-en-1-yl)phenoxy)ethyl)carbamate (700 g, 0.93 mol) in methanol (3.5 L) was added at 0° C., conc.HCl (2.1 L, 3 vol). The reaction mixture was stirred for 16 h at room temperature. After completion of reaction, reaction mixture was concentrated under reduced pressure. Gummy reaction mass was basified with saturated Na$_2$CO$_3$, extracted with dichloromethane (3×2 L). Combined organic layers were dried over anhydrous sodium sulphate and concentrated under reduced pressure to afford crude compound, which was purified by column chromatography over 60-120 mesh silica-gel using 5-7% MeOH in dichloromethane to afford desired compound (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide (260 g) 65.3% pure by HPLC.

Obtained compound was further purified by combi flash column chromatography to afford the title compound with >92% HPLC.

Step-7A: Synthesis of (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide hydrochloride

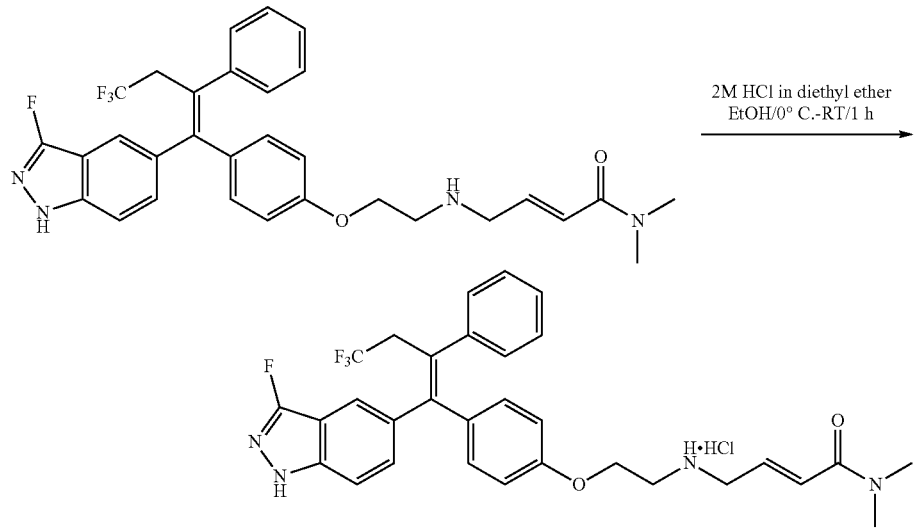

To a stirred solution of (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide (5.6 g, 9.88 mmol) in ethanol (6.6 mL) was added 2M HCl in diethyl ether (56 mL) at 0° C. A white solid was observed after stirring for 1 h at room temperature. Reaction mixture was concentrated under vacuum at 30° C. to remove the excess of ether HCl and ethanol. The solid obtained was dried at 50° C. for 1 h, the residue was triturated with diethyl ether and ether layer was decanted (500 mL×3). Solid obtained was co-distilled with ethyl acetate (300 mL×4), followed by triturated with ethyl acetate (500 mL), filtered and dried under reduced pressure to obtain the title compound (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide hydrochloride (5.4 g, 90%).

Compound 69 (hydrochloride salt): $^1$H NMR (400 MHz, DMSO-d$_6$): δ 12.70 (s, 1H), 9.15 (s, 2H), 7.57 (s, 1H), 7.54 (m, 2H), 7.25-7.14 (m, 6H), 6.86-6.79 (m, 3H), 6.69 (d, J=5.8 Hz, 2H), 6.61-6.54 (m, 1H), 4.13 (t, J=4.4 Hz, 2H), 3.79 (m, 2H), 3.48-3.37 (m, 2H), 3.26 (m, 2H) 3.03 (s, 3H), 2.87 (s, 3H). LCMS: 567.2 [M+H]$^+$.

Steps 8A-12A report synthesis of the intermediate tert-butyl (E)-(4-(dimethylamino)-4-oxobut-2-en-1-yl)(2-(4-iodophenoxy)ethyl)carbamate Step 8A: Synthesis of tert-butyl (E)-(4-(dimethylamino)-4-oxobut-2-en-1-yl)(2-(4-iodophenoxy)ethyl)carbamate

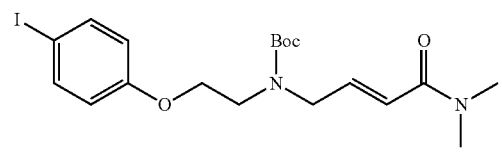 [SMILES: CN(C)C(=O)/C=C/CN(CCOc1ccc(I)cc1)C(=O)OC(C)(C)C]

Step-9A: Synthesis of tert-butyl (2-bromoethyl)carbamate

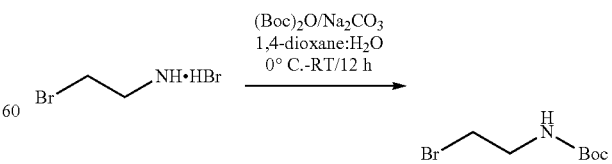

Bromoethylamine hydrobromide (1 Kg, 4.88 mol) was added to a stirred solution of sodium carbonate (1.55 Kg, 14.6 mol), di-t-butyl dicarbonate (1.6 Kg, 7.32 mol) in 1,4-dioxane-water mixture (2:1, 3 L) at 0° C. and the mixture was stirred at room temperature for 12 h. After completion of reaction, excess of 1,4-dioxane was removed under reduced pressure. Reaction mixture was extracted with ethylacetate (2×4 L), organic layer was washed with water followed by brine, dried over anhydrous sodium sulphate, filtered and concentrated under reduced pressure. The crude product was used in next step without further purification (1.1 Kg, %). $^1$H NMR (400 MHz, DMSO-d$_6$): δ 7.07 (bs, 1H), 3.42 (t, 2H), 3.31 (t, 2H), 1.38 (s, 9H).

Step-10A: Synthesis of tert-butyl (2-(4-iodophenox)ethyl)carbamate

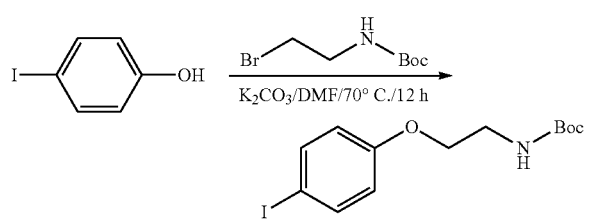

To a stirred solution of 4-iodophenol (1 Kg, 4.54 mol) in DMF (15 L) was added potassium carbonate (1.8 Kg, 13.6 mol) and stirred for 30 min at room temperature, to the above mixture tert-butyl (2-bromoethyl)carbamate (1.48 Kg, 6.36 mol) was added. The contents were stirred at 70° C. for 12 h. After completion of reaction, reaction mixture was poured onto ice cold water, solid separated was filtered and dried under reduced pressure to obtain desired compound tert-butyl (2-(4-iodophenoxy)ethyl)carbamate as an off-white solid (1.4 Kg, 84%). $^1$H NMR (400 MHz, DMSO-d$_6$): δ 7.58 (d, J=8.8 Hz, 2H), 7.01 (t, J=5.2 Hz, 1H), 7.78 (d, J=8.8 Hz, 2H), 3.92 (t, J=5.6 Hz, 2H), 1.37 (s, 9H).

Step-11A: Synthesis of 2-(4-iodophenoxy)ethan-1-amine

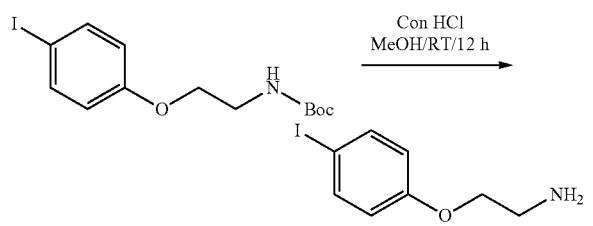

To a stirred solution of tert-butyl (2-(4-iodophenoxy)ethyl)carbamate (1.4 Kg, 3.85 mol) in methanol (10 L) was added at 0° C., Con.HCl (2.8 L). The reaction mixture was stirred for 12 h at room temperature. After completion of reaction, methanol was evaporated, residue was basified with saturated Na$_2$CO$_3$, extracted with 10% MeOH in DCM. Organic layer was concentrated under reduced pressure and the crude material was used in next step without further purification (700 g, 70% yield, 98% pure by HPLC). $^1$H NMR (400 MHz, DMSO-d$_6$): δ 7.59-7.55 (m, 2H), 6.80-6.76 (m, 2H), 3.88 (t, J=5.8 Hz, 2H), 3.85 (t, J=6.0 Hz, 2H), 1.61 (bs, 2H).

Step-12A: Synthesis of (E)-4-((2-(4-iodophenoxy)ethyl)amino)-N,N-dimethylbut-2-enamide

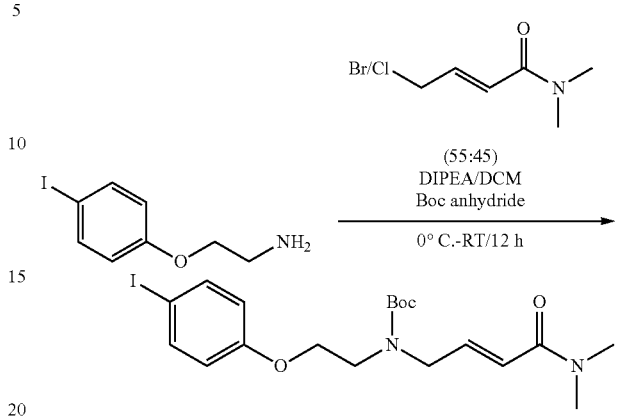

To a stirred solution of 2-(4-iodophenoxy)ethan-1-amine (700 g, 2.66 mol) in DCM (4 L) was added DIPEA (1 L, 7.98 mol) and cooled to 0° C. Then, (E)-4-bromo-(chloro)-N,N-dimethylbut-2-enamide (505 g, 2.66 mol) in DCM (2 L) was added dropwise at 0° C. The reaction mixture was stirred for 12 h at room temperature. After that, reaction mixture was cooled to 0° C. and Boc anhydride (870 g, 3.9 mol) in DCM (2 L) was added dropwise and stirred at room temperature for 12 h. Upon completion by TLC, the reaction mixture was cooled to 0° C., quenched with ice cold water (5 L) and extracted with dichloromethane (2 L). The combined organic extracts were washed with water, followed by brine, dried over anhydrous sodium sulphate and concentrated under reduced pressure. The crude material was purified by column chromatography over 60-120 mesh silica using 20% EtOAc in Hexane as an eluent to afford tert-butyl (E)-(4-(dimethylamino)-4-oxobut-2-en-1-yl)(2-(4-iodophenoxy)ethyl)carbamate (480 g, 37% yield). 69% pure by HPLC. $^1$H NMR (400 MHz, DMSO-d$_6$): δ 7.58 (d, J=8.8 Hz, 2H), 6.79 (d, J=6.8 Hz, 2H), 6.51-6.39 (m, 2H), 4.0-3.99 (m, 2H), 3.95 (t, J=5.6 Hz, 2H), 3.38 (d, J=5.6 Hz, 2H), 2.96 (s, 3H), 2.84 (s, 3H), 1.37 (s, 9H). LCMS: 595.4 [M+H]$^+$.

Example 70: There is no Example 70

Example 71: There is no Example 71

Example 72: Synthesis of (E)-4-((2-((5-((Z)-2-cyclobutyl-1-(3-fluoro-1H-indazol-5-yl)-2-phenylvinyl)pyridin-2-yl)oxy)ethyl)amino)-N,N-dimethylbut-2-enamide (Compound 72)

The compound was synthesized following the approach as outlined in Example 14 by substituting into Step-4 tert-butyl (E)-(4-(dimethylamino)-4-oxobut-2-en-1-yl)(2-((5-iodopyridin-2-yl)oxy)ethyl)carbamate (as prepared in Example 25, Step-2) for compound 234 and substituting Step-5 with the reaction conditions described in Scheme 2, Step-6b to deliver Compound 72 (0.09 g, 11%).

Compound 72: $^1$H NMR (400 MHz, DMSO-d$_6$): δ 12.59 (s, 1H), 7.67 (d, J=2.0 Hz, 1H), 7.54 (s, 1H), 7.49 (dd, J$_1$=8.8 Hz, J$_2$=1.6 Hz, 1H), 7.28-7.12 (m, 7H), 6.61-6.44 (m, 3H), 4.09 (t, J=6.0 Hz, 2H), 3.42-3.38 (m, 1H), 3.28-3.27 (m, 2H), 2.97 (s, 3H), 2.83 (s, 3H), 2.73 (t, J=5.8 Hz, 2H), 1.83-1.76 (m, 4H), 1.63-1.58 (m, 1H), 1.35-1.33 (m, 1H). LCMS: 540.3 [M+H]$^+$.

Example 73: Synthesis of (E)-4-((2-(4-((E)-2-(2-chlorophenyl)-1-(3-fluoro-1H-indazol-5-yl)but-1-en-1-yl)phenoxy)ethyl)amino)-N,N-dimethylbut-2-enamide (Compound 73)

The compound was synthesized following the approach as outlined in Example 60 by substituting into Step-1 (i) 5-(but-1-yn-1-yl)-3-fluoro-1-(tetrahydro-2H-pyran-2-yl)-1H-indazole (as prepared in Example 2, Step-3) for compound 275, (ii) tert-butyl (E)-(4-(dimethylamino)-4-oxobut-2-en-1-yl)(2-(4-iodophenoxy)ethyl)carbamate (as prepared in Example 14, Step-3) for compound 263, and (iii) 1-chloro-2-iodobenzene for compound 264 to deliver Compound 73 (0.23 g, 5.6%) as an off-white solid.

Compound 73: $^1$H NMR (400 MHz, DMSO-$d_6$): δ 12.59 (s, 1H), 7.54 (s, 1H), 7.49 (dd, $J_1$=8.8 Hz, $J_2$=2.0 Hz, 1H), 7.35 (dd, $J_1$=7.4 Hz, $J_2$=1.4 Hz, 1H), 7.27-7.16 (m, 4H), 6.83 (d, J=8.8 Hz, 2H), 6.60 (d, J=8.8 Hz, 2H), 6.57-6.47 (m, 2H), 3.86 (t, J=5.6 Hz, 2H), 2.98 (s, 3H), 2.84 (s, 3H), 2.77 (t, J=5.4 Hz, 2H), 2.43-2.32 (m, 4H), 0.88 (t, J=7.4 Hz, 3H). LCMS: 547.2 [M+H]$^+$

Example 74: Synthesis of (E)-4-((2-(4-((E)-2-(2-chloro-4-fluorophenyl)-1-(1H-indazol-5-yl)but-1-en-1-yl)phenoxy)ethyl)amino)-N,N-dimethylbut-2-enamide (Compound 74)

The compound was synthesized following the approach as outlined in Example 60 by substituting into Step-1 (i) 5-(but-1-yn-1-yl)-1-(tetrahydro-2H-pyran-2-yl)-1H-indazole (as prepared in Example 1, Step-3) for compound 275, (ii) tert-butyl (E)-(4-(dimethylamino)-4-oxobut-2-en-1-yl)(2-(4-iodophenoxy)ethyl)carbamate (as prepared in Example 14, Step-3) for compound 263 and (iii) 2-chloro-4-fluoro-1-iodobenzene for compound 264 to isolate Compound 74 (0.26 g, 31%).

Compound 74: $^1$H NMR (400 MHz, DMSO-$d_6$): δ 13.08 (s, 1H), 8.08 (s, 1H), 7.65 (s, 1H), 7.53 (d, J=8.8 Hz, 1H), 7.34-7.17 (m, 2H), 7.16-7.10 (m, 2H), 6.81 (d, J=8.8 Hz, 2H), 6.62-6.47 (m, 4H), 3.86 (t, J=5.6 Hz, 2H), 2.98 (s, 3H), 2.83 (s, 3H), 2.76 (t, J=5.4 Hz, 2H), 2.38-2.33 (m, 3H), 0.88 (t, J=7.4 Hz, 3H). LCMS: 547.3 [M+H]$^+$.

Example 75: Synthesis of (E)-4-((2-(4-((E)-1-(3-fluoro-1H-indazol-5-yl)-2-(pyridin-4-yl)but-1-en-1-yl)phenoxy)ethyl)amino)-N-(2-hydroxyethyl)-N-methylbut-2-enamide (Compound 75)

The compound was synthesized following the approach as outlined in Example 14 by (a) substituting into Step-4 (i) (Z)-5-(1,2-bis(4,4,5,5-tetramethyl-1,3,2-dioxaborolan-2-yl)but-1-en-1-yl)-3-fluoro-1-(tetrahydro-2H-pyran-2-yl)-1H-indazole (as prepared in Example 3, Step-1) for compound 233, (ii) tert-butyl (E)-(4-((2-hydroxyethyl)(methyl)amino)-4-oxobut-2-en-1-yl)(2-(4-iodophenoxy)ethyl)carbamate (preparation shown below in Ex. 75 Step 1-2) for compound 234, (iii) 4-iodopyridine for compound 262, and (b) substituting the reaction conditions described in Scheme 2, Step-6b in Ex. 14 Step-5 to afford Compound 75 (0.1 g, 20.6%).

Step-1: Synthesis of (E)-N-(2-hydroxyethyl)-4-((2-(4-iodophenoxy)ethyl)amino)-N-methylbut-2-enamide

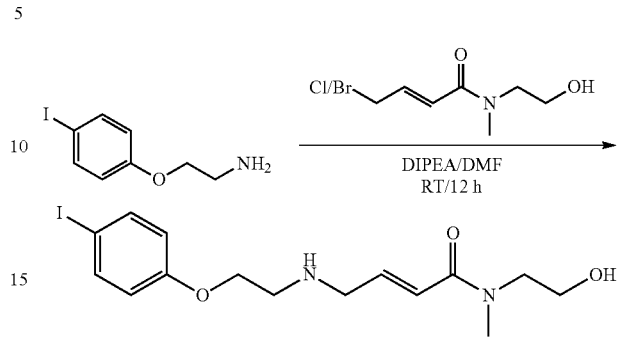

The reaction was carried out according to Scheme 3, Step-3 using 2-(4-iodophenoxy)ethan-1-amine (7.3 g, 27 mmol, Example 14, Step-3) for compound 217 and (E)-4-bromo-N-(2-hydroxyethyl)-N-methylbut-2-enamide for compound 214 and (E)-4-chloro-N-(2-hydroxyethyl)-N-methylbut-2-enamide (5 g, 27 mmol, Example 50, Step-1) for compound 214. The crude material was used in next step without further purification (9.5 g, crude).

Step-2: Synthesis of tert-butyl (E)-(4-((2-hydroxyethyl)(methyl)amino)-4-oxobut-2-en-1-yl) (2-(4-iodophenoxy)ethyl)carbamate

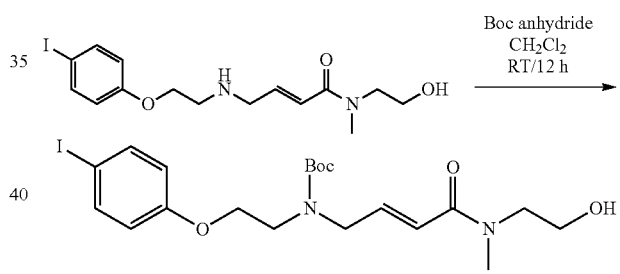

The reaction was carried out according to Scheme 3, Step-4 using (E)-N-(2-hydroxyethyl)-4-((2-(4-iodophenoxy)ethyl)amino)-N-methylbut-2-enamide (9.5 g, 23.5 mmol) for compound 218. The crude material was purified by column chromatography over 230-400 mesh silica using 3% MeOH in dichloromethane as an eluent to afford the title compound of Ex. 75 Step-2 (2.5 g, 21%).

Compound 75: $^1$H NMR (400 MHz, DMSO-$d_6$): δ 12.60 (s, 1H), 8.38 (dd, $J_1$=4.4 Hz, $J_2$=1.7 Hz, 1H), 7.53 (s, 1H), 7.49 (d, J=1.6 Hz, 1H), 7.47 (d, J=2.0 Hz, 1H), 7.22 (d, J=1.6 Hz, 1H), 7.20 (d, J=1.6 Hz, 1H), 7.13 (dd, J=4.2 Hz, $J_2$=1.4 Hz, 2H), 6.79 (d, J=8.8 Hz, 2H), 6.65 (d, J=8.8 Hz, 2H), 6.60-6.51 (m, 2H), 3.88 (t, J=5.4 Hz, 2H), 3.50-3.48 (m, 2H), 3.47-3.34 (m, 2H), 3.03-2.85 (m, 4H), 2.86-2.78 (m, 2H), 2.42 (q, J=7.4 Hz, 2H), 0.87 (t, J=7.2 Hz, 3H). LCMS: 544.3 [M+H]$^+$.

Example 76: Synthesis of (E)-4-((2-(4-((E)-1-(7-fluoro-1H-indazol-5-yl)-2-phenylbut-1-en-1-yl)phenoxy)ethyl)amino)-N,N-dimethylbut-2-enamide (Compound 76)

The compound was synthesized following the approach as outlined in Example 14 by substituting into Step-2 5-(but- 1-yn-1-yl)-7-fluoro-1-(tetrahydro-2H-pyran-2-yl)-1H-indazole (preparation shown below in Ex. 76 Step 1-5) for compound 271 and substituting Step-5 with reaction conditions outlined in Scheme 2, Step-6c to deliver Compound 76 (0.195 g, 17.7%) as an off-white solid.

Step-1: Synthesis of
5-bromo-2,3-difluorobenzaldehyde

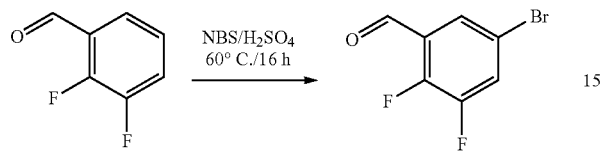

To a stirred solution of 2,3-difluorobenzaldehyde (30 g, 211 mmol) in H₂SO₄ (120 mL) was added N-bromo succinamide (45 g, 253 mmol) at 0° C. The reaction mixture was stirred for 16 h at 60° C., after completion of reaction (monitored by TLC), the reaction mixture was diluted with EtOAc. Organic layer was washed with water followed by brine, dried over anhydrous sodium sulphate, filtered and concentrated under reduced pressure. The crude product was purified by column chromatography by using 0.8% EtOAc in n-hexane to afford 5-bromo-2,3-difluorobenzaldehyde (11.7 g, 23.5%) as a white solid.

Step-2: Synthesis of
(E)-5-bromo-2,3-difluorobenzaldehyde O-methyl oxime

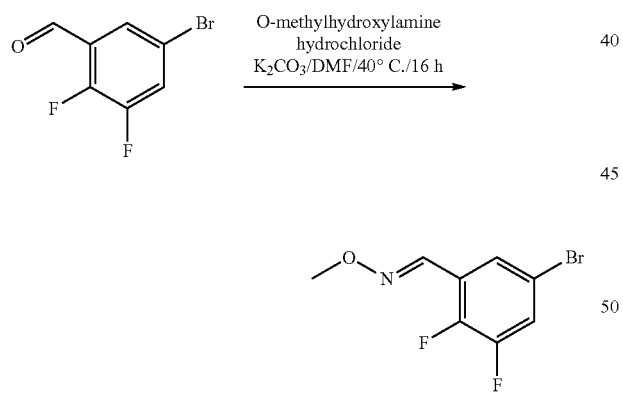

To a stirred solution of 5-bromo-2,3-difluorobenzaldehyde (2 g, 9 mmol) in DMF (20 mL) was added O-methylhydroxylamine hydrochloride (1.51 g, 18 mmol) and K₂CO₃ (2.75 g, 19.9 mmol), contents were stirred at 40° C. for 16 h. After completion of reaction (monitored by TLC), the reaction mixture was cooled to 0° C., diluted with ethyl acetate and the organic layer was washed with water followed by brine. The organic layer was dried over anhydrous Na₂SO₄ and concentrated under reduced pressure. The crude compound was purified by combi-flash using 2% ethyl acetate in n-hexane as an eluent to obtain title compound of Ex. 76 Step-2 (1 g, 44%).

Step-3: Synthesis of 5-bromo-7-fluoro-1H-indazole

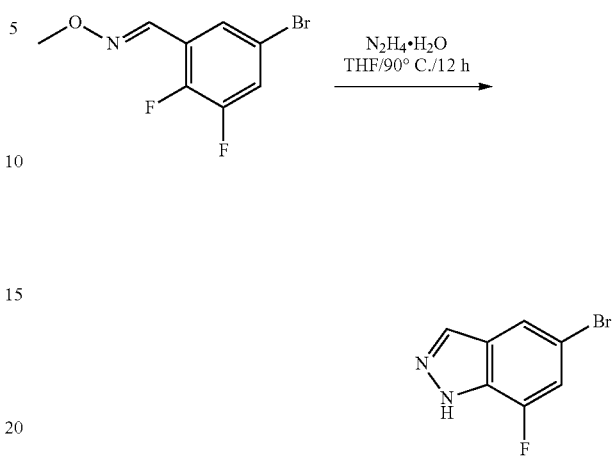

To a stirred solution of (E)-5-bromo-2,3-difluorobenzaldehyde O-methyl oxime (1 g, 4 mmol) in THF (10 mL) was added hydrazine hydrate (4 mL), contents were stirred at 90° C. for 12 h. After completion of reaction (monitored by TLC), the reaction mixture was cooled to 0° C., diluted with ethyl acetate and the organic layer was washed with water followed by brine. The organic layer was dried over anhydrous Na₂SO₄ and concentrated under reduced pressure. The crude compound was purified by combi-flash using 10% ethyl acetate in n-hexane as an eluent to obtain title compound of Ex. 76 Step-3 (0.2 g, 21%).

Step-4: Synthesis of 5-bromo-7-fluoro-1-(tetrahydro-2H-pyran-2-yl)-1H-indazole

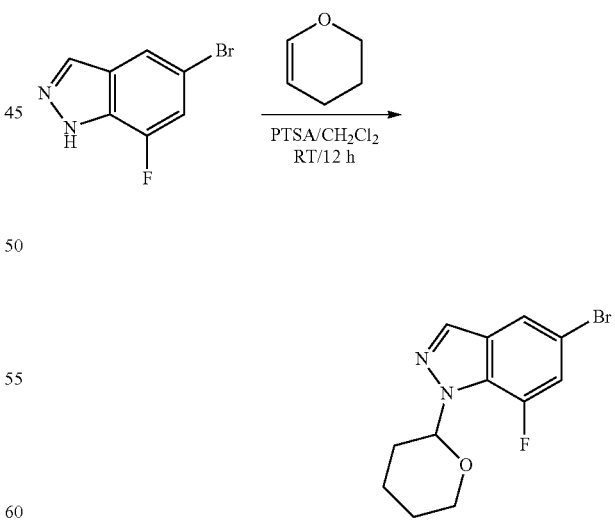

The reaction was carried out according to Scheme 1, Step-1 using 5-bromo-7-fluoro-1H-indazole (1.82 g, 8.46 mmol). The crude compound was purified by combi-flash using 5% ethyl acetate in n-hexane as an eluent to obtain the title compound of Ex. 76 Step-4 (2.39 g, 94%).

Step-5: Synthesis of 5-(but-1-yn-1-yl)-7-fluoro-1-(tetrahydro-2H-pyran-2-yl)-1H-indazole

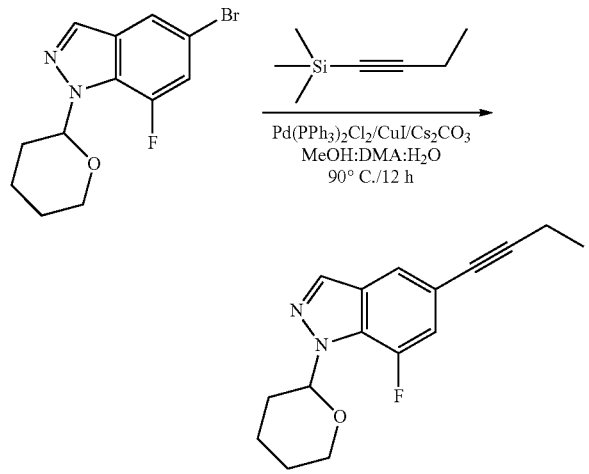

The reaction was carried out according to Scheme 1, Step-2 using 5-bromo-7-fluoro-1-(tetrahydro-2H-pyran-2-yl)-1H-indazole (4.49 g, 15 mmol) and but-1-yn-1-yltrimethylsilane (3.8 g, 30 mmol, Example 1, Step-2). The crude product was purified over 230-400 mesh silica column chromatography using 20% ethyl acetate in n-hexane to afford the title compound of Ex. 76 Step-5 (3.2 g).

Compound 76: $^1$H NMR (400 MHz, DMSO-$d_6$): δ 13.66 (s, 1H), 8.19 (d, J=2.4 Hz, 1H), 7.48 (s, 1H), 7.22-7.21 (m, 2H), 7.19-7.11 (m, 3H), 6.90 (d, J=12.0 Hz, 1H), 6.76 (d, J=8.4 Hz, 2H), 6.63-6.59 (m, 3H), 6.57-6.47 (m, 1H), 3.87 (t, J=5.4 Hz, 2H), 3.37-3.30 (m, 2H), 2.98 (s, 3H), 2.84 (s, 3H), 2.77 (t, J=5.6 Hz, 2H), 2.41 (q, J=7.2 Hz, 2H), 2.32-2.10 (m, 1H), 0.87 (t, J=7.2 Hz, 3H). LCMS: 513.3 [M+H]$^+$.

Example 77: Synthesis of (E)-4-((2-(4-((E)-1-(3-fluoro-1H-indazol-5-yl)-2-phenylpent-1-en-1-yl)phenoxy)ethyl)amino)-N,N-dimethylbut-2-enamide (Compound 77)

The compound was synthesized following the approach as outlined in Example 59 by (i) substituting into Step-4 3-fluoro-5-(pent-1-yn-1-yl)-1-(tetrahydro-2H-pyran-2-yl)-1H-indazole (preparation shown below in Ex. 77 Step 1-2) for compound 276 and tert-butyl (E)-(4-(dimethylamino)-4-oxobut-2-en-1-yl)(2-(4-iodophenoxy)ethyl)carbamate (as prepared in Example 14, Step-3) for compound 277 and (ii) substituting into Step-5 iodobenzene for compound 265 to afford Compound 77 (0.06 g, 19.3%) as an off-white solid.

Step-1: Synthesis of trimethyl(pent-1-yn-1-yl)silane

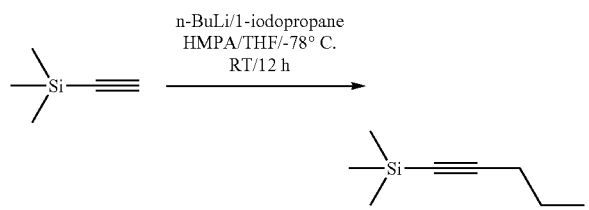

To a stirred solution of (trimethylsilyl)acetylene (29 g, 295 mmol) in dry THF (100 mL) was added n-BuLi (2.5M in THF, 125 mL) at −78° C. over 2 h. The resulting mixture was warmed to 0° C. and stirred for 10 min. The reaction mixture was again cooled to −78° C., HMPA (58 g, 324 mmol) was added to the above mixture and stirred at −78° C. for 30 min. To the above reaction mixture 1-iodopropane (53 g, 315 mmol) was added and the resulting mixture was stirred at room temperature for 12 h. After completion of reaction, the reaction mixture was quenched with water, extracted with ethyl acetate (500 mL). The organic layer was washed with brine, dried over anhydrous sodium sulphate and concentrated under reduced pressure. The product but-1-yn-1-yltrimethylsilane was distilled between 110-160° C. to afford the desired product (38 g).

Step-2: Synthesis of 3-fluoro-5-(pent-1-yn-1-yl)-1-(tetrahydro-2H-pyran-2-yl)-1H-indazole

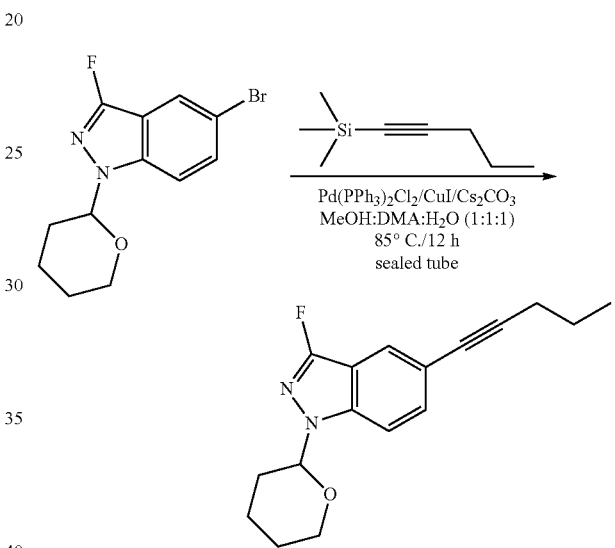

The reaction was carried out according to Scheme 1, Step-2 using 5-bromo-3-fluoro-1-(tetrahydro-2H-pyran-2-yl)-1H-indazole (4 g, 13.4 mmol, Example 2, Step-2) for compound 202 and trimethyl(pent-1-yn-1-yl)silane (2.8 g, 20.1 mmol) for compound 203. The crude product was purified over 230-silica gel chromatography using 5% ethyl acetate in n-hexane to afford 3-fluoro-5-(pent-1-yn-1-yl)-1-(tetrahydro-2H-pyran-2-yl)-1H-indazole (1.18 g, 30.8%).

Compound 77: $^1$H NMR (400 MHz, DMSO-$d_6$): δ 12.56 (s, 1H), 7.49 (s, 1H), 7.47 (d, J=6.8 Hz, 1H), 7.46-7.11 (m, 6H), 6.77 (d, J=8.8 Hz, 2H), 6.62-6.48 (m, 4H), 3.87 (t, J=5.6 Hz, 2H), 3.33-3.31 (m, 2H), 2.98 (s, 3H), 2.84 (s, 3H), 2.78 (t, J=5.6 Hz, 2H), 2.36-2.32 (m, 2H), 1.29-1.23 (m, 2H), 0.74 (t, J=7.4 Hz, 3H). LCMS: 527.3 [M+H]$^+$.

Example 78: There is no Example 78

Example 79: Synthesis of (E)-4-((2-(4-((E)-1-(3,7-difluoro-1H-indazol-5-yl)-2-phenylbut-1-en-1-yl)phenoxy)ethyl)amino)-N,N-dimethylbut-2-enamide (Compound 79)

The compound was synthesized following the approach as outlined in Example 14 by substituting into Step-2 5-(but-1-yn-1-yl)-3,7-difluoro-1-(tetrahydro-2H-pyran-2-yl)-1H-indazole (preparation shown below in Ex. 79 Step-1) for compound 271 and substituting Step-5 of Ex. 14 with reaction conditions described in Scheme 2, Step-6b to isolate Compound 79 (0.046 g) as an off-white solid.

Step-1: Synthesis of 5-(but-1-yn-1-yl)-3,7-difluoro-1-(tetrahydro-2H-pyran-2-yl)-1H-indazole

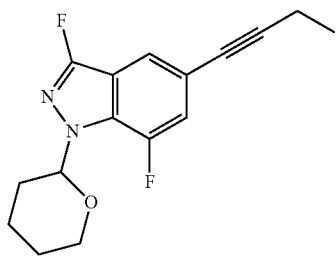 [SMILES: CCC#Cc1cc(F)c2c(c1)c(F)nn2C1CCCCO1]

The compound was synthesized following the approach as outlined in Example 2 by substituting into Step-1 5-bromo-7-fluoro-1-(tetrahydro-2H-pyran-2-yl)-1H-indazole for compound 270 and continuing with Steps 2-3 of Ex. 2 to deliver the title compound of Ex. 79 Step-1 (0.78 g, 76%).

Compound 79: $^1$H NMR (400 MHz, DMSO-$d_6$): δ 13.20 (s, 1H), 7.40 (s, 1H), 7.22-7.21 (m, 2H), 7.19-7.11 (m, 3H), 6.90 (d, J=12.0 Hz, 1H), 6.8 (d, J=8.4 Hz, 2H), 6.63-6.59 (m, 3H), 6.57-6.47 (m, 1H), 3.87 (t, J=5.4 Hz, 2H), 3.37-3.30 (m, 2H), 2.98 (s, 3H), 2.84 (s, 3H), 2.77 (t, J=5.6 Hz, 2H), 2.41 (q, J=7.2 Hz, 2H), 0.87 (t, J=7.2 Hz, 3H) LCMS: 531.3 $[M+H]^+$.

Example 80: Synthesis of (E)-4-((2-(4-((E)-2-(2,5-difluorophenyl)-1-(3-fluoro-1H-indazol-5-yl)but-1-en-1-yl)phenoxy)ethyl)amino)-N,N-dimethylbut-2-enamide (Compound 80)

The compound was synthesized following the approach as outlined in Example 14 by substituting into Step-4 (i) (Z)-5-(1,2-bis(4,4,5,5-tetramethyl-1,3,2-dioxaborolan-2-yl)but-1-en-1-yl)-3-fluoro-1-(tetrahydro-2H-pyran-2-yl)-1H-indazole (as prepared in Example 3, Step-1) for compound 233, (ii) tert-butyl (E)-(4-(dimethylamino)-4-oxobut-2-en-1-yl)(2-(4-iodophenoxy)ethyl)carbamate (as prepared in Example 14, Step-3) for compound 234, (iii) 1,4-difluoro-2-iodobenzene for compound 262 and (iv) substituting Ex. 14 Step-5 with reaction conditions described in Scheme 2, Step-6b to isolate Compound 80 (0.16 g, 23.7%) as an off-white solid.

Compound 80: $^1$H NMR (400 MHz, DMSO-$d_6$): δ 12.60 (s, 1H), 7.52 (s, 1H), 7.49 (dd, $J_1$=8.8 Hz, $J_2$=1.2 Hz, 1H), 7.23-7.12 (m, 1H), 7.11-7.02 (m, 3H), 6.83 (d, J=8.4 Hz, 2H), 6.65 (d, J=8.4 Hz, 2H), 6.62-6.48 (m, 2H), 3.88 (t, J=5.6 Hz, 2H), 3.32-3.31 (m, 2H), 2.99 (s, 3H), 2.84 (s, 3H), 2.79 (t, J=5.4 Hz, 2H), 2.35 (q, J=7.0 Hz, 2H), 0.91 (t, J=7.4 Hz, 3H). LCMS: 549.3 $[M+H]^+$.

Example 81: Synthesis of (E)-4-((2-(4-((E)-1-(3-fluoro-1H-indazol-5-yl)-2-(3-fluoropyridin-4-yl)but-1-en-1-yl)phenoxy)ethyl)amino)-N,N-dimethylbut-2-enamide (Compound 81)

The compound was synthesized following the approach as outlined in Example 14 by substituting into Step-4 (i) (Z)-5-(1,2-bis(4,4,5,5-tetramethyl-1,3,2-dioxaborolan-2-yl)but-1-en-1-yl)-3-fluoro-1-(tetrahydro-2H-pyran-2-yl)-1H-indazole (as prepared in Example 3, Step-1) for compound 233, (ii) tert-butyl (E)-(4-(dimethylamino)-4-oxobut-2-en-1-yl)(2-(4-iodophenoxy)ethyl)carbamate (Example 14, Step-3) for compound 234, and (iii) 3-fluoro-4-iodopyridine for compound 262, and (iv) substituting Ex. 14 Step-5 with reaction conditions described in Scheme 2, Step-6b to isolate Compound 81 (0.24 g, 34%) as an off-white solid.

Compound 81: $^1$H NMR (400 MHz, DMSO-$d_6$): δ 12.60 (s, 1H), 8.4 (s, 1H), 8.30 (s, 1H), 7.6 (m, 2H), 7.49 (d, J=1.6 Hz, 1H), 7.22 (d, J=1.6 Hz, 1H), 6.8 (d, J=8.8 Hz, 2H), 6.65 (d, J=8.8 Hz, 3H), 6.40 (m, 1H), 3.88 (t, J=5.4 Hz, 2H), 3.03 (s, 3H), 2.80 (s, 3H), 2.78 (t, J=5.4 Hz, 2H), 2.42 (q, J=7.4 Hz, 2H), 0.87 (t, J=7.2 Hz, 3H). LCMS: 532.3 $[M+H]^+$.

Example 82: Synthesis of (E)-4-((2-(4-((E)-1-(3-fluoro-1H-indazol-5-yl)-3-methyl-2-phenylbut-1-en-1-yl)phenoxy)ethyl)amino)-N,N-dimethylbut-2-enamide (Compound 82)

The compound was synthesized following the approach as outlined in Example 50 by (i) substituting into Step-3 (E)-2-(4-(1-(3-fluoro-1-(tetrahydro-2H-pyran-2-yl)-1H-indazol-5-yl)-3-methyl-2-phenylbut-1-en-1-yl)phenoxy)ethan-1-amine (preparation shown below in Ex. 82 Step 1-3) for compound 258 and (ii) substituting Ex. 50 Step-5 with reaction conditions described in Scheme 2, Step-6c to isolate Compound 82 (0.07 g).

Step-1: Synthesis of (E)-2-(4-(1-(3-fluoro-1-(tetrahydro-2H-pyran-2-yl)-1H-indazol-5-yl)-3-methyl-2-phenylbut-1-en-1-yl)phenoxy)ethan-1-amine

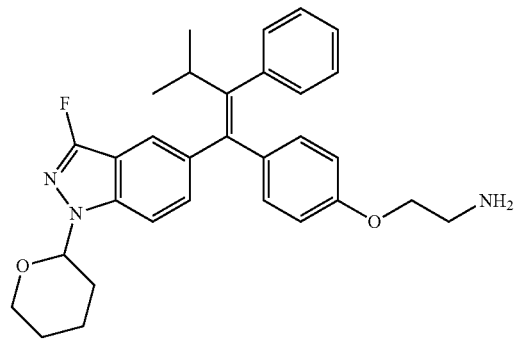 [SMILES: CC(C)/C(=C(/c1ccc(OCCN)cc1)c1ccc2c(c1)c(F)nn2C1CCCCO1)c1ccccc1]

The compound was synthesized following the approach as outlined in Example 2 by (i) substituting into Step-3 3-methylbut-1-yne for compound 278, (ii) substituting into Step-4 tert-butyl (2-(4-(4,4,5,5-tetramethyl-1,3,2-dioxaborolan-2-yl)phenoxy)ethyl)carbamate (as prepared in Example 63, Step-5) for compound 274, and (iii) continuing with Ex. 2 Step 6 to isolate the title compound of Ex. 82 Step-1.

227

Step-2: Synthesis of (E)-2-(4-(1-(3-fluoro-1-(tetra-hydro-2H-pyran-2-yl)-1H-indazol-5-yl)-3-methyl-2-phenylbut-1-en-1-yl)phenoxy)ethan-1-amine

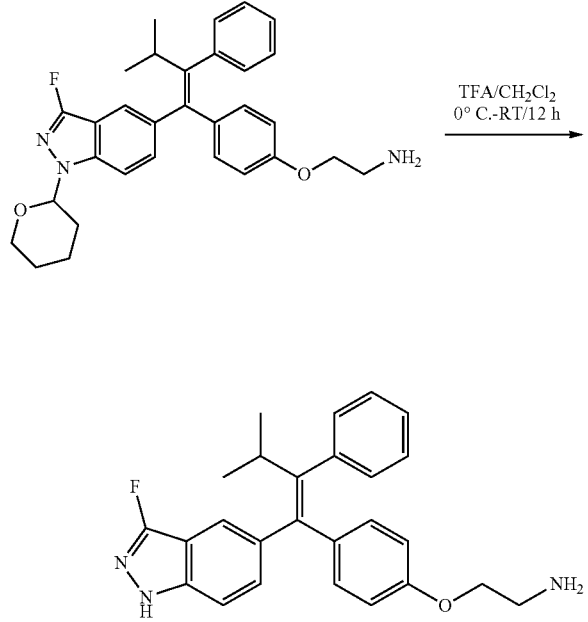

To a stirred solution of (E)-2-(4-(1-(3-fluoro-1-(tetrahydro-2H-pyran-2-yl)-1H-indazol-5-yl)-3-methyl-2-phenylbut-1-en-1-yl)phenoxy)ethan-1-amine (1.5 g, 3 mmol) in dichloromethane (20 mL) was added at 0° C., TFA (3.4 mL, 45 mmol). The reaction mixture was stirred for 12 h at room temperature. After completion of reaction, reaction mixture was basified with saturated NaHCO$_3$, extracted with 10% MeOH in dichloromethane. Organic layer was concentrated under reduced pressure and the crude material was purified by combi-flash using 10% MeOH in dichloromethane to afford the title compound of Ex. 82 Step-2 (1.1 g).

Compound 82: $^1$H NMR (400 MHz, DMSO-d$_6$): δ 12.55 (s, 1H), 7.56 (s, 1H), 7.48 (d, J=8.8 Hz, 1H), 7.30 (d, J=8.8 Hz, 1H), 7.23-7.19 (m, 2H), 7.14-7.10 (m, 3H), 6.84 (d, J=8.8 Hz, 2H), 6.61-6.46 (m, 4H), 3.83 (t, J=5.6 Hz, 2H), 3.31 (bs, 2H), 2.97 (s, 3H), 2.83 (m, 4H), 2.75 (t, J=5.4 Hz, 2H), 0.88 (m, 6H). LCMS: 527.3 [M+H]$^+$.

Example 83: There is no Example 83

Example 84: Synthesis of (E)-5-((2-(4-((E)-4-fluoro-1-(3-fluoro-1H-indazol-5-yl)-2-phenylbut-1-en-1-yl)phenoxy)ethyl)amino)-N,N-dimethylpent-2-enamide (Compound 84)

The compound was synthesized following the approach as outlined in Example 60 by substituting into Step-1 3-fluoro-5-(4-fluorobut-1-yn-1-yl)-1-(tetrahydro-2H-pyran-2-yl)-1H-indazole (preparation shown below in Ex. 84 Step 1-2) for compound 275 and tert-butyl (E)-(4-(dimethylamino)-4-oxobut-2-en-1-yl)(2-(4-iodophenoxy)ethyl)carbamate (as prepared in Example 14, Step-3) for compound 263 to isolate Compound 84 (0.075 g, 10%).

228

Step-1: Synthesis of 4-(3-fluoro-1-(tetrahydro-2H-pyran-2-yl)-1H-indazol-5-yl)but-3-yn-1-ol

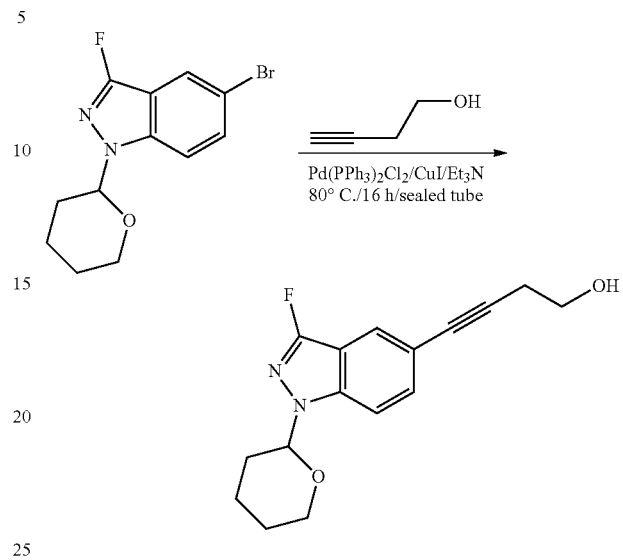

The reaction was carried out according to Scheme 1, Step-2 using 5-bromo-3-fluoro-1-(tetrahydro-2H-pyran-2-yl)-1H-indazole (10 g, 33 mmol, as prepared in Example 2, Step-2) and but-3-yn-1-ol (3.52 g, 50 mmol) for compound 202. The crude product was purified over silica-gel column chromatography using 30% ethyl acetate in n-hexane to afford the title compound of Ex. 84 Step-1 (5.7 g, 59%).

Step-2: Synthesis of 3-fluoro-5-(4-fluorobut-1-yn-1-yl)-1-(tetrahydro-2H-pyran-2-yl)-1H-indazole

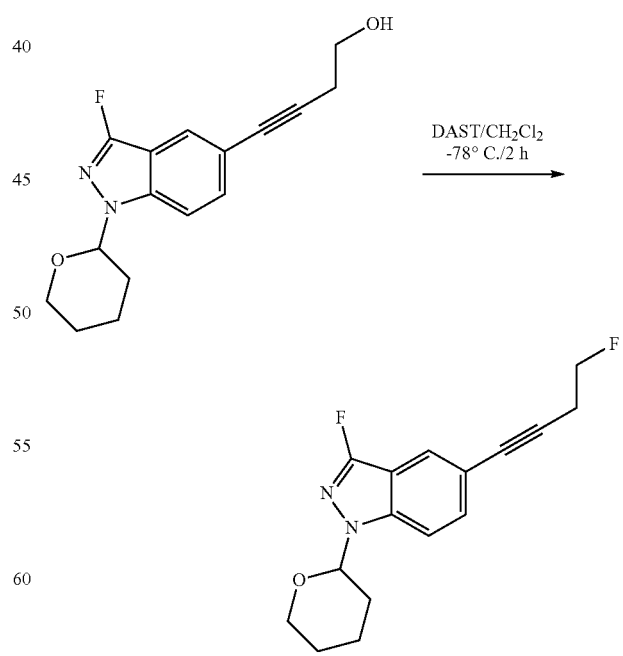

To a stirred solution of 4-(3-fluoro-1-(tetrahydro-2H-pyran-2-yl)-1H-indazol-5-yl)but-3-yn-1-ol (4 g, 13 mmol) in 40 mL of dichloromethane, was added DAST (3.35 g) at -78° C., reaction mixture was stirred for 2 h. Upon completion by TLC, the reaction mixture was diluted with water (100 mL) and extracted with ethyl acetate (250 mL). The combined organic extracts were washed with water, brine, dried over anhydrous sodium sulphate and concentrated under reduced pressure. The crude product was purified over 230-400 mesh silica column chromatography using 6% ethyl acetate in n-hexane to afford the title compound of Ex. 84 Step-2 (1.2 g, 30%).

Compound 84: $^1$H NMR (400 MHz, DMSO-$d_6$): δ 12.61 (s, 1H), 7.60 (s, 1H), 7.47 (dd, $J_1$=8.6 Hz, $J_2$=1.8 Hz, 1H), 7.25-7.13 (m, 6H), 6.9-6.75 (m, 2H), 6.64-6.57 (m, 2H), 6.52-6.48 (m, 2H), 4.36 (t, J=6 Hz, 1H), 4.25 (t, J=6.2 Hz, 1H), 3.87 (t, J=5.6 Hz, 2H), 3.37-3.31 (m, 2H), 2.99 (s, 3H), 2.84 (s, 3H), 2.82-2.70 (m, 4H). LCMS: 531.3 [M+H]$^+$.

Example 85: Synthesis of (E)-5-((2-(4-((E)-2-(2-chloro-4-fluorophenyl)-1-(3-fluoro-(3-fluoro-1H-indazol-5-yl)but-1-en-1-yl)phenoxy)ethyl)amino)-N,N-dimethylpent-2-enamide (Compound 85)

The compound was synthesized following the approach as outlined in Example 60 by substituting into Step-1 (i) tert-butyl (E)-(5-(dimethylamino)-5-oxopent-3-en-1-yl)(2-(4-iodophenoxy)ethyl)carbamate (preparation shown below in Ex. 85 Step 1-7) for compound 263, 5-(but-1-yn-1-yl)-3-fluoro-1-(tetrahydro-2H-pyran-2-yl)-1H-indazole (as prepared in Example 2, Step-3) for compound 275, and 2-chloro-4-fluoro-1-iodobenzene for compound 264 to isolate Compound 85 (0.046 g).

Step-1: Synthesis of 1-(2-chloroethoxy)-4-iodobenzene

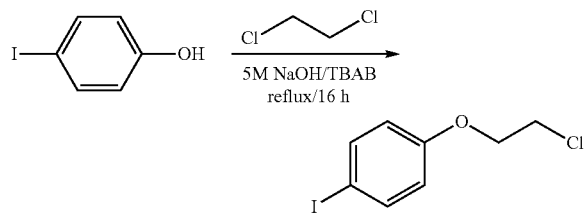

To a stirred solution of 4-iodophenol (15 g, 68 mmol) was added 5M NaOH (90 mL) and stirred for 10 min at 0° C., to the above mixture 1,2-dichloroethane (225 mL) followed by TBAB (0.43 g, 1.36 mmol) were added. The contents were stirred at reflux for 16 h. After completion of reaction, reaction mixture was poured onto ice cold water, and extracted with ethyl acetate. The combined organic layers were washed with water followed by saturated NaCl solution, dried over anhydrous Na$_2$SO$_4$ and concentrated under reduced pressure to obtain desired compound 1-(2-chloroethoxy)-4-iodobenzene (20 g, crude).

Step-2: Synthesis of 3-((2-(4-iodophenoxy) ethyl)amino)propan-1-ol

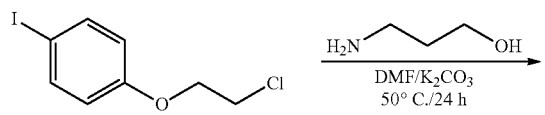

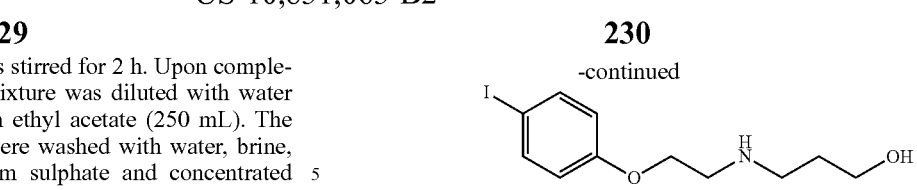

To a stirred solution of 1-(2-chloroethoxy)-4-iodobenzene (10 g, 35 mmol) in DMF (25 mL) was added potassium carbonate (19.5 g, 141 mmol) and 3-aminopropan-1-ol (26.6 g, 350 mmol). The reaction mixture was stirred for 24 h at 50° C., after completion of reaction (monitored by TLC), reaction mixture was diluted with cold water (50 mL) solid separated was filtered and dried under reduced pressure. The crude product was used in next step without further purification (8.6 g, crude).

Step-3: Synthesis of tert-butyl (3-hydroxypropyl)(2-(4-iodophenoxy)ethyl)carbamate

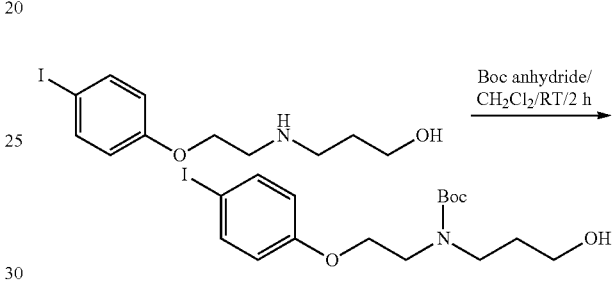

To a stirred solution of 3-((2-(4-iodophenoxy)ethyl)amino)propan-1-ol (8.6 g, 26 mmol) in dichloromethane (86 mL) was added boc anhydride (6.4 g, 29 mmol). The reaction mixture was stirred for 2 h at room temperature, after completion of reaction (monitored by TLC), reaction mixture was diluted with cold water (100 mL) and extracted with dichloromethane (250 mL). The organic layer was washed with water followed by saturated NaCl solution, dried over anhydrous Na$_2$SO$_4$ and concentrated under reduced pressure. The crude product purified by combi-flash using 40% EtOAc in n-hexane to get the title compound of Ex. 85 Step-3 (9.5 g).

Step-4: Synthesis of tert-butyl (2-(4-iodophenoxy)ethyl) (3-oxopropyl)carbamate

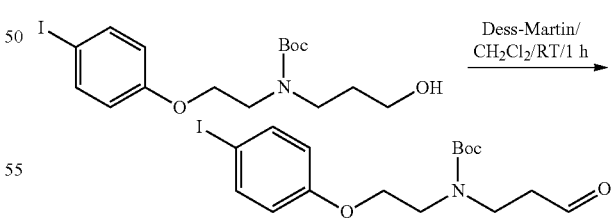

To a stirred solution of tert-butyl (3-hydroxypropyl)(2-(4-iodophenoxy)ethyl)carbamate (9 g, 21 mmol) in dichloromethane (90 mL) was added Dess-Martin periodinane (11.78 g, 27 mmol). The reaction mixture was stirred for 1 h at room temperature, after completion of reaction (monitored by TLC), reaction mixture was diluted with 1:1 mixture of hypo and NaHCO$_3$ solution and extracted with dichloromethane (250 mL). The organic layer was washed with water followed by saturated NaCl solution, dried over Step-5: Synthesis of ethyl (E)-5-((tert-butoxycarbonyl)(2-(4-iodophenoxy)ethyl)amino)pent-2-enoate

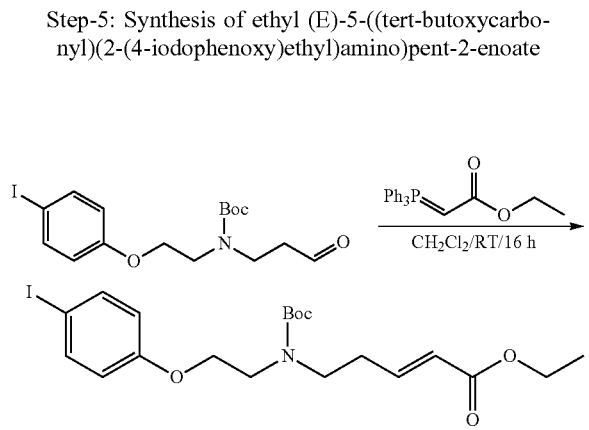

To a stirred solution of tert-butyl (2-(4-iodophenoxy)ethyl)(3-oxopropyl)carbamate (9 g, 28 mmol) in dichloromethane (90 mL) was added ethyl 2-(triphenyl-15-phosphanylidene)acetate (9.8 g, 28 mmol). The reaction mixture was stirred for 16 h at room temperature, after completion of reaction (monitored by TLC), reaction mixture was diluted with water and extracted with dichloromethane (250 mL). The organic layer was washed with water followed by saturated NaCl solution, dried over anhydrous $Na_2SO_4$ and concentrated under reduced pressure. The crude product was purified by combi-flash eluting with 9% EtOAc in n-hexane to afford the title compound of Ex. 85 Step-5 (6.7 g).

Step-6: Synthesis of (E)-5-((tert-butoxycarbonyl)(2-(4-iodophenoxy)ethyl)amino)pent-2-enoic acid

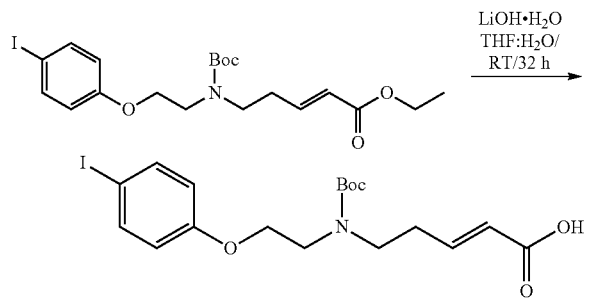

To a stirred solution of ethyl (E)-5-((tert-butoxycarbonyl)(2-(4-iodophenoxy)ethyl)amino)pent-2-enoate (6.7 g, 13 mmol) in THF (100 mL) was added $LiOH \cdot H_2O$ (2.87 g, 68 mmol) and water (33 mL). The reaction mixture was stirred for 32 h at room temperature, after completion of reaction (monitored by TLC), reaction mixture was diluted with water and neutralized with citric acid, extracted with EtOAc (250 mL). The organic layer was washed with water followed by saturated NaCl solution, dried over anhydrous $Na_2SO_4$ and concentrated under reduced pressure. The crude product was used in next step without further purification (5.4 g).

Step-7: Synthesis of tert-butyl (E)-(5-(dimethylamino)-5-oxopent-3-en-1-yl) (2-(4-iodophenoxy)ethyl)carbamate

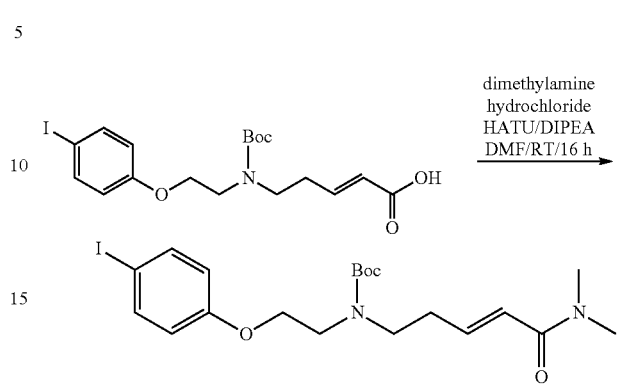

To a stirred solution of (E)-5-((tert-butoxycarbonyl)(2-(4-iodophenoxy)ethyl)amino)pent-2-enoic acid (2.5 g, 5.3 mmol) in DMF (25 mL) was added DIPEA (2.32 mL, 13 mmol), HATU (2.45 g, 6.4 mmol) and dimethylamine hydrochloride (0.526 g, 6.4 mmol). The reaction mixture was stirred for 16 h at room temperature, after completion of reaction (monitored by TLC), reaction mixture was diluted with water and extracted with EtOAc (100 mL). The organic layer was washed with water followed by saturated NaCl solution, dried over anhydrous $Na_2SO_4$ and concentrated under reduced pressure to afford title compound of Ex. 85 Step-7 (2 g, 71%).

Compound 85: $^1H$ NMR (400 MHz, DMSO-$d_6$): δ 12.62 (s, 1H), 7.54 (s, 1H), 7.49 (dd, $J_1$=8.8 Hz, $J_2$=1.2 Hz, 1H), 7.36-7.35 (m, 2H), 7.34-7.31 (m, 1H), 7.15-7.11 (m, 1H), 6.82 (d, J=8.8 Hz, 2H), 6.65-6.58 (m, 3H), 6.43-6.39 (m, 1H), 3.85 (t, J=5.7 Hz, 2H), 2.98 (s, 3H), 2.83 (s, 3H), 2.79-2.78 (m, 2H), 2.62 (t, J=6.8 Hz, 2H), 2.33-2.27 (m, 4H), 0.88 (t, J=7.4 Hz, 3H). LCMS: 579.3 $[M+H]^+$.

Example 86: Synthesis of (E)-4-((2-(4-((E)-2-(2-chloro-4-fluorophenyl)-1-(3-fluoro-(3-fluoro-1H-indazol-5-yl)but-1-en-1-yl)phenoxy)ethyl)amino)-N,N,2-trimethylbut-2-enamide (Compound 86)

The compound was synthesized following the approach as outlined in Example 59 by substituting into Step-4 5-(but-1-yn-1-yl)-3-fluoro-1-(tetrahydro-2H-pyran-2-yl)-1H-indazole (as prepared in Example 2, Step-3) for compound 276 and tert-butyl (E)-(4-(dimethylamino)-3-methyl-4-oxobut-2-en-1-yl)(2-(4-iodophenoxy)ethyl)carbamate (preparation shown below in Ex. 86 Step 1-3) for compound 277 to isolate Compound 86 (0.11 g, 7.6%).

Step-1: Synthesis of methyl (E)-4-((tert-butoxycarbonyl) (2-(4-iodophenoxy)ethyl)amino)-2-methylbut-2-enoate

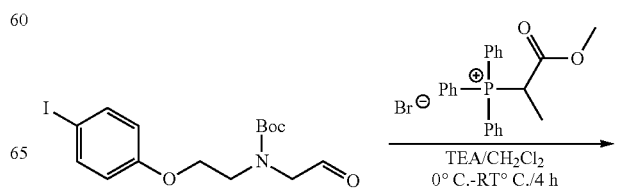

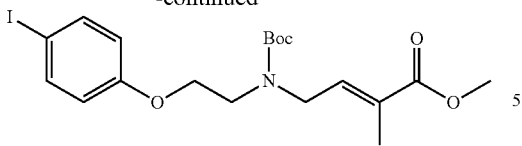

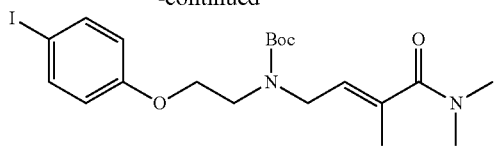

To a stirred solution of (1-methoxy-1-oxopropan-2-yl) triphenylphosphonium bromide (10.8 g, 25 mmol) in dichloromethane (50 mL) was added triethyl amine (6.35 g, 62 mmol) at 0° C., stirred for 30 min. To the above solution, tert-butyl (2-(4-iodophenoxy)ethyl)(2-oxoethyl)carbamate (8.5 g, 20 mmol, Example 22, Step-4) in dichloromethane (35 mL) was added dropwise. The reaction mixture was stirred for 3.5 h at room temperature, after completion of reaction (monitored by TLC), reaction mixture was diluted with ammonium chloride solution and extracted with EtOAc (100 mL). The organic layer was washed with water followed by saturated NaCl solution, dried over anhydrous $Na_2SO_4$ and concentrated under reduced pressure. The crude product was purified by column chromatography over 230-400 mesh silica-gel by eluting with 5% EtOAc in n-hexane to afford the title compound of Ex. 86 Step-1 (7.1 g, 71.7%).

Step-2: Synthesis of (E)-4-((tert-butoxycarbonyl)(2-(4-iodophenoxy)ethyl)amino)-2-methylbut-2-enoic acid

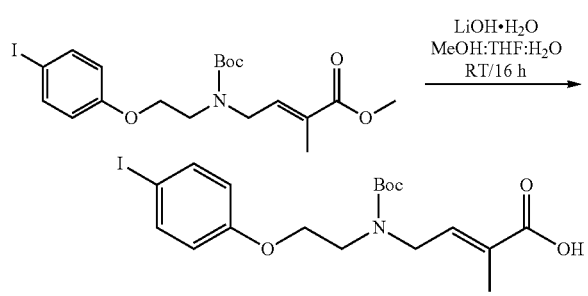

To a stirred solution of methyl (E)-4-((tert-butoxycarbonyl)(2-(4-iodophenoxy)ethyl)amino)-2-methylbut-2-enoate (7.1 g, 14.9 mmol) in MeOH:THF:$H_2O$ (1:1:1) mixture (70 mL) was added LiOH.$H_2O$ (3.13 g, 74 mmol). The reaction mixture was stirred for 16 h at room temperature, after completion of reaction (monitored by TLC), reaction mixture was diluted with water followed by acidified with 0.5 M HCl and extracted with EtOAc (250 mL). The organic layer was washed with water followed by saturated NaCl solution, dried over anhydrous $Na_2SO_4$ and concentrated under reduced pressure. The crude product was used in next step without further purification (6.5 g, 94%).

Step-3: Synthesis of tert-butyl (E)-(4-(dimethylamino)-3-methyl-4-oxobut-2-en-1-yl) (2-(4-iodophenoxy)ethyl)carbamate

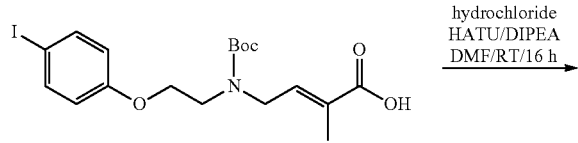

To a stirred solution of (E)-4-((tert-butoxycarbonyl)(2-(4-iodophenoxy)ethyl)amino)-2-methylbut-2-enoic acid (3 g, 6.5 mmol) in DMF (30 mL) was added DIPEA (3.1 g, 16.25 mmol), HATU (2.96 g, 7.8 mmol) and dimethylamine hydrochloride (0.63 g, 7.8 mmol). The reaction mixture was stirred for 16 h at room temperature, after completion of reaction (monitored by TLC), reaction mixture was diluted with water and extracted with dichloromethane (100 mL). The organic layer was washed with water followed by saturated NaCl solution, dried over anhydrous $Na_2SO_4$ and concentrated under reduced pressure. The crude product was purified by column chromatography over 230-400 mesh silica-gel by eluting with 70% EtOAc in n-hexane to afford the title compound of Ex. 86 Step-3 (2.6 g, 82%).

Compound 86: $^1$H NMR (400 MHz, DMSO-$d_6$): δ 12.63 (s, 1H), 7.54 (s, 1H), 7.49 (dd, $J_1$=8.6 Hz, $J_2$=1.8 Hz, 1H), 7.36-7.31 (m, 2H), 7.24 (dd, $J_1$=8.8 Hz, $J_2$=1.2 Hz, 1H), 7.14 (dd, $J_1$=8.0 Hz, $J_2$=2.4 Hz, 1H), 6.82 (d, J=8.8 Hz, 2H), 6.62 (d, J=8.8 Hz, 2H), 5.43-5.40 (m, 1H), 3.86 (t, J=5.6 Hz, 2H), 3.21 (d, J=6.4 Hz, 2H), 2.87-2.75 (m, 8H), 2.33 (q, J=7.2 Hz, 2H), 2.08-1.85 (m, 1H), 1.70 (s, 3H), 0.88 (t, J=7.6 Hz, 3H). LCMS: 579.3 [M+H]$^+$.

Example 87: Synthesis of (E)-4-((2-(4-((E)-2-(2-chloro-4-fluorophenyl)-4,4,4-trifluoro-1-(3-fluoro-1H-indazol-5-yl)but-1-en-1-yl)phenoxy)ethyl)amino)-N,N-dimethylbut-2-enamide (Compound 87)

The compound was synthesized following the approach as outlined in Example 59 by substituting into Step-4 tert-butyl (E)-(4-(dimethylamino)-4-oxobut-2-en-1-yl)(2-(4-iodophenoxy)ethyl)carbamate (as prepared in Example 14, Step-3) for compound 277 to isolate Compound 87 (0.17 g, 24%).

Compound 87: $^1$H NMR (400 MHz, DMSO-$d_6$): δ 12.69 (s, 1H), 7.59 (s, 1H), 7.55 (dd, $J_1$=8.6 Hz, $J_2$=1.8 Hz, 1H), 7.53 (dd, J=8.6 Hz, $J_2$=1.8 Hz, 1H), 7.43 (dd, J=8.6 Hz, $J_2$=1.8 Hz, 1H), 7.36-7.21 (m, 2H), 6.85 (d, J=8.9 Hz, 2H), 6.67-6.57 (m, 3H), 6.51-6.47 (m, 1H), 3.88 (t, J=5.7 Hz, 2H), 3.45 (q, J=10.8 Hz, 2H), 2.98 (s, 3H), 2.84 (s, 3H), 2.78 (t, J=5.6 Hz, 2H). LCMS: 619.3 [M+H]$^+$.

Example 88: Synthesis of (E)-4-((2-(4-((E)-1-(1H-indazol-5-yl)-2-(phenyl-d5)but-1-en-1-yl)phenoxy)ethyl)amino)-N,N-dimethylbut-2-enamide (Compound 88)

The compound was synthesized following the approach as outlined in Example 59 by substituting into Step-5 tert-butyl ((E)-4-(dimethylamino)-4-oxobut-2-en-1-yl)(2-(4-((Z)-1-(1-(tetrahydro-2H-pyran-2-yl)-1H-indazol-5-yl)-2-(4,4,5,5-tetramethyl-1,3,2-dioxaborolan-2-yl)but-1-en-1-yl)phenoxy)ethyl)carbamate (as prepared in Example 33, Step-1) for compound 278 and iodobenzene-$d_5$ for compound 265 to isolate Compound 88 (0.023 mg) as an off-white solid.

Compound 88: $^1$H NMR (400 MHz, DMSO-$d_6$) δ 13.05 (s, 1H), 8.06 (s, 1H), 7.60 (s, 1H), 7.50 (d, J=8.8 Hz, 1H), 7.11 (d, J=8.4 Hz, 2H), 6.73 (d, J=8.8, 2H), 6.59-6.51 (m, 3H), 6.47 (d, J=8.8 Hz, 1H), 3.86 (t, J=5.2 Hz, 2H), 3.31 (d, J=4.8 Hz, 2H), 2.98 (s, 3H), 2.83 (s, 3H), 2.78-2.75 (m, 2H), 2.40 (q, J=7.6 Hz, 2H), 0.89 (t, J=7.6 Hz, 3H). LCMS: 500.4 [M+H]⁺.

Example 89: Synthesis of (E)-4-((2-(4-((E)-1-(1H-indazol-5-yl)-2-phenylbut-1-en-1-yl)phenoxy)ethyl)amino)-N,N-dimethylpent-2-enamide (Compound 89)

The compound was synthesized following the approach as outlined in Example 59 by substituting into Step-4 5-(but-1-yn-1-yl)-1-(tetrahydro-2H-pyran-2-yl)-1H-indazole (Example 1, Step-3) for compound 276 and tert-butyl (E)-(5-(dimethylamino)-5-oxopent-3-en-2-yl)(2-(4-iodophenoxy)ethyl)carbamate (preparation shown below in Ex. 89 Step 1-4) for compound 277 and substituting into Step-5 iodobenzene for compound 265 to isolate Compound 89 (0.08 g, 5.5%).

Step-1: Synthesis of (E)-4-bromopent-2-enoic acid

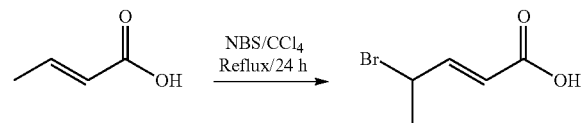

To a stirred solution of (E)-but-2-enoic acid (5 g, 50 mmol) in carbontetrachloride (50 mL) was added N-Bromo succinamide (8.6 g, 65 mmol). The reaction mixture was heated to reflux for 24 h, which resulted in precipitation of succinamide crystals. The crystals were filtered off and the filtrate was concentrated. The crude was recrystallized with minimum amount of hexane and washed with hexane to afford (E)-4-bromopent-2-enoic acid (4 g, 45%) as a white solid.

Step-2: Synthesis of (E)-4-bromo-N,N-dimethylpent-2-enamide

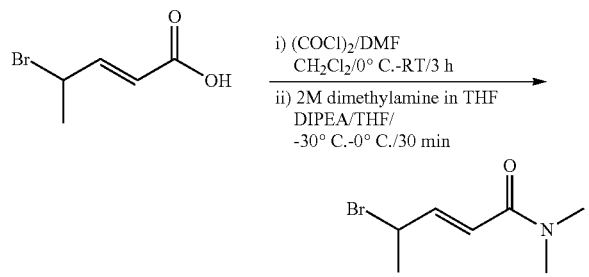

(E)-4-bromopent-2-enoic acid (4 g, 24.2 mmol) was taken in dichloromethane (40 mL) and cooled to 0° C. To this solution oxalyl chloride (3.6 g, 29 mmol), DMF (0.5 mL) were added and stirred for 3 h at room temperature. The reaction mixture was concentrated under nitrogen atmosphere, residue was diluted with dichloromethane (40 mL), cooled to −30° C. and was basified with DIPEA (7.7 mL, 43 mmol). To this mixture 2M dimethylamine in THF (14.3 mL, 28.6 mmol) was added slowly and the contents were stirred at 0° C. for 30 min. The volatiles were removed by concentration under reduced pressure and the residue was partitioned between water and ethyl acetate. The organic layer was washed with water, brine, dried over sodium sulphate and concentrated. The crude material was purified by combi-flash to afford (E)-4-bromo-N,N-dimethylpent-2-enamide (2.3 g, 50%).

Step-3: Synthesis of (E)-4-((2-(4-iodophenoxy) ethyl)amino)-N,N-dimethylpent-2-enamide

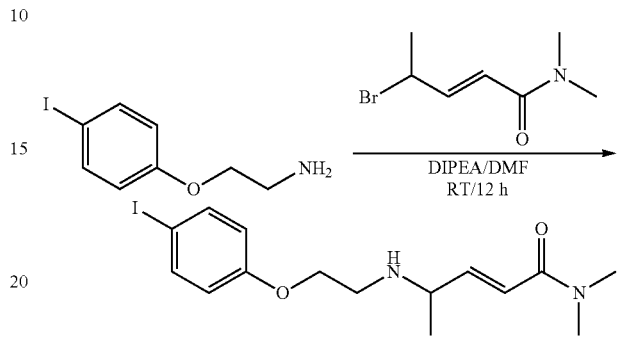

The reaction was carried out according to Scheme 3, Step-3 using 2-(4-iodophenoxy)ethan-1-amine (1.5 g, 5.86 mmol, Example 14, Step-3.1) for compound 217 and (E)-4-bromo-N,N-dimethylpent-2-enamide (1.8 g, 5.86 mmol) for compound 214. The crude material was used in next step (3 g, crude).

Step-4: Synthesis of tert-butyl (E)-(5-(dimethylamino)-5-oxopent-3-en-2-yl) (2-(4-iodophenoxy)ethyl)carbamate

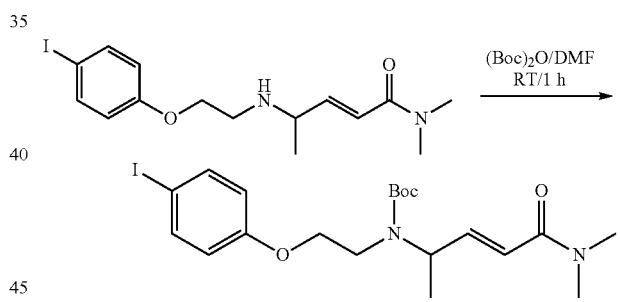

The reaction was carried out according to Scheme 3, Step-4 using (E)-4-((2-(4-iodophenoxy)ethyl)amino)-N,N-dimethylpent-2-enamide (4.5 g, 12 mmol) for compound 218 to afford the crude product was purified by combi-flash eluting with 70% ethyl aceate in n-hexane to afford the title compound in Ex. 90 Step-4 (2.8 g, 50%).

Compound 89: ¹H NMR (400 MHz, DMSO-d₆): δ 13.05 (s, 1H), 8.06 (s, 1H), 7.60 (s, 1H), 7.51 (d, J=8.8 Hz, 1H), 7.22-7.10 (m, 6H), 6.74 (d, J=8.8 Hz, 2H), 6.57 (d, J=8.8 Hz, 2H), 6.47-6.41 (m, 2H), 3.84 (t, J=5.6 Hz, 2H), 3.30 (bs, 2H), 2.98 (s, 3H), 2.83 (s, 3H), 2.75-2.66 (m, 2H), 2.43-2.32 (m, 2H), 1.07 (d, J=6.8 Hz, 3H), 0.87 (t, J=7.2 Hz, 3H). LCMS: 509.3 [M+H]⁺.

Example 90: Synthesis of (E)-4-((2-(4-((E)-1-(1H-indazol-5-yl)-2-phenylbut-1-en-1-yl)phenoxy)propyl)amino)-N,N-dimethylbut-2-enamide (Compound 90)

The compound was synthesized following the approach as outlined in Example 59 by substituting into Step-4 5-(but- 1-yn-1-yl)-1-(tetrahydro-2H-pyran-2-yl)-1H-indazole (Example 1, Step-3) for compound 276 and tert-butyl (E)-(4-(dimethylamino)-4-oxobut-2-en-1-yl)(2-(4-iodophenoxy)propyl)carbamate (preparation shown below Ex. 90 Step 1-5) for compound 277 and substituting into Step-5 iodobenzene for compound 265 to afford Compound 90 (0.06 g, 10%).

Step-1: Synthesis of tert-butyl (2-hydroxypropyl)carbamate

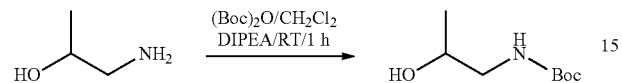

To a stirred solution of 1-aminopropan-2-ol (5 g, 66.6 mmol) in dichloromethane (50 mL), was added boc anhydride (17 mL, 79.92 mmol) and DIPEA (18 mL, 99.9 mmol), the reaction mixture was stirred at room temperature for about 1 h. After completion of reaction, reaction mixture was concentrated under reduced pressure and the crude product was purified by combi-flash eluting with 50% ethyl acetate in n-hexane to afford the title compound in Ex. 90 Step-1 (10 g, 86%).

Step-2: Synthesis of tert-butyl (2-(4-iodophenoxy)propyl)carbamate

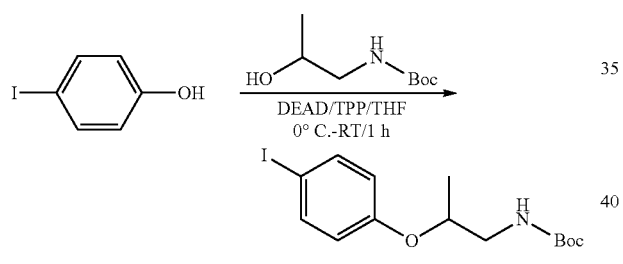

To a mixture of 4-iodophenol (4 g, 18.1 mmol), tert-butyl (2-hydroxypropyl)carbamate (2.6 g, 21.8 mmol), triphenyl phosphine (5.7 g, 21.8 mmol) in THF (40 mL) was added DEAD (3.8 g, 21.8 mmol) dropwise then the reaction mixture was stirred at room temperature for 1 h. After completion of reaction, reaction mixture was quenched with water extracted with ethyl acetate (2×100 mL), combined organic layer was washed with brine solution and dried over anhydrous sodium sulphate. Organic layer was concentrated to afford the crude product which was purified through column chromatography over 100-200 mesh silica gel, eluting with 10% EtOAc in n-hexane to afford the title compound in Ex. 90 Step-2 (2.1 g, 32%).

Step-3: Synthesis of 2-(4-iodophenoxy)propan-1-amine

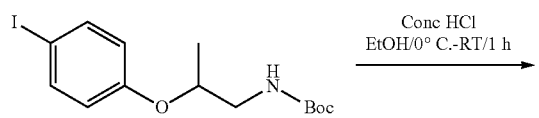

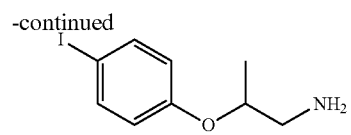

The reaction was carried out according to Scheme 3, Step-2 using tert-butyl (2-(4-iodophenoxy)propyl)carbamate (4.8 g, 12.76 mmol) for compound 207b to afford the crude material, which was used in next step without further purification (2.8 g).

Step-4: Synthesis of (E)-4-((2-(4-iodophenoxy)propyl)amino)-N,N-dimethylbut-2-enamide

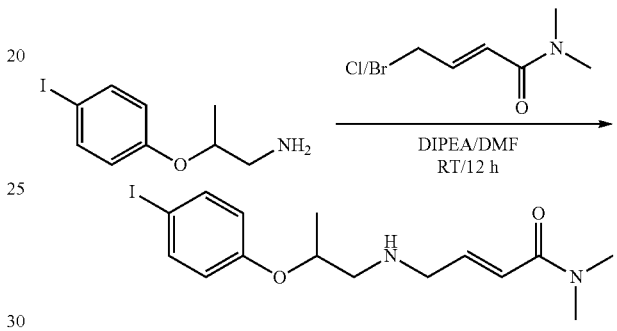

The reaction was carried out according to Scheme 3, Step-3 using 2-(4-iodophenoxy)propan-1-amine (1 g, 3.6 mmol) for compound 217 in DMF (10 mL) and (E)-4-chloro-N,N-dimethylbut-2-enamide for compound 214 and (E)-4-bromo-N,N-dimethylbut-2-enamide mixture (0.7 g, 3.6 mmol, Example 63, Step-7) for compound 214. The crude material was used in next step (0.5 g, crude).

Step-5: Synthesis of tert-butyl (E)-(4-(dimethylamino)-4-oxobut-2-en-1-yl) (2-(4-iodophenoxy)propyl)carbamate

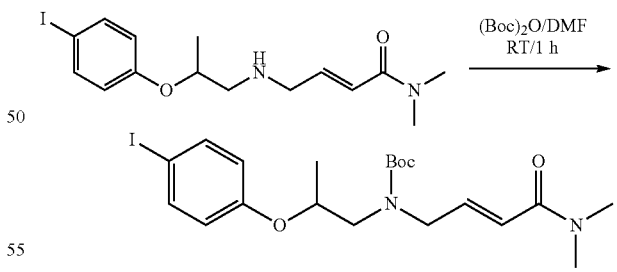

The reaction was carried out according to Scheme 3, Step-4 using (E)-4-((2-(4-iodophenoxy)propyl)amino)-N,N-dimethylbut-2-enamide (2 g, 5.3 mmol) for compound 218 to afford the crude product, which was purified by combi-flash eluting with 70% ethyl aceate in n-hexane to afford the title compound in Ex. 90 Step-5 (0.5 g, 20%).

Compound 90: $^1$H NMR (400 MHz, DMSO-$d_6$): δ 13.07 (s, 1H), 8.07 (s, 1H), 7.61 (s, 1H), 7.52 (d, J=11.2 Hz, 1H), 7.22-7.11 (m, 6H), 6.78 (d, J=8.8 Hz, 2H), 6.71-6.52 (m, 4H), 4.52-4.31 (m, 1H), 3.61 (d, J=4.4 Hz, 2H), 3.96-3.04

(m, 5H), 2.86 (s, 3H), 2.42-2.32 (m, 2H), 1.14 (d, J=6.0 Hz, 3H), 0.87 (t, J=7.6 Hz, 3H). LCMS: 509.3 [M+H]+.

Example 91: There is no Example 91

Example 92: Synthesis of (E)-4-((1-(4-((E)-1-(1H-indazol-5-yl)-2-phenylbut-1-en-1-yl)phenoxy)propan-2-yl)amino)-N,N-dimethylbut-2-enamide (Compound 92)

The compound was synthesized following the approach as outlined in Example 59 by (i) substituting into Step-4 5-(but-1-yn-1-yl)-1-(tetrahydro-2H-pyran-2-yl)-1H-indazole (as prepared in Example 1, Step-3) for compound 276 and tert-butyl (E)-(4-(dimethylamino)-4-oxobut-2-en-1-yl)(1-(4-iodophenoxy)propan-2-yl)carbamate (preparation shown below in Ex. 92 Step 1-4) for compound 277 and (ii) substituting into Step-5 iodobenzene for compound 265 to isolate Compound 92 (0.015 g).

Step-1: Synthesis of 2-(3-(4-iodophenyl)propyl)isoindoline-1,3-dione

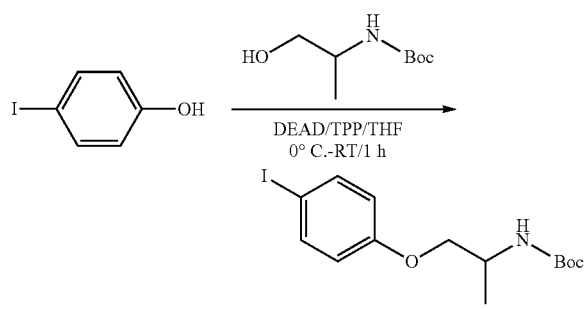

To a mixture of 4-iodophenol (5 g, 22 mmol), tert-butyl (1-hydroxypropan-2-yl)carbamate (4.66 g, 26 mmol), triphenyl phosphine (7.12 g, 26 mmol) in THF (100 mL) was added DEAD (4.66 g, 26 mmol) dropwise then the reaction mixture was stirred at room temperature for 1 h. After completion of reaction, reaction mixture was quenched with water extracted with ethyl acetate (2×100 mL), combined organic layer was washed with brine solution and dried over anhydrous sodium sulphate. Organic layer was concentrated to afford the crude product which was purified through column chromatography over 100-200 mesh silica gel, eluting with 10% EtoAc in n-hexane to afford the title compound in Ex. 92 Step-1 (2 g).

Step-2: Synthesis of 1-(4-iodophenoxy)propan-2-amine

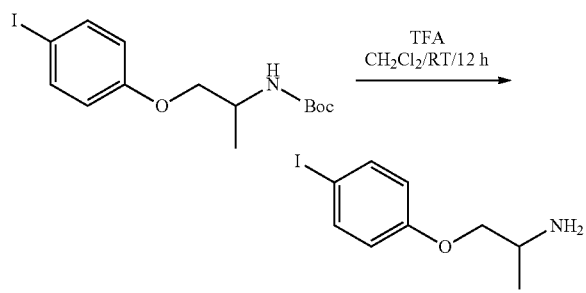

The reaction was carried out according to Scheme 3, Step-2 using tert-butyl (1-(4-iodophenoxy)propan-2-yl)carbamate (4 g, 10.6 mmol) for compound 207b to afford the crude material, which was used in next step without further purification (2 g).

Step-3: Synthesis of (E)-4-((2-(4-iodophenoxy)ethyl)amino)-N,N-dimethylpent-2-enamide

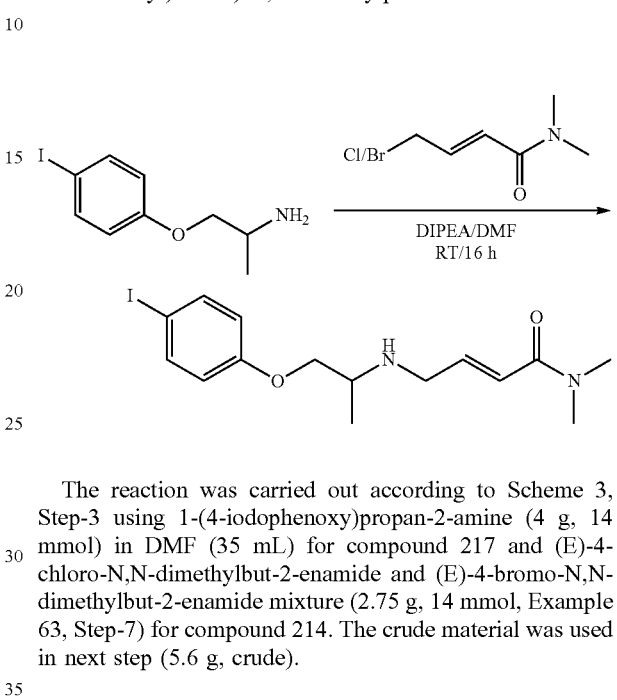

The reaction was carried out according to Scheme 3, Step-3 using 1-(4-iodophenoxy)propan-2-amine (4 g, 14 mmol) in DMF (35 mL) for compound 217 and (E)-4-chloro-N,N-dimethylbut-2-enamide and (E)-4-bromo-N,N-dimethylbut-2-enamide mixture (2.75 g, 14 mmol, Example 63, Step-7) for compound 214. The crude material was used in next step (5.6 g, crude).

Step-4: Synthesis of tert-butyl (E)-(4-(dimethylamino)-4-oxobut-2-en-1-yl)(1-(4-iodophenoxy)propan-2-yl) carbamate

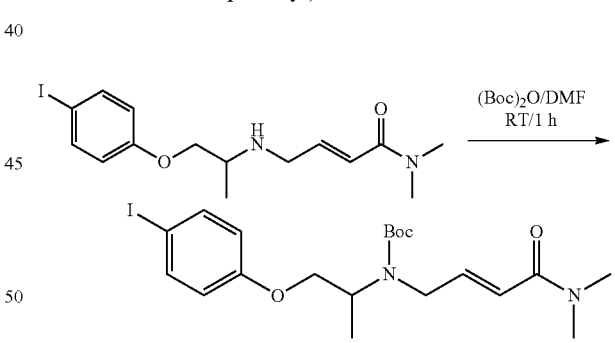

The reaction was carried out according to (E)-4-((1-(4-iodophenoxy)propan-2-yl)amino)-N,N-dimethylbut-2-enamide (5.6 g, 14 mmol) to afford the crude, which was purified by silica gel chromatography with 40% ethyl aceate in n-hexane to afford the title compound in Ex. 92 Step-4 (2.5 g).

Compound 92: $^1$H NMR (400 MHz, DMSO-$d_6$): δ 13.05 (s, 1H), 8.06 (s, 1H), 7.60 (s, 1H), 7.51 (d, J=8.0 Hz, 1H), 7.22-7.11 (m, 6H), 6.75 (d, J=8.4 Hz, 2H), 6.6-6.47 (m, 4H), 3.74-3.71 (m, 1H), 3.65-3.61 (m, 1H), 3.39-3.32 (m, 2H), 2.97 (s, 3H), 2.91-2.83 (m, 4H), 2.43-2.23 (m, 2H), 1.07 (d, J=6.4 Hz, 3H), 0.87 (t, J=7.2 Hz, 3H). LCMS: 509.3 [M+H]+.

241

Example 93: Synthesis of (E)-4-((2-((6-((Z)-1-(3-fluoro-1H-indazol-5-yl)-2-phenylbut-1-en-1-yl)pyridin-3-yl)oxy)ethyl)amino)-N,N-dimethylbut-2-enamide (Compound 93)

The compound was synthesized following the approach as outlined in Example 3 by (i) substituting into Step-3 of Ex. 3 tert-butyl (E)-(4-(dimethylamino)-4-oxobut-2-en-1-yl)(2-((6-iodopyridin-3-yl)oxy)ethyl)carbamate (preparation shown below in Ex. 93 Step 1-5) for compound 256, (ii) substituting into Ex. 3 Step-4 of Ex. 3 iodobenzene for compound 227, and (iii) substituting Step-5 of Ex. 3 with reaction conditions described in Scheme 2, Step-6b to afford Compound 93 (0.12 g).

Step-1: Synthesis of tert-butyl (2-((6-bromopyridin-3-yl)oxy)ethyl)carbamate

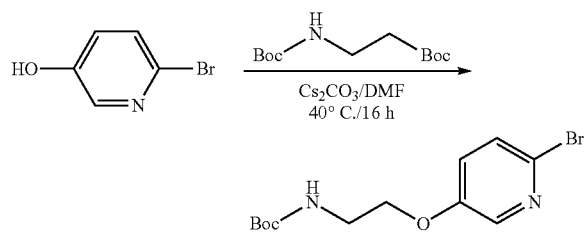

To a stirred solution of 6-bromopyridin-3-ol (5 g, 28.9 mmol) in 50 ml of DMF, cesium carbonate (28.2 g, 86 mmol) and tert-butyl (2-bromoethyl)carbamate (12.89 g, 57.8 mmol) were added. The mixture was then stirred for 16 h at 40° C. After completion of reaction, reaction mixture was added to ice cold water. Solid separated was filtered and dried to obtain tert-butyl (2-((6-bromopyridin-3-yl)oxy)ethyl)carbamate (8.2 g).

Step-2: Synthesis of tert-butyl (2-((6-iodopyridin-3-yl)oxy)ethyl)carbamate

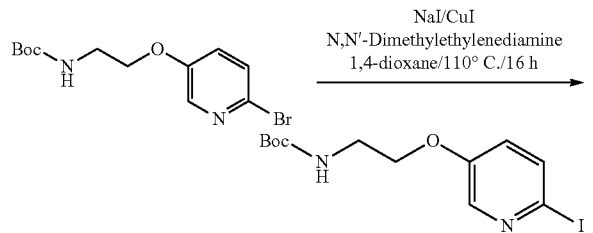

To a stirred solution of tert-butyl (2-((6-bromopyridin-3-yl)oxy)ethyl)carbamate (8.1 g, 25 mmol) in 1,4-dioxane (80 mL) were added sodium iodide (19.2 g, 128 mmol), copper iodide (0.244 g, 1.28 mmol) and N,N'-Dimethylethylenediamine (0.28 mL, 2.5 mmol) stirred for 16 h at 110° C. After completion of reaction, reaction mixture was diluted with ethyl acetate, organic layer was washed with a saturated aqueous solution of sodium chloride, dried over anhydrous sodium sulfate, and then concentrated under reduced pressure. The obtained crude product was used in next step without further purification (8.7 g, crude).

242

Step-3: Synthesis of 2-((6-iodopyridin-3-yl)oxy)ethan-1-amine

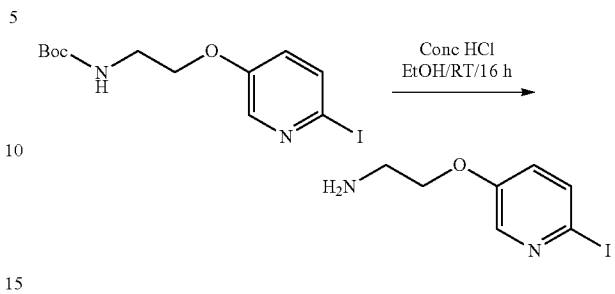

To a stirred solution of tert-butyl (2-((6-iodopyridin-3-yl)oxy)ethyl)carbamate (8 g, 21.97 mmol) in ethanol (2 mL) was added at 0° C., conc HCl (20 mL). The reaction mixture was stirred for 16 h at room temperature. After completion of reaction, reaction mixture was basified with saturated NaHCO$_3$, extracted with ethyl acetate. Organic layer was concentrated under reduced pressure and the crude material was used in next step without further purification (5 g, crude).

Step-4: Synthesis of (E)-4-((2-((6-iodopyridin-3-yl)oxy)ethyl)amino)-N,N-dimethylbut-2-enamide

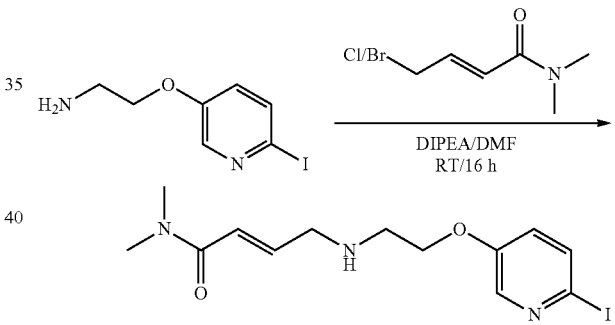

The reaction was carried out according to Scheme 3, Step-3 using 2-((6-iodopyridin-3-yl)oxy)ethan-1-amine (5 g, 18.9 mmol) in DMF (50 mL) for compound 217 and (E)-4-bromo-N,N-dimethylbut-2-enamide and (E)-4-chloro-N,N-dimethylbut-2-enamide mixture (2.63 g, 15 mmol, Example 63, Step-7) for compound 214. The crude material was used in next step without further purification (7.08 g, crude).

Step-5: Synthesis of tert-butyl (E)-(4-(dimethylamino)-4-oxobut-2-en-1-yl) (2-((6-iodopyridin-3-yl)oxy) ethyl)carbamate

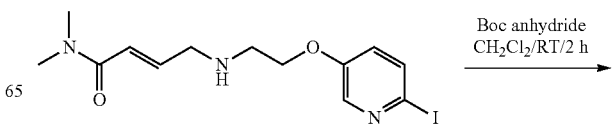

-continued

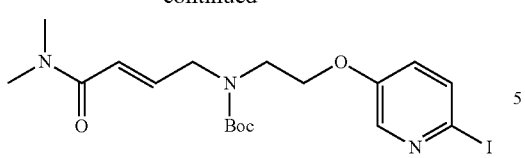

The reaction was carried out according to Scheme 3, Step-4 using (E)-4-((2-(((6-iodopyridin-3-yl)oxy)ethyl)amino)-N,N-dimethylbut-2-enamide (7.08 g, 18.9 mmol) for compound 218. The crude material was purified by combiflash eluting with 1.5% MeOH in dichloromethane as an eluent to afford the title compound of Ex. 93 Step-5 (2.7 g, 30%).

Compound 93: $^1$H NMR (400 MHz, DMSO-$d_6$): δ 12.5 (s, 1H), 8.03 (s, 1H), 7.48-7.44 (m, 2H), 7.25 (dd, J=8.8 Hz, $J_2$=1.6 Hz, 2H), 7.21-7.10 (m, 4H), 7.02-6.99 (m, 1H), 6.78 (d, J=8.0 Hz, 1H), 6.62-6.47 (m, 2H), 3.94 (t, J=5.6 Hz, 2H), 2.98 (s, 3H), 2.84-2.78 (m, 5H), 2.47-2.42 (m, 2H), 0.87 (t, J=7.2 Hz, 3H). LCMS: 514.3 [M+H]$^+$.

Example 94: There is no Example 94

Example 95: Synthesis of (E)-4-((3-(4-((E)-1-(1H-indazol-5-yl)-2-phenylbut-1-en-1-yl)phenoxy)propyl)amino)-N,N-dimethylbut-2-enamide (Compound 95)

The compound was synthesized following the approach as outlined in Example 59 by (i) substituting into Step-4 of Ex. 59 5-(but-1-yn-1-yl)-1-(tetrahydro-2H-pyran-2-yl)-1H-indazole (as prepared in Example 1, Step-3) for compound 276 and tert-butyl (E)-(4-(dimethylamino)-4-oxobut-2-en-1-yl) (3-(4-iodophenoxy)propyl)carbamate (preparation shown below in Ex. 95 Step 1-5) for compound 277 and (ii) substituting into Step-5 of Ex. 59 iodobenzene for compound 265 to isolate Compound 95 (0.035 g).

Step-1: Synthesis of 1-(3-chloropropoxy)-4-iodobenzene

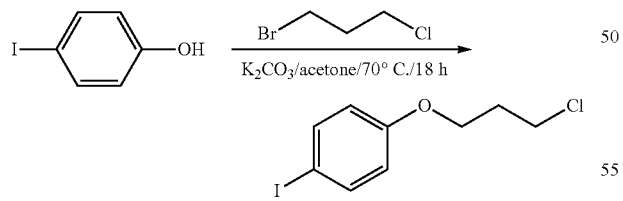

To a stirred solution of 4-iodophenol (10 g, 45.5 mmol) in acetone (150 mL) was added potassium carbonate (12.6 g, 91 mmol) and stirred for 30 min at room temperature, to the above mixture 1-bromo-3-chloropropane (10.75 g, 68.2 mmol) was added. The contents were stirred at 70° C. for 18 h. After completion of reaction, reaction mixture filtered through celite bed, filterate was concentrated under reduced pressure to obtain desired compound 1-(3-chloropropoxy)-4-iodobenzene as a glassy solid (13.3 g, 98%).

Step-2: Synthesis of 2-(3-(4-iodophenoxy)propyl)isoindoline-1,3-dione

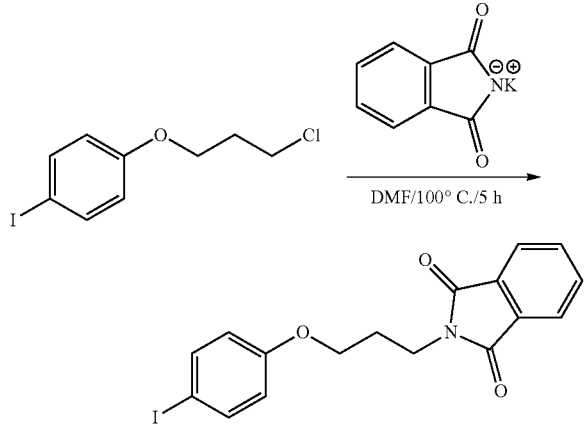

To a stirred solution of 1-(3-chloropropoxy)-4-iodobenzene (12 g, 40.5 mmol) in DMF (100 mL) was added potassium phthalimide (9 g, 48.6 mmol) in one portion at room temperature and the reaction mixture was stirred at 100° C. for 5 h. The reaction mixture cooled to room temperature, diluted with water, solid separated was filtered and dried under reduced pressure to afford the title compound of Ex. 95 Step-2 (15.2 g, 92%).

Step-3: Synthesis of 3-(4-iodophenoxy)propan-1-amine

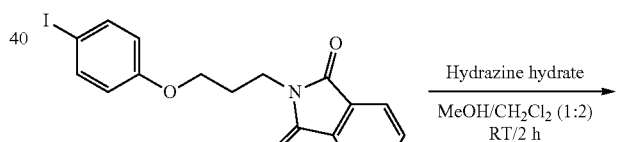

To a solution of 2-(3-(4-iodophenoxy)propyl)isoindoline-1,3-dione (16 g, 39 mmol) in MeOH/CH$_2$Cl$_2$ (160 mL/1:2) was added hydrazine hydrate (28 mL) at room temperature. The reaction mixture was stirred for 2 h and was quenched with water and extracted with dichloromethane. The organic layer was washed with water, saturated NaCl solution, dried over anhydrous Na$_2$SO$_4$ and concentrated under reduced pressure to afford 3-(4-iodophenoxy)propan-1-amine (10.6 g, 97%) as a light brown liquid.

Step-4: Synthesis of (E)-4-((3-(4-iodophenoxy)propyl)amino)-N,N-dimethylbut-2-enamide

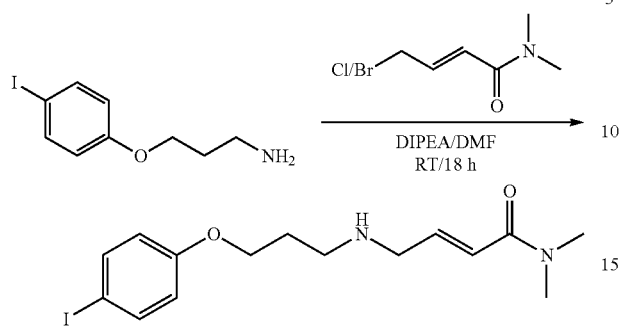

The reaction was carried out according to Scheme 3, Step-3 using 3-(4-iodophenoxy)propan-1-amine (10.6 g, 38 mmol) for compound 217 and (E)-4-chloro-N,N-dimethylbut-2-enamide and (E)-4-bromo-N,N-dimethylbut-2-enamide mixture (5.2 g, 30.6 mmol, Example 63, Step-7) for compound 214. The crude material was used in next step (14.7 g, crude).

Step-5: Synthesis of tert-butyl (E)-(4-(dimethylamino)-4-oxobut-2-en-1-yl) (3-(4-iodophenoxy)propyl)carbamate

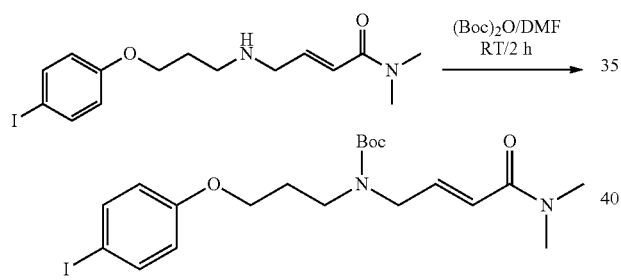

The reaction was carried out according to Scheme 3, Step-4 using (E)-4-((3-(4-iodophenoxy)propyl)amino)-N,N-dimethylbut-2-enamide (14.7 g, 37.8 mmol) for compound 218 to afford crude product, which was purified by column chromatography over 60-120 mesh silica-gel, eluting with 60-80% ethyl aceate in n-hexane to afford the title compound of Ex. 95 Step-5 (7.1 g, 39%).

Compound 95: $^1$H NMR (400 MHz, DMSO-d$_6$): δ 13.05 (s, 1H), 8.06 (s, 1H), 7.60 (s, 1H), 7.52 (d, J=8.4 Hz, 1H), 7.20 (d, J=7.6 Hz, 2H), 7.15-7.11 (m, 4H), 6.74 (d, J=8.4 Hz, 2H), 6.58-6.48 (m, 4H), 3.86 (t, J=6.0 Hz, 2H), 3.25 (d, J=4.8 Hz, 2H), 2.96 (s, 3H), 2.83 (s, 3H), 2.56 (t, J=6.8 Hz, 2H), 2.41 (m, 2H), 1.90 (bs, 1H), 1.76 (t, J=6.0 Hz, 2H), 0.89 (t, J=7.6 Hz, 3H). LCMS: 509.4 [M+H]$^+$.

Example 96: Synthesis of (E)-4-((3-(4-((E)-1-(1H-indazol-5-yl)-2-phenylbut-1-en-1-yl)phenoxy)butan-2-yl)amino)-N,N-dimethylbut-2-enamide (Compound 96)

The compound was synthesized following the approach as outlined in Example 59 by substituting into Step-4 of Ex. 59 5-(but-1-yn-1-yl)-1-(tetrahydro-2H-pyran-2-yl)-1H-indazole (as prepared in Example 1, Step-3) for compound 276 and tert-butyl (E)-(4-(dimethylamino)-4-oxobut-2-en-1-yl) (3-(4-iodophenoxy)butan-2-yl)carbamate (preparation shown below in Ex. 96 Step 1-4) for compound 277 and substituting into Step-5 of Ex. 59 iodobenzene for compound 265 to isolate Compound 96 (0.165 g).

Step-1: Synthesis of 3-(4-iodophenoxy)butan-2-one

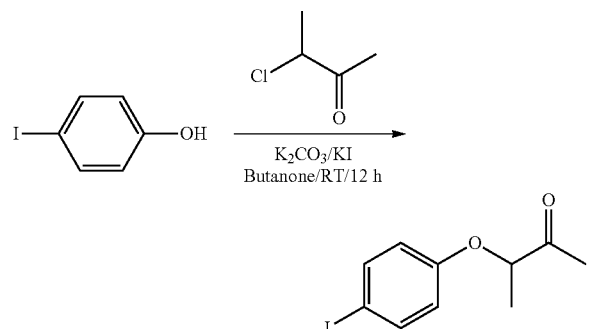

To a stirred solution of 4-iodophenol (5 g, 22.7 mmol) in butanone (100 mL) were added potassium carbonate (4.7 g, 34 mmol) and potassium iodide (0.376 g, 2.27 mmol). Reaction mixture was stirred for 30 min at room temperature, to the above mixture 3-chlorobutan-2-one (2.4 g, 22.7 mmol) was added. The contents were stirred at room temperature for 12 h. After completion of reaction, reaction mixture was poured onto ice cold water and extracted with ethyl acetate (2×250 mL). The combined organic extracts were washed with water, brine, dried over anhydrous sodium sulphate and concentrated under reduced pressure to obtain desired compound 3-(4-iodophenoxy)butan-2-one (6 g, 86%).

Step-2: Synthesis of 3-(4-iodophenoxy)butan-2-amine

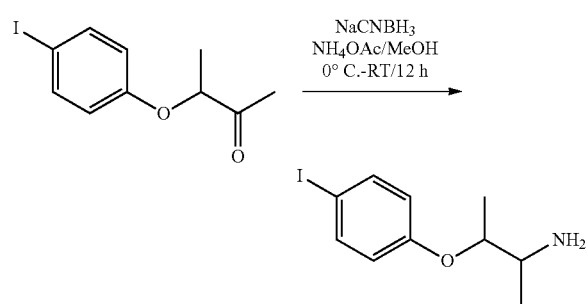

To a stirred solution of 3-(4-iodophenoxy)butan-2-one (3 g, 10.3 mmol) in methanol (50 mL) were added at 0° C., sodium cyanoborohydride (0.98 g, 15.5 mmol) and ammonium acetate (11.8 g, 154.5 mmol). The reaction mixture was stirred for 12 h at room temperature. After completion of reaction, reaction mixture was diluted with conc HCl and water, extracted with diethyl ether. Aqueous layer was basified with 5% NaOH solution, extracted with ethyl acetate. Organic layer was concentrated under reduced pressure and the crude material was used in next step without further purification (2.2 g, 70%).

Step-3: Synthesis of (E)-4-((3-(4-iodophenoxy)butan-2-yl)amino)-N,N-dimethylbut-2-enamide

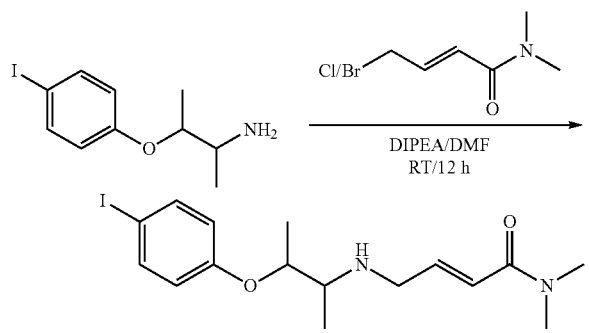

The reaction was carried out according to Scheme 3, Step-3 using 3-(4-iodophenoxy)butan-2-amine (2.9 g, 10.03 mmol) and (E)-4-chloro-N,N-dimethylbut-2-enamide and (E)-4-bromo-N,N-dimethylbut-2-enamide mixture (1.73 g, 9.03 mmol, Example 63, Step-7). The crude material was used in next step (4 g, crude).

Step-4: Synthesis of tert-butyl (E)-(4-(dimethylamino)-4-oxobut-2-en-1-yl) (3-(4-iodophenoxy) butan-2-yl)carbamate

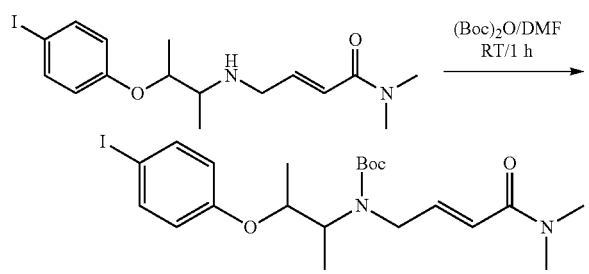

The reaction was carried out according to Scheme 3, Step-4 using (E)-4-((3-(4-iodophenoxy)butan-2-yl)amino)-N,N-dimethylbut-2-enamide (4 g, 9.9 mmol) for compound 218. The crude product was purified by combi-flash eluting with 70% ethyl aceate in n-hexane to afford the title compound of Ex. 96 Step-4 (2.9 g, 60%).

Compound 96: $^1$H NMR (400 MHz, DMSO-$d_6$): δ 13.05 (s, 1H), 8.06 (s, 1H), 7.61 (s, 1H), 7.51 (d, J=11.2 Hz, 1H), 7.22-7.10 (m, 6H), 6.74-6.71 (m, 2H), 6.61-6.43 (m, 4H), 4.23-4.20 (m, 1H), 3.35-3.28 (m, 2H), 2.94-2.81 (m, 6H), 2.71-2.67 (m, 1H), 2.42-2.32 (m, 2H), 1.09-0.84 (m, 9H). LCMS: 523.3 [M+H]$^+$.

Example 97: There is no Example 97

Example 98: Synthesis of (E)-4-((1-(4-((E)-1-(1H-indazol-5-yl)-2-phenylbut-1-en-1-yl)phenoxy)-2-methylpropan-2-yl)amino)-N,N-dimethylbut-2-enamide (Compound 98)

The compound was synthesized following the approach as outlined in Example 3 by (i) substituting into Step-1 of Ex. 3 5-(but-1-yn-1-yl)-1-(tetrahydro-2H-pyran-2-yl)-1H-indazole (as prepared in Example 1, Step-3) for compound 252, (ii) proceeding directly from Step-1 to Step-3 and substituting into Step-3 of Ex. 3 tert-butyl (1-(4-iodophenoxy)-2-methylpropan-2-yl)carbamate (preparation shown below in Ex. 98 Step 1-4) for compound 256, (iii) substituting into Step-4 of Ex. 3 Iodobenzene for compound 227, (iv) substituting Step-5 of Ex. 3 with reaction conditions described in Scheme 2, Step-6b, and (v) substituting into Step-6 of Ex. 3 (E)-4-chloro-N,N-dimethylbut-2-enamide and (E)-4-bromo-N,N-dimethylbut-2-enamide mixture (as prepared in Example 49, Step-4) for compound 251 to afford Compound 98 (0.035 g).

Step-1: Synthesis of 2-methyl-1-(4-nitrophenoxy)propan-2-amine

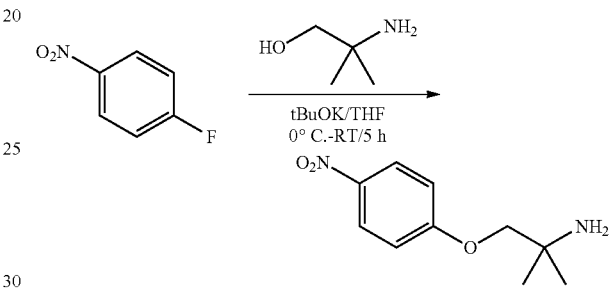

To a stirred solution of 2-amino-2-methylpropan-1-ol (4.5 g) in THF (25 mL) was added a solution of potassium tert-butoxide (5.7 g, 51 mmol) in THF (25 mL) at 0° C., stirred for 1 h at the same temperature. 1-Fluoro-4-nitrobenzene (5 g, 35.4 mmol) was added to the above reaction mixture and the reaction mixture was stirred at room temperature for 4 h. After completion of reaction, reaction mixture was diluted with ice cold water, extracted with EtOAc. The organic layer was dried over anhydrous sodium sulphate and concentrated under reduced pressure to afford the title compound in Ex. 98 Step-1 (6 g, 80%).

Step-2: Synthesis of tert-butyl (2-methyl-1-(4-nitrophenoxy)propan-2-yl)carbamate

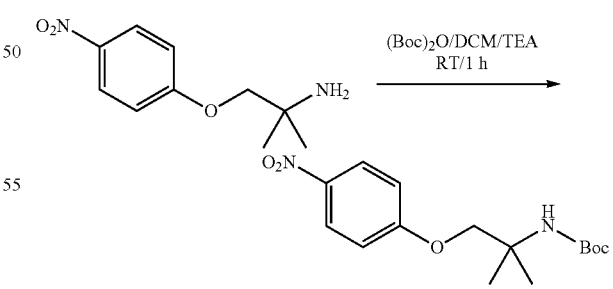

To a stirred solution of 2-methyl-1-(4-nitrophenoxy)propan-2-amine (5 g, 23.5 mmol) in DCM (50 mL) was added TEA (6.3 mL, 35.3 mmol) at room temperature, stirred for 15 min. Boc anhydride (6.1 mL, 28.2 mmol) was added and the reaction mixture was stirred at room temperature for 1 h. After completion of reaction, reaction mixture was diluted with ice cold water, extracted with EtOAc. The organic layer

249 was dried over anhydrous sodium sulphate and concentrated under reduced pressure to afford the title compound in Ex. 98 Step-2 (7.3 g).

Step-3: Synthesis of tert-butyl (1-(4-aminophenoxy)-2-methylpropan-2-yl)carbamate

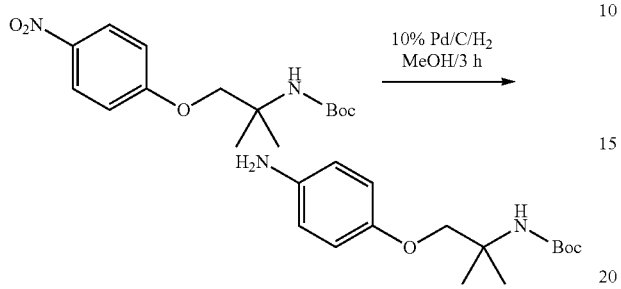

To a solution of tert-butyl (2-methyl-1-(4-nitrophenoxy)propan-2-yl)carbamate (6 g, 19.35 mmol) in methanol (70 mL) was added 10% Pd/C (1.5 g). Reaction mixture was stirred at room temperature under hydrogen atmosphere for 3 h. After completion of reaction, reaction mixture was filtered through celite, filterate was concentrated under reduced pressure to afford the crude product, crude compound was used in next step without further purification (6 g, crude).

Step-4: Synthesis of tert-butyl (1-(4-iodophenoxy)-2-methylpropan-2-yl)carbamate

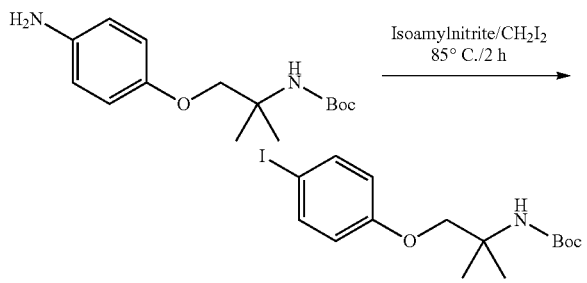

A mixture of tert-butyl (1-(4-aminophenoxy)-2-methylpropan-2-yl)carbamate (4 g, 14.2 mmol), isoamylnitrite (19 mL, 142 mmol) and diiodomethane (11.4 mL, 142 mmol) stirred at 85° C. for 2 h. After completion of reaction, reaction mixture was diluted with ice cold water, extracted with EtOAc. The organic layer was dried over anhydrous sodium sulphate and concentrated under reduced pressure to afford the crude product, crude compound was purified by combi-flash eluting with 5% ethyl acetate in n-hexane to afford title compound in Ex. 98 Step-4 (0.9 g, 37%).

Compound 98: $^1$H NMR (400 MHz, DMSO-$d_6$): δ 13.05 (s, 1H), 8.06 (s, 1H), 7.60 (s, 1H), 7.51 (d, J=8.8 Hz, 1H), 7.20 (d, J=7.2 Hz, 1H), 7.15-7.10 (m, 5H), 6.74 (d, J=8 Hz, 2H), 6.65-6.58 (m, 3H), 6.49 (d, J=15.2 Hz, 1H), 3.60 (s, 2H), 3.28-3.06 (m, 2H), 2.98 (s, 3H), 2.89 (s, 3H), 2.40 (d, J=8 Hz, 2H), 1.04 (s, 6H), 0.87 (t, J=7.2 Hz, 3H). LCMS: 523.4 [M+H]$^+$.

250

Example 99: Synthesis of (E)-4-((2-(4-((E)-1-(1H-indazol-5-yl)-2-phenylbut-1-en-1-yl)phenoxy)-2-methylpropyl)amino)-N,N-dimethylbut-2-enamide (Compound 99)

The compound was synthesized following the approach as outlined in Example 59 by (i) substituting into Step-4 of Ex. 59 5-(but-1-yn-1-yl)-1-(tetrahydro-2H-pyran-2-yl)-1H-indazole (sa prepared in Example 1, Step-3) for compound 276 and tert-butyl (E)-(4-(dimethylamino)-4-oxobut-2-en-1-yl) (2-(4-iodophenoxy)-2-methylpropyl)carbamate (preparation shown below Ex. 99 Step 1-5) for compound 277, and (ii) substituting into Step-5 of Ex. 59 iodobenzene for compound 265 to afford Compound 99 (0.19 g).

Step-1: Synthesis of ethyl 2-(4-iodophenoxy)-2-methylpropanoate

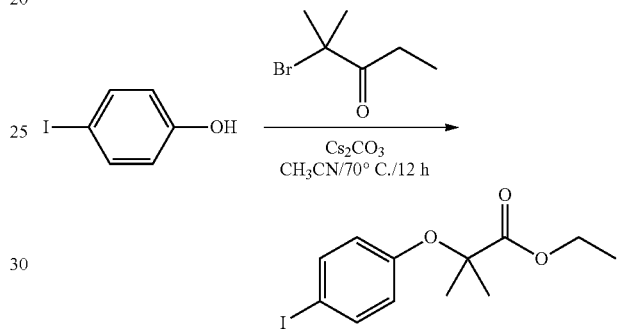

To a stirred solution of 4-iodophenol (10 g, 45.45 mmol) in acetonitrile (100 mL) were added cesium carbonate (29.5 g, 90 mmol) and 2-bromo-2-methylpentan-3-one (8.86 g, 45.45 mmol). The contents were stirred at 70° C. for 12 h. After completion of reaction, reaction mixture was poured onto ice cold water and extracted with ethyl acetate (2×250 mL). The combined organic extracts were washed with water, brine, dried over anhydrous sodium sulphate and concentrated under reduced pressure to obtain desired compound ethyl 2-(4-iodophenoxy)-2-methylpropanoate (15 g).

Step-2: Synthesis of 2-(4-iodophenoxy)-2-methylpropanoic acid

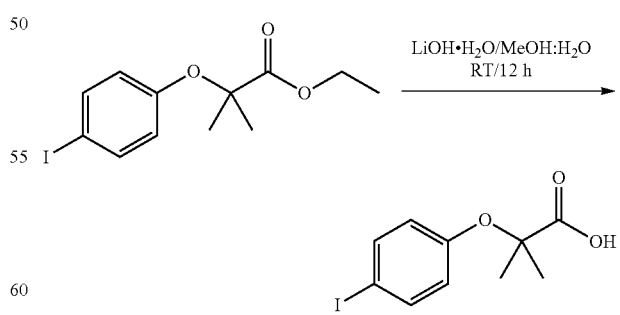

To a stirred solution of ethyl 2-(4-iodophenoxy)-2-methylpropanoate (15 g, 44.91 mmol) in MeOH:H$_2$O (60 mL, 3:1) was added LiOH.H$_2$O (3.77 g, 89.82 mmol). The reaction mixture was stirred for 12 h at room temperature, after completion of reaction (monitored by TLC), reaction mixture was diluted with water and acidified with 2M HCl, extracted with EtOAc (300 mL). The organic layer was washed with water followed by saturated NaCl solution, dried over anhydrous Na$_2$SO$_4$ and concentrated under reduced pressure. The crude product was used in next step without further purification (12 g).

Step-3: Synthesis of 2-(4-iodophenoxy)-2-methylpropanamide

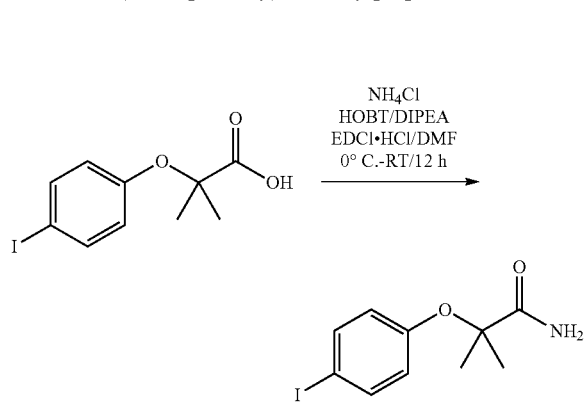

To a stirred solution of 2-(4-iodophenoxy)-2-methylpropanoic acid (13 g, 42.48 mmol) in DMF (25 mL) was added DIPEA (14.6 mL, 84.96 mmol), EDCI.HCl (12.21 g, 63.72 mmol), HOBT (8.6 g, 63.72 mmol) and ammonium chloride (4.58 g, 84.96 mmol). The reaction mixture was stirred for 12 h at room temperature, after completion of reaction (monitored by TLC), reaction mixture was diluted with water and extracted with EtOAc (500 mL). The organic layer was washed with water followed by saturated NaCl solution, dried over anhydrous Na$_2$SO$_4$ and concentrated under reduced pressure to afford crude compound, crude compound was purified by combi-flash using 2% MeOH in dichloromethane to afford the title compound of Ex. 99 Step-3 (12 g, 97%).

Step-4: Synthesis of 2-(4-iodophenoxy)-2-methylpropan-1-amine

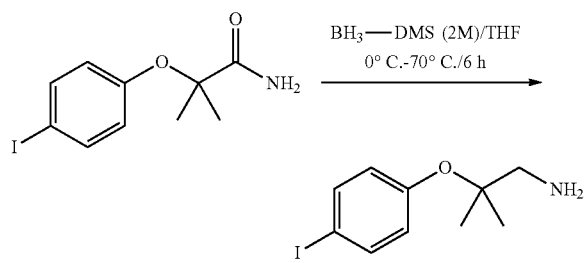

A solution of 2-(4-iodophenoxy)-2-methylpropanamide (11.2 g, 36.72 mmol), in THF (110 mL) was added to a solution of borane-methyl sulphide complex (36.7 mL, 73.44 mmol) was added drop wise and the contents were stirred for 6 h at 70° C. The reaction mixture was quenched with methanol, water was added to the reaction mixture, extracted twice with ethyl acetate. The combined organic layers were washed with water followed by brine solution and dried over anhydrous sodium sulphate. The solvent was removed under reduced pressure to obtain the title compound in Ex. 99 Step-4 (8.5 g, 80%).

Step-5: Synthesis of tert-butyl (E)-(4-(dimethylamino)-4-oxobut-2-en-1-yl) (2-(4-iodophenoxy)-2-methylpropyl)carbamate

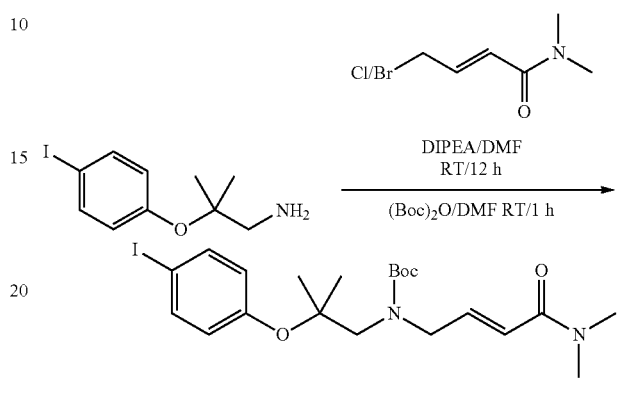

The reaction was carried out according to Scheme 3, Step-3 using 2-(4-iodophenoxy)-2-methylpropan-1-amine (5 g, 17.18 mmol) in DMF (50 mL) and (E)-4-chloro-N,N-dimethylbut-2-enamide and (E)-4-bromo-N,N-dimethylbut-2-enamide mixture (2.39 g, 13.74 mmol, Example 63, Step-7). The crude product was purified by combi-flash eluting with 2% MeOH in dichloromethane to afford the title product of Ex. 99 Step 5 (5 g, 58%).

Compound 99: $^1$H NMR (400 MHz, DMSO-d$_6$): δ 13.06 (s, 1H), 8.07 (s, 1H), 7.63 (s, 1H), 7.52 (d, J=8.8 Hz, 1H), 7.11-7.10 (m, 5H), 7.09 (d, J=2 Hz, 1H), 6.75 (d, J=8.4 Hz, 2H), 6.63-6.60 (m, 2H), 6.51 (t, J=5.4 Hz, 1H), 6.50 (s, 1H), 2.98 (s, 3H), 2.84 (s, 3H), 2.41 (q, J=7.2 Hz, 2H), 1.12 (s, 6H), 0.87 (t, J=7.2 Hz, 3H). LCMS: 523.3 [M+H]$^+$.

Example 100: There is no Example 100

EXAMPLES

Example 101—Compounds that Inhibit ERα$^{T/MUT}$ Activity In Vitro

Cell Culture

MCF7 BUS cells (Coser, et al., (2003) *PNAS* 100(24): 13994-13999) were maintained in Dulbecco's Modified Eagle Medium supplemented with 10% FBS, 4 mM L-glutamine and 1× non-essential amino acids. Lenti-X 293T cells (Clontech, Cat #632180) were routinely cultured in Dulbecco's Modified Eagle Medium supplemented with 10% FBS.

Site-Direct Mutagenesis and Cell Line Engineering

The QuikChange II XL Site-Directed Mutagenesis Kit (Agilent Technologies, Cat #200523) was used to generate Y537S, Y537C, Y537N and D538G mutations within the ERα exon 8. Wild-type ESR1 cDNA (GeneCopoeia Inc., Cat #GC-A0322, accession no. NM 000125) was used as a template with the following mutagenesis primers (where the underlined nucleotides represent site mutations); Y537S: F-AAG AAC GTG GTG CCC CTC TCT GAC CTG CTG CTG GAG ATG (SEQ ID NO: 1), R-CAT CTC CAG CAG CAG GTC AGA GAG GGG CAC CAC GTT CTT (SEQ ID NO: 2); Y537N: F-AAG AAC GTG GTG CCC CTC AAT GAC CTG CTG CTG GAG ATG (SEQ ID NO: 3), R-CAT CTC CAG CAG CAG GTC AT$\underline{T}$ GAG GGG CAC CAC GTT CTT (SEQ ID NO: 4); Y537C: F-AAG AAC GTG GTG CCC CTC T$\underline{G}$T GAC CTG CTG CTG GAG ATG (SEQ ID NO: 5), R-CAT CTC CAG CAG CAG GTC AC$\underline{A}$ GAG GGG CAC CAC GTT CTT (SEQ ID NO: 6); D538G: F-AAC GTG GTG CCC CTC TAT G$\underline{G}$C CTG CTG CTG GAG ATG CTG (SEQ ID NO: 7), R-CAG CAT CTC CAG CAG CAG G$\underline{C}$C ATA GAG GGG CAC CAC GTT (SEQ ID NO: 8). WT and mutant ESR1 cDNAs were cloned into the designation lentiviral vector pLenti6.3/V5-Dest (Invitrogen, Cat #V533-06). To make lentivirus, DNAs (WT and mutant ESR1) were co-transfected with packaging plasmids into Lenti-X 293T cells using TransIT (Mirus, Cat #MIR 2700). 48 h post-transfection, virus containing media was filtered and added to MCF7 cells in the presence of 8 g/ml polybrene overnight. Two days following infection, cells were placed under selection with 10 μg/ml blasticidin for 2 weeks for stable expression.

In Vitro Proliferation Assays

MCF7-WT and -Y537S cells were seeded at 1500 cells/well in black-walled 96-well plates (assay plates, Costar, Cat #3904). In parallel, cells were also seeded in a separate 96-well plate (8 wells/cell line, control plate) for which a CTG (CellTiter-Glo® Luminescent Viability Assay, Promega, Cat #G7572) was measured the following day (day 0 reading). The day 0 reading was used for the $GI_{50}$ calculation at the termination of the experiment. The day following seeding, compounds were added to assay plates. Briefly, a 1:4 serial dilution was prepared in DMSO at 200× final concentration for a total of 10 concentrations (9 dilutions containing compound and one is DMSO only). Serially diluted compounds were pipetted into medium to prepare a compound-medium mix at 10× final concentration. 10 μl of compound-medium mix was added to MCF7-WT and -Y537S cells at 3 wells/concentration (triplicate for each concentration). On day 3, media/compound was removed and replaced with fresh media/compound as described above. On day 6, CTG was measured and compared to day 0 readings from control plate to assess $GI_{50}$.

Results

FIG. 1 shows that ectopic expression of $ER\alpha^{Y537S/N/C, D538G}$ in MCF7 cells conferred phenotypic resistance to currently marketed therapies tamoxifen (SERM), raloxifene (SERM) and fulvestrant (SERD). Similar observations were also recently published by several independent labs (Jeselsohn et al., (2014) *Clin Cancer Res. Apr.* 1; 20(7):1757-67; Toy et al., (2013) *Nat Genet.* 2013 December; 45(12): 1439-45; Robinson et al., (2013) *Nat Genet. December;* 45(12): 1446-51; Merenbakh-Lamin et al., (2013) *Cancer Res. December* 1; 73(23):6856-64; Yu et al., (2014) *Science July* 11; 345(6193):216-20). Having confirmed that $ER\alpha^{MUT}$ drive resistance to current endocrine therapies, identification of novel compounds that would reduce proliferation of the $ER\alpha^{MUT}$-bearing MCF7 cells more efficaciously than the corresponding clinical compound 4-hydroxytamoxifen was sought. Using the WT and mutant viability assay as a screening tool, compounds were identified that were more potent towards the Y537S-bearing MCF7 line relative to 4-hydroxytamoxifen. The results of the viability assay screen are shown in Table 1 above.

In Vivo Xenograft Methods

Methods and Materials

In the following examples (Examples 102-109) and in the figures that are referred to in those examples, references to compound 1, compound 60, and compound 69 refer to a hydrochloride salt of the respectively numbered compounds. These hydrochloride salts were prepared as outlined above in Examples 1A, 60A, and 69A.

MCF7 Xenograft Study

The ESR1 wild-type human ER+ breast cancer cell line MCF7 (ATCC) was cultured in DMEM media supplemented with 10% FBS at 37° C. in a 5% CO2 atmosphere and kept in the exponential growth phase. The cells were collected in trypsin and re-suspended in a 1:1 mixture of matrigel and HBSS at a final concentration of $5\times10^7$ cells/mL. A 0.2 mL aliquot of cells was injected subcutaneously into the $3^{rd}$ mammary fat pad of 6-8 week old female Balb/c nude mice, giving $1\times10^7$ cells/mouse. When the average tumor volume reached approximately 155 mm³, 92 animals were randomized prior to treatment.

Anti-tumor activity in the MCF7 xenograft model was examined using compound 1, compound 60, and compound 69. All of the compounds were dosed orally every day at doses ranging from 1 to 30 mg/kg. Each treatment was started on Day 0 and the administration schedule was continued for 17 days. The administration volume was calculated from the individual mouse body weights prior to dose administration. The body weights were measured daily while the tumor volumes were measured twice a week. Tumor volumes (TV) were calculated based on the formula:

$$TV = length \times width^2 \times 0.5$$

length: largest diameter of tumor (mm)
width: diameter perpendicular to length (mm)

The Tumor Growth Inhibition % (TGI) was calculated according to the following formula:

$$\text{Tumor Growth Inhibition \% } (TGI) = \frac{\text{Average Control TV Day } X - \text{Treatment TV Day } X}{\text{Average Control TV Day } X} \times 100$$

Where Day X is the endpoint measurement.

Y537S Positive PDx Xenograft Study

A Patient-Derived Xenograft (PDX) tumor model representing an ESR1-Y537S mutated human ER+ breast cancer, designated as PDX-Y537S, was propagated subcutaneously in immunocompromised mice. The tumors were excised within 60 days of implantation and processed to mixed tumor fragments. Solid tumor tissues were depleted of necrotic components, cut into 70 mg fragments, mixed with matrigel and subcutaneously implanted into the right flank of 6-12 week old female athymic Nude (Crl:NU(NCr)-Foxn1nu) mice. The precise number of fragments and volume of matrigel was determined on a case by case basis. When the average tumor volume reached approximately 200 mm³, animals were randomized prior to treatment. All of the primary human tumors utilized in this study had undergone approximately 7 passages in vivo.

Anti-tumor activity in the PDX-Y537S model was examined using compound 1, compound 60, and compound 69. Estrogen was not supplemented in the studies. All compounds were dosed orally every day at doses ranging from 3 to 200 mg/kg. Each treatment was started on Day 0 and the administration schedule was continued for up to 35 days. The administration volume was calculated from the individual mouse body weights prior to dose administration. The body weights were measured daily while the tumor volumes were measured twice a week. Tumor volumes were calculated based on the previously described formula.

WHIM20 Xenograft Study

The Patient-Derived Xenograft (PDX) tumor model, WHIM20, representing an ESR1-Y537S mutated human ER+ breast cancer was propagated in mice. The tumors were excised and processed to mixed tumor fragments and the fragments were re-implanted subcutaneously into new recipient mice. For the current work, solid tumor tissues were depleted of necrotic components, cut into fragments, mixed with matrigel and subcutaneously implanted into the right flank of 6-8 week old female SCID-bg mice. The precise number of fragments and volume of matrigel was determined on a case by case basis. When the average tumor volume reached approximately 370 mm$^3$, animals were randomized prior to treatment. All of the primary human tumors utilized in this study had undergone approximately 4 passages in vivo.

Anti-tumor activity in the WHIM20 patient derived xenograft model was examined using compound 1 and compound 60 in separate studies. Estrogen was not supplemented in WHIM20 studies. Compounds 1 and 60 were dosed orally every day at the indicated doses. Each treatment was started on Day 0 and the administration schedule was continued for the indicated days. The administration volume was calculated from the individual mouse body weights prior to dose administration. The body weights were measured daily while the tumor volumes were measured twice a week. Tumor volumes were calculated based on the previously described formula.

Statistical Analysis

Data are expressed as the mean±SEM for tumor volume and the mean±SEM for body weight.

The differences in tumor volume during the study period between the vehicle treated and compound treated groups were analyzed by two-way analysis of variance (ANOVA) followed by the Dunnett multiple comparison post hoc test. Statistical analyses were performed using the GraphPad Prism® version 5.04 (GraphPad Software, La Jolla, Calif.).

Example 102

Figure 2:
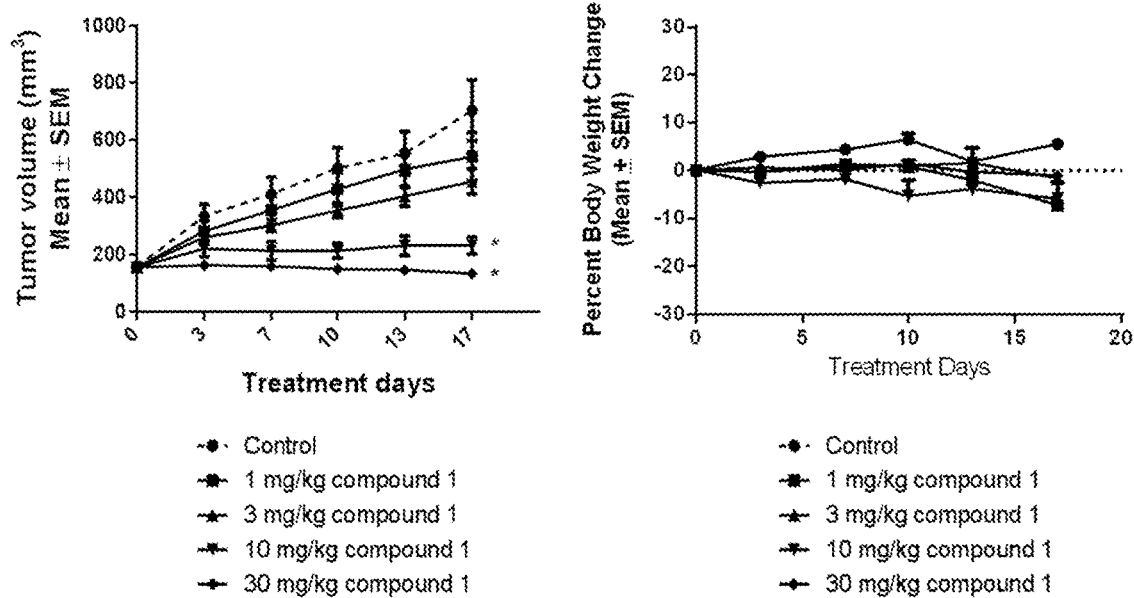
FIG. 2 shows antitumor and body weight effects of oral Compound 1 in MCF7 xenograft bearing female balb/c nude mice.

FIG. 2 shows the anti-tumor and body weight effects of compound 1 in the MCF7 xenograft model carrying the wild-type ER grown in immunocompromised mice. Compound 1 inhibited xenograft growth in a dose dependent manner with 10 mg/kg QD and 30 mg/kg QD significantly inhibiting growth on day 17 compared to the control (TGI of 68% and 83% and p<0.0001 for both doses, respectively). Compound 1 treatment of 1 mg/kg QD and 3 mg/kg QD was not statistically different from the control treated group (TGI of 19% and 41%, respectively). All doses and regimens were well tolerated with no significant body weight loss.

Compound 1 was given orally once daily for the duration of the study. Data in FIG. 2 represent the mean±SEM (Tumor Volume), or the mean±SEM (Body Weight) (N=6 for treatment groups, N=8 for Vehicle control). * p<0.0001 versus vehicle control on Day 17 (Two-Way ANOVA followed by the Dunnett multiple comparison test).

Example 103

Figure 3:
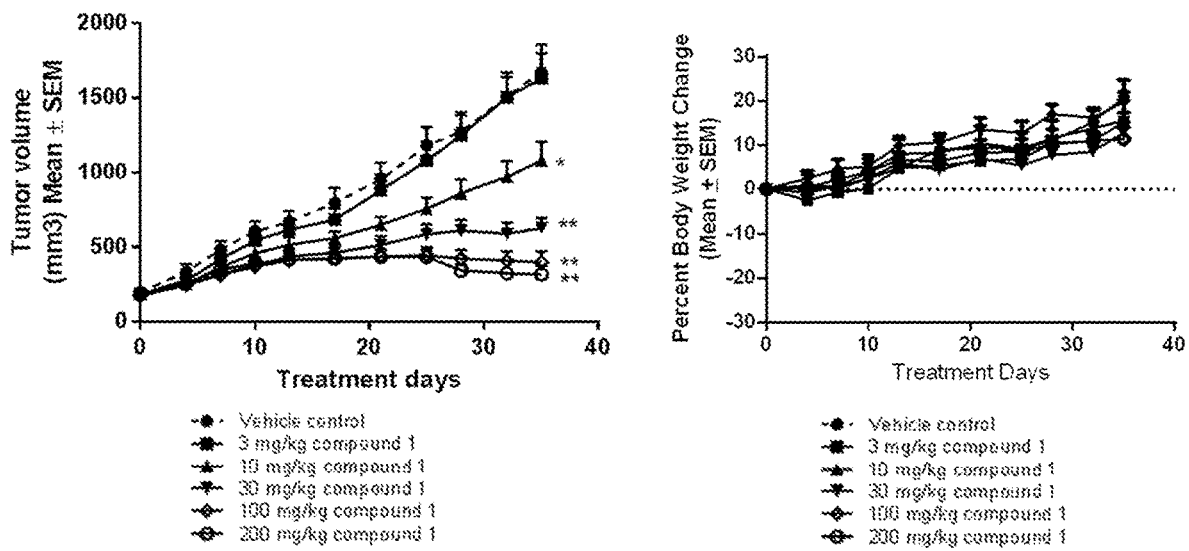
FIG. 3 shows antitumor and body weight effects of oral Compound 1 in PDX-Y537S xenograft bearing athymic nude (Crl:NU(NCr)-Foxn1nu) female mice.

FIG. 3 shows the anti-tumor and body weight effects of compound 1 in the PDX-Y537S model bearing a heterozygous Y537S mutation. Compound 1 dosed daily inhibited xenograft growth in a dose dependent manner with 10 mg/kg, 30 mg/kg, 100 mg/kg and 200 mg/kg treatments significantly inhibiting growth on day 35 (TGI of 35%, 63%, 76% and 81% and p<0.01, p<0.0001, p<0.0001 and p<0.0001, respectively). Compound 1 treated daily at 3 mg/kg was not statistically different from the Vehicle treated group (TGI of 3%). All doses and regimens were well tolerated with no significant body weight loss.

Compound 1 was given orally once daily for the duration of the study. Data represent the mean±SEM (Tumor Volume) or mean±SEM (Body Weight) (N=8 for all groups). *p<0.01, **p<0.0001 versus vehicle control on Day 35 (Two-Way ANOVA followed by the Dunnett multiple comparison post hoc test).

Example 104

Figure 4:
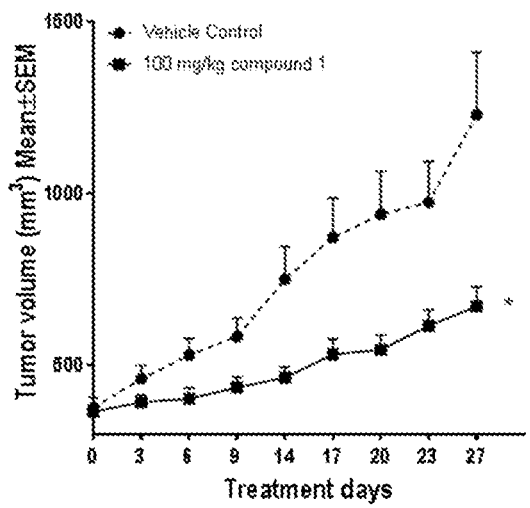
FIG. 4 shows antitumor and body weight effects of oral Compound 1 in WHUM20 xenograft bearing SCID-bg female mice.
Figure 4:
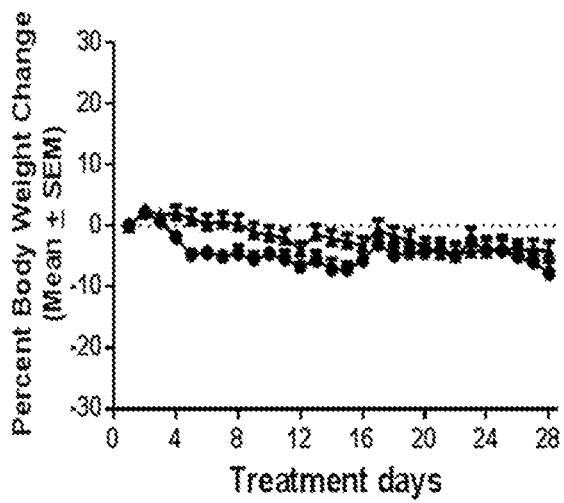

FIG. 4 shows the anti-tumor and body weight effects of compound 1 in the ER+ WHIM20 PDX model bearing a homozygous Y537S mutation. Daily treatment with compound 1 at 100 mg/kg significantly reduced tumor growth relative to the vehicle control (TGI of 45%; p<0.05). This dose of compound 1 was tolerated in accordance with internal animal care and use committee guidelines.

Compound 1 was given orally once daily for the duration of the study. Data represent the mean±SEM (Tumor Volume) or mean±SEM (Body Weight) (N=9 for all groups). *p<0.05 versus vehicle control on Day 27 (Two-Way ANOVA followed by the Dunnett multiple comparison post hoc test).

Example 105

Figure 5:
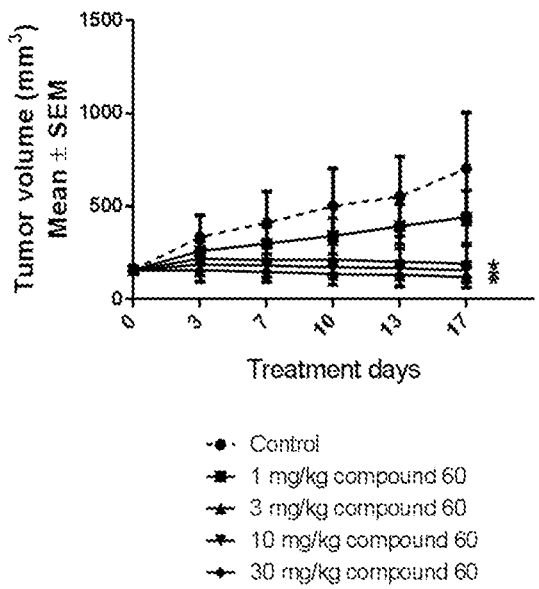
FIG. 5 shows antitumor and body weight effects of oral Compound 60 in MCF7 xenograft bearing female Balb/c nude mice.
Figure 5:
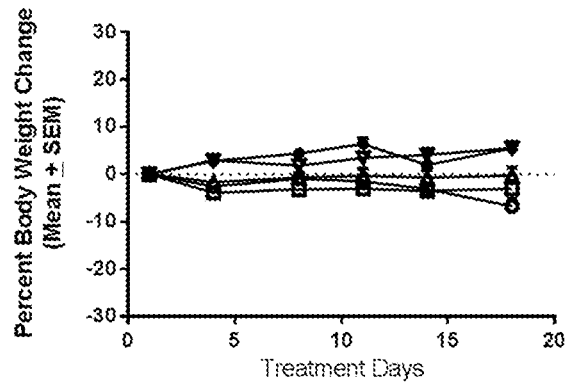

FIG. 5 shows the antitumor and body weight effects of compound 60 in the MCF7 subcutaneous xenograft model carrying wild-type ER grown in immunocompromised mice. Compound 60 inhibited xenograft growth in a dose dependent manner with 3 mg/kg QD, 10 mg/kg QD and 30 mg/kg QD treatments inhibiting growth on day 17 (TGI of 75%, 80% and 85% and p<0.0001 for all doses, respectively). Compound 60 treatment of 1 mg/kg QD×18 did not show a statistically meaningful difference from the control treated group (TGI of 36%, p>0.05). All doses and regimens were well tolerated with no significant body weight loss or clinical signs.

Compound 60 was given orally once daily for the duration of the study. Data represent the mean±SEM (Tumor Volume) or mean±SEM (Body Weight) (N=6 for treatment groups, N=8 for Vehicle control). * p<0.0001 versus vehicle control on Day 17 (Two-Way ANOVA followed by the Dunnett multiple comparison test).

Example 106

Figure 6:
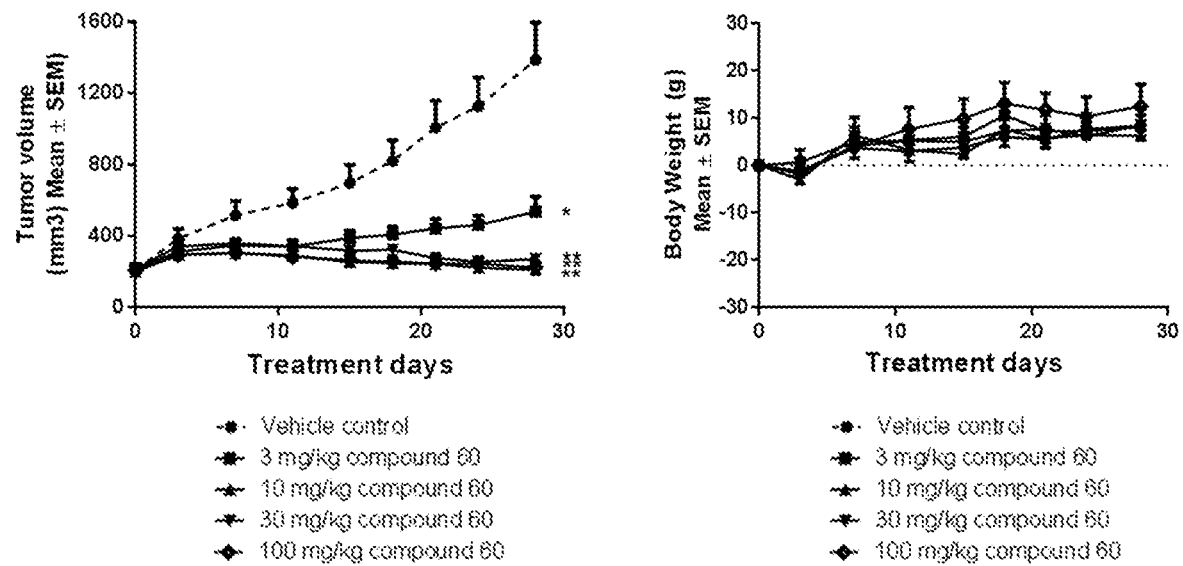
FIG. 6 shows antitumor and body weight effects of oral Compound 60 in PDX-Y537S xenograft bearing athymic nude (Crl:NU(NCr)-Foxn1nu) female mice.

FIG. 6 shows the antitumor and body weight effects of compound 60 in a repeat study in the ER+ PDX-Y537S model bearing a heterozygous Y537S mutation. Compound 60 inhibited xenograft growth in a dose dependent manner with 3 mg/kg QD, 10 mg/kg QD, 30 mg/kg QD and 100 mg/kg QD treatments significantly inhibiting growth on day 28 (TGI of 61%, 85%, 81% and 84% and p<0.001, p<0.0001, p<0.0001 and p<0.0001, respectively). All doses were well tolerated with no significant body weight loss or clinical signs.

Compound 60 was given orally once daily for the duration of the study. Data represent the mean±SEM (Tumor Volume) or mean±SEM (Body Weight) (N=6 for compound 60 and N=8 for vehicle). * p<0.001, ** p<0.0001 versus vehicle control on Day 28 (Two-Way ANOVA followed by the Dunnett multiple comparison test).

Example 107

Figure 7:
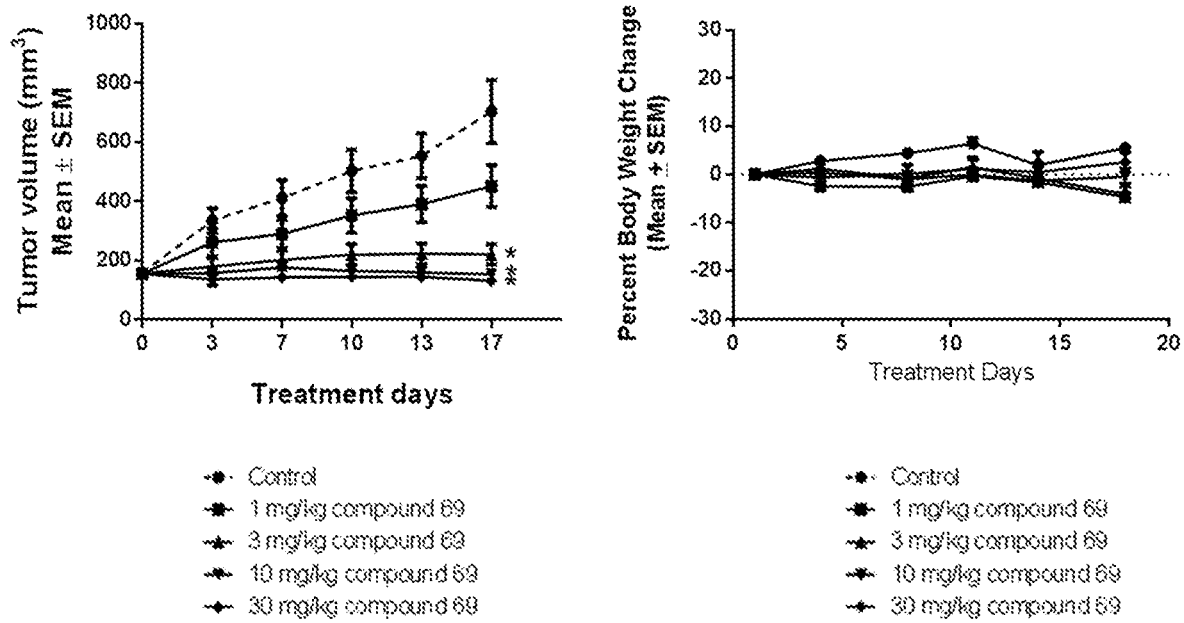
FIG. 7 shows antitumor and body weight effects of oral Compound 69 in MCF7 xenograft bearing female Balb/c nude mice.

FIG. 7 shows the antitumor and body weight effects of compound 69 in the MCF7 subcutaneous xenograft model carrying wild-type ER grown in immunocompromised mice. Compound 69 inhibited xenograft growth in a dose dependent manner with 3 mg/kg QD, 10 mg/kg QD and 30 mg/kg QD treatments inhibiting growth on day 17 (TGI of 72%, 80% and 83% and p<0.0001 for all doses, respectively). Compound 69 treatment of 1 mg/kg QD did not show statistically meaningful difference from the control treated group (TGI of 42%). All doses were well tolerated with no significant body weight loss or clinical signs.

Compound 69 was given orally once daily for the duration of the study. Data represent the mean±SEM (Tumor Volume) or mean±SEM (Body Weight) (N=6 for treatment groups, N=8 for Vehicle control). * p<0.0001 versus vehicle control on Day 17 (Two-Way ANOVA followed by the Dunnett multiple comparison test).

Example 108

Figure 8:
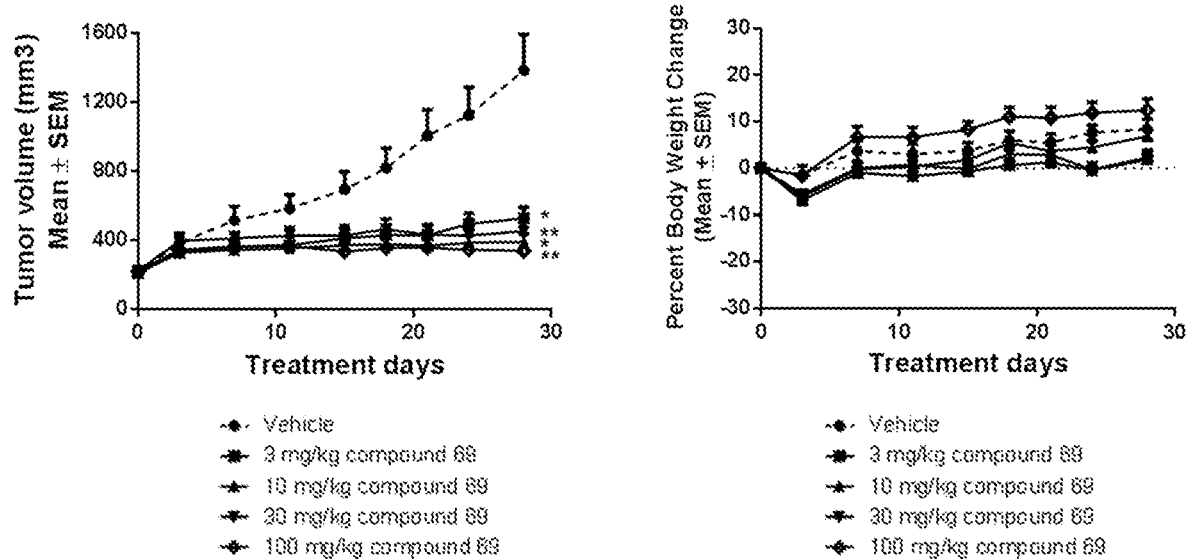
FIG. 8 shows antitumor and body weight effects of oral Compound 69 in PDX-Y537S xenograft bearing athymic nude (Crl:NU(NCr)-Foxn1nu) female mice.

FIG. 8 shows the antitumor and body weight effects of compound 69 in the ER+ PDX-Y537S model bearing a heterozygous Y537S mutation. Compound 69 showed significant efficacy with 3 mg/kg QD, 10 mg/kg QD, 30 mg/kg QD and 100 mg/kg QD treatments inhibiting growth on day 28 relative to vehicle treatment group (TGI of 62%, 72%, 67% and 76% and p<0.001, p<0.0001, p<0.001 and p<0.0001, respectively). All doses were well tolerated with no significant body weight loss or clinical signs.

Compound 69 was given orally once daily for the duration of the study. Data represent the mean±SEM (Tumor Volume) or mean±SEM (Body Weight) (N=8). * p<0.001, ** p<0.0001 versus vehicle control on Day 28 (Two-Way ANOVA followed by the Dunnett multiple comparison test).

Example 109

Figure 9:
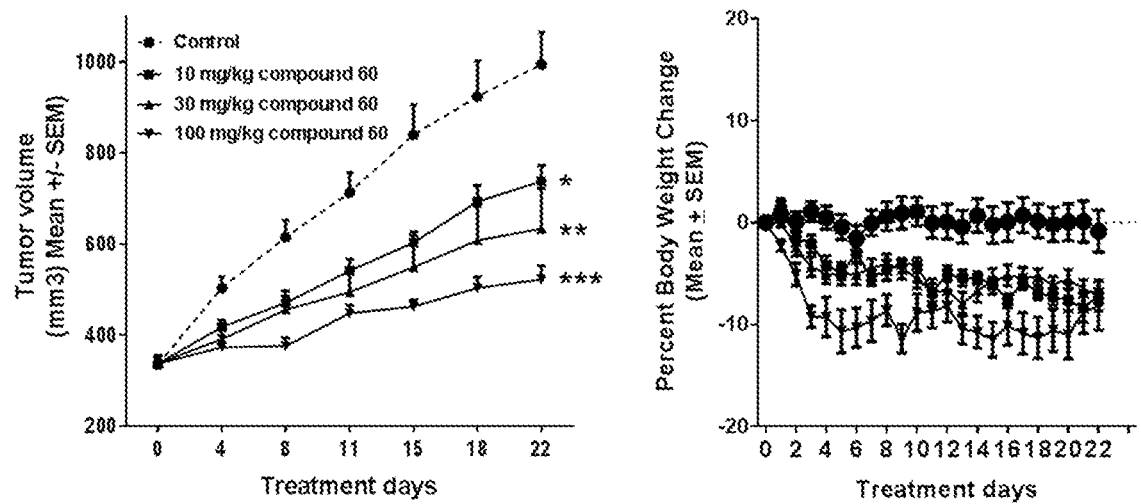
FIG. 9 shows the anti-tumor and body weight effects of Compound 60 in the ER+ WHIM20 PDX model bearing a homozygous Y537S mutation.

FIG. 9 shows the anti-tumor and body weight effects of compound 60 in the ER+ WHIM20 PDX model bearing a homozygous Y537S mutation. Compound 60 inhibited xenograft growth in a dose dependent manner with 10 mg/kg QD, 30 mg/kg QD and 100 mg/kg QD treatments significantly inhibiting growth on day 22 (TGI of 26%, 36%, and 48% and p<0.05, p<0.01 and p<0.0001, respectively). This dose of compound 60 was tolerated in accordance with internal animal care and use committee guidelines.

Compound 60 was given orally once daily for the duration of the study. Data represent the mean±SEM (Tumor Volume) or mean±SEM (Body Weight) (N=8 for all groups). *p<0.05, p<0.01 and *p<0.0001 respectively versus vehicle control on Day 22 (Two-Way ANOVA followed by the Dunnett multiple comparison test).

It will now be apparent that new, improved, and nonobvious compositions have been described in this specification with sufficient particularity as to be understood by one of ordinary skill in the art. Moreover, it will be apparent to those skilled in the art that modifications, variations, substitutions, and equivalents exist for features of the compositions which do not materially depart from the spirit and scope of the embodiments disclosed herein. Accordingly, it is expressly intended that all such modifications, variations, substitutions, and equivalents which fall within the spirit and scope of the invention as defined by the appended claims shall be embraced by the appended claims.

What is claimed is:

1. A compound or pharmaceutically acceptable salt thereof, given by formula I:

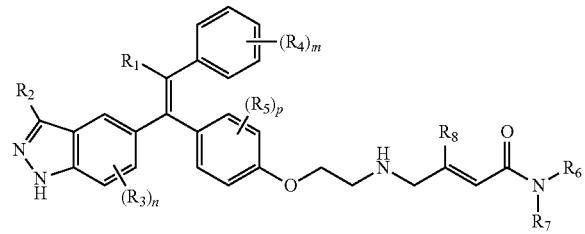

wherein:
$R_1$ is selected from the group consisting of cyclobutyl and —$CH_2CF_3$;
$R_2$ is selected from the group consisting of H and F;
n is 0-1;
$R_3$ is F when n=1;
m is 0-2;
$R_4$ are the same or different and are independently selected from the group consisting of F, $CF_3$, Cl, isopropyl, —$OCH_3$, —$OCHF_2$, —$OCF_3$, ethyl and methyl;
p is 0-1;
$R_5$ is F when p=1;
$R_6$ and $R_7$ are the same or different and are independently selected from the group consisting of methyl, ethyl, propyl, —$CH_2CH_2OH$ and

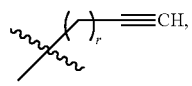

wherein r is 1 or 2;
or, wherein $R_6$ and $R_7$ form a 4-6 membered heterocyclic ring with the N to which they are attached, wherein said heterocyclic ring optionally includes an oxygen atom, and wherein said heterocyclic ring is optionally substituted with F, or —$CH_2F$;
$R_8$ is selected from the group consisting of H and $CH_3$;
or a pharmaceutically acceptable salt thereof.

2. A compound selected from the group consisting of (E)-4-((2-(4-((E)-1-(1H-indazol-5-yl)-2-phenylbut-1-en-1-yl)phenoxy) ethyl) amino)-N,N-dimethylbut-2-enamide; (E)-4-((2-(4-((E)-1-(3-fluoro-1H-indazol-5-yl)-2-phenyl but-1-en-1-yl) phenoxy)ethyl)amino)-N,N-dimethylbut-2-enamide; (E)-4-((2-(4-((E)-1-(3-fluoro-1H-indazol-5-yl)-2-(3-fluoro-5-(trifluoromethyl) phenyl)but-1-en-1-yl)phenoxy)ethyl)amino)-N,N-dimethylbut-2-enamide; (E)-4-((2-(4-((E)-1-(4-fluoro-1H-indazol-5-yl)-2-phenyl but-1-en-1-yl) phenoxy) ethyl)amino)-N,N-dimethylbut-2-enamide; (E)-4-((2-(4-((E)-2-(3,5-difluorophenyl)-1-(1H-indazol-5-yl)but-1-en-1-yl) phenoxy)ethyl)amino)-N,N-dimethylbut-2-enamide; (E)-4-((2-(4-((E)-2-(3,4-difluorophenyl)-1-(1H-indazol-5-yl)but-1-en-1-yl) phenoxy)ethyl)amino)-N,N-dimethylbut-2-enamide; (E)-4-((2-(4-((E)-2-(3-chloro-5-fluorophenyl)-1-(1H-indazol-5-yl)but-1-en-1-yl) phenoxy) ethyl)amino)-N,N-dimethylbut-2-enamide; (E)-4-((2-(4-((E)-1-(1H-indazol-5-yl)-2-phenylbut-1-en-1-yl)phenoxy) ethyl) amino)-N-methyl-N-(prop-2-yn-1-yl)but-2-enamide; (E)-4-((2-(4-((E)-1-(1H-indazol-5-yl)-2-phenylbut-1-en-1-yl)phenoxy)ethyl) amino)-N-(but-3-yn-1-yl)-N-methylbut-2-enamide; (E)-4-((2-(4-((E)-1-(1H-indazol-5-yl)-2-phenylbut-1-en-1-yl)phenoxy)ethyl) amino)-1-(azetidin-1-yl)but-2-en-1-one; (E)-4-((2-(4-((E)-1-(1H-indazol-5-yl)-2-phenylbut-1-en-1-yl)phenoxy)ethyl) amino)-1-(pyrrolidin-1-yl)but-2-en-1-one; (E)-4-((2-(4-((E)-1-(1H-indazol-5-yl)-2-phenylbut-1-en-1-yl)phenoxy)ethyl) amino)-1-(piperidin-1-yl)but-2-en-1-one; (E)-4-((2-(4-((E)-2-cyclobutyl-1-(1H-indazol-5-yl)-2-phenylvinyl)phenoxy) ethyl)amino)-N,N-dimethylbut-2-enamide; (E)-4-((2-(4-((E)-2-cyclobutyl-1-(3-fluoro-1H-indazol-5-yl)-2-phenylvinyl) phenoxy)ethyl) amino)-N,N-dimethylbut-2-enamide 2,2,2-trifluoro acetate; (E)-4-((2-(4-((E)-1-(1H-indazol-5-yl)-2-phenylbut-1-en-1-yl)phenoxy)ethyl) amino)-1-morpholinobut-2-en-1-one; (E)-4-((2-(4-((E)-1-(1H-indazol-5-yl)-2-phenylbut-1-en-1-yl)phenoxy)ethyl) amino)-N-ethyl-N-methylbut-2-enamide; (E)-4-((2-(4-((E)-1-(1H-indazol-5-yl)-2-phenylbut-1-en-1-yl)phenoxy)ethyl) amino)-N-methyl-N-propylbut-2-enamide; (E)-4-((2-(4-((E)-1-(1H-indazol-5-yl)-2-phenylbut-1-en-1-yl)phenoxy)ethyl)amino)-N-(2-hydroxyethyl)-N-methylbut-2-enamide; (E)-4-((2-(4-((E)-2-(2-chloro-4-fluorophenyl)-1-(3-fluoro-1H-indazol-5-yl)but-1-en-1-yl) phenoxy)ethyl)amino)-N,N-dimethylbut-2-enamide; (E)-4-((2-(4-((E)-1-(1H-indazol-5-yl)-2-phenylbut-1-en-1-yl) phenoxy)ethyl) amino)-N,N,3-trimethylbut-2-enamide; (Z)-4-((2-(4-((E)-1-(1H-indazol-5-yl)-2-phenylbut-1-en-1-yl) phenoxy)ethyl) amino)-N,N-dimethylbut-2-enamide; (E)-4-((2-(4-((E)-2-cyclobutyl-1-(1H-indazol-5-yl)-2-phenylvinyl)phenoxy)ethyl)amino)-1-morpholinobut-2-en-1-one; (E)-4-((2-(4-((E)-2-cyclobutyl-1-(4-fluoro-1H-indazol-5-yl)-2-phenylvinyl) phenoxy)ethyl)amino)-N,N-dimethylbut-2-enamide; (E)-4-((2-((5-((Z)-1-(1H-indazol-5-yl)-2-phenylbut-1-en-1-yl)pyridin-2-yl) oxy)ethyl) amino)-N,N-dimethylbut-2-enamide; (E)-4-((2-(4-((E)-1-(1H-indazol-5-yl)-2-(o-tolyl)but-1-en-1-yl)phenoxy) ethyl) amino)-N-(2-hydroxyethyl)-N-methylbut-2-enamide; (E)-4-((2-(4-((E)-2-(2-chloro-4-fluorophenyl)-1-(3-fluoro-1H-indazol-5-yl)but-1-en-1-yl)phenoxy)ethyl)amino)-N-(2-hydroxyethyl)-N-methylbut-2-enamide; (E)-4-((2-(4-((E)-1-(1H-indazol-5-yl)-2-(4-isopropyl phenyl)but-1-en-1-yl) phenoxy)ethyl)amino)-N,N-dimethylbut-2-enamide; (E)-4-((2-(4-((E)-4-chloro-1-(1H-indazol-5-yl)-2-phenyl but-1-en-1-yl)phenoxy) ethyl)amino)-N,N-dimethylbut-2-enamide; (E)-4-((2-(4-((E)-1-(1H-indazol-5-yl)-2-(4-isopropyl phenyl)but-1-en-1-yl) phenoxy)ethyl)amino)-N,N-dimethylbut-2-enamide; (E)-4-((2-(4-((E)-2-(2-(difluoromethoxy) phenyl)-1-(1H-indazol-5-yl)but-1-en-1-yl)phenoxy)ethyl) amino)-N,N-dimethylbut-2-enamide; (E)-4-((2-(4-((E)-1-(1H-indazol-5-yl)-2-(2-(trifluoro-methoxy)phenyl)but-1-en-1-yl)phenoxy)ethyl)amino)-N,N-dimethylbut-2-enamide; (E)-4-((2-(4-((E)-1-(1H-indazol-5-yl)-2-(2-isopropyl phenyl)but-1-en-1-yl) phenoxy)ethyl)amino)-N,N-dimethylbut-2-enamide; (E)-4-((2-(4-((E)-2-(2-ethylphenyl)-1-(1H-indazol-5-yl) but-1-en-1-yl)phenoxy) ethyl)amino)-N,N-dimethylbut-2-enamide; (E)-4-((2-(4-((E)-1-(1H-indazol-5-yl)-2-(o-tolyl)but-1-en-1-yl)phenoxy) ethyl) amino)-N,N-dimethylbut-2-enamide; (E)-4-((24(5-((Z)-1-(1H-indazol-5-yl)-2-phenylbut-1-en-1-yl)pyrimidin-2-yl) oxy)ethyl)amino)-N,N-dimethylbut-2-enamide; (E)-1-(azetidin-1-yl)-4(2-(4-((E)-2-cyclobutyl-1-(1H-indazol-5-yl)-2-phenylvinyl) phenoxy)ethyl)amino)but-2-en-1-one; (E)-1-(azetidin-1-yl)-4-((2-(4-((E)-2-cyclobutyl-1-(3-fluoro-1H-indazol-5-yl)-2-phenylvinyl)phenoxy)ethyl) amino)but-2-en-1-one; (E)-4-((2-(4-((E)-2-cyclobutyl-1-(1H-indazol-5-yl)-2-phenylvinyl) phenoxy) ethyl)amino)-N-(2-hydroxyethyl)-N-methylbut-2-enamide; (E)-1-

(azetidin-1-yl)-4-((2-(4-((E)-2-cyclobutyl-1-(1H-indazol-5-yl)-2-(o-tolyl) vinyl)phenoxy)ethyl)amino)but-2-en-1-one; (E)-4-((2-(4-((E)-1-(3-fluoro-1H-indazol-5-yl)-2-(2-fluorophenyl)but-1-en-1-yl)phenoxy)ethyl)amino)-N,N-dimethylbut-2-enamide; (E)-4-((2-(4-((E)-1-(3-fluoro-1H-indazol-5-yl)-2-(3-fluoro phenyl)but-1-en-1-yl) phenoxy)ethyl) amino)-N,N-dimethylbut-2-enamide; (E)-4-((2-(4-((E)-1-(3-fluoro-1H-indazol-5-yl)-2-(3-fluorophenyl)but-1-en-1-yl) phenoxy)ethyl)amino)-N,N-dimethylbut-2-enamide; (E)-4-((2-(4-((E)-2-(2-chloro-4-fluorophenyl)-2-cyclobutyl-1-(3-fluoro-1H-indazol-5-yl)vinyl)phenoxy)ethyl)amino)-N,N-dimethylbut-2-enamide; (E)-4-((2-(2-fluoro-4-((Z)-1-(3-fluoro-1H-indazol-5-yl)-2-phenylbut-1-en-1-yl) phenoxy)ethyl)amino)-N,N-dimethylbut-2-enamide; (E)-4-((2-(4-((E)-2-(2,6-difluorophenyl)-1-(3-fluoro-1H-indazol-5-yl)but-1-en-1-yl)phenoxy)ethyl)amino)-N,N-dimethylbut-2-enamide; (E)-4-((2-(4-((E)-1-(3-fluoro-1H-indazol-5-yl)-2-(pyridin-3-yl)but-1-en-1-yl)phenoxy)ethyl) amino)-N,N-dimethylbut-2-enamide; (E)-4-((2-(4-((E)-1-(3-fluoro-1H-indazol-5-yl)-2-(pyridin-4-yl)but-1-en-1-yl) phenoxy)ethyl)amino)-N, N-dimethylbut-2-enamide; (E)-4-((2-(4-((E)-1-(1H-indazol-5-yl)-2-phenylprop-1-en-1-yl) phenoxy)ethyl)amino)-N,N-dimethylbut-2-enamide; (E)-4-((2-(4-((E)-2-cyclopropyl-1-(1H-indazol-5-yl)-2-phenylvinyl)phenoxy)ethyl)amino)-N,N-dimethylbut-2-enamide; (E)-4-((2-(4-((E)-2-(2-chloro-4-fluorophenyl)-1-(4-fluoro-1H-indazol-5-yl)but-1-en-1-yl)phenoxy)ethyl) amino)-N,N-dimethylbut-2-enamide; (E)-4-((2-((5-((Z)-2-(2-chloro-4-fluorophenyl)-1-(3-fluoro-1H-indazol-5-yl)but-1-en-1-yl)pyridin-2-yl)oxy)ethyl)amino)-N,N-dimethylbut-2-enamide; (E)-4-((2-((5-((Z)-2-(2-chloro-4-fluorophenyl)-4,4,4-trifluoro-1-(3-fluoro-1H-indazol-5-yl)but-1-en-1-yl) pyridin-2-yl)oxy)ethyl)amino)-N,N-dimethylbut-2-enamide; (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide; (E)-N,N-dimethyl-4-((2-(4-((E)-4,4,4-trifluoro-1-(3-fluoro-1H-indazol-5-yl)-2-(3-fluoropyridin-4-yl)but-1-en-1-yl)phenoxy)ethyl)amino) but-2-enamide; (E)-N,N-dimethyl-4-((2-((5-((Z)-4,4,4-trifluoro-1-(3-fluoro-1H-indazol-5-yl)-2-(3-fluoropyridin-4-yl)but-1-en-1-yl)pyridin-2-yl)oxy)ethyl)amino)but-2-enamide; (E)-N,N-dimethyl-4-((2-(4-((E)-2-phenyl-1-(1H-pyrazolo[4,3-b]pyridin-5-yl)but-1-en-1-yl)phenoxy)ethyl) amino)but-2-enamide; (E)-4-((2-(3-fluoro-4-((Z)-1-(3-fluoro-1H-indazol-5-yl)-2-phenylbut-1-en-1-yl)phenoxy) ethyl)amino)-N,N-dimethylbut-2-enamide; (E)-4-((2-(4-((E)-2-(2,4-difluorophenyl)-1-(3-fluoro-1H-indazol-5-yl) but-1-en-1-yl)phenoxy)ethyl)amino)-N,N-dimethylbut-2-enamide; (E)-4-((2-(4-((E)-1-(3,6-difluoro-1H-indazol-5-yl)-2-phenylbut-1-en-1-yl)phenoxy)ethyl)amino)-N,N-dimethylbut-2-enamide; (E)-4-((2-(4-((E)-1-(3-fluoro-1H-indazol-5-yl)-2-(pyridin-2-yl)but-1-en-1-yl)phenoxy)ethyl) amino)-N,N-dimethylbut-2-enamide; (E)-4-((2-((5-((Z)-1-(3-fluoro-1H-indazol-5-yl)-2-phenylbut-1-en-1-yl)pyridin-2-yl)oxy)ethyl)amino)-N,N-dimethylbut-2-enamide; (E)-N, N-dimethyl-4-((2-(4-((E)-4,4,4-trifluoro-1-(3-fluoro-1H-indazol-5-yl)-2-phenylbut-1-en-1-yl)phenoxy)ethyl)amino) but-2-enamide; (E)-4-((2-((5-((Z)-2-cyclobutyl-1-(3-fluoro-1H-indazol-5-yl)-2-phenylvinyl)pyridin-2-yl)oxy)ethyl) amino)-N,N-dimethylbut-2-enamide; (E)-4-((2-(4-((E)-2-(2-chlorophenyl)-1-(3-fluoro-1H-indazol-5-yl)but-1-en-1-yl)phenoxy)ethyl)amino)-N,N-dimethylbut-2-enamide; (E)-4-((2-(4-((E)-2-(2-chloro-4-fluorophenyl)-1-(1H-indazol-5-yl)but-1-en-1-yl)phenoxy)ethyl)amino)-N,N-dimethylbut-2-enamide; (E)-4-((2-(4-((E)-1-(3-fluoro-1H-indazol-5-yl)-2-(pyridin-4-yl)but-1-en-1-yl)phenoxy)ethyl)amino)-N-(2-hydroxyethyl)-N-methylbut-2-enamide; (E)-4-((2-(4-((E)-1-(7-fluoro-1H-indazol-5-yl)-2-phenylbut-1-en-1-yl)phenoxy)ethyl)amino)-N,N-dimethylbut-2-enamide; (E)-4-((2-(4-((E)-1-(3-fluoro-1H-indazol-5-yl)-2-phenylpent-1-en-1-yl)phenoxy)ethyl)amino)-N,N-dimethylbut-2-enamide; (E)-4-((2-(4-((E)-1-(3,7-difluoro-1H-indazol-5-yl)-2-phenylbut-1-en-1-yl)phenoxy)ethyl)amino)-N,N-dimethylbut-2-enamide; (E)-4-((2-(4-((E)-2-(2,5-difluorophenyl)-1-(3-fluoro-1H-indazol-5-yl)but-1-en-1-yl) phenoxy)ethyl)amino)-N,N-dimethylbut-2-enamide; (E)-4-((2-(4-((E)-1-(3-fluoro-1H-indazol-5-yl)-2-(3-fluoropyridin-4-yl)but-1-en-1-yl)phenoxy)ethyl)amino)-N,N-dimethylbut-2-enamide; (E)-4-((2-(4-((E)-1-(3-fluoro-1H-indazol-5-yl)-3-methyl-2-phenylbut-1-en-1-yl) phenoxy)ethyl)amino)-N,N-dimethylbut-2-enamide; (E)-5-((2-(4-((E)-4-fluoro-1-(3-fluoro-1H-indazol-5-yl)-2-phenylbut-1-en-1-yl)phenoxy)ethyl)amino)-N,N-dimethylpent-2-enamide; (E)-5-((2-(4-((E)-2-(2-chloro-4-fluorophenyl)-1-(3-fluoro-1H-indazol-5-yl)but-1-en-1-yl) phenoxy)ethyl)amino)-N,N-dimethylpent-2-enamide; (E)-4-((2-(4-((E)-2-(2-chl oro-4-fluorophenyl)-1-(3-fluoro-1H-indazol-5-yl)but-1-en-1-yl)phenoxy)ethyl)amino)-N,N,2-trimethylbut-2-enamide; (E)-4-((2-(4-((E)-2-(2-chloro-4-fluorophenyl)-4,4,4-trifluoro-1-(3-fluoro-1H-indazol-5-yl) but-1-en-1-yl)phenoxy)ethyl)amino)-N,N-dimethylbut-2-enamide; (E)-4-((2-(4-((E)-1-(1H-indazol-5-yl)-2-(phenyl-d5)but-1-en-1-yl)phenoxy)ethyl)amino)-N,N-dimethylbut-2-enamide; (E)-4-((2-(4-((E)-1-(1H-indazol-5-yl)-2-phenylbut-1-en-1-yl)phenoxy)ethyl)amino)-N,N-dimethylpent-2-enamide; (E)-4-((2-(4-((E)-1-(1H-indazol-5-yl)-2-phenylbut-1-en-1-yl)phenoxy)propyl)amino)-N,N-dimethylbut-2-enamide; (E)-4-((1-(4-((E)-1-(1H-indazol-5-yl)-2-phenylbut-1-en-1-yl)phenoxy)propan-2-yl)amino)-N,N-dimethylbut-2-enamide; (E)-4-((2-((6-((Z)-1-(3-fluoro-1H-indazol-5-yl)-2-phenylbut-1-en-1-yl)pyridin-3-yl)oxy) ethyl)amino)-N,N-dimethylbut-2-enamide; (E)-4-((3-(4-((E)-1-(1H-indazol-5-yl)-2-phenylbut-1-en-1-yl)phenoxy) propyl)amino)-N,N-dimethylbut-2-enamide; (E)-4-((3-(4-((E)-1-(1H-indazol-5-yl)-2-phenylbut-1-en-1-yl)phenoxy) butan-2-yl)amino)-N,N-dimethylbut-2-enamide; (E)-4-((1-(4-((E)-1-(1H-indazol-5-yl)-2-phenylbut-1-en-1-yl) phenoxy)-2-methylpropan-2-yl)amino)-N,N-dimethylbut-2-enamide; (E)-4-((2-(4-((E)-1-(1H-indazol-5-yl)-2-phenylbut-1-en-1-yl)phenoxy)-2-methylpropyl)amino)-N,N-dimethylbut-2-enamide; and (E)-4-((2-(4-((E)-2-cyclobutyl-1-(3-fluoro-1H-indazol-5-yl)-2-phenylvinyl) phenoxy)ethyl)amino)-N-(2-hydroxyethyl)-N-methylbut-2-enamide; or a pharmaceutically acceptable salt thereof.

3. A compound given by formula III:

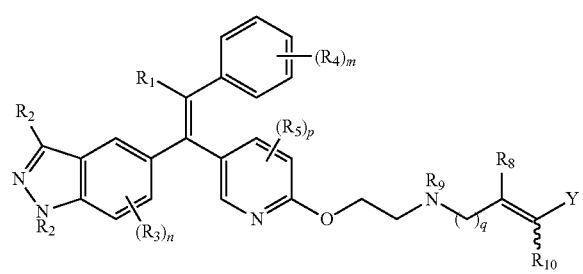

III wherein:
R$_1$ is selected from the group consisting of —CH$_2$CF$_3$, —CH$_2$CH$_3$, and cyclobutyl;

$R_2$ is selected from the group consisting of H, halogen, hydroxy, $C_1$-$C_3$ alkyl, $C_3$-$C_4$ cycloalkyl and $C_4$ heterocyclic ring;

when n is not 0, $R_3$ are the same or different, and are independently selected from the group consisting of H, halogen, $C_1$-$C_6$ alkyl and $C_1$-$C_3$ alkoxy optionally substituted with at least one halogen;

n is 0-3;

when m is not zero, $R_4$ are the same or different and are independently selected from the group consisting of H, halogen, $C_1$-$C_6$ alkyl, and $OR_{ii}$, wherein $R_{11}$ is selected from the group consisting of $C_3$-$C_6$ cycloalkyl, $C_1$-$C_6$ alkyl, aryl, heteroaryl and a 4-6 membered heterocyclic ring;

m is 0-5;

when p is not 0, $R_5$ are the same or different and are independently selected from the group consisting of H, halogen, $C_1$-$C_4$ alkyl, C alkoxy, $C_3$-$C_4$ cycloalkyl, $C_3$-$C_6$ cycloalkoxy and $C_4$ heterocycle;

p is 0-3;

q is 1-2;

$R_8$ and $R_{10}$ are the same or different and are independently selected from the group consisting of halogen, H and $C_1$-$C_3$ alkyl;

$R_9$ is selected from the group consisting of H, $C_1$-$C_6$ alkyl and $C_3$-$C_6$ cycloalkyl;

Y is selected from the group consisting of —$S(O)_2R_6$, —$S(O)_2NR_6R_7$, —$C(O)NR_6R_7$, —$C(O)R_6$, —$C(O)OR_6$, —CN; or wherein Y and $R_{10}$ both represent —$CF_3$;

$R_6$ and $R_7$ are the same or different and are independently selected from the group consisting of H, $C_1$-$C_6$ alkyl, $C_3$-$C_6$ cycloalkyl, aryl, heteroaryl and a 4-6 membered heterocyclic ring wherein said alkyl is saturated or unsaturated or wherein $R_6$ and $R_7$ form a 4-6 membered heterocyclic ring with the N to which they are attached, optionally also containing an O atom;

$R_{12}$ is selected from the group consisting of H, $C_3$-$C_4$ cycloalkyl and $C_1$-$C_6$ alkyl; and wherein any carbon containing moiety of $R_1$-$R_{12}$ may be optionally substituted with one or more halogen atoms, fluoromethane, difluoromethane or trifluoromethane, or —OH;

or a pharmaceutically acceptable salt thereof.

4. The compound or pharmaceutically acceptable salt of claim 3, wherein $R_1$ is —$CH_2CF_3$.

5. The compound or pharmaceutically acceptable salt of claim 3, wherein $R_1$ is cyclobutyl.

6. A method of treating breast cancer comprising administering to a subject the compound or pharmaceutically acceptable salt of claim 1.

7. The method of claim 6, wherein said breast cancer is an ER-positive breast cancer.

8. The method of claim 7, wherein said subject expresses a mutant ER-a protein.

9. A method of treating breast cancer comprising administering to a subject a compound or pharmaceutically acceptable salt of claim 2.

10. A method of treating breast cancer comprising administering to a subject the compound or pharmaceutically acceptable salt of claim 3.

11. The method of claim 10, wherein said breast cancer is an ER-positive breast cancer.

12. The method of claim 10, wherein said subject expresses a mutant ER-a protein.

13. The compound or pharmaceutically acceptable salt of claim 3, wherein $R_8$ is H.

14. The compound or pharmaceutically acceptable salt of claim 3, wherein $R_2$ is F.

15. The compound or pharmaceutically acceptable salt thereof of claim 3, wherein $R_2$ is H.

16. The compound or pharmaceutically acceptable salt of claim 3, wherein m is 2, and one of R4 is F and the other R4 is Cl.

17. The compound or pharmaceutically acceptable salt of claim 3, wherein $R_{10}$ is —H and Y is —$C(O)NR_6R_7$.

18. The compound or pharmaceutically acceptable salt of claim 17, wherein $R_6$ and $R_7$ are both methyl.

19. The compound or pharmaceutically acceptable salt of claim 3, wherein n is 0, p is 0, and $R_9$ is H.

20. The compound or pharmaceutically acceptable salt of claim 3, wherein m is 0.

* * * * *